(12) United States Patent
Katagiri et al.

(10) Patent No.: US 10,669,310 B2
(45) Date of Patent: Jun. 2, 2020

(54) PEPTIDE FOR CANCER TREATMENT AND PHARMACEUTICAL COMPOSITION CONTAINING SAME

(71) Applicants: TOKUSHIMA UNIVERSITY, Tokushima-shi (JP); ONCOTHERAPY SCIENCE, INC., Kawasaki-shi (JP)

(72) Inventors: Toyomasa Katagiri, Tokushima (JP); Takashi Miyamoto, Kawasaki (JP); Rie Hayashi, Kawasaki (JP)

(73) Assignees: TOKUSHIMA UNIVERSITY, Tokushima-shi (JP); ONCOTHERAPY SCIENCE, INC., Kawasaki-shi (JP)

( * ) Notice: Subject to any disclaimer, the term of this patent is extended or adjusted under 35 U.S.C. 154(b) by 0 days.

(21) Appl. No.: 16/070,896

(22) PCT Filed: Jan. 16, 2017

(86) PCT No.: PCT/JP2017/001187
§ 371 (c)(1),
(2) Date: Jul. 18, 2018

(87) PCT Pub. No.: WO2017/126461
PCT Pub. Date: Jul. 27, 2017

(65) Prior Publication Data
US 2019/0023739 A1    Jan. 24, 2019

(30) Foreign Application Priority Data
Jan. 19, 2016    (JP) ................. 2016-007686

(51) Int. Cl.
| | | |
|---|---|---|
| A61K 38/10 | (2006.01) | |
| C07K 7/04 | (2006.01) | |
| A61K 38/00 | (2006.01) | |
| C07K 7/00 | (2006.01) | |
| A61P 35/00 | (2006.01) | |
| A61K 38/03 | (2006.01) | |

(52) U.S. Cl.
CPC ............ *C07K 7/04* (2013.01); *A61K 38/00* (2013.01); *A61K 38/10* (2013.01); *A61P 35/00* (2018.01); *C07K 7/00* (2013.01); *A61K 38/03* (2013.01)

(58) Field of Classification Search
None
See application file for complete search history.

(56) References Cited

U.S. PATENT DOCUMENTS

| | | |
|---|---|---|
| 2009/0175844 A1 | 7/2009 | Nakamura et al. |
| 2011/0135647 A1 | 6/2011 | Nakamura et al. |
| 2012/0014996 A1 | 1/2012 | Nakamura et al. |
| 2013/0011933 A1 | 1/2013 | Nakamura et al. |
| 2014/0162952 A1* | 6/2014 | Katagiri ............ G01N 33/5011 514/10.2 |
| 2015/0045310 A1 | 2/2015 | Link et al. |

FOREIGN PATENT DOCUMENTS

| | | |
|---|---|---|
| EP | 2738255 A1 | 6/2014 |
| WO | 2006/085684 A2 | 8/2006 |
| WO | 2008/018642 A2 | 2/2008 |
| WO | 2013/018690 A1 | 2/2013 |

OTHER PUBLICATIONS

Walensky et al., "Hydrocarbon-Stapled Peptides: Principles, Practice ad Progress", Journal of Medicinal Chemistry, 2014, pp. 6275-6288 (Year: 2014).*
Aihara, et al; Synthesis of lactam-bridged cyclic peptides using sequential olefin metathesis and diimide reduction reactions; Tetrahedron (Jun. 2015); vol. 71; Issue 24, 17; 4183-4191.
Blackwell, et al; Highly Efficient Synthesis of Covalently Cross-Linked Peptide Helices by Ring-Closing Metathesis; Angew. Chem. Int. Ed. (1998); 37, No. 23; 3281-3284.
Chlebowski, et al; Clinical perspectives on the utility of aromatase inhibitors for the adjuvant treatment of breast cancer; The Breast; 18 (2009) 52, S1-S11.
Clarke, et al; Cellular and Molecular Pharmacology of Antiestrogen Action and Resistance; Pharmacol. Reviews; (2001) vol. 53, No. 1; 25-71.
Chumsri, et al; Aromatase, Aromatase Inhibitors, and Breast Cancer; J. Steroid Biochem Mol. Biol.; (May 2011) 125(1-2): 13-22.
Fisher, et al; Five Versus More Than Five Years of Tamoxifen for Lymph Node-Negative Breast Cancer: Updated Findings From the National Surgical Adjuvant Breast and Bowel Project B-14 Randomized Trial; Jour. of the National Cancer Inst.; (May 2001) vol. 93, No. 9; 684-690.
Fisher, et al; Tamoxifen for the Prevention of Breast Cancer: Current Status of the National Surgical Adjuvant Breast and Bowel Project P-1 Study; Jour. of the National Cancer Inst.; (Nov. 2005) vol. 97, No. 22; 1652-1662.
Johnston; New Strategies in Estrogen Receptor-Positive Breast Cancer; Clin. Cancer Res. (2010) 16:1979-1987.
Jordan; Tamoxifen: A Most Unlikely Pioneering Medicine; Nature Reviews; (Mar. 2003) vol. 2; 205-213.
Kim et al; Abstract of the annual meeting of the Japanese Cancer Assoc. (2008); 67; 309;0-414.
Kim, et al; Activation of an estrogen/estrogen receptor signaling by BIG3 through its inhibitory effect on nuclear transport of PHB2/REA in breast cancer; Cancer Sci (Aug. 2009) vol. 100, No. 8; 1468-1478.

(Continued)

*Primary Examiner* — Lianko G Garyu
(74) *Attorney, Agent, or Firm* — Kilpatrick Townsend & Stockton LLP

(57) ABSTRACT

The present invention provides peptides containing a structure in which a portion of the dominant negative peptide of BIG3 which inhibits the interaction between BIG3 and PHB2 is substituted with stapling structure(s). Peptides of the present invention have excellent cell growth inhibitory actions. Furthermore, their cell growth inhibitory actions continue for a longer time than the actions of peptides without stapling structures. Therefore, these peptides have features suitable for clinical applications in cancer therapy.

13 Claims, 55 Drawing Sheets

Specification includes a Sequence Listing.

(56) References Cited

OTHER PUBLICATIONS

Kim, et al; BIG3 Inhibits the Estrogen-Dependent Nuclear Translocation of PHB2 via Multiple Karyopherin-Alpha Proteins in Breast Cancer Cells; PLoS One; (Jun. 2015) 8:10(6); 1-16.

Lau, et al; Peptide stapling techniques based on different macrocyclisation chemistries; Chem Soc Rev.; (Jan. 2015) 7:44(1):91-102.

Yoshimaru, et al; Therapeutic advances in BIG3-PHB2 inhibition targeting the crosstalk between estrogen and growth factors in breast cancer; Cancer Sci (May 2015); vol. 106, No. 5; 550-558.

Yoshimaru, et al; Xanthohumol suppresses oestrogen-signalling in breast cancer through the inhibition of BIG3-PHB2 interactions; Scientific Reports (Dec. 2014); 4:7355; 1-9.

Yoshimaru, et al; Targeting BIG3-PHB2 interaction to overcome tamoxifen resistance in breast cancer cells; Nature Communications (Sep. 2013); 4:2443; 1-13.

Yoshimaru, et al; Development of Intramolecularly-Crosslinked BIG3-PHB2 Interaction Inhibiting Peptide Aiming at Treatment of Hormonal Therapy-Resistant Breast Cancer; The 20th Annual Meeting of the Japanese Assoc. for Molecular Target Therapy of Cancer (May 2016); entire text.

Japan Patent Office; International Search Report of PCT/JP2017/001187; dated Apr. 18, 2017.

U.S. Appl. No. 16/631,141, filed Jan. 14, 2020, Oncotherapy Science, Inc.

Yoshimaru, et al; Stapled BIG3 helical peptide ERAP potentiates anti-tumour activity for breast cancer therapeutics; Sci Rep.; May 12, 2017; 7(1):1821.

* cited by examiner

| | Concentration (μM) | Percentage of Cell Growth Inhibition (%) | | | | | | | |
|---|---|---|---|---|---|---|---|---|---|
| | | MCF-7 Cell | | | | MCF-10A Cell | | | |
| | | 24 | 48 | 72 | 96 | 24 | 48 | 72 | 96 (Hours) |
| 11R-ERAP: 11R-GGG-QMLSDLTLQLRQR (SEQ ID NO: 33) | 0.5 | 0 | 0 | 13 | 2 | 0 | 0 | 1 | 0 |
| | 1 | 41 | 6 | 0 | 0 | 0 | 0 | 0 | 1 |
| | 10 | 100 | 48 | 61 | 61 | 0 | 0 | 0 | 0 |
| No. 2 : QXLSDXTLQLRQR (SEQ ID NO: 2) | 0.5 | 0 | 21 | 32 | 59 | 0 | 6 | 12 | 4 |
| | 1 | 100 | 53 | 34 | 70 | 0 | 5 | 10 | 5 |
| | 10 | 100 | 99 | 64 | 81 | 0 | 6 | 12 | 6 |
| No. 3 : QMXSDLXLQLRQR (SEQ ID NO: 3) | 0.5 | 38 | 51 | 40 | 63 | 1 | 8 | 11 | 4 |
| | 1 | 100 | 99 | 59 | 68 | 0 | 5 | 12 | 9 |
| | 10 | 100 | 100 | 79 | 77 | 2 | 4 | 6 | 8 |
| No. 4 : QMLXDLTXQLRQR (SEQ ID NO: 4) | 0.5 | 11 | 22 | 16 | 46 | 3 | 5 | 6 | 7 |
| | 1 | 100 | 75 | 37 | 66 | 7 | 43 | 71 | 55 |
| | 10 | 100 | 99 | 90 | 79 | 12 | 55 | 71 | 57 |
| No. 5 : QMLSXLTLXLRQR (SEQ ID NO: 5) | 0.5 | 0 | 16 | 13 | 13 | 0 | 0 | 8 | 3 |
| | 1 | 0 | 0 | 3 | 11 | 1 | 1 | 73 | 53 |
| | 10 | 62 | 16 | 45 | 65 | 12 | 44 | 73 | 54 |
| No. 6 : QMLSDXTLQXRQR (SEQ ID NO: 6) | 0.5 | 18 | 20 | 42 | 55 | 9 | 54 | 72 | 55 |
| | 1 | 100 | 46 | 82 | 81 | 10 | 58 | 73 | 58 |
| | 10 | 100 | 100 | 86 | 86 | 7 | 53 | 71 | 56 |

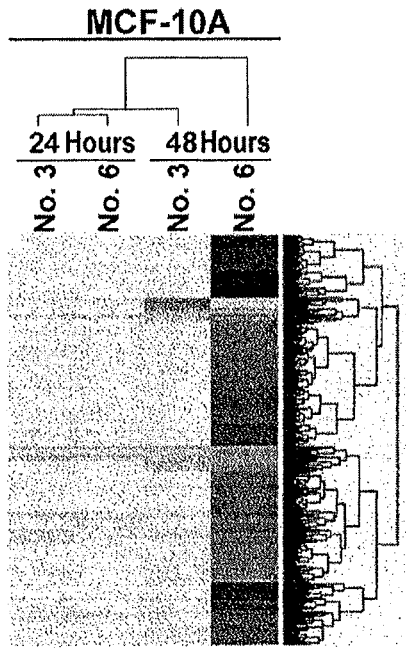

DAVID

| Term | Count | P Value | Bonferroni | Benjamini | FDR |
|---|---|---|---|---|---|
| cell adhesion | 27 | 3.8E-10 | 1.3E-07 | 1.3E-07 | 5.2E-07 |
| extracellular region part | 42 | 8.3E-10 | 1.8E-07 | 1.8E-07 | 1.1E-06 |
| signal | 85 | 9.6E-09 | 3.3E-06 | 1.7E-06 | 1.3E-05 |
| extracellular matrix | 18 | 6.7E-08 | 2.3E-05 | 7.8E-06 | 9.2E-05 |
| biological adhesion | 34 | 1.7E-08 | 2.9E-05 | 9.8E-06 | 2.8E-05 |
| signal peptide | 85 | 1.3E-08 | 1.3E-05 | 1.3E-05 | 2.0E-05 |
| cell motion | 28 | 8.0E-09 | 1.4E-05 | 1.4E-05 | 1.4E-05 |
| Secreted | 52 | 1.9E-07 | 6.5E-05 | 1.6E-05 | 2.5E-04 |
| calcium binding | 12 | 2.4E-07 | 8.4E-05 | 1.7E-05 | 3.3E-04 |
| inflammatory response | 22 | 4.8E-08 | 8.4E-05 | 2.1E-05 | 8.1E-05 |
| extracellular region | 59 | 3.5E-07 | 7.7E-05 | 2.6E-05 | 4.5E-04 |
| response to wounding | 28 | 7.8E-08 | 1.4E-04 | 2.7E-05 | 1.3E-04 |
| extracellular matrix | 21 | 2.6E-07 | 5.8E-05 | 2.9E-05 | 3.4E-04 |
| ectoderm development | 17 | 1.1E-07 | 1.9E-04 | 3.1E-05 | 1.8E-04 |
| epidermis development | 16 | 2.3E-07 | 4.0E-04 | 5.7E-05 | 3.8E-04 |
| proteinaceous extracellular matrix | 19 | 1.7E-06 | 3.7E-04 | 7.4E-05 | 2.1E-03 |
| extracellular space | 29 | 1.4E-06 | 3.1E-04 | 7.7E-05 | 1.8E-03 |
| epithelium development | 16 | 3.2E-06 | 5.7E-03 | 7.1E-04 | 5.5E-03 |
| glycoprotein | 92 | 2.2E-05 | 7.6E-03 | 8.4E-04 | 3.0E-02 |
| defense response | 27 | 4.7E-06 | 8.2E-03 | 9.2E-04 | 7.9E-03 |
| regulation of cell proliferation | 31 | 6.6E-06 | 1.2E-02 | 1.2E-03 | 1.1E-02 |
| cell migration | 17 | 8.2E-06 | 1.4E-02 | 1.3E-03 | 1.4E-02 |
| regulation of cell adhesion | 12 | 1.1E-05 | 1.9E-02 | 1.6E-03 | 1.9E-02 |
| epithelial cell differentiation | 12 | 1.1E-05 | 1.94E-02 | 1.63E-03 | 1.88E-02 |

FIG. 2F

Gene MANIA

| Feature | FDR | Coverage Ratio |
|---|---|---|
| extracellular matrix organization | 1.1E-27 | 25/290 |
| extracellular structure organization | 1.1E-27 | 25/291 |
| extracellular matrix | 2.6E-22 | 20/208 |
| extracellular matrix disassembly | 9.6E-18 | 15/119 |
| proteinaceous extracellular matrix | 1.1E-14 | 13/110 |
| hemidesmosome assembly | 1.9E-12 | 7/12 |
| cell junction assembly | 1.9E-12 | 13/164 |
| cell junction organization | 5.3E-12 | 13/181 |
| extracellular matrix part | 5.7E-12 | 10/67 |
| collagen catabolic process | 2.8E-10 | 9/65 |
| multicellular organismal catabolic process | 5.9E-10 | 9/71 |
| cell-substrate junction assembly | 1.4E-09 | 8/49 |
| collagen | 1.5E-09 | 7/28 |
| extracellular matrix structural constituent | 2.4E-09 | 8/53 |
| collagen metabolic process | 2.6E-09 | 9/86 |
| multicellular organismal macromolecule metabolic process | 3.7E-09 | 9/90 |
| multicellular organismal metabolic process | 6.3E-09 | 9/96 |
| cell-substrate adhesion | 1.3E-08 | 10/152 |
| endoplasmic reticulum lumen | 1.7E-07 | 9/140 |
| cell-cell adhesion | 1.9E-06 | 10/256 |
| collagen fibril organization | 5.3E-06 | 5/24 |
| cell-matrix adhesion | 1.3E-05 | 7/103 |
| fibrillar collagen | 1.5E-05 | 4/11 |
| low-density lipoprotein particle binding | 4.3E-05 | 1/14 |

FIG. 2F-(cont.)

1. KPL-3C Orthotopic Breast Cancer Xenograft Transplantation in Nude Mouse (1 x 10$^7$ cells/mouse)
2. Every Day Injection of E2 Solution into the Neck Skin
3. Every Day or Every 4 Days Intraperitoneal Injection of Peptide Stapled ERAP No. 12 (SEQ ID NO:12): QMXSDLXLQLRQR
Stapled-D-ERAP No.12 (SEQ ID NO:34): qmxsdlxlqlrqr
Stapled Retro-inverso ERAP No.12 (SEQ ID NO:35): rqrlqlxldsxmq
Short Stapled Retro-inverso ERAP No.12 (SEQ ID NO:36): xldsxmq

FIG. 6A

PEPTIDE FOR CANCER TREATMENT AND PHARMACEUTICAL COMPOSITION CONTAINING SAME

CROSS-REFERENCE TO RELATED APPLICATIONS

The present application is a § 371 National Phase Application of PCT/JP2017/001187, filed Jan. 16, 2017, which application claims the benefit of Japanese Patent Application No. JP 2016-007686, filed on Jan. 19, 2016, the entire contents of which are incorporated by reference in their entireties for all purposes herein.

TECHNICAL FIELD

The present invention relates to peptides useful in cancer therapy, and pharmaceutical compositions containing them.

BACKGROUND ART

Estrogen-receptor α (ERα) plays a key role in the development and progression of breast cancer. The current endocrine therapies for breast cancer mainly target ERα signaling, and use selective ERα modulators (for example, tamoxifen and raloxifene), ERα down-regulators (for example, fulvestrant), and aromatase inhibitors (AI) (Non-patent Literatures 1 to 3). Among these therapies, a method that uses tamoxifen, which inhibits breast cancer cell proliferation through competitive binding to ERα, is a standard therapy for patients with ERα-positive breast cancer. However, tamoxifen therapy is often ineffective, and the patient may die from recurrent endocrine therapy-resistant tumors (Non-patent Literatures 4 and 5). Furthermore, compared with tamoxifen, AI, which blocks estrogen synthesis, provides substantial clinical effects such as good efficacy, significant increase in relapse-free survival period, and a prolonged time to disease recurrence in postmenopausal women; however, some patients who have undergone AI treatment still relapse (Non-patent Literatures 6 and 7). The precise molecular events having effects on the efficacy of these endocrine therapies remain unknown.

A complex formed between brefeldin A-inhibited guanine nucleotide-exchange protein 3 (BIG3), which is a cancer specific protein, and prohibitin 2 (PHB2), which is a tumor suppressor, plays a key role in estrogen signaling regulation in ERα-positive breast cancer (Non-patent Literatures 8 and 9). BIG3 binds to PHB2 to inhibit the ability of PHB2, which suppresses the estrogen-dependent transcriptional activation, and thereby causes constitutive ERα activation. Based on these findings, strategies of making PHB2 exhibit its tumor suppressive activity by dissociating PHB2 from its complex with BIG3 through inhibition of the BIG3-PHB2 interaction, may become a novel therapy for breast cancer. Based on this strategy, the present inventors have previously developed a dominant negative peptide of BIG3, which specifically inhibits the BIG3-PHB2 interaction (Patent Literature 1). This peptide has been confirmed to suppress breast cancer growth by reactivating the tumor suppressive activity of PHB2 to inhibit ERα-signaling pathways that bring about the growth of breast cancer (Patent Literature 1).

CITATION LIST

Patent Literatures

[Patent Literature 1] WO 2013/018690

Non-Patent Literatures

[Non-patent Literature 1] Johnston, S. R., Clin. Cancer Res. 16, 1979-1987 (2010).
[Non-patent Literature 2] Fisher, B. et al., J. Natl. Cancer Inst. 97, 1652-1662 (2005).
[Non-patent Literature 3] Jordan, V. C., Nature Rev. Drug Discov. 2, 205-213 (2003).
[Non-patent Literature 4] Clarke, R. et al., Pharmacol. Rev. 53, 25-71 (2001).
[Non-patent Literature 5] Fisher, B. et al., J. Natl. Cancer Inst. 93, 684-690 (2001).
[Non-patent Literature 6] Chlebowski, R. et al., Breast 2, S1-11 (2009).
[Non-patent Literature 7] Chumsri, S. et al., J. Steroid Biochem. Mol. Biol. 125, 13-22 (2011).
[Non-patent Literature 8] Kim, J. W. et al., Cancer Sci. 100, 1468-1478 (2009).
[Non-patent Literature 9] Yoshimaru, T. et al., Nat. Commun. 4, 2443 (2013).

SUMMARY OF THE INVENTION

Problems to be Solved by the Invention

However, the stability of the above-mentioned dominant negative peptide cannot be said to be high and the duration of inhibitory effects on the BIG3-PHB2 interaction is not that long. Inhibitory effects that last longer are desired for clinical applications.

Therefore, an objective of the present invention is to provide peptides having longer lasting inhibitory effects on the BIG3-PHB2 interaction.

Means for Solving the Problems

The present inventors completed the present invention by discovering that the duration of inhibitory effects on the BIG3-PHB2 interaction is improved by introducing stapling structure(s) into the dominant negative peptide molecule. More specifically, the present invention provides the following peptides and uses thereof:

[1] a peptide comprising an amino acid sequence in which an n pair (n is a natural number) of amino acid residues is substituted with an n number of stapling structures in the amino acid sequence of SEQ ID NO: 9 or a partial sequence thereof, or a salt thereof;

[2] the peptide or the salt thereof of [1], wherein the n pair of amino acid residues is one pair of amino acid residues of (a) or (b) below:
  (a) the third and seventh amino acid residues from the N terminus of the amino acid sequence of SEQ ID NO: 9; or
  (b) the second and sixth amino acid residues from the N terminus of the amino acid sequence of SEQ ID NO: 9;

[3] the peptide or the salt thereof of [1] or [2], wherein the partial sequence of the amino acid sequence of SEQ ID NO: 9 is the amino acid sequence of SEQ ID NO: 13;

[4] the peptide or the salt thereof of [3], wherein the n pair of amino acid residues is one pair of amino acid residues of (a) or (b) below:
  (a) the third and seventh amino acid residues from the N terminus of the amino acid sequence of SEQ ID NO: 13; or
  (b) the second and sixth amino acid residues from the N terminus of the amino acid sequence of SEQ ID NO: 13;

[5] the peptide or the salt thereof of any one of [1] to [4], wherein the stapling structure is represented by Formula (I) below:

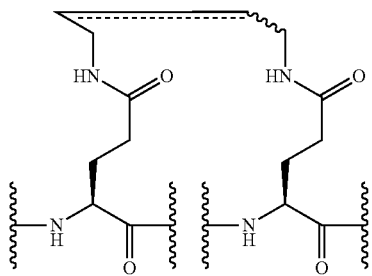

(I)

(wherein, the double line drawn by a solid line and a dashed line indicates a single bond or a double bond);

[6] the peptide or the salt thereof of [5], which is represented by Formula (II) below:

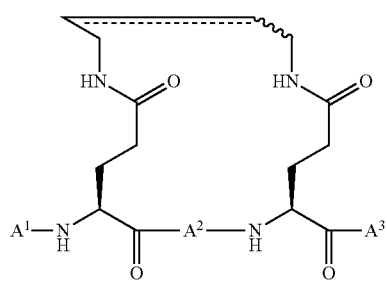

(II)

(wherein, the double line drawn by a solid line and a dashed line indicates a single bond or a double bond;
the combination of $A^1$, $A^2$, and $A^3$ is selected from the following:
$A^1$=Q, $A^2$=LSD, and $A^3$=TLQLRQR (SEQ ID NO: 14);
$A^1$=QM, $A^2$=SDL, and $A^3$=LQLRQR (SEQ ID NO: 15);
$A^1$=QM, $A^2$=SDL, and $A^3$=—OH; and
$A^1$=Q, $A^2$=LSD, and $A^3$=T);

[7] the peptide or the salt thereof of any one of [1] to [6], wherein either one or both of N-terminal and C-terminal amino acid residues have been modified;

[8] the peptide or the salt thereof of [7], wherein either one or both of N-terminal and C-terminal amino acid residues have been modified by any one or a combination of acetylation, amidation, and HA tagging;

[9] the peptide or the salt thereof of [8], wherein the N-terminal amino acid residue is acetylated and the C-terminal amino acid residue is amidated;

[10] the peptide or the salt thereof of any one of [1] to [9], wherein all the amino acid residues have been substituted with D-form amino acid residues;

[11] a peptide which is a retro-inverso form of the peptide of any one of [1] to [9], or a salt thereof;

[12] a pharmaceutical composition comprising the peptide or the salt thereof of any one of [1] to [11] and a pharmaceutically acceptable carrier;

[13] the pharmaceutical composition of [12], which is for cancer therapy;

[14] the pharmaceutical composition of [13], wherein the cancer is breast cancer or prostate cancer; and

[15] the pharmaceutical composition of [13] or [14], wherein the cancer is estrogen receptor-positive cancer.

Alternatively, the present invention provides a method for cancer therapy, which comprises the step of administering the peptide or the salt thereof of any one of the above-mentioned [1] to [11] to a subject in need of the therapy. Furthermore, the present invention relates to use of the peptide or the salt thereof of any one of the above-mentioned [1] to [11] in the production of pharmaceutical compositions for cancer therapy. The present invention also relates to use of the peptide or the salt thereof of any one of the above-mentioned [1] to [11] in cancer therapy. Additionally, the present invention relates to a method of producing a pharmaceutical composition for cancer therapy, which comprises the step of mixing or formulating the peptide or the salt thereof of any one of the above-mentioned [1] to [11] with a carrier.

Effects of the Invention

Peptides having longer lasting inhibitory effects on the BIG3-PHB2 interaction are provided by the present invention. Pharmaceutical compositions comprising a peptide of the present invention may be applied to cancer therapy.

BRIEF DESCRIPTION OF THE DRAWINGS

FIG. 1 shows schematic diagrams for stapled ERAP synthesis.

and filled diamond: 10 μM peptide. These data represent the mean±SD of three independent experiments (***P<0.001, two-sided Student's t-test).

Figure 2A:
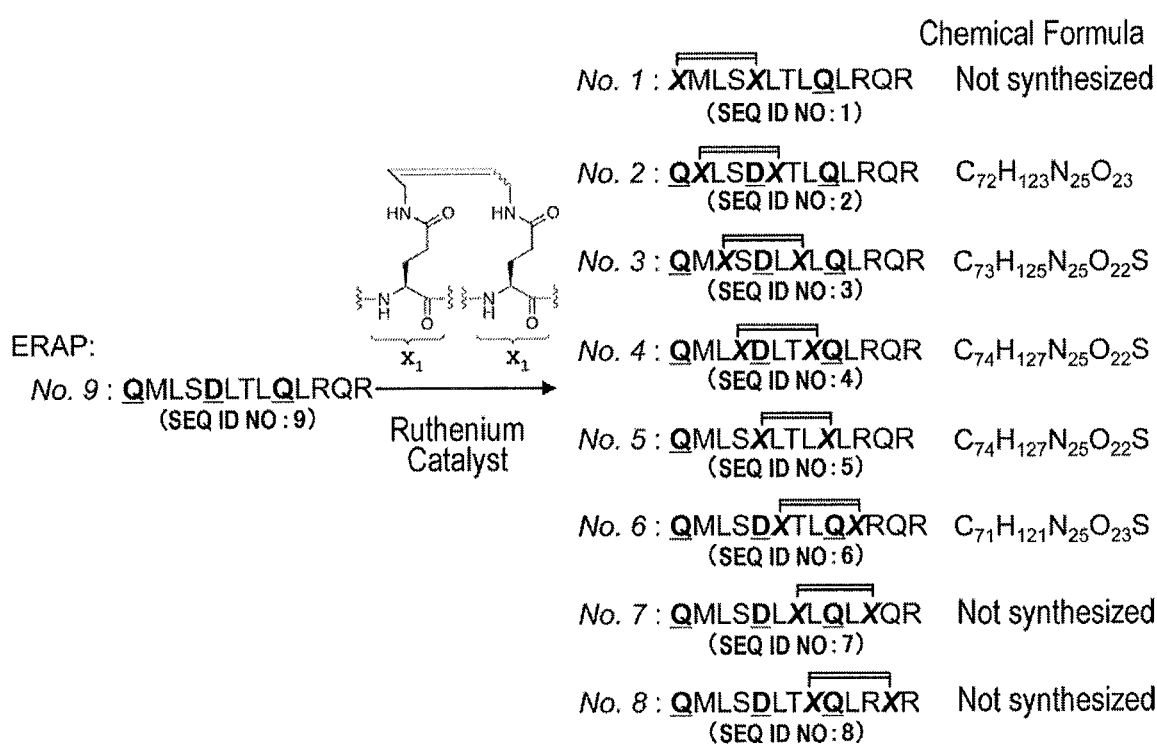
FIG. 2A shows the primary structures of ERAP (No. 9) and stapled ERAPs (Nos. 1 to 8). In the amino acid sequences, the underlined bold letters indicate the amino acid residues important for PHB2-binding, and the italicized bold letters indicate the stapled amino acid residues. All amino acid sequences are described starting from the N terminus at the far left to the C-terminus on the right.
Figure 2B:
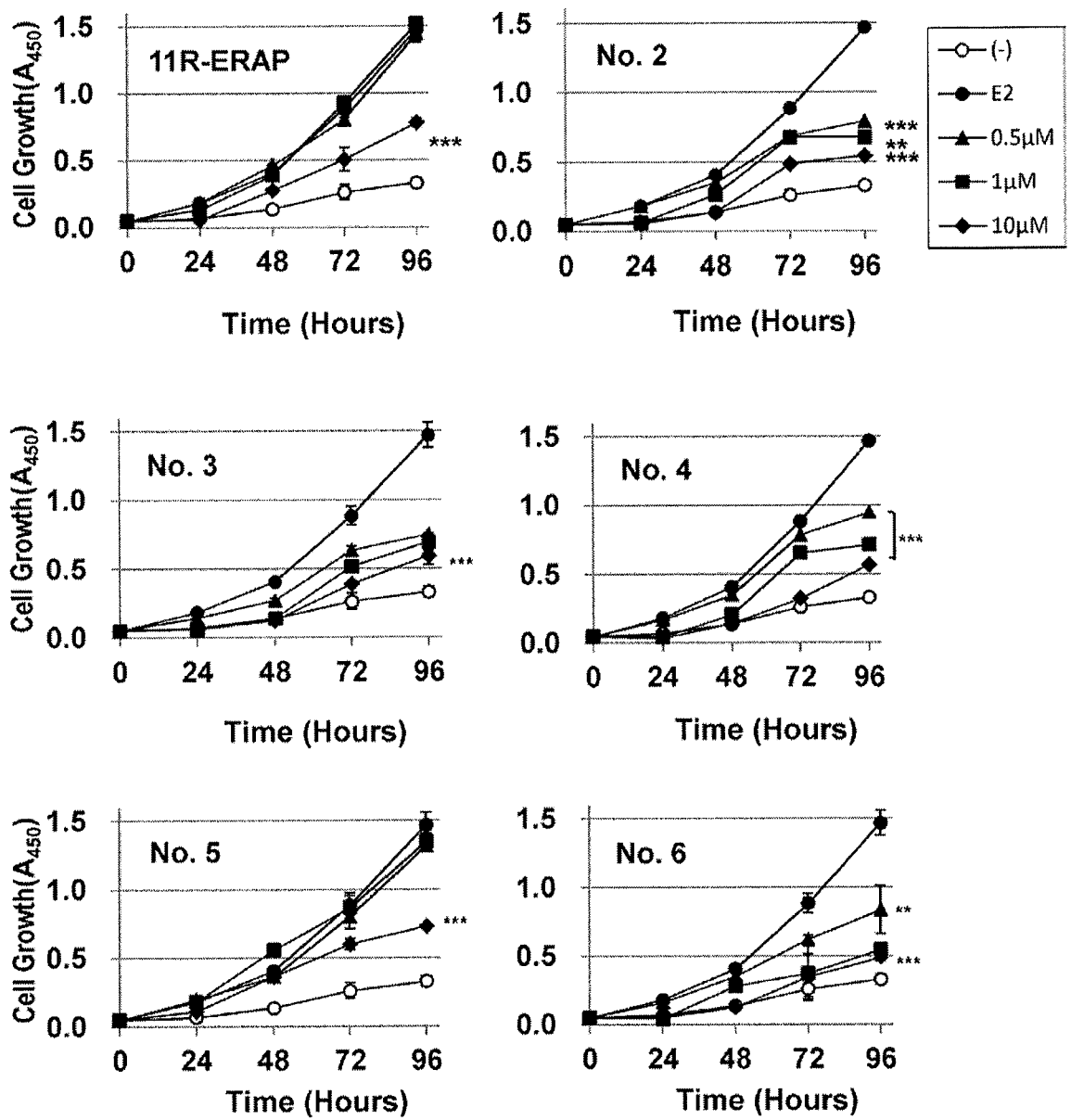
FIG. 2B shows the results of MIT assays which evaluated the inhibitory effects of 11R-ERAP and stapled ERAPs (Nos. 2 to 6) on the 17β-estradiol (E2)-dependent growth of human breast cancer cell line MCF-7. In the E2-added groups, 10 nM E2 was added. The type of the added peptide is indicated at the upper left in each graph. Each symbol in each graph indicates the following: open circle: untreated; filled circle: E2 alone; filled triangle: E2+0.5 µM peptide; filled square: E2+1 µM peptide; and filled diamond: E2+10 µM peptide. These data represent the mean±SD of three independent experiments (P<0.01, *P<0.001, two-sided Student's t-test).
Figure 2C:
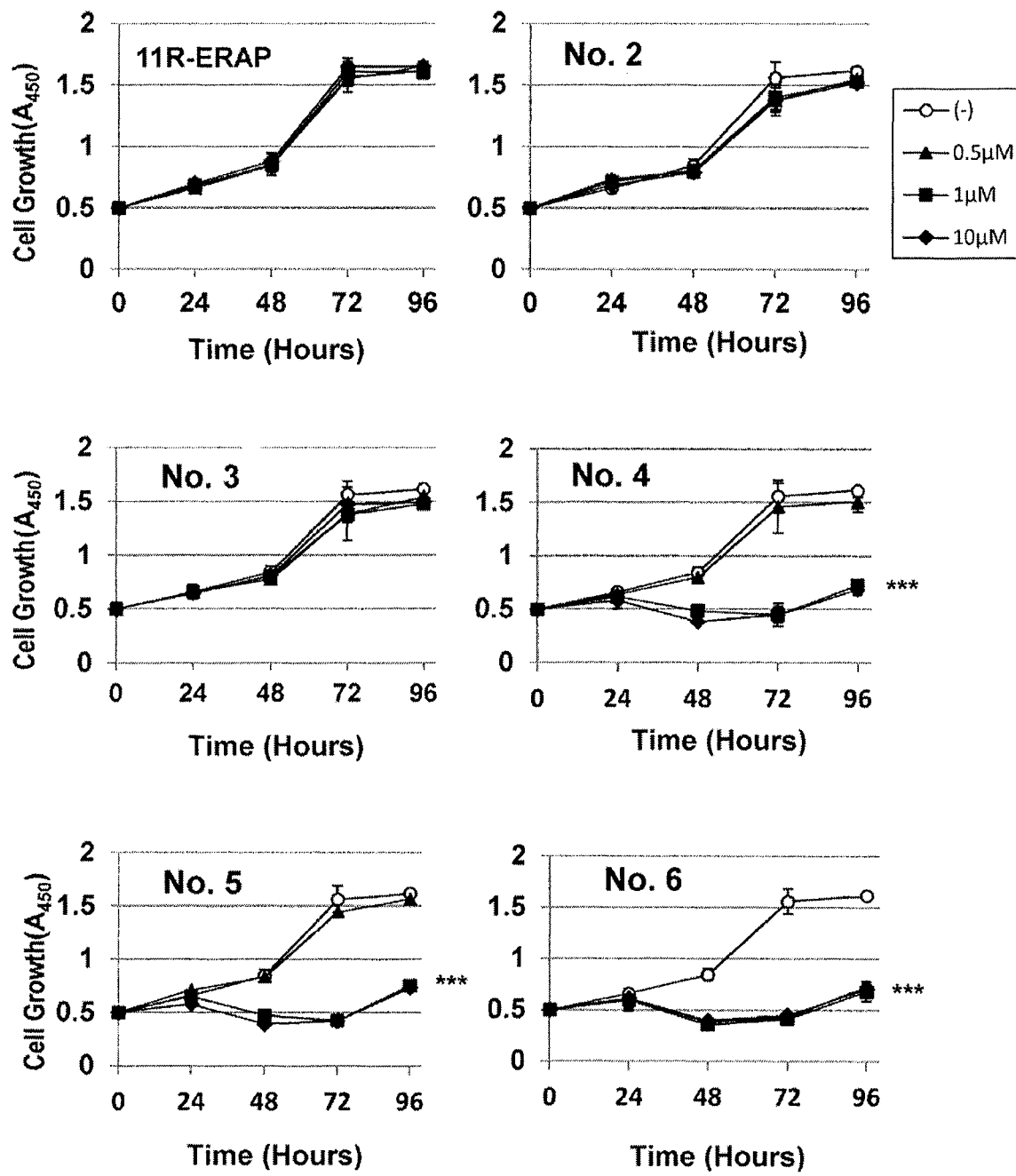
FIG. 2C shows the results of MTT assays which evaluated the inhibitory effects of 11R-ERAP and stapled ERAPs (Nos. 2 to 6) on the growth of human mammary epithelial cell line MCF-10A. The type of the added peptide is indicated at the upper left in each graph. Each symbol in each graph indicates the following: open circle: untreated; filled triangle: 0.5 µM peptide; filled square: 1 µM peptide.
Figure 2D:
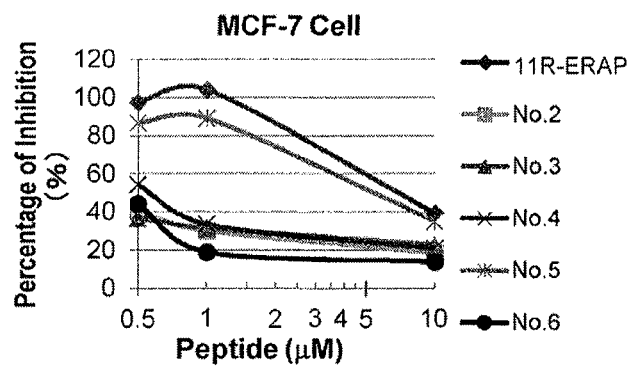
FIG. 2 shows that stapled ERAPs had long-term stable inhibitory actions on the BIG3-PHB2 interaction.
Figure 2D:
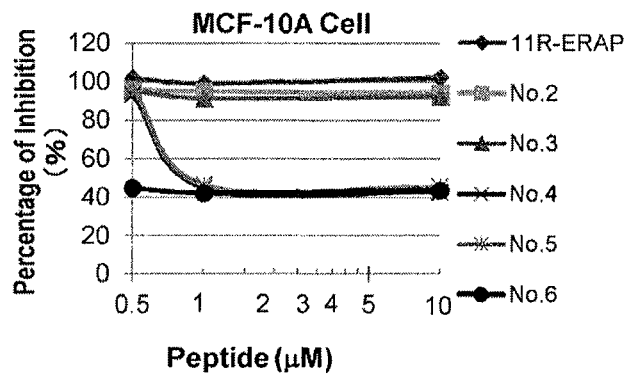

FIG. 2D shows the percentage of cell growth inhibition of E2-dependent MCF-7 cells and MCF-10A cells caused by 11R-ERAP or stapled ERAP (Nos. 2 to 6) addition. The numerical values of the percentage of inhibition were calculated from the results of MTT assays of FIGS. 2B and 2C. In the amino acid sequences of each of the peptides indicated in the table in the upper part of the figure, the underlined bold letters indicate the amino acid residues important for PHB2-binding, and the italicized bold letters indicate the stapled amino acid residues.

Figure 2E:
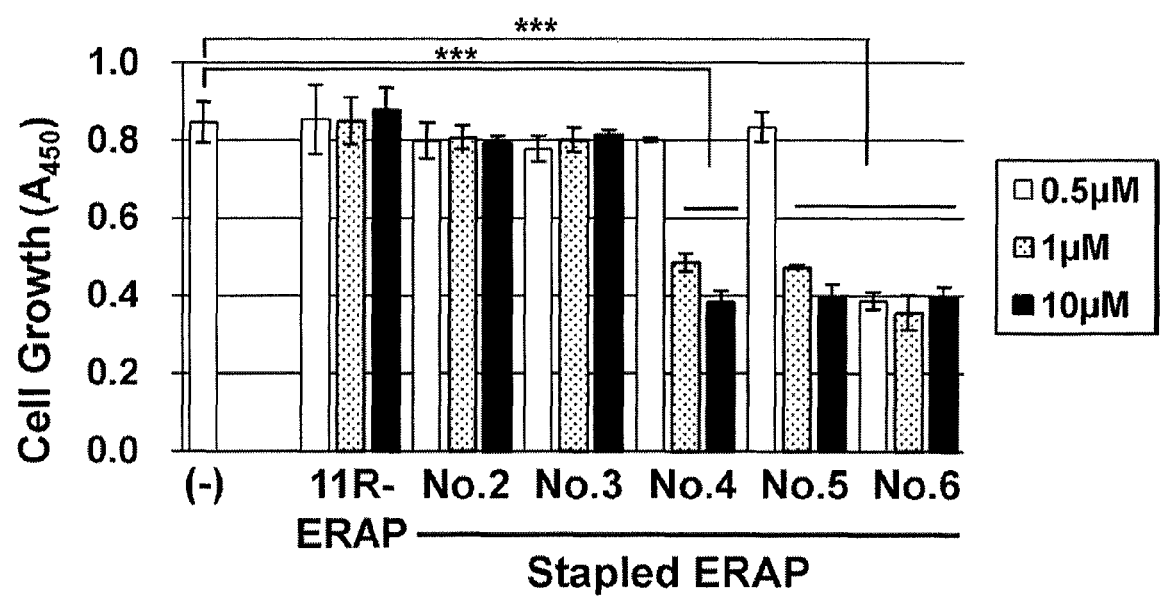

FIG. 2E shows the results of MTT assays which evaluated the inhibitory effects of 11R-ERAP and stapled ERAPs (Nos. 2 to 6) on the growth of MCF-10A cells. The values at 48 hours shown in FIG. 2C are presented as a bar graph. In the graph, "(−)" indicates untreated cells. The data represent the mean±SD of three independent experiments (***P<0.001, two-sided Student's t-test).

FIG. 2F shows the results of analyzing the genes differentially expressed between stapled ERAP No. 3-treated and stapled ERAP No. 6-treated MCF-10A cells. The upper panel shows a heat-map image obtained by analyzing the gene expression in stapled ERAP No. 3-treated or stapled ERAP No. 6-treated MCF-10A cells at 24 hours and 48 hours after the treatment. The lower panel shows the results of performing gene annotation enrichment analysis based on DAVID on the 284 genes that were significantly up-regulated or down-regulated by 100-fold or more in MCF-10A cells subjected to stapled ERAP No. 6 treatment, compared to stapled ERAP No. 3 treatment, at 48 hours after the treatment.

FIG. 2F-(cont.) shows the results of performing an analysis based on GeneMANIA software on the 284 genes that were significantly up-regulated or down-regulated by 100-fold or more in MCF-10A cells subjected to stapled ERAP No. 6 treatment, compared to stapled ERAP No. 3 treatment, at 48 hours after the treatment.

Figure 2G:
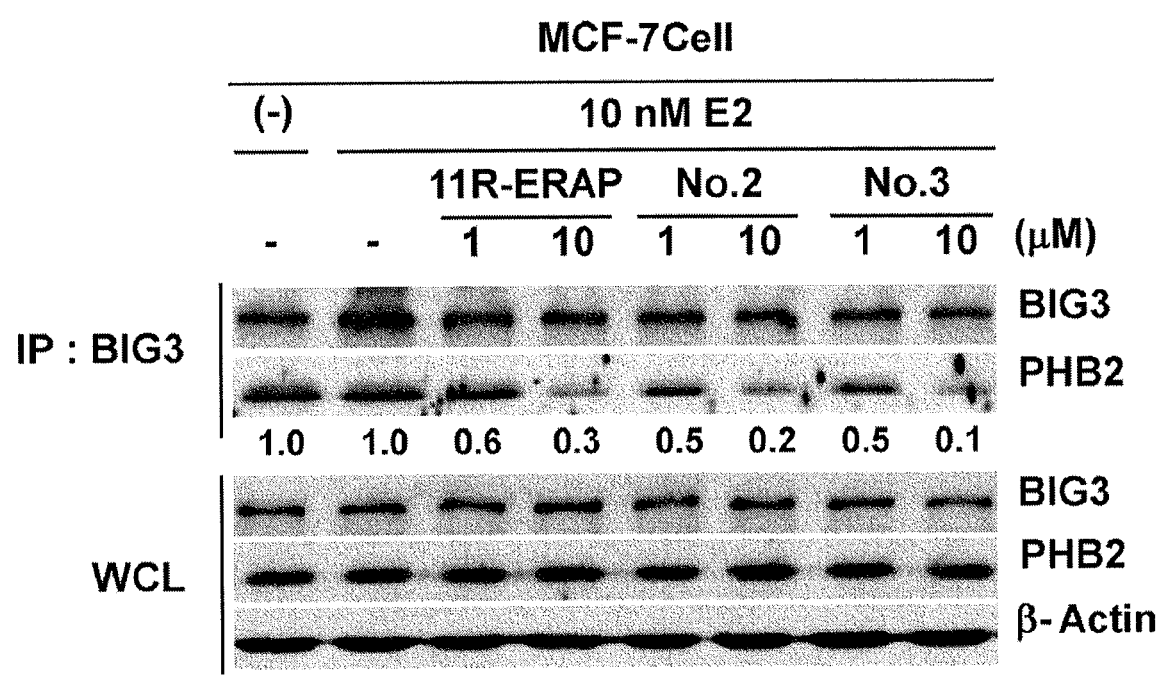

FIG. 2G shows the results of co-immunoprecipitation which evaluated the inhibitory effects of stapled ERAP (No. 2 and No. 3) treatments on the BIG3-PHB2 interaction in MCF-7 cells. 11R-ERAP was used as a positive control for the inhibition of the BIG3-PHB2 interaction. In the figure, "IP" indicates the antibody used for immunoprecipitation, "WCL" indicates whole cell lysate, "(−)" indicates E2-untreated cells, and "−" indicates peptide-untreated cells. The antibodies reacted on the membrane are shown at the far right. The numerical values below the membrane indicate the relative values of reaction intensity for each of the lanes when the reaction intensity of the far-left lane is defined as 1.0.

Figure 2H:
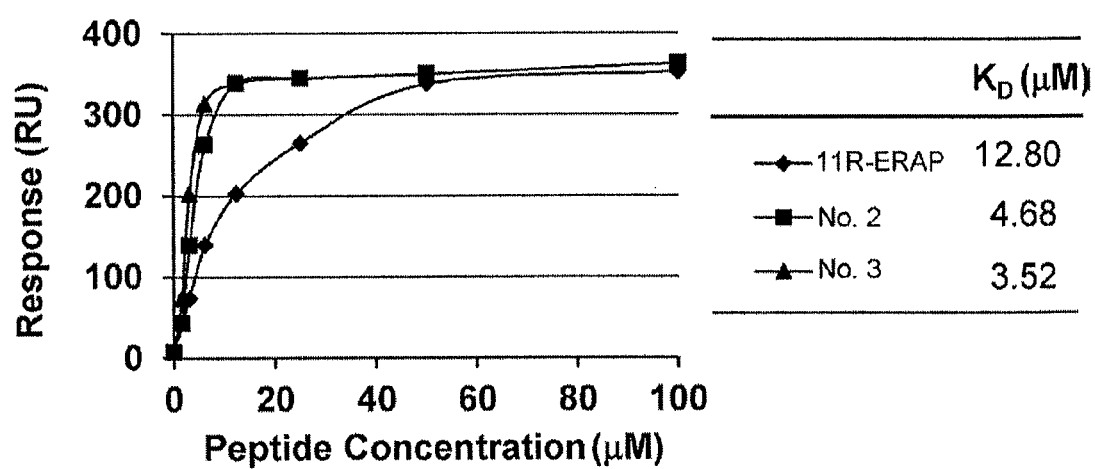

FIG. 2H shows the results of surface plasmon resonance interaction analysis which evaluated the affinities of 11R-ERAP and stapled ERAPs (No. 2 and No. 3) for a His-tagged recombinant PHB2.

Figure 2I:
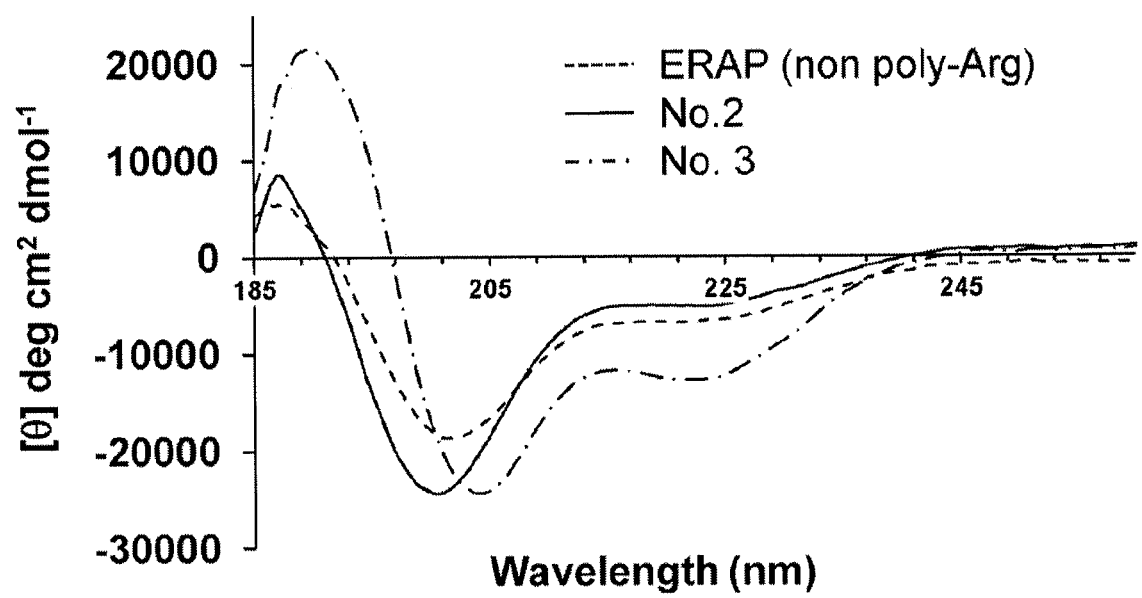

FIG. 2I shows the CD spectra of ERAP and stapled ERAPs (No. 2 and No. 3) in a 10 mM sodium phosphate buffer (pH 7.0).

Figure 2J:
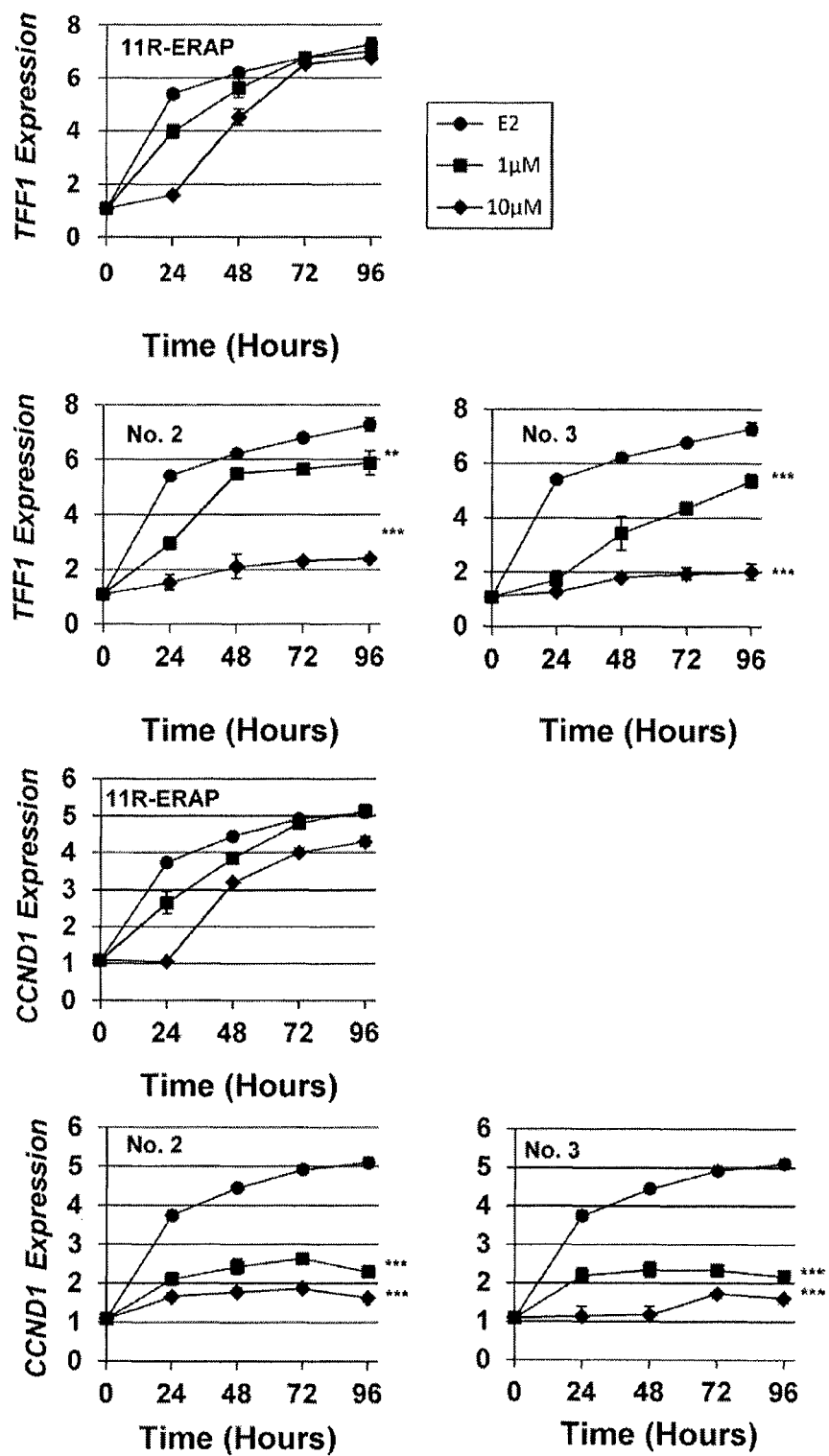

FIG. 2J shows the duration of inhibitory effects of 11R-ERAP and stapled ERAPs (No. 2 and No. 3) on ERα target gene expression measured in MCF-7 cells. The results were presented as multiples of the expression level in untreated cells at time zero, with that level being defined as 1.0. The upper three graphs show TFF1 gene expression and the lower three graphs show CCND1 gene expression. The type of peptide added is indicated at the upper left in each graph. Each symbol in each graph indicates the following: filled circle: E2 alone; filled square: E2+1 μM peptide; and filled diamond: E2+10 μM peptide. These data represent the mean±SD of three independent experiments (P<0.01, *P<0.001, two-sided Student's t-test).

FIG. 3 indicates that stapled ERAP (No. 12) without olefin stably suppressed E2-dependent responses for a long time. FIG. 3A shows the primary structures of stapled ERAP No. 12 which is a stapled ERAP without olefin and its HA-tagged peptide, HA-tagged stapled ERAP No. 12. In the amino acid sequences, the underlined bold letters indicate the amino acid residues important for PHB2-binding and the italicized bold letters indicate the stapled amino acid residues. Both amino acid sequences are described from the N terminus at the far left to the C terminus on the right.

Figure 3A:
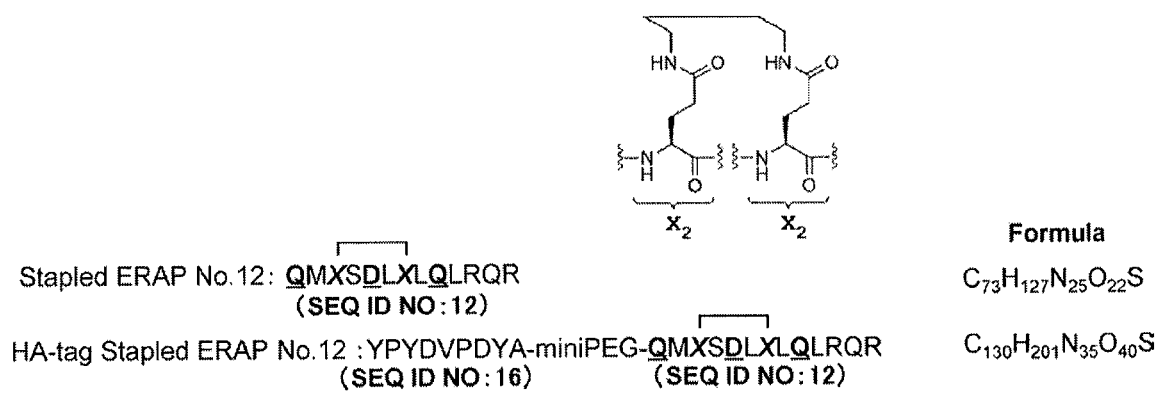
Figure 3B:
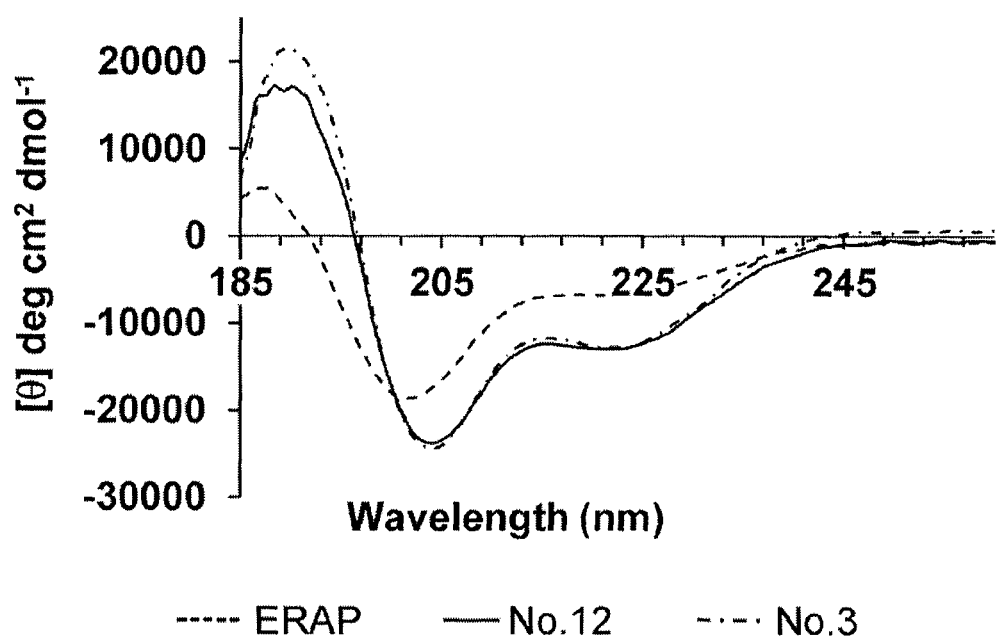

FIG. 3B indicates the CD spectra of ERAP and stapled ERAPs (No. 3 and No. 12).

Figure 3C:
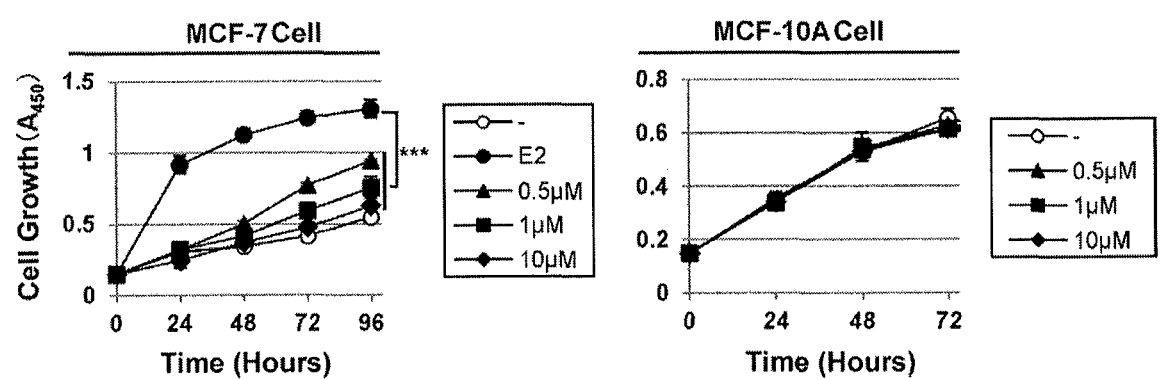

FIG. 3C shows the results of MTT assays which evaluated the inhibitory effects of stapled ERAP No. 12 on the E2-dependent growth of MCF-7 cells (left panel) and the growth of MCF-10A cells (right panel). In the E2-added groups, 10 nM E2 was added. Each symbol in each graph indicates the following: open circle: untreated; filled circle: E2 alone; filled triangle: E2+0.5 μM peptide (left panel) or 0.5 μM peptide (right panel); filled square: E2+1 μM peptide (left panel) or 1 μM peptide (right panel); and filled diamond: E2+10 μM peptide (left panel) or 10 μM peptide (right panel). These data represent the mean±SD of three independent experiments (***P<0.001, two-sided Student's t-test).

Figure 3D:
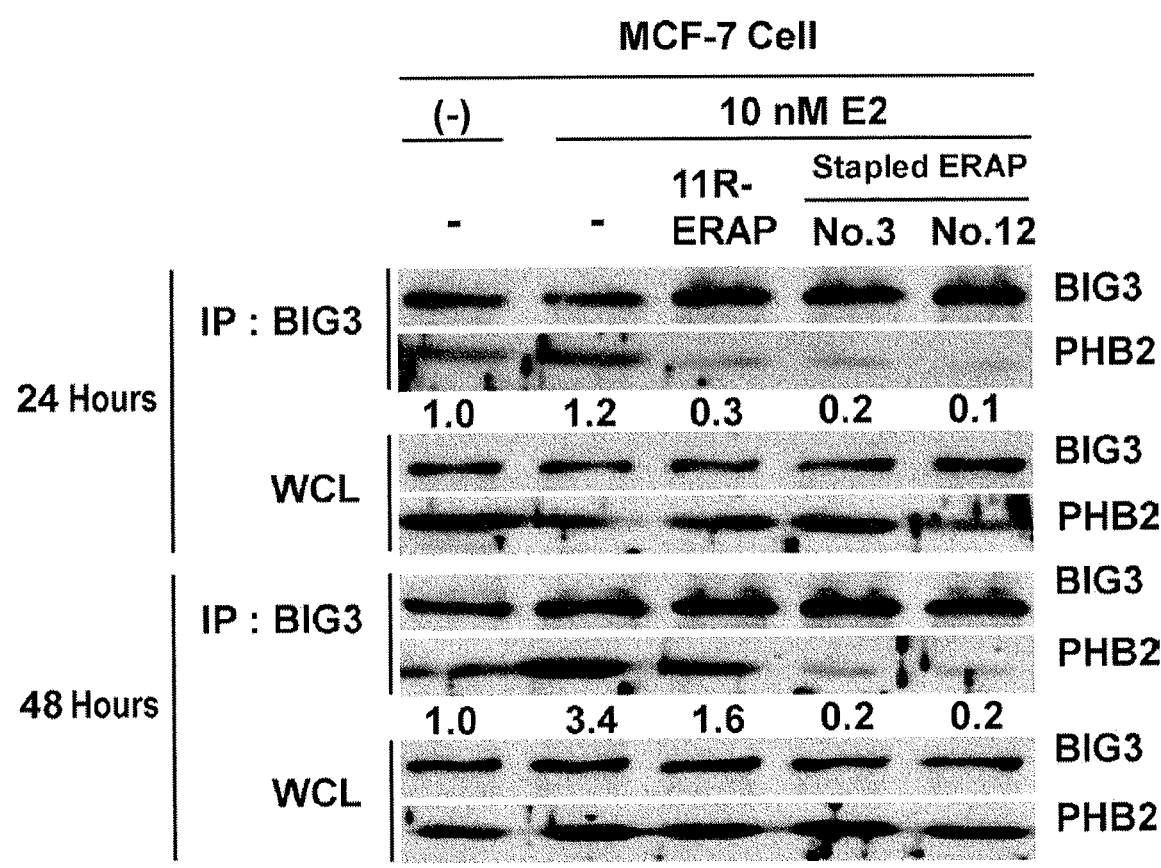

FIG. 3D shows the results of co-immunoprecipitation which evaluated the inhibitory effects of 11R-ERAP and stapled ERAP (No. 3 and No. 12) treatments on the BIG3-PHB2 interaction in MCF-7 cells. In the figure, "IP" indicates the antibody used for immunoprecipitation, "WCL" indicates whole cell lysate, "(−)" indicates E2-untreated cells, and "−" indicates peptide-untreated cells. The antibodies reacted on the membrane are shown at the far right. The numerical values below the membrane indicate the relative values of reaction intensity for each of the lanes when the reaction intensity of the far-left lane is defined as 1.0.

Figure 3E:
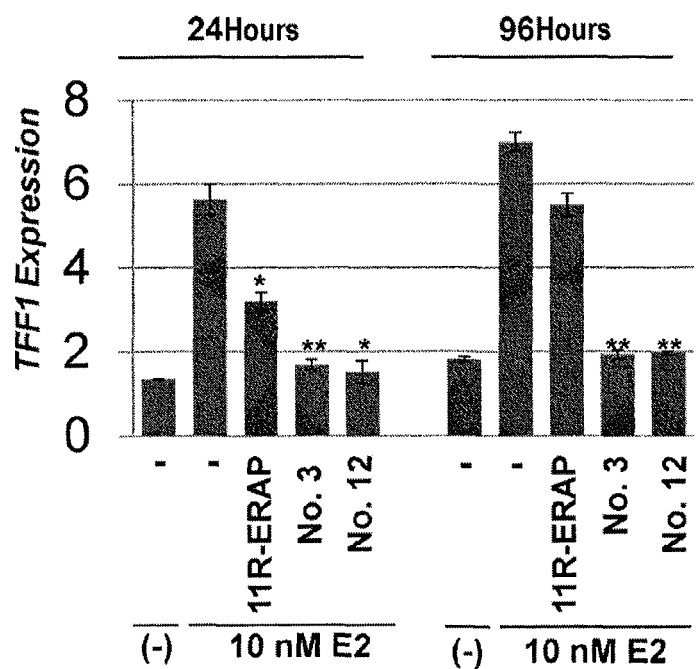
Figure 3E:
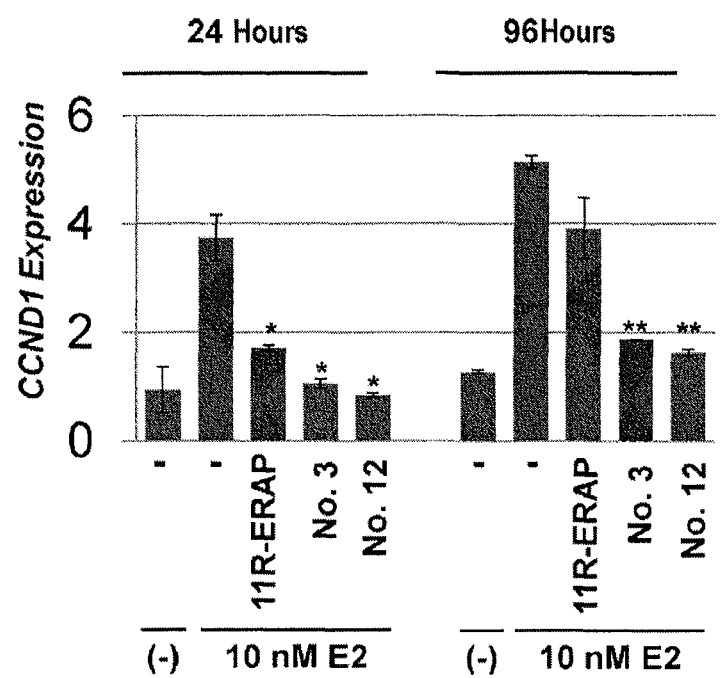

FIG. 3E shows the inhibitory effects of 11R-ERAP and stapled ERAPs (No. 3 and No. 12) on ERα target gene expression. The results were presented as multiples of the expression level in untreated cells at each time, with that level being defined as 1.0. In the figure, "(−)" indicates E2-untreated cells and "−" indicates peptide-untreated cells. The upper panel indicates the TFF1 gene expression and the lower panel indicates the CCND1 gene expression. These data represent the mean±SD of three independent experiments (*P<0.05, **P<0.01, two-sided Student's t-test).

Figure 3F:
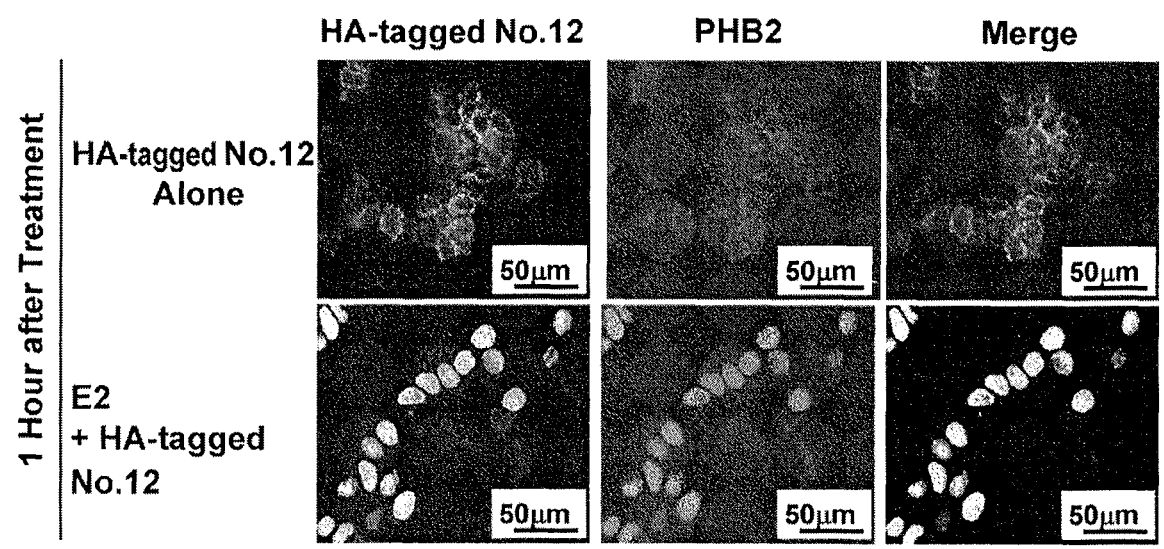

FIG. 3F shows representative immunofluorescence images indicating the intracellular localization of stapled ERAP No. 12 and PHB2 in the presence or absence of E2. MCF-7 cells were treated with HA-tagged stapled ERAP No. 12 in the presence or absence of E2, and one hour after the treatment, immunofluorescent staining was carried out using an anti-HA tag antibody and an anti-PHB2 antibody.

Figure 3G:
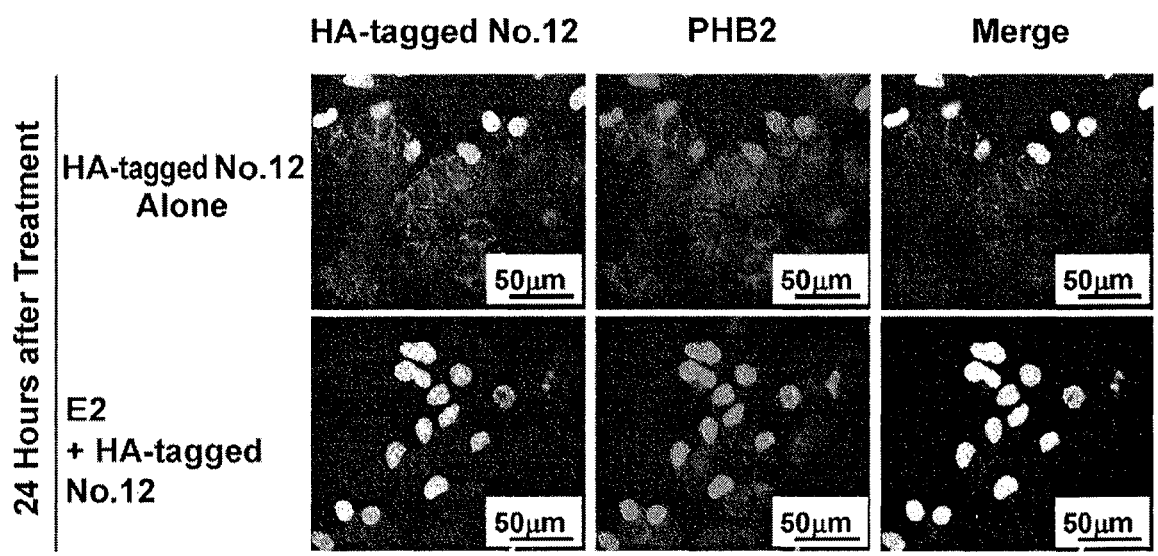

FIG. 3G shows representative immunofluorescence images indicating the intracellular localization of stapled ERAP No. 12 and PHB2 in the presence or absence of E2. MCF-7 cells were treated with HA-tagged stapled ERAP No. 12 in the presence or absence of E2, and 24 hours after the treatment, immunofluorescent staining was carried out using an anti-HA tag antibody and an anti-PHB2 antibody.

Figure 3H:
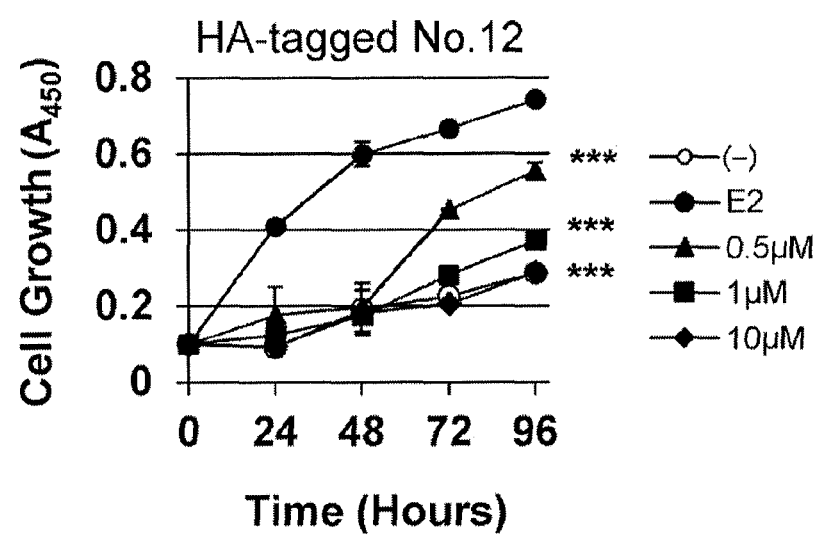

FIG. 3H shows the results of MTT assays which evaluated the inhibitory effects of HA-tagged stapled ERAP No. 12 on E2-dependent growth of MCF-7 cells. Each symbol in the graph indicates the following: open circle: untreated; filled circle: E2 alone; filled triangle: E2+0.5 μM peptide; filled square: E2+1 μM peptide; and filled diamond: E2+10 μM peptide. The data represent the mean±SD of three independent experiments (***$P<0.001$, two-sided Student's t-test).

Figure 3I:
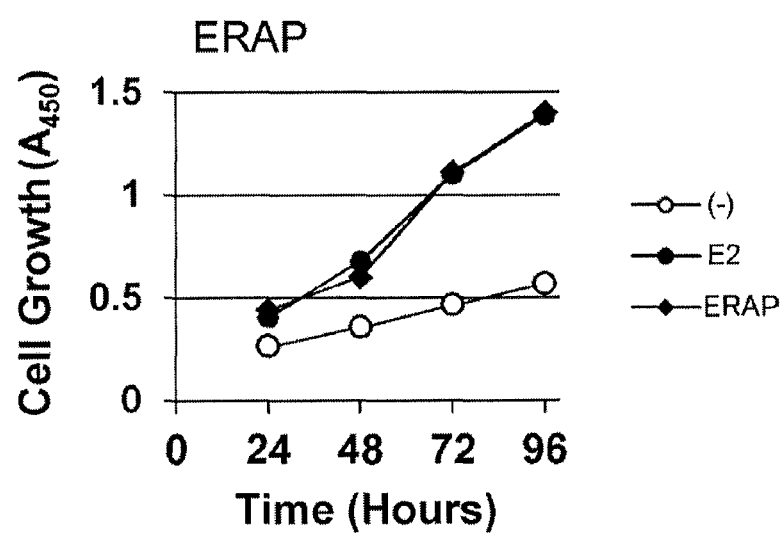

FIG. 3I shows the results of MIT assays which evaluated the inhibitory effects of ERAP on E2-dependent growth of MCF-7 cells. Each symbol in the graph indicates the following: open circle: untreated; filled circle: E2 alone; and filled diamond: E2+10 μM peptide. The data represent the mean±SD of three independent experiments.

Figure 3J:
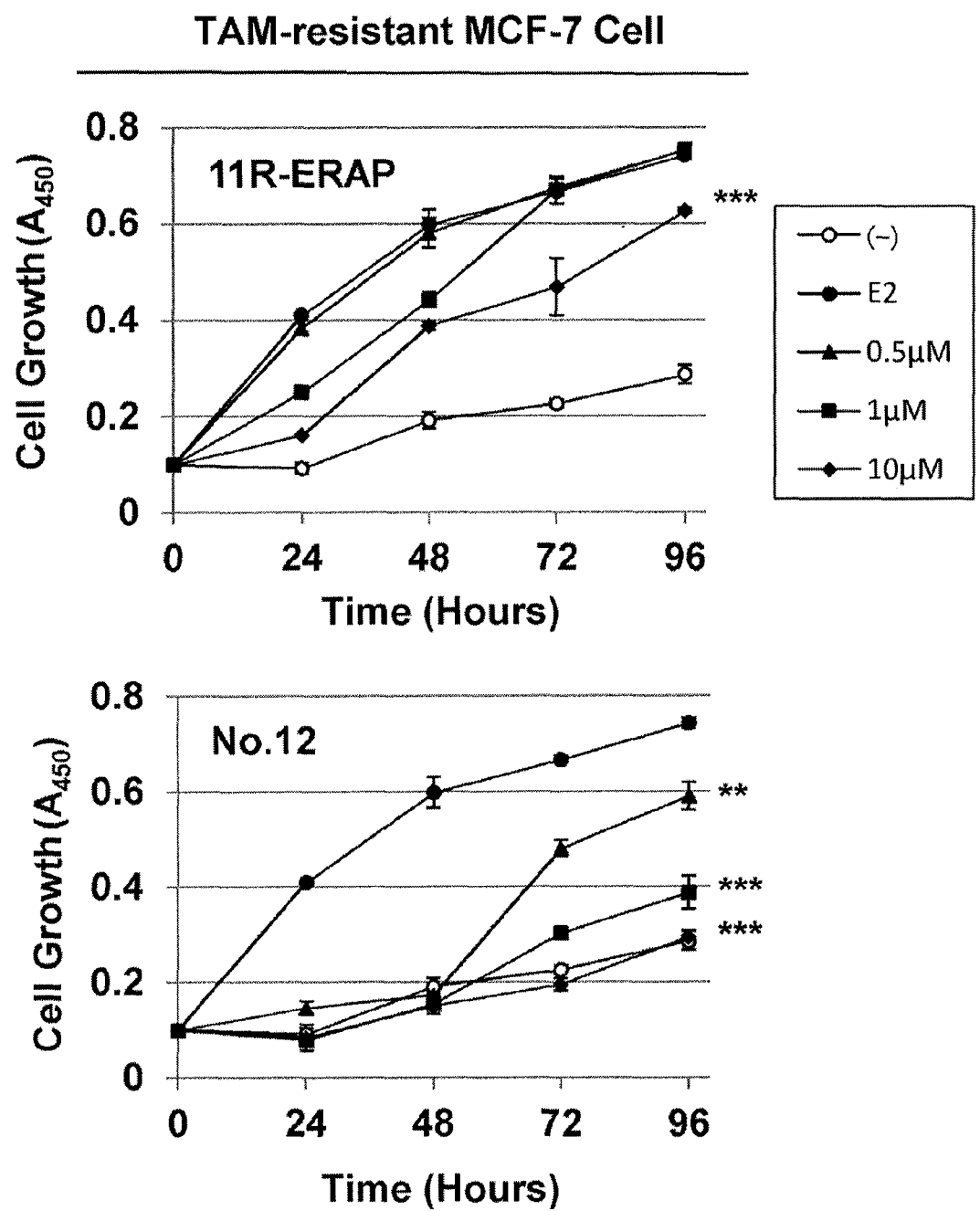

FIG. 3J shows the results of MTT assays which evaluated the inhibitory effects of 11R-ERAP (upper panel) and stapled ERAP No. 12 (lower panel) on the E2-dependent growth of tamoxifen-resistant (TAM-R) MCF-7 cells. TAM-R MCF-7 cells were treated with each concentration of 11R-ERAP or stapled ERAP-No. 12 in the presence of 1 μM tamoxifen. In the E2-added groups, 10 nM E2 was added. Each symbol in the graphs indicates the following: open circle: untreated; filled circle: E2 alone; filled triangle: E2+0.5 μM peptide; filled square: E2+1 μM peptide; and filled diamond: E2+10 μM peptide. These data represent the mean±SD of three independent experiments ($P<0.01$, *$P<0.001$, two-sided Student's t-test).

Figure 3K:
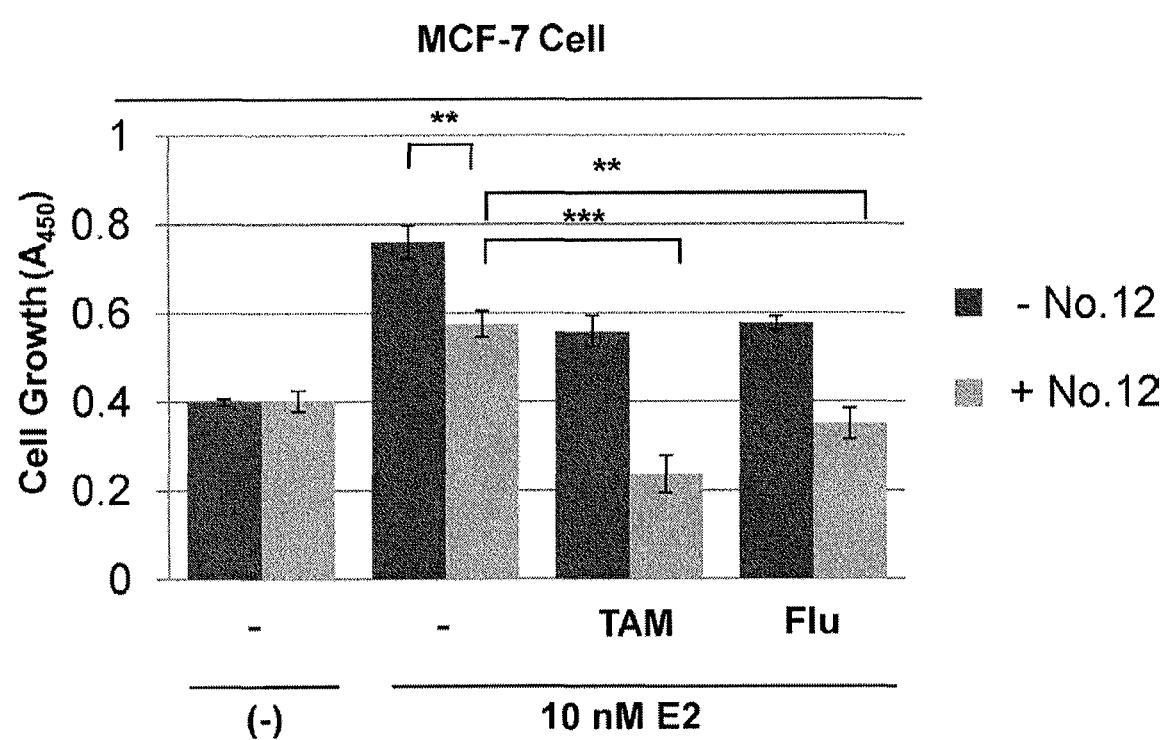

FIG. 3K shows the result of MTT assay which evaluated the combined inhibitory effects of stapled ERAP No. 12 with tamoxifen or fulvestrant on the E2-dependent growth of MCF-7 cells. In the figure, the dark gray bars represent stapled ERAP No. 12-untreated, and the light gray bars represent treatment with 0.5 μM stapled ERAP No. 12. Furthermore, "TAM" indicates 10 nM tamoxifen, "Flu" indicates 2 μM fulvestrant, "(−)" indicates E2-untreated cells, and "−" indicates cells not treated with either tamoxifen or fulvestrant. The graph shows the results obtained 24 hours after the treatment. The data represent the mean±SD of three independent experiments ($P<0.01$, *$P<0.001$, two-sided Student's t-test).

FIG. 4 shows that stapled ERAP has in vivo antitumor effects in an orthotopic xenograft mouse model of human ERα-positive breast cancer. FIG. 4A shows a schematic diagram of the in vivo experiments.

Figure 4A:
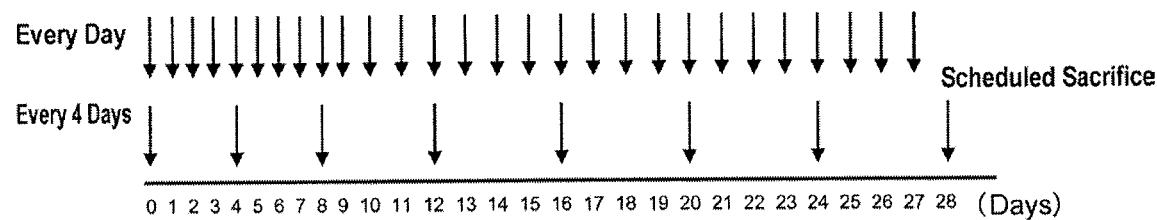
Figure 4B:
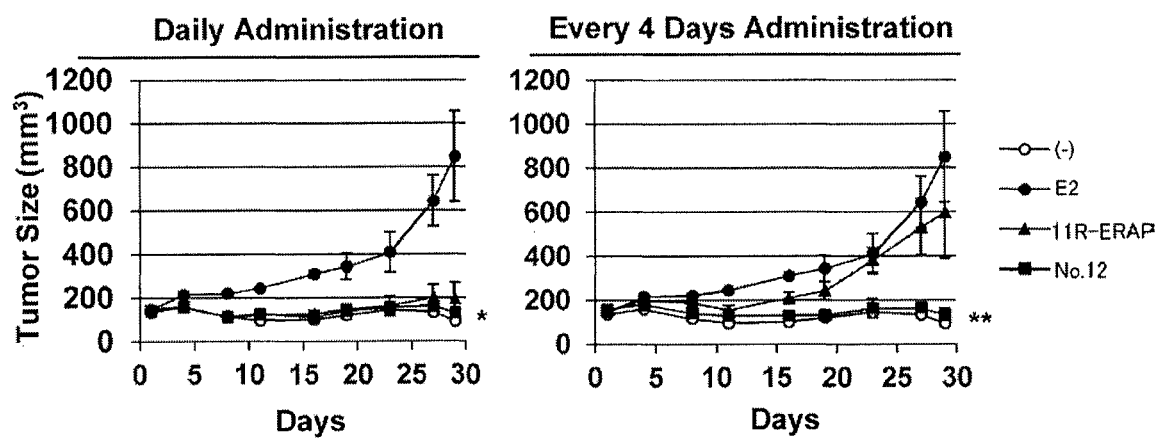

FIG. 4B shows the inhibitory effects of stapled ERAP No. 12 treatment at 1.4 mg/kg on tumor growth in a human breast cancer cell line KPL-3C orthotopic xenograft mouse model. The left panel shows the results in the group with daily administration of the peptide and the right panel shows the results in the group with every four days administration of the peptide. Each symbol in each graph indicates the following: open circle: untreated; filled circle: E2 alone; filled triangle: E2+11R-ERAP; and filled square: E2+stapled ERAP No. 12. The data on tumor sizes represent the mean±SE of each group (n=5, *$P<0.05$, **$P<0.01$, two-sided Student's t-test).

Figure 4C:
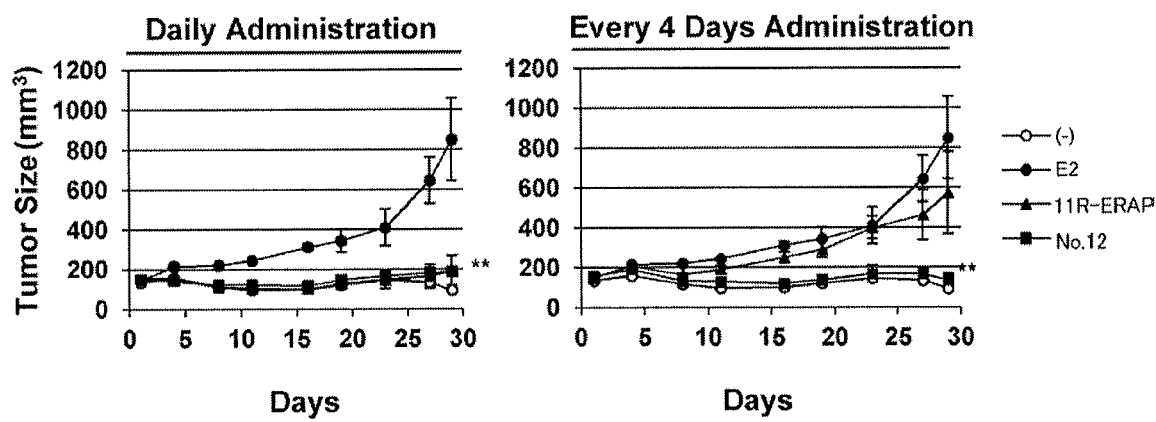

FIG. 4C shows the inhibitory effects of stapled ERAP No. 12 treatment at 14 mg/kg on tumor growth in a human breast cancer cell line KPL-3C orthotopic xenograft mouse model. The left panel shows the results in the group with daily administration of the peptide and the right panel shows the results in the group with every four days administration of the peptide. Each symbol in each graph indicates the following: open circle: untreated; filled circle: E2 alone; filled triangle: E2+11R-ERAP; and filled square: E2+stapled ERAP No. 12. The data on tumor sizes represent the mean±SE of each group (n=5, **$P<0.01$, two-sided Student's t-test).

Figure 4D:
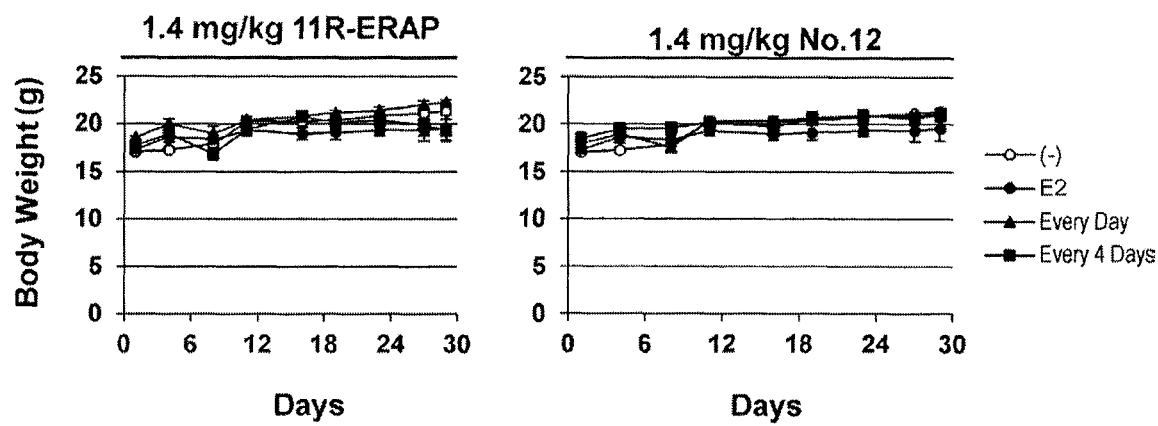

FIG. 4D shows the variation in body weight of the KPL-3C orthotopic xenograft mice treated with 1.4 mg/kg 11R-ERAP (left panel) or stapled ERAP No. 12 (right panel). Each symbol in each graph indicates the following: open circle: untreated; filled circle: E2 alone; filled triangle: E2+daily peptide treatment; and filled square: E2+peptide treatment every four days. The data on body weight represent the mean±SE of each group (n=5).

Figure 4E:
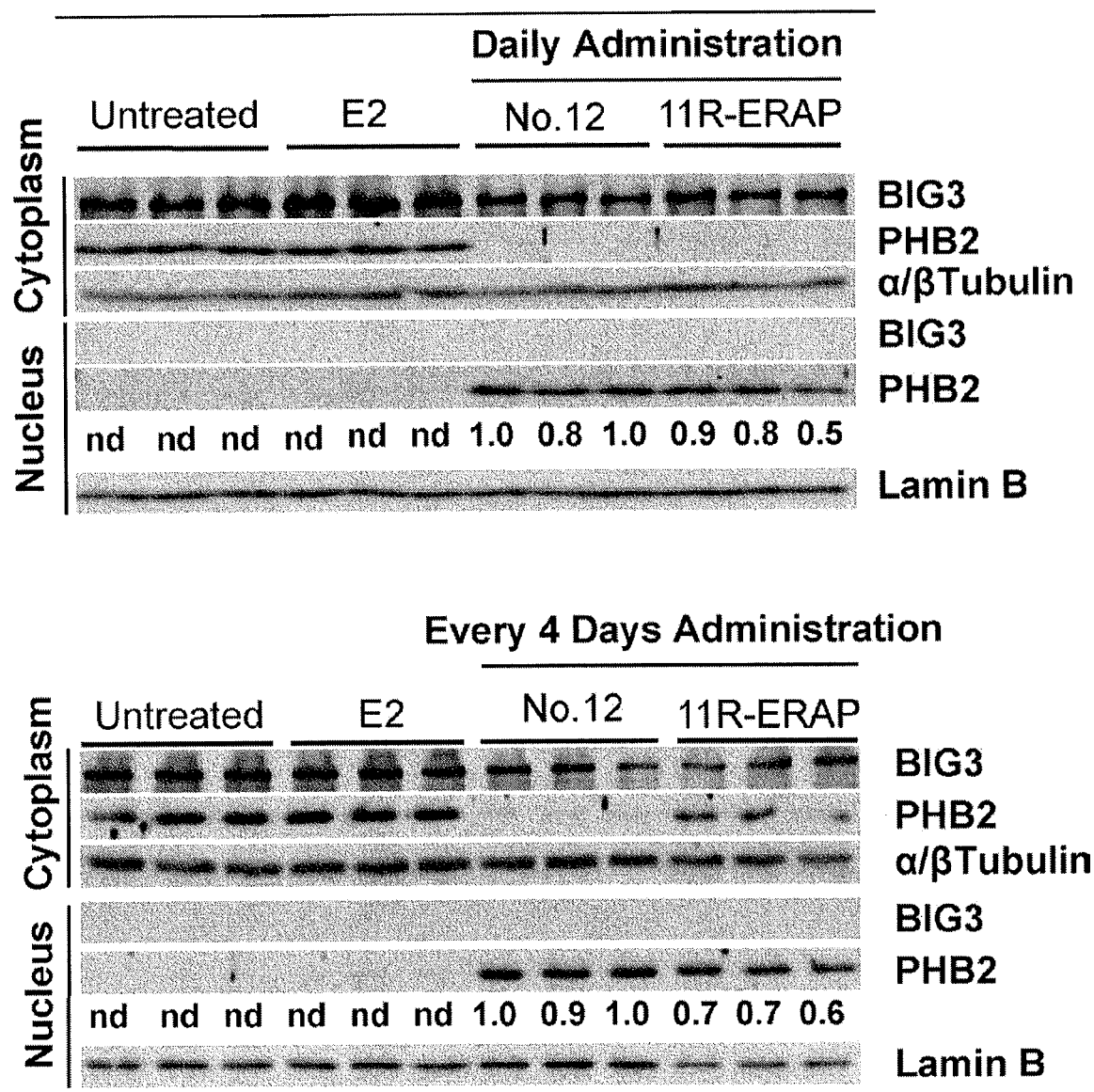

FIG. 4E shows the results of immunoblotting which examined the intracellular localization of PHB2 in tumors. The immunoblotting was performed using tumors removed from KPL-3C orthotopic xenograft mice treated with 1.4 mg/kg 11R-ERAP or stapled ERAP No. 12 every day (upper panel) or every four days (lower panel). α/β-Tubulin and lamin B were used as the loading controls of the cytoplasmic fraction and the nuclear fraction, respectively. The antibodies reacted on the membrane are shown at the far right. The numerical values below the membrane indicate the relative values of reaction intensity for each of the lanes when the reaction intensity of the far-left lane of the stapled ERAP No. 12-treated lanes is defined as 1.0, and "nd" indicates not detected.

Figure 4F:
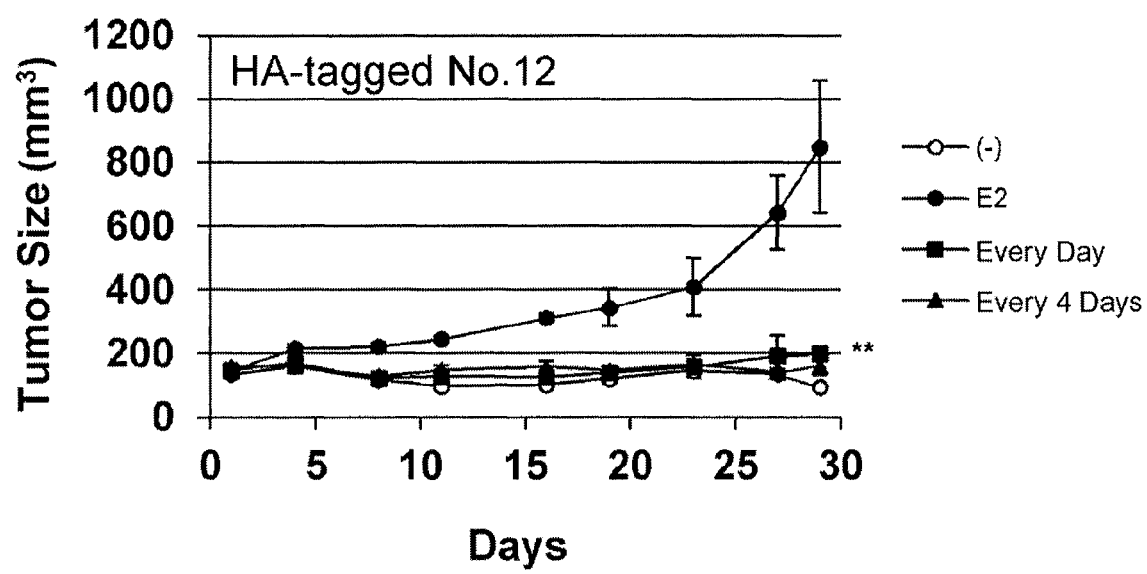

FIG. 4F shows the tumor growth inhibitory effects in a KPL-3C orthotopic xenograft mouse model treated with 14 mg/kg HA-tagged stapled ERAP No. 12 every day or every four days. Each symbol in the graph indicates the following: open circle: untreated; filled circle: E2 alone; filled triangle: E2+daily peptide treatment; and filled square: E2+peptide treatment every four days. The data on tumor size represent the mean±SE of each group (n=5, **$P<0.01$, two-sided Student's t-test).

Figure 4G:
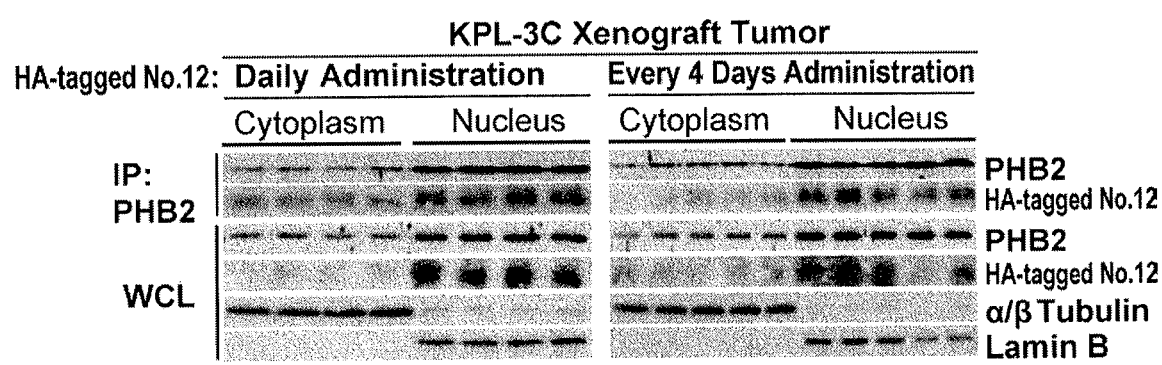

FIG. 4G shows the results of co-immunoprecipitation which examined the intracellular localization of PHB2 and stapled ERAP No. 12 in tumors. The co-immunoprecipitation was performed using tumors removed from KPL-3C orthotopic xenograft mice treated with 1.4 mg/kg HA-tagged stapled ERAP No. 12 every day (left panel) or every four days (right panel). In the figure, "IP" indicates the antibody used for immunoprecipitation and "WCL" indicates whole cell lysate. The antibodies reacted on the membrane are shown at the far right. α/β-Tubulin and lamin B were used as the loading controls of the cytoplasmic fraction and the nuclear fraction, respectively.

Figure 4H:
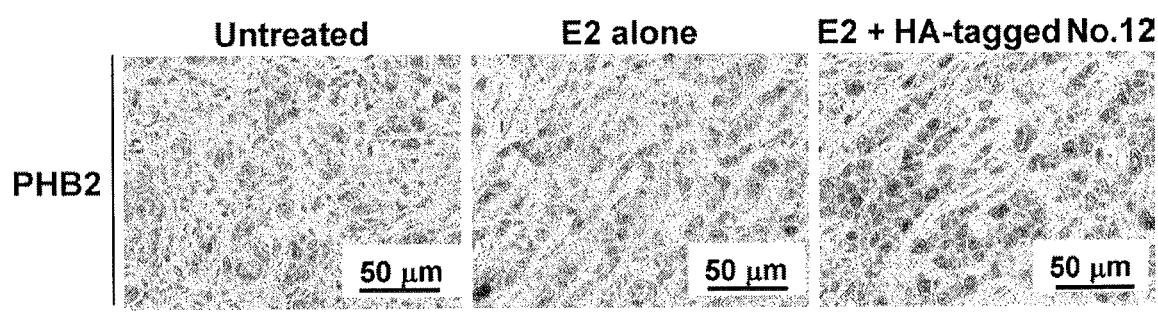

FIG. 4H shows representative immunohistochemical staining images which examined the intracellular localization of PHB2 and stapled ERAP No. 12 in tumors. The immunohistochemical staining was performed using tumors removed from KPL-3C orthotopic xenograft mice treated with 14 mg/kg HA-tagged stapled ERAP No. 12 (HA-tagged No. 12) every four days. An anti-PHB2 antibody was used for the staining.

Figure 4I:
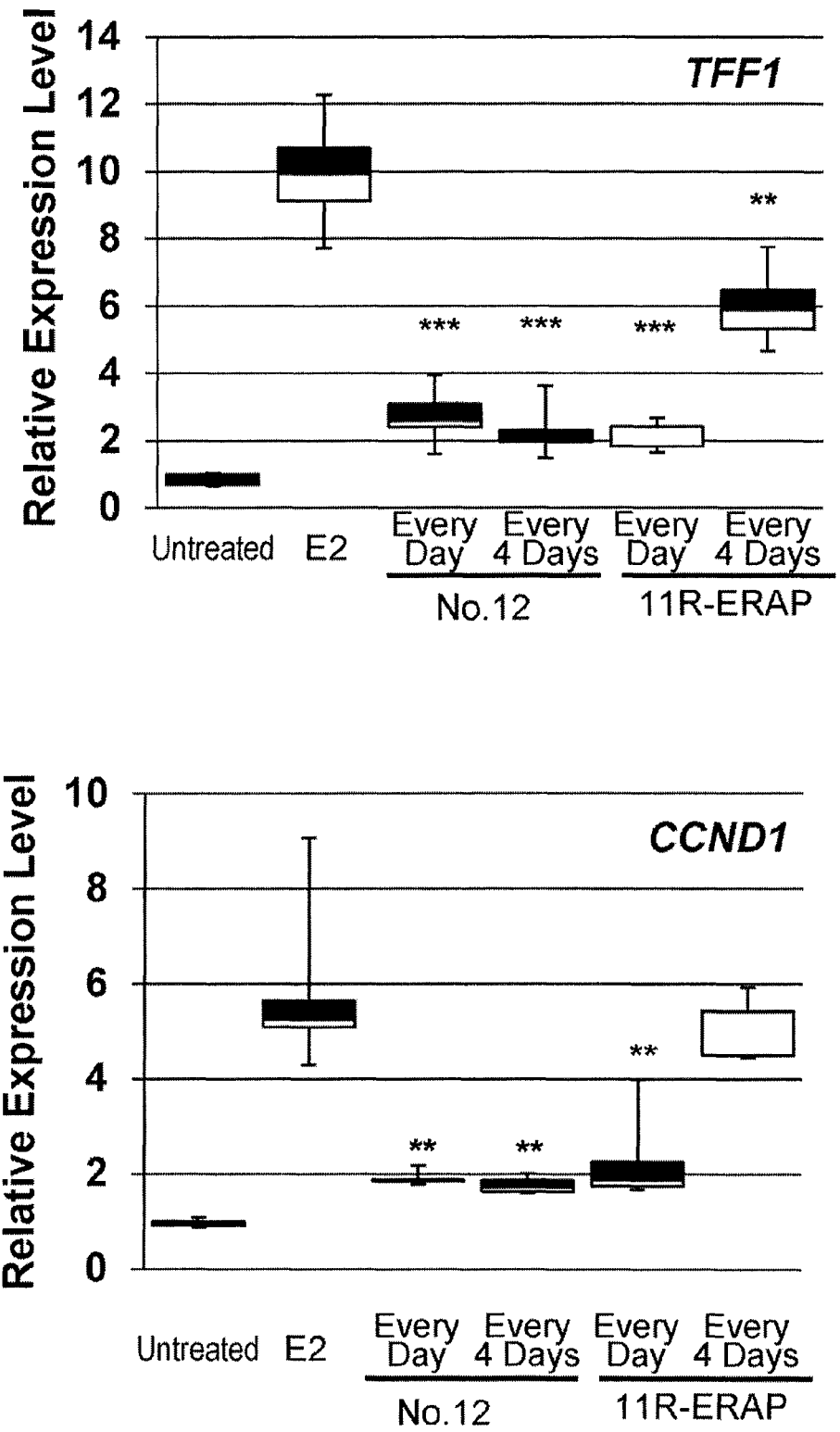

FIG. 4I shows a box plot which evaluated the inhibitory effects of stapled ERAP No. 12 on ERα target gene expression in tumors. The upper panel indicates TFF1 expression and the lower panel indicates CCND1 expression. The analysis was carried out using tumors removed from KPL-3C orthotopic xenograft mice treated with 1.4 mg/kg stapled ERAP No. 12 every day or every four days. The results were presented as multiples of the expression level in untreated tumors, with that level being defined as 1.0. These data represent the mean±SD of five independent tumors ($P<0.01$, *$P<0.0001$, two-sided Student's t-test).

Figure 4J:
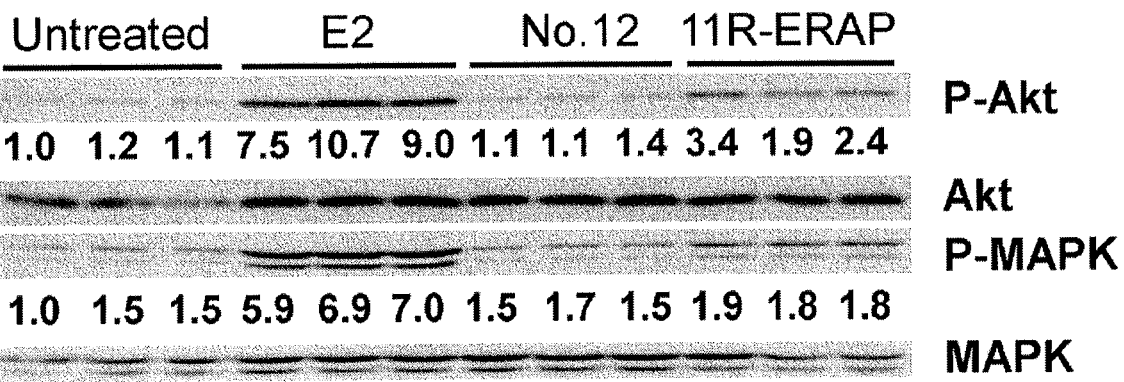
Figure 4J:
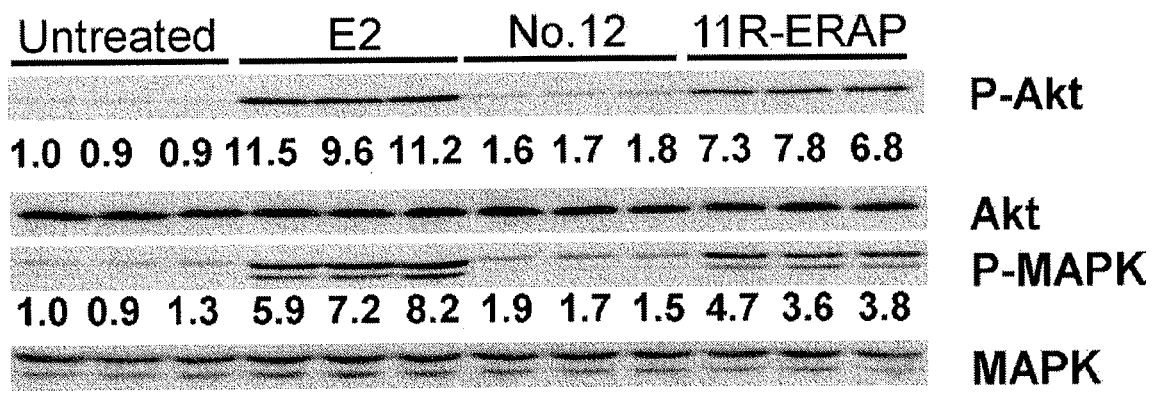

FIG. 4J shows the results of immunoblotting which examined the phosphorylation levels of Akt and MAPK in tumors treated with stapled ERAP. The immunoblotting was performed using tumors removed from KPL-3C orthotopic xenograft mice treated with 1.4 mg/kg stapled ERAP No. 12 every day (upper panel) or every four days (lower panel). The antibodies reacted on the membrane are shown at the far right. The numerical values below the membrane indicate the relative values of reaction intensity for each of the lanes when the reaction intensity of the far-left lane is defined as 1.0.

Figure 4K:
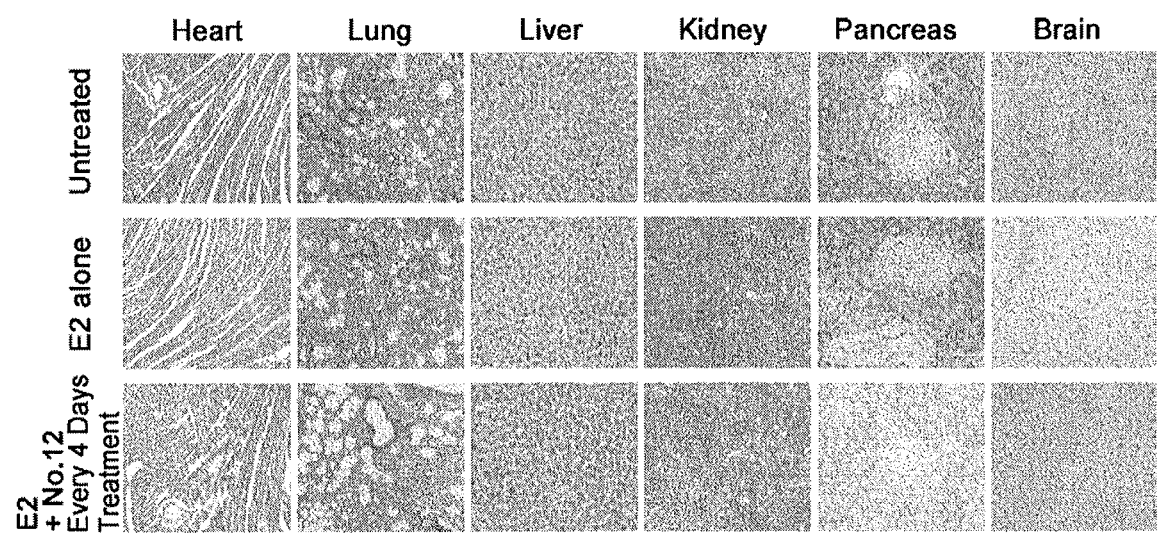

FIG. 4K shows representative hematoxylin-eosin staining images of the heart, lung, liver, kidney, pancreas, and brain removed from KPL-3C orthotopic xenograft mice treated every four days with 14 mg/kg stapled ERAP No. 12.

Figure 4L:
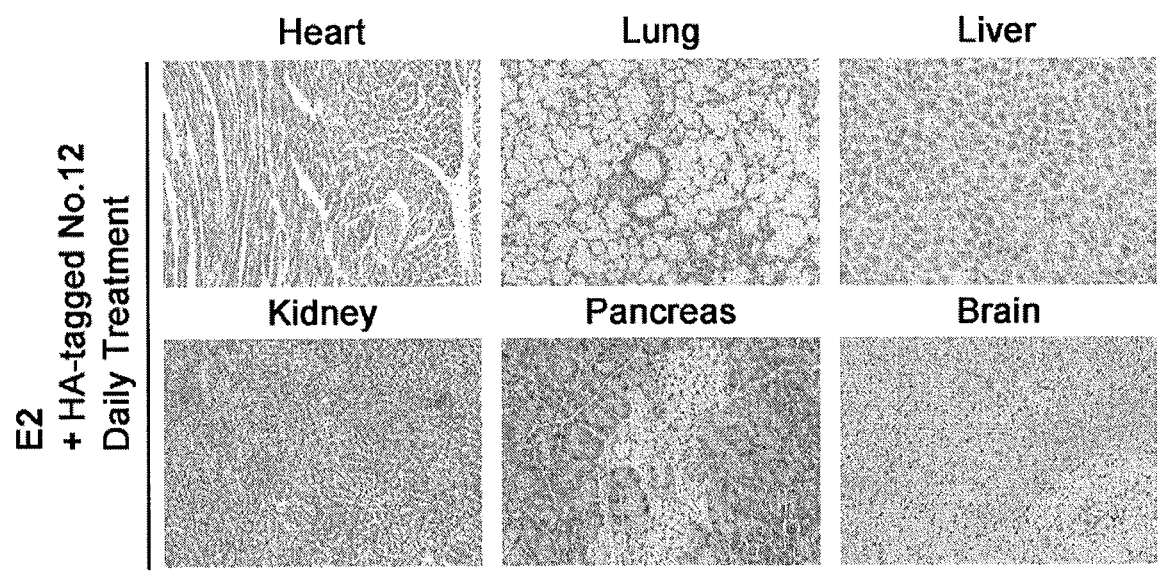

FIG. 4L shows representative hematoxylin-eosin staining images of the heart, lung, liver, kidney, pancreas, and brain removed from KPL-3C orthotopic xenograft mice treated every day with 14 mg/kg HA-tagged stapled ERAP No. 12.

Figure 4M:
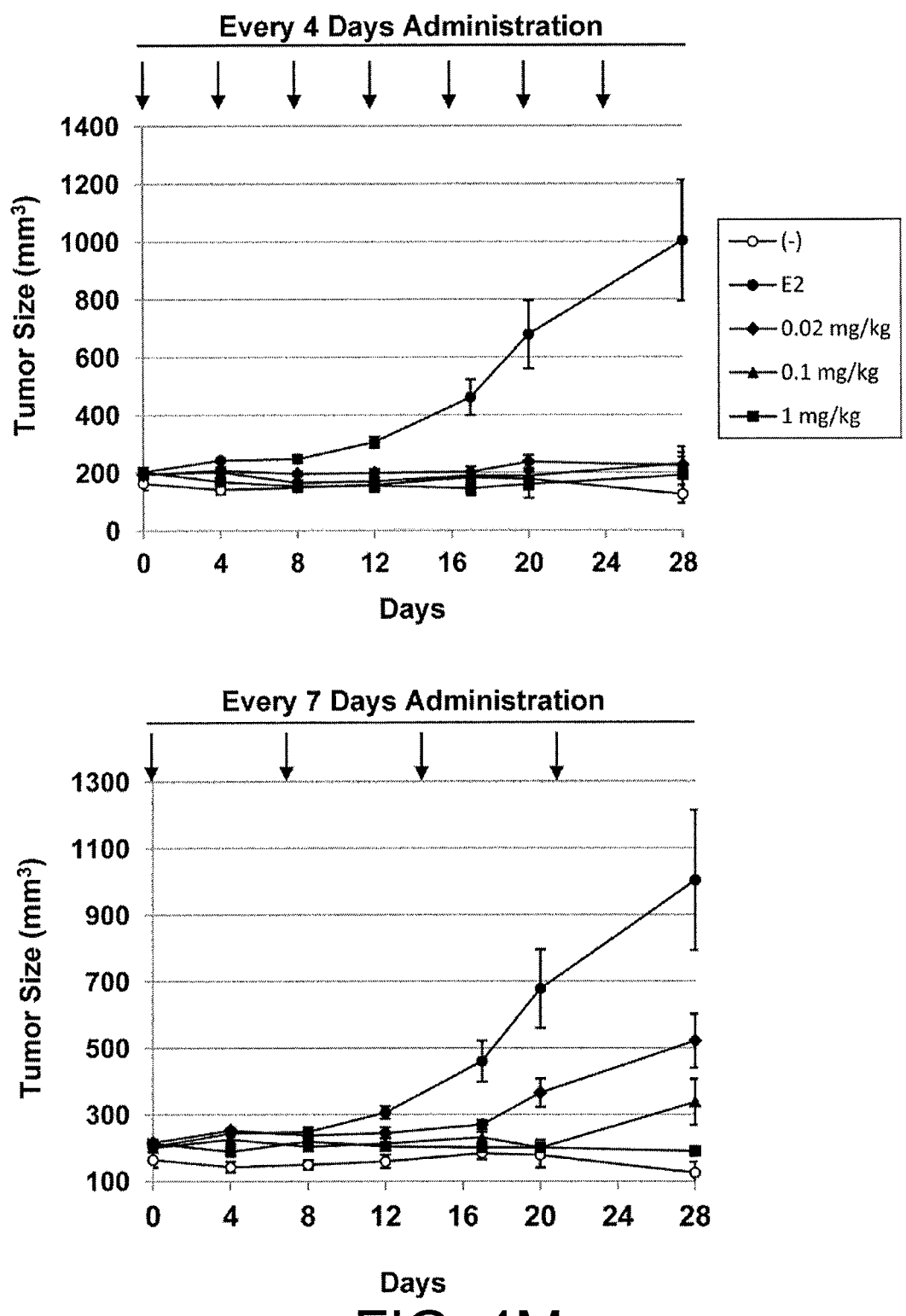

FIG. 4M shows the inhibitory effects of treatment with stapled ERAP No. 12 every four days (upper panel) or every seven days (lower panel) on tumor growth in KPL-3C orthotopic xenograft mice. Each symbol in each graph indicates the following: open circle: untreated; filled circle: E2 alone; filled diamond: E2+0.02 mg/kg peptide; filled triangle: E2+0.1 mg/kg peptide; and filled square: E2+1 mg/kg peptide. The data on tumor sizes represent the mean±SE of each group (n=5).

Figure 4N:
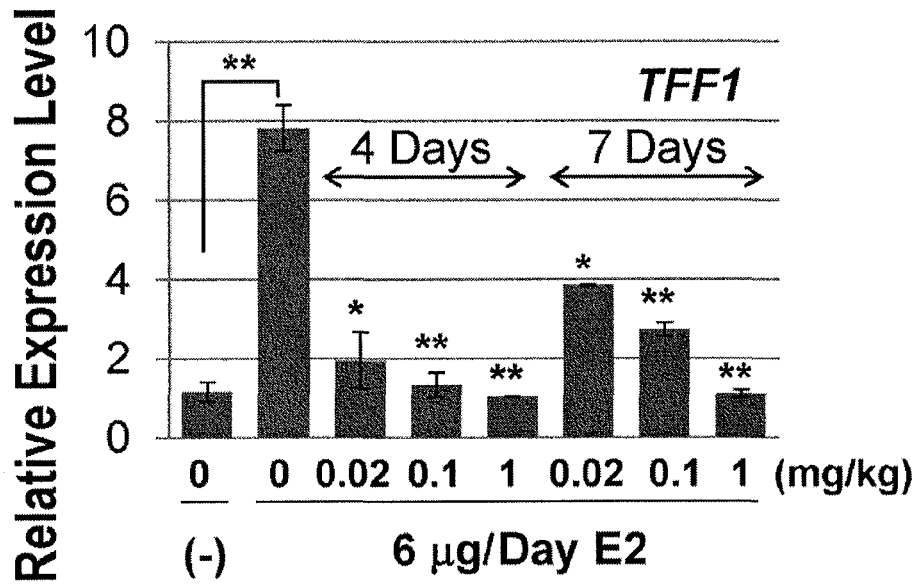
Figure 4N:
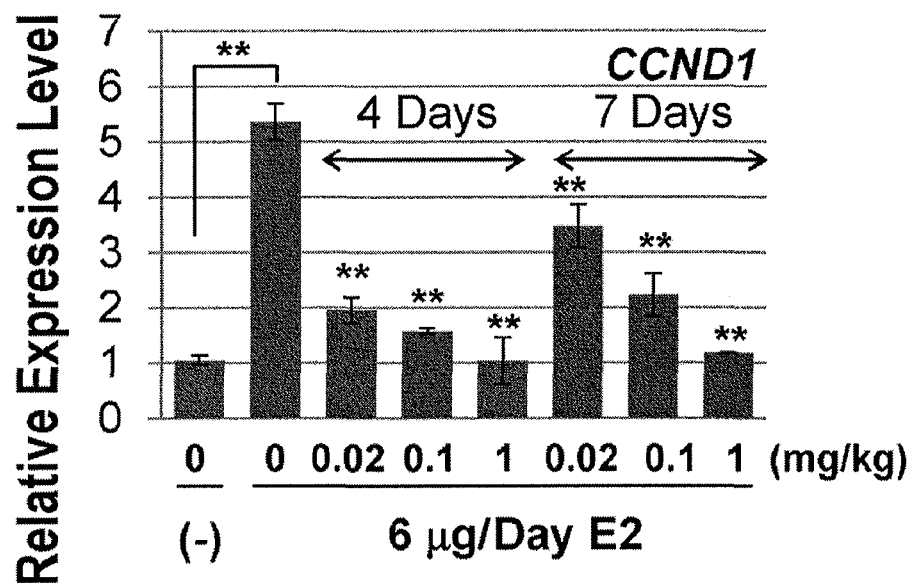

FIG. 4N shows the results of examining ERα target gene expression in tumors removed from KPL-3C orthotopic xenograft mice treated every four days or every seven days with stapled ERAP No. 12. The upper panel indicates TFF1 expression and the lower panel indicates CCND1 expression. The horizontal axis of the graphs indicates the dose at a single treatment of stapled ERAP No. 12. In the figure, "(−)" indicates E2-untreated cells. The results were presented as multiples of the expression level in untreated tumors, with that level being defined as 1.0. The data represent the mean±SD of five independent tumors (*P<0.05, **P<0.01, two-sided Student's t-test).

Figure 5A:
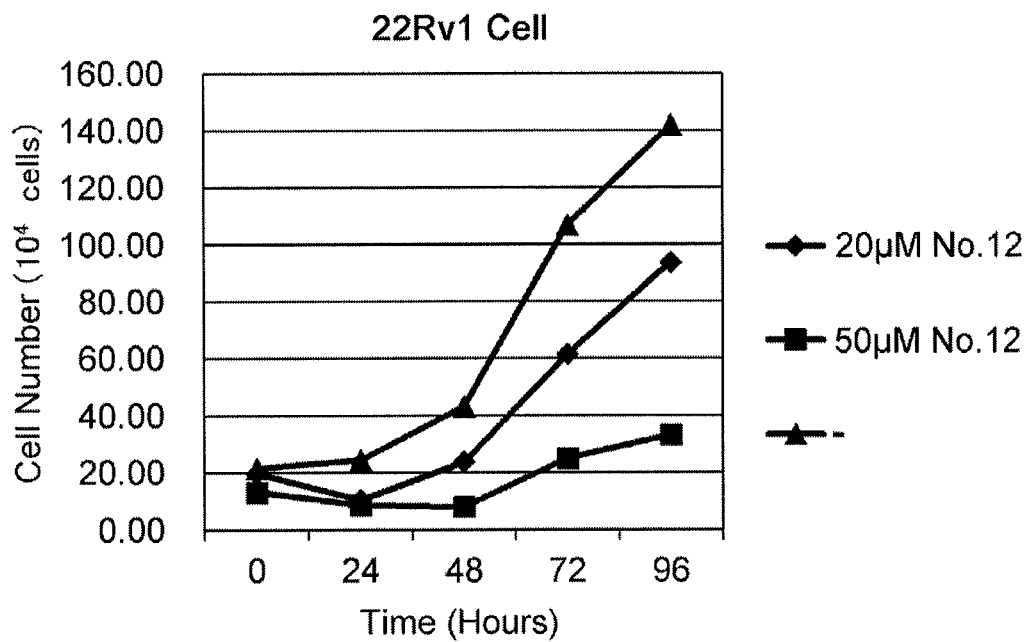

FIG. 5 shows that stapled ERAP No. 12 suppressed cell growth of human prostate cancer cell line 22Rv1 and inhibited the BIG3-PHB2 interaction. FIG. 5A shows the results of examinations which evaluated the inhibitory effects of stapled ERAP No. 12 on 22Rv1 cell growth. Each symbol in the graph indicates the following: filled diamond: 20 µM stapled ERAP No. 12; filled square: 50 µM stapled ERAP No. 12; and filled triangle: untreated.

Figure 5B:
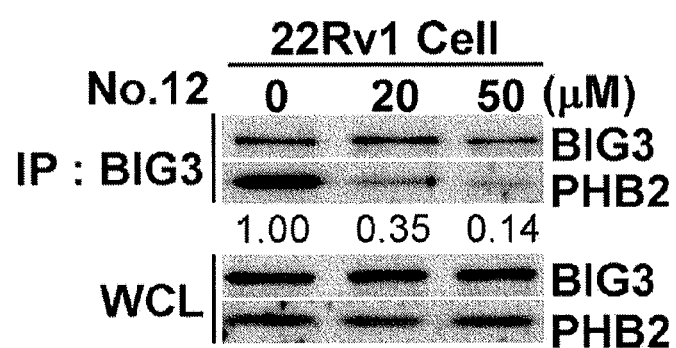

FIG. 5B shows the results of co-immunoprecipitation experiments which evaluated the inhibitory effects of stapled ERAP No. 12 on the endogenous BIG3-PHB2 interaction in 22Rv1 cells. In the figure, "IP" indicates the antibody used for immunoprecipitation and "WCL" indicates whole cell lysate. The antibodies reacted on the membrane are shown at the far right. The numerical values below the membrane indicate the relative values of reaction intensity for each of the lanes when the reaction intensity of the far-left lane is defined as 1.00.

Figure 5C:
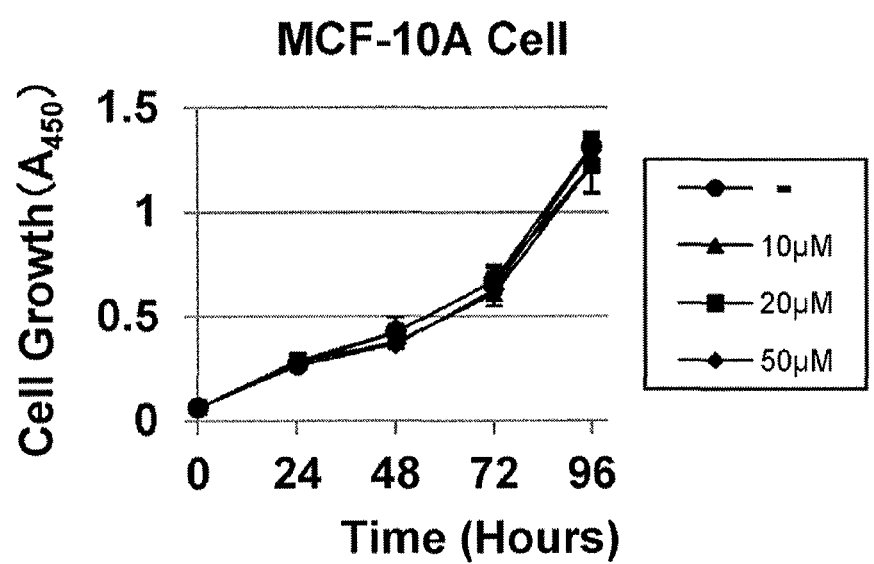

FIG. 5C shows the results of examinations which evaluated the inhibitory effects of stapled ERAP No. 12 on MCF-10A cell growth. Each symbol in the graph indicates the following: filled circle: untreated; filled triangle: 10 µM stapled ERAP No. 12; filled square: 20 µM stapled ERAP No. 12; and filled diamond: 50 µM stapled ERAP No. 12.

FIG. 6 shows that stapled-D-ERAP No. 12 (D-No. 12), stapled retro-inverso ERAP No. 12 (RI-No. 12), and short stapled retro-inverso ERAP No. 12 (shRI-No. 12) stably inhibited the BIG3-PHB2 interaction for a long time. FIG. 6A shows the primary structures of stapled ERAP analogs. In the amino acid sequences, the underlined bold letters indicate the amino acid residues important for PHB2-binding and the italicized bold letters indicate the stapled amino acid residues. The lower-case letters indicate D-amino acids. All amino acid sequences are described from the N terminus at the far left to the C terminus on the right.

Figure 6B:
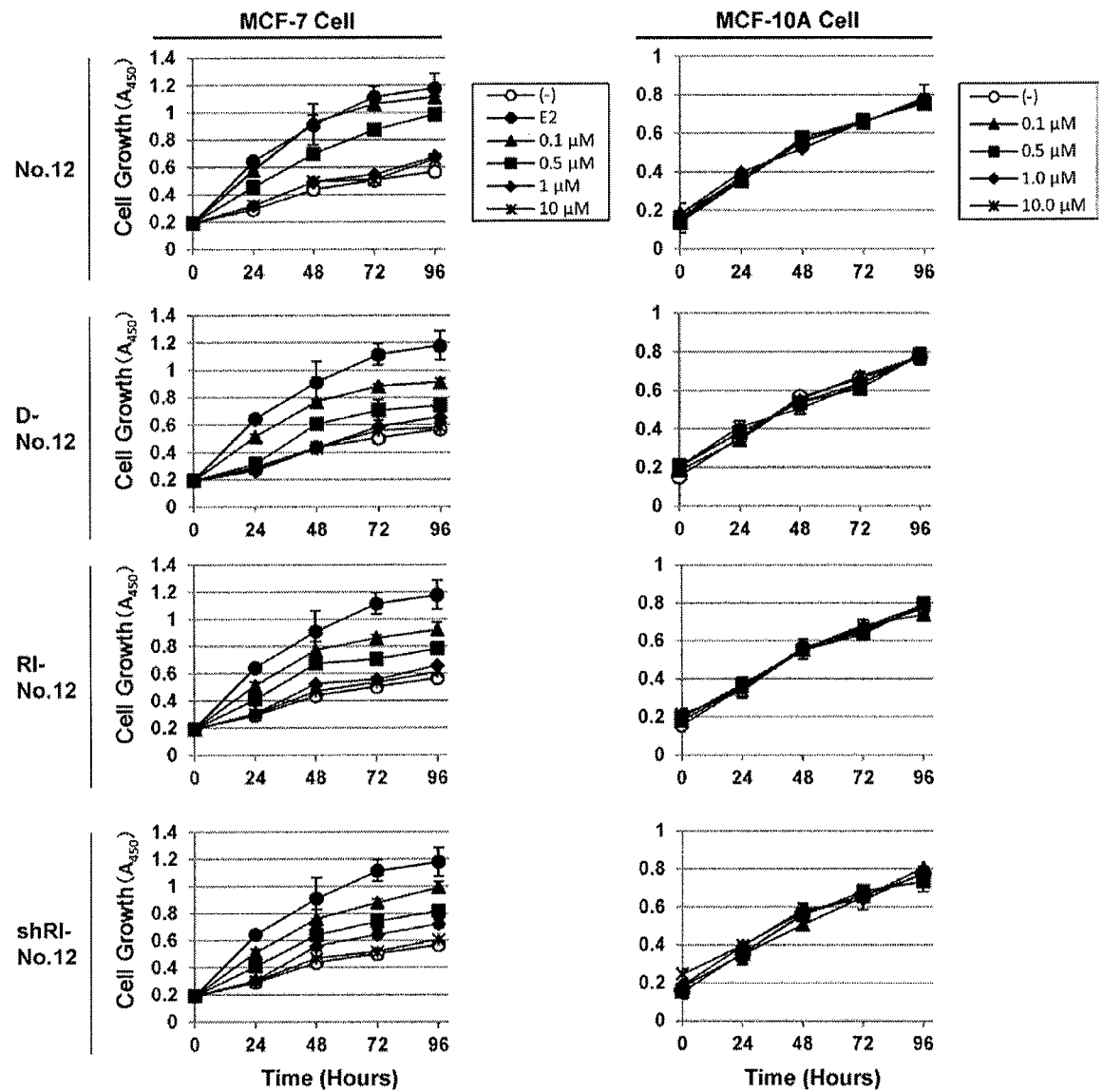

FIG. 6B shows the results of MTT assays which evaluated the inhibitory effects of stapled ERAP No. 12 (first row), D-No. 12 (second row), RI-No. 12 (third row), and shRI-No. 12 (fourth row) on E2-dependent growth of MCF-7 cells (left panels) and growth of MCF-10A cells (right panels). In the E2-added groups, 10 nM E2 was added. Each symbol in each graph indicates the following: open circle: untreated; filled circle: E2 alone; filled triangle: E2+0.1 µM peptide (left panels) or 0.1 µM peptide (right panels); filled square: E2+0.5 µM peptide (left panels) or 0.5 µM peptide (right panels); filled diamond: E2+1.0 µM peptide (left panels) or 1.0 µM peptide (right panels); and asterisk: E2+10 µM peptide (left panels) or 10 µM peptide (right panels).

Figure 6C:
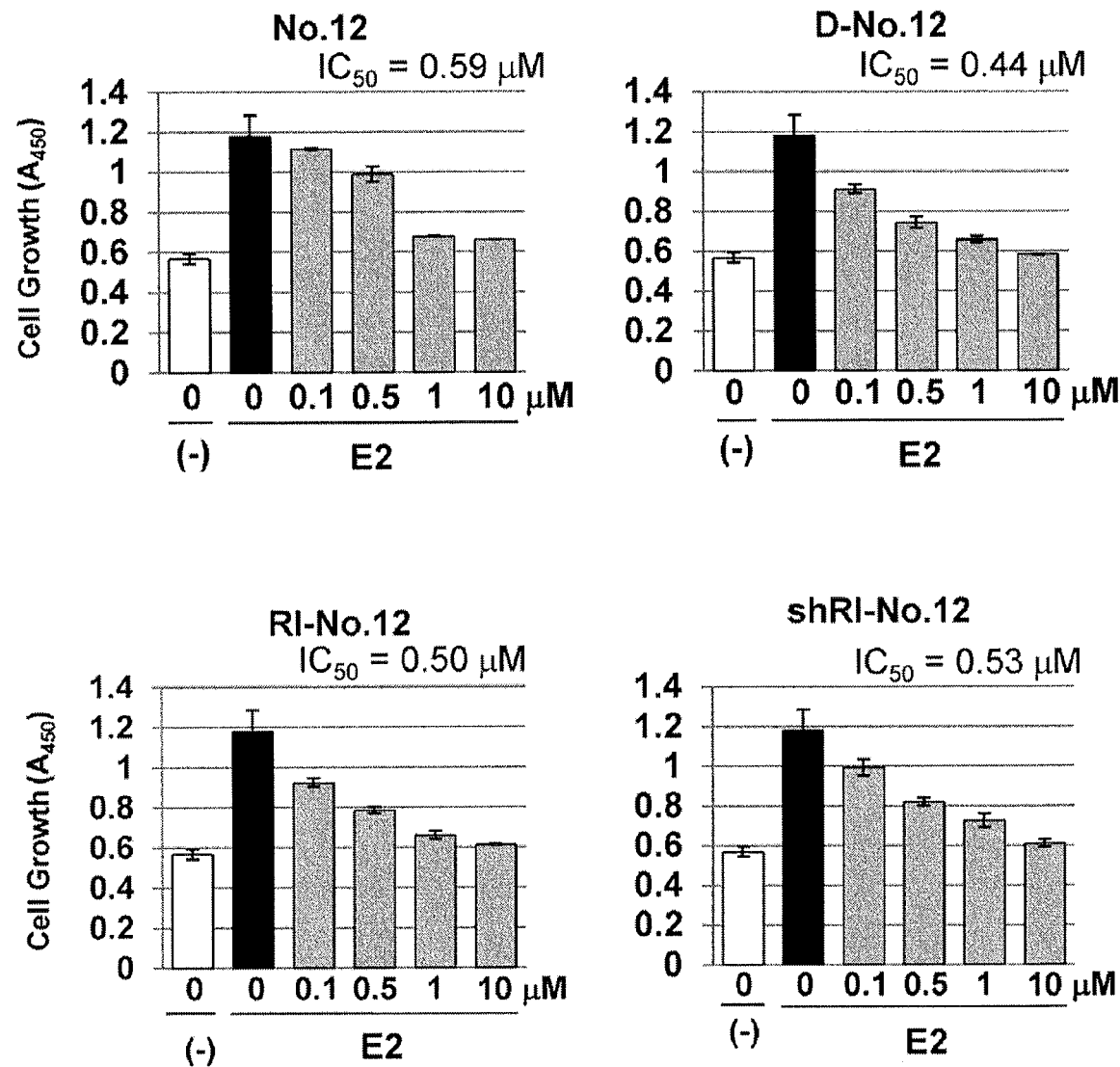

FIG. 6C shows the inhibitory effects of stapled ERAP No. 12 (upper left panel), D-No. 12 (upper right panel), RI-No. 12 (lower left panel), or shRI-No. 12 (lower right panel) on E2-dependent growth of MCF-7 cells at 96 hours after treatment of the cells with the above stapled ERAPs. In the E2-added groups, 10 nM E2 was added. The horizontal axis of the graphs indicates the concentrations of the peptides used for the treatment. In the figure, "(−)" indicates E2-untreated cells.

Figure 6D:
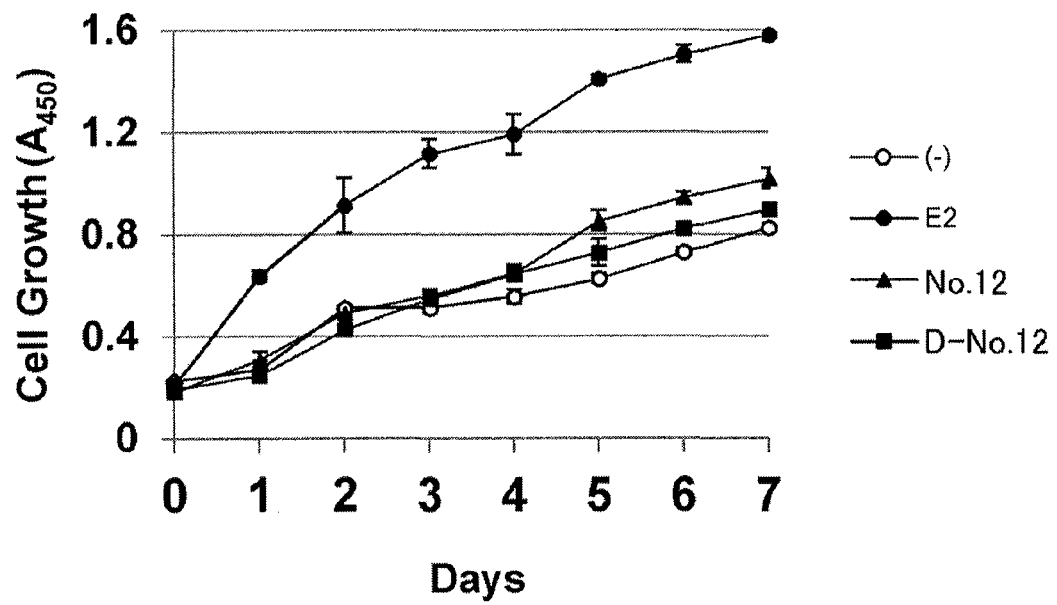
Figure 6D:
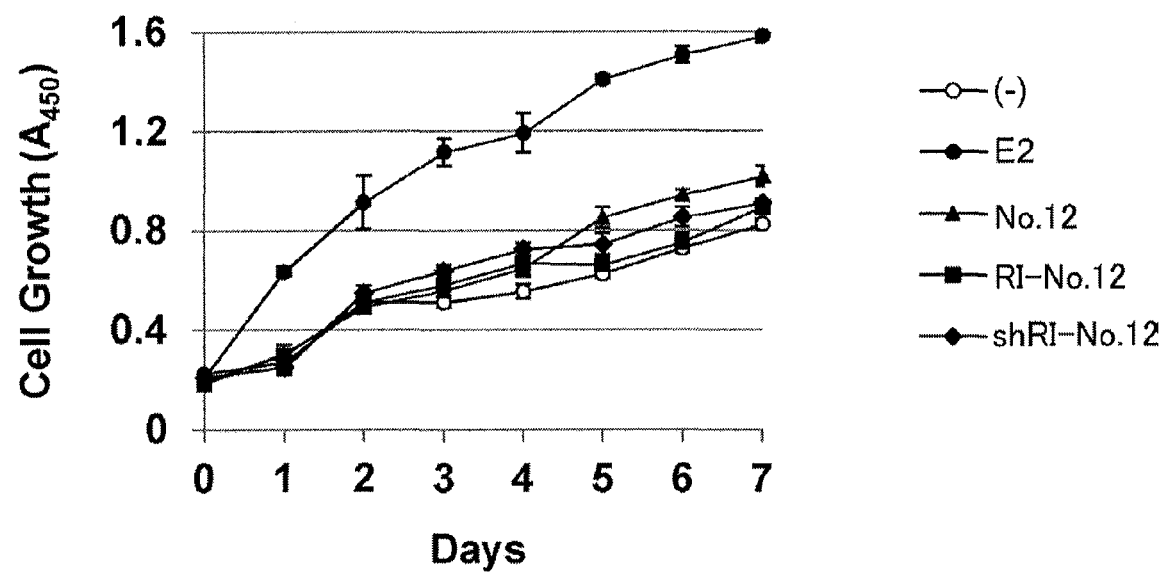

FIG. 6D shows the results of evaluating the inhibitory effects of D-No. 12 (upper panel), RI-No. 12 (lower panel), or shRI-No. 12 (lower panel) on E2-dependent growth of MCF-7 cells for seven days after treatment of the cells with the above peptides. In the E2-added groups, 10 nM E2 was added and each peptide was added at 1 µM. Each symbol in each graph indicates the following: open circle: untreated; filled circle: E2 alone; filled triangle: E2+No. 12; filled square: E2+D-No. 12 (upper panel) or E2+RI-No. 12 (lower panel); and filled diamond: E2+shRI-No. 12.

Figure 6E:
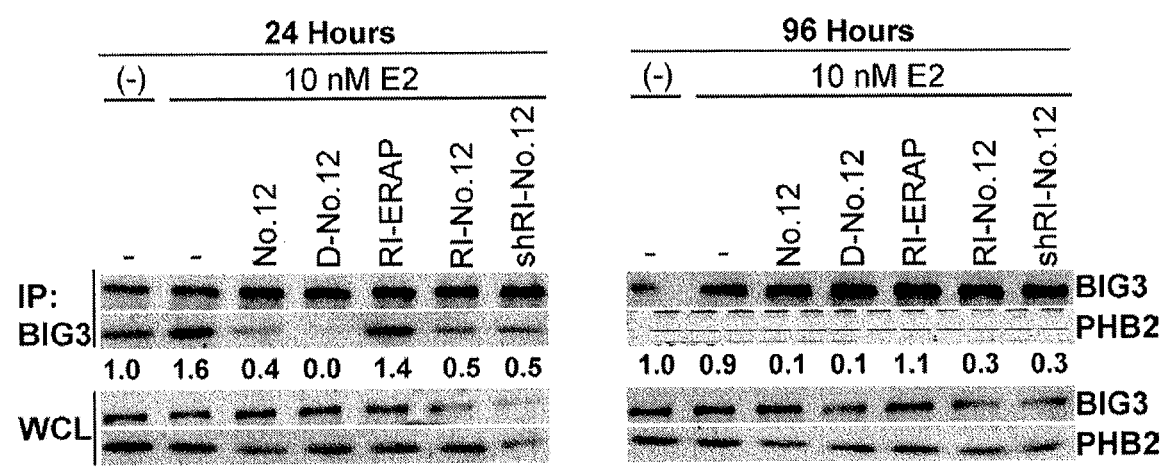

FIG. 6E shows the results of co-immunoprecipitation using an anti-BIG3 antibody, which was performed to evaluate the inhibitory effects of D-No. 12, RI-No. 12, and shRI-No. 12 on the BIG3-PHB2 interaction. The co-immunoprecipitation was performed using MCF-7 cells 24 hours (left panel) or 96 hours (right panel) after the treatment with the respective peptides at 1 µM. In the figure, "IP" indicates the antibody used for immunoprecipitation and "WCL" indicates whole cell lysate. The antibodies reacted on the membrane are shown at the far right. The numerical values below the membrane indicate the relative reaction intensity values for each of the lanes when the reaction intensity of the far-left lane is defined as 1.0. In the figure, "(−)" indicates E2-untreated cells and "−" indicates peptide-untreated cells.

Figure 6F:
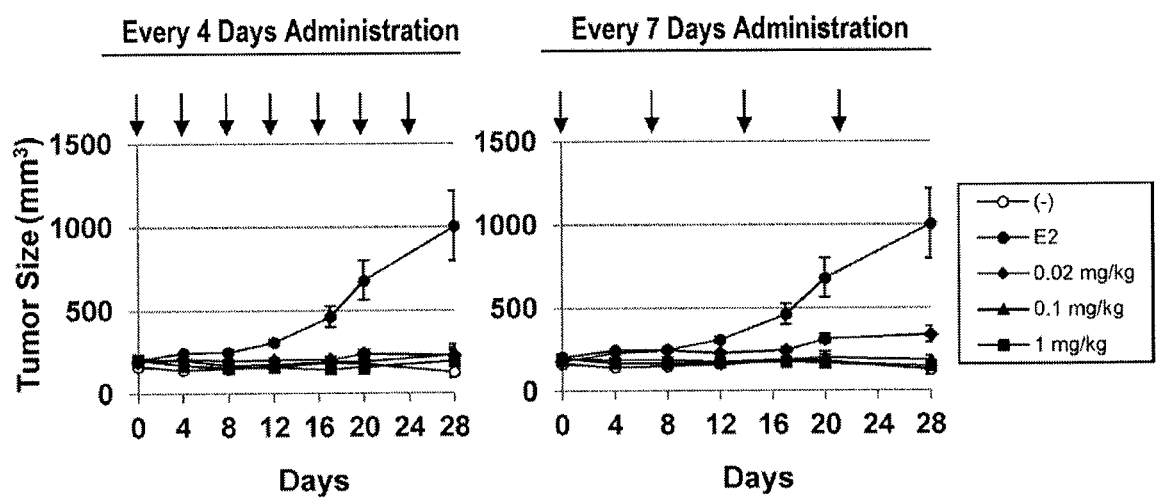

FIG. 6F shows the inhibitory effects of RI-No. 12 treatments every four days (left panel) and every seven days (right panel) on tumor growth in a KPL-3C orthotopic xenograft mouse model. Each symbol in each graph indicates the following: open circle: untreated; filled circle: E2 alone; filled diamond: E2+0.02 mg/kg RI-No. 12; filled triangle: E2+0.1 mg/kg RI-No. 12; and filled square: E2+1 mg/kg RI-No. 12. The data on tumor sizes represent the mean±SE of each group (n=5).

Figure 6G:
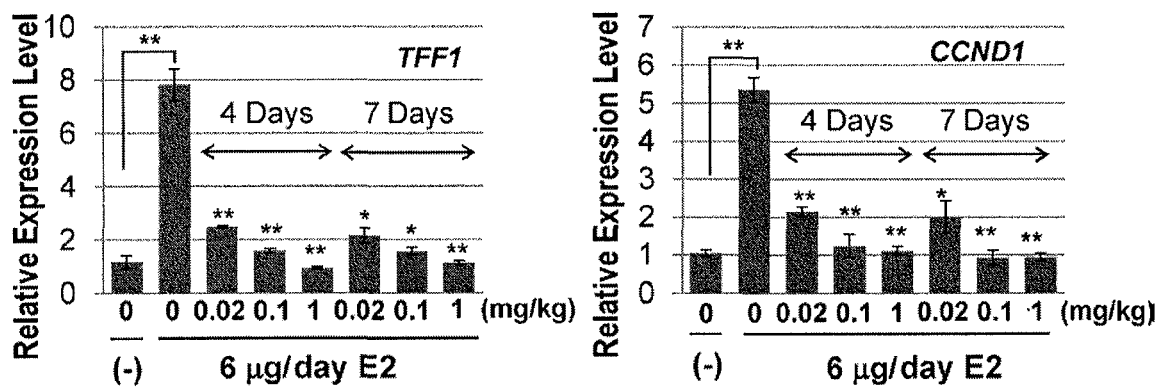

FIG. 6G shows the suppression of expression of ERα target genes TFF1 (left panel) and CCND1 (right panel) in tumors removed from KPL-3C orthotopic xenograft mice treated with RI-No. 12 every four days or every seven days. The horizontal axis of the graphs indicates a single treatment dose of RI-No. 12. In the figure, "(−)" indicates E2-untreated cells. The results were presented as multiples of the expression level in untreated tumors, with that level being defined as 1.0. The data represent the mean±SD of five independent tumors (*P<0.05, **P<0.01, two-sided Student's t-test).

Figure 7:
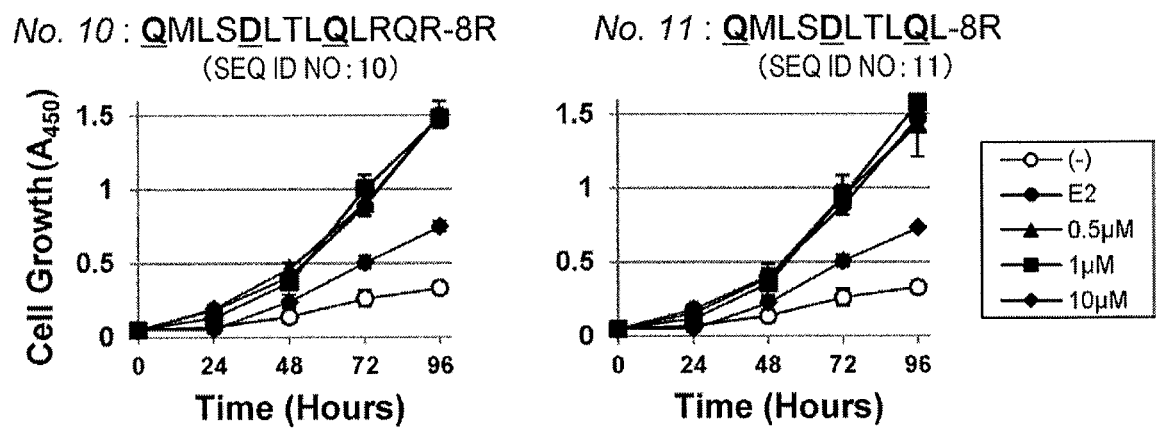

FIG. 7 shows the results of MTT assays which evaluated the inhibitory effects of ERAP-8R (No. 10; left panel) and partial ERAP-8R (No. 11; right panel) on E2-dependent growth of MCF-7 cells. In the E2-added groups, 10 nM E2 was added. In the amino acid sequences indicated above each graph, the underlined bold letters indicate the amino acid residues important for PHB2-binding. Each symbol in each graph indicates the following: open circle: untreated; filled circle: E2 alone; filled triangle: E2+0.5 μM peptide; filled square: E2+1 μM peptide; and filled diamond: E2+10 μM peptide. These data represent the mean±SD of three independent experiments (***P<0.001, two-sided Student's t-test).

Figure 8:
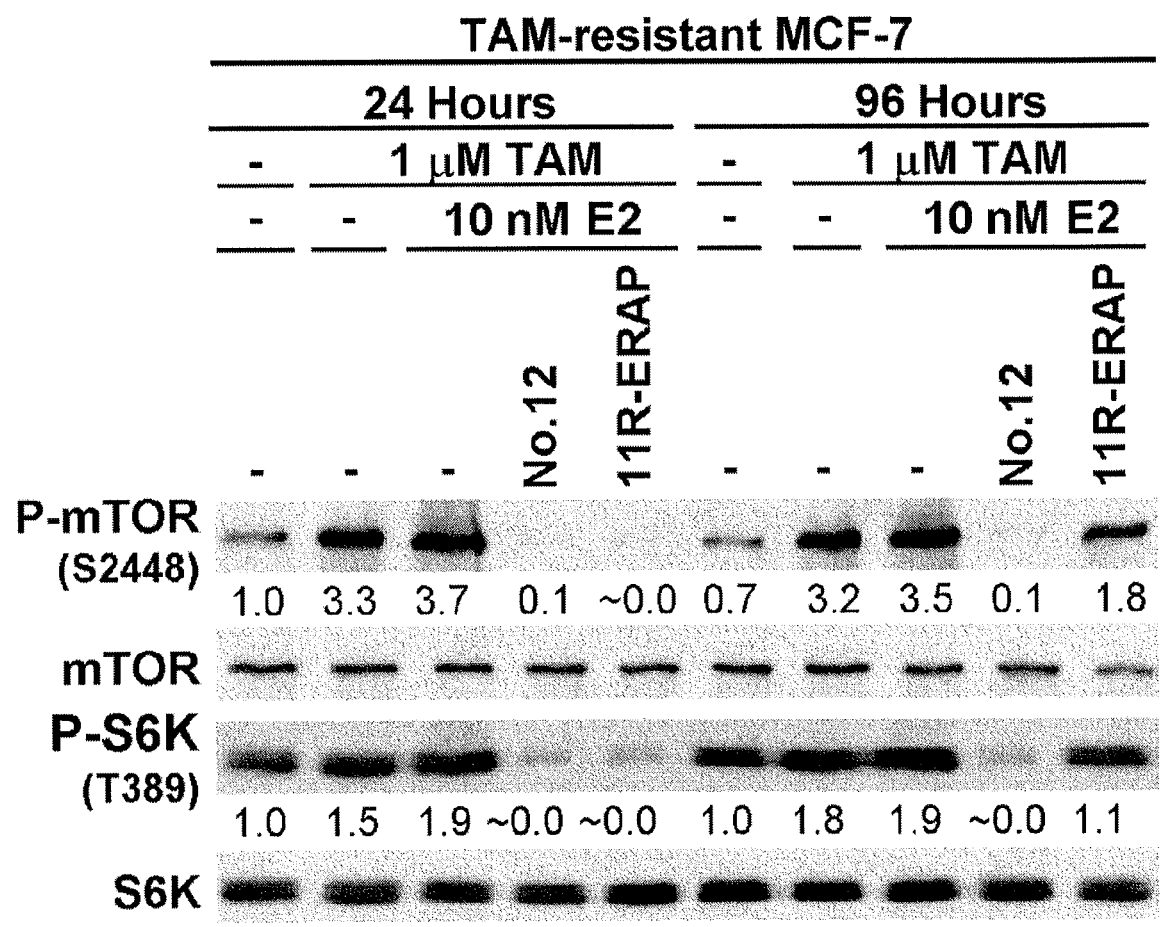

FIG. 8 shows the results of immunoblotting which examined the phosphorylation levels of mTOR and S6K in tamoxifen-resistant breast cancer cell line treated with stapled ERAP (No. 12). The antibodies reacted on the membrane are shown at the far left. The numerical values below the membrane indicate the relative values of reaction intensity for each of the lanes when the reaction intensity of the far-left lane is defined as 1.0.

Figure 9:
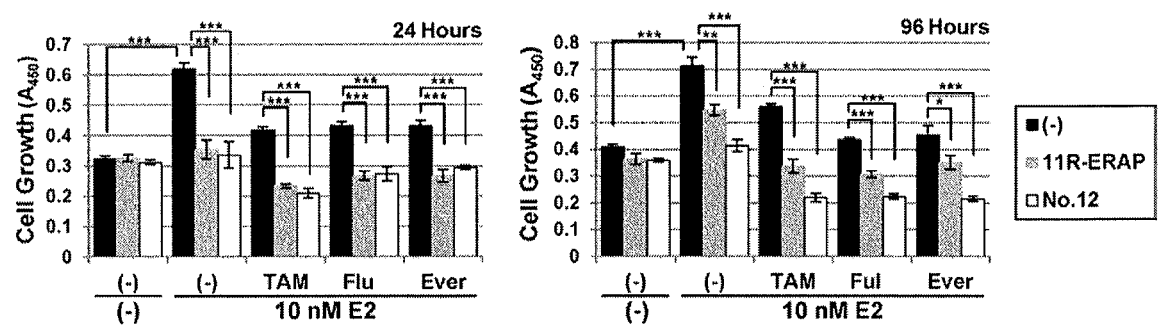

FIG. 9 shows the results of MIT assays which evaluated the effects of combined use of stapled ERAP (No. 12) with tamoxifen, fulvestrant, or everolimus on the E2-dependent growth of MCF-7 cells. In the figure, the dark gray bars indicate untreated cells, the light gray bars indicate 11R-ERAP-treated cells, and the open bars indicate stapled ERAP No. 12-treated cells. Furthermore, "TAM", "Flu", and "Ever" refer to tamoxifen, fulvestrant, and everolimus, respectively. The graph shows the results obtained 24 hours (left panel) and 96 hours (right panel) after the treatment. The data represent the mean±SD of three independent experiments (P<0.01, *P<0.001, two-sided Student's t-test).

Figure 10:
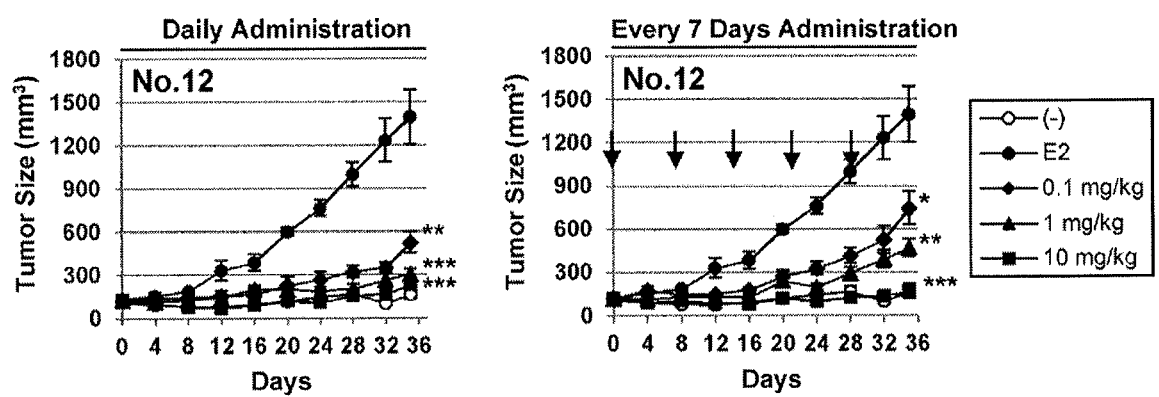

FIG. 10 shows the antitumor effects of tail vein administration of stapled ERAP (No. 12). Each symbol in the graphs indicates the following: open circle: untreated; filled circle: E2 alone; filled diamond: E2+0.1 mg/kg peptide; filled triangle: E2+1 mg/kg peptide; and filled square: E2+10 mg/kg peptide.

Figure 11:
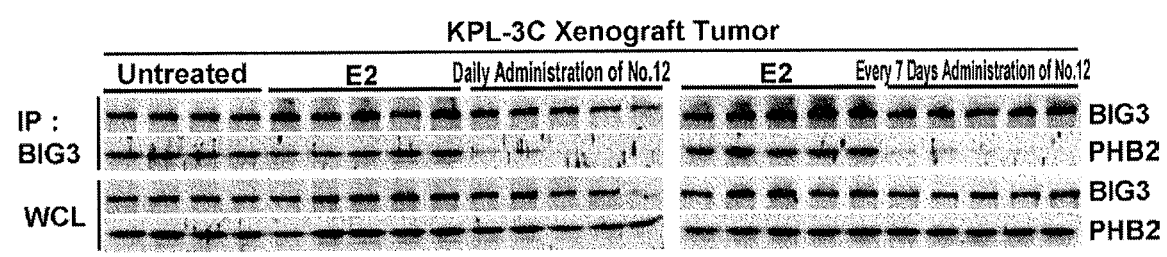

FIG. 11 shows the results of co-immunoprecipitation experiments which evaluated the BIG3-PHB2 interaction in tumors isolated from grafted mice treated with stapled ERAP (No. 12). In the figure, "IP" indicates the antibody used for immunoprecipitation and "WCL" indicates whole cell lysate. The antibodies reacted on the membrane are shown at the far right.

Figure 12:
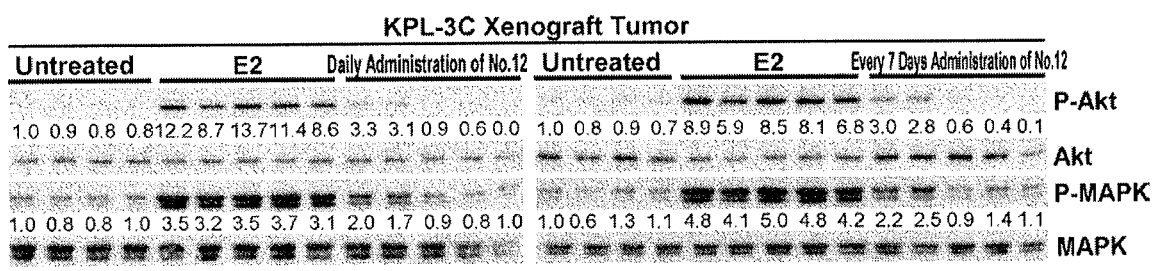

FIG. 12 shows the results of immunoblotting which examined the phosphorylation levels of Akt and MAPK in tumors removed from grafted mice treated with stapled ERAP (No. 12). The antibodies reacted on the membrane are shown at the far right. The numerical values below the membrane indicate the relative reaction intensity values for each of the lanes when the reaction intensity of the far-left lane is defined as 1.0.

MODE FOR CARRYING OUT THE INVENTION

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Definitions

The words "a", "an", and "the" used herein mean "at least one" unless otherwise specifically indicated.

Herein, unless otherwise specifically indicated, amino acids represented by capital letters indicate L-amino acids. Amino acids represented by lower-case letters indicate D-amino acids. Furthermore, L-amino acids and D-amino acids represented herein may include amino acids in which any of amino group, carboxyl group, and side chains has been modified. Examples of preferred modifications include acetylation of the amino group, amidation of the carboxyl group, tag peptide addition such as FLAG-tagging and HA-tagging, and such.

Herein, numbers indicating the positions of amino acid residues in amino acid sequences have been given in order from the N-terminal amino acid residue unless otherwise specifically indicated.

The term "BIG3" used herein refers to brefeldin A-inhibited guanine nucleotide-exchange protein 3. BIG3 forms a complex with PHB2 to inhibit the E2-dependent transcriptional activation-suppressing function of PHB2. BIG3 is also referred to as "ARFGEF family member 3 (ARFGEF3)" or "A7322". An example of a representative nucleotide sequence of the human BIG3 gene is shown in SEQ ID NO: 23 (GenBank Accession No. NM_020340.4), and the amino acid sequence encoded by the gene is shown in SEQ ID NO: 24. In the present invention, BIG3 is not limited to that encoded by the aforementioned nucleotide sequence and also encompasses their isoforms and mutants.

The term "PHB2" used herein refers to prohibitin 2. PHB2 binds to estrogen receptors to inhibit estrogen receptor signaling pathways and suppresses estrogen-dependent cell growth. PHB2 is also referred to as "Repressor of Estrogen Activity (REA)". Examples of representative nucleotide sequences of the human PHB2 gene are shown in SEQ ID NO: 25 (GenBank Accession No. NM_001144831.1) and SEQ ID NO: 27 (GenBank Accession No. NM_001267700.1), and the amino acid sequences encoded by the genes are shown in SEQ ID NO: 26 and SEQ ID NO: 28, respectively. In the present invention, PHB2s are not limited to those encoded by the aforementioned nucleotide sequences and also encompass their isoforms and mutants.

The term "estrogen receptor" used herein encompasses both estrogen receptor α (ERα) and estrogen receptor β (ERβ). Estrogen receptors translocate into the nucleus when bound by estrogen, and bind to the enhancer sequence ERE on a DNA to cause transcriptional activation of genes relating to cell growth. This induces estrogen-dependent cell growth. ERα and ERβ are encoded by the ESR1 gene and ESR2 gene, respectively. The nucleotide sequence of a representative human ESR1 gene is shown in SEQ ID NO: 29 (GenBank Accession No. NM_000125.3). Furthermore, the nucleotide sequence of a representative human ESR2 gene is shown in SEQ ID NO: 31 (GenBank Accession No. NM_001437.2). In the present invention, ERα and ERβ are not limited to those encoded by the aforementioned nucleotide sequences and also encompass their isoforms and mutants. In a preferred embodiment of the present invention, the estrogen receptor is ERα.

The term "ERAP" used herein refers to a peptide consisting of the amino acid sequence of SEQ ID NO: 9. Furthermore, the term "short ERAP" indicates a peptide consisting of a partial sequence of the amino acid sequence of SEQ ID NO: 9. The amino acid sequence of SEQ ID NO: 9 is a sequence consisting of the amino acid residues of positions 165 to 177 in the amino acid sequence of BIG 3 (SEQ ID NO: 24), and contains amino acid residues important for binding with PHB2 (glutamine (Q) at position 165, aspartic acid (D) at position 169, and glutamine (Q) at position 173 in the amino acid sequence of SEQ ID NO: 24). ERAP has an ability to bind to PHB2 and inhibits formation of the BIG3-PHB2 complex by binding competitively to PHB2. Furthermore, herein, peptides formed by linking polyarginine to the N terminus or the C terminus of ERAP as cell-permeable peptides are described as 11R-ERAP, ERAP-8R (the numeric character before "R" refers to the number of arginine residues), or such.

The term "stapling structure" used herein refers to a structure in which two (a pair of) amino acid residues in an amino acid sequence constituting a peptide are crosslinked. Herein, a peptide in which original amino acid residues are substituted with one or a plurality of stapling structures is referred to as "a stapled peptide". For example, a stapled ERAP is a peptide in which at least one pair of amino acid residues in the peptide consisting of the amino acid sequence of SEQ ID NO: 9 (ERAP) has been substituted with a stapling structure. A short stapled ERAP refers to a peptide in which at least one pair of amino acid residues in a peptide consisting of a partial sequence of the amino acid sequence of SEQ ID NO: 9 (short ERAP) has been substituted with a stapling structure. Herein, a short stapled ERAP is also written as "sh stapled ERAP".

The term "therapy" used herein encompasses alleviation/improvement of at least one symptom caused by a target disease, suppression of progression of the disease, suppression of enlargement of the disease site, and such. For example, "cancer therapy" includes cancer cell growth suppression, suppression of cancer progression, induction of regression/remission of cancer, alleviation/improvement of symptoms accompanying cancer, suppression of cancer metastasis, suppression of postoperative recurrence, and induction of prolonged survival time.

Peptides of the Present Invention

A peptide of the present invention is a peptide comprising an amino acid sequence in which an n pair (n is a natural number) of amino acid residues is substituted with n number of stapling structure(s) in the amino acid sequence of SEQ ID NO: 9 or its partial sequences. Here, n is preferably 3 or less, more preferably 2, and even more preferably 1. Therefore, in the present invention, n pair(s) of amino acid residues normally refer(s) to one to three pairs, or one or two pairs, and preferably one pair of amino acid residues.

In peptides of the present invention, the partial sequence of the amino acid sequence of SEQ ID NO: 9 is preferably a sequence of six or more continuous residues and more preferably a sequence of seven or more continuous residues of the amino acid sequence of SEQ ID NO: 9. Furthermore, glutamine (Q) at position 1, aspartic acid (D) at position 5, and glutamine (Q) at position 9 from the N terminus of the amino acid sequence of SEQ ID NO: 9 are amino acid residues important for binding to PHB2; therefore, the partial sequences preferably include at least one, or more preferably two or more of these amino acid residues. A preferred example of the partial sequence of the amino acid sequence of SEQ ID NO: 9 includes the amino acid sequence of SEQ ID NO: 13 (QMLSDLT).

In the peptides of the present invention, the amino acid residues substituted by the stapling structure are not particularly limited; however, from the viewpoint of binding affinity for PHB2, they are preferably selected from amino acid residues other than glutamine (Q) at position 1, aspartic acid (D) at position 5, and glutamine (Q) at position 9 from the N terminus of the amino acid sequence of SEQ ID NO: 9 (QMLSDLTLQLRQR).

Examples of the amino acid residues substituted by the stapling structure include the following pairs of amino acid residues:

(a) the third (L) and seventh (T) amino acid residues from the N terminus of the amino acid sequence of SEQ ID NO: 9;

(b) the second (M) and sixth (L) amino acid residues from the N terminus of the amino acid sequence of SEQ ID NO: 9;

(c) the fourth (S) and eighth (L) amino acid residues from the N terminus of the amino acid sequence of SEQ ID NO: 9; and (d) the sixth (L) and tenth (L) amino acid residues from the N terminus of the amino acid sequence of SEQ ID NO: 9.

Among (a) to (d) mentioned above, particularly preferred pairs of amino acid residues include the amino acid residue pairs of (a) and (b).

When the amino acid sequence (QMLSDLT) of SEQ ID NO: 13 is used as the partial sequence of the amino acid sequence of SEQ ID NO: 9, examples of the amino acid residues substituted by the stapling structure include the following pairs of amino acid residues:

(a) the third (L) and seventh (T) amino acid residues from the N terminus of the amino acid sequence of SEQ ID NO: 13; and (b) the second (M) and sixth (L) amino acid residues from the N terminus of the amino acid sequence of SEQ ID NO: 13.

In the peptides of the present invention, the stapling structures are not particularly limited. Peptide stapling techniques are known (for example, Blackwell, H. E. et al., Angew. Chem., Int. Ed. 37, 3281-3284 (1994); Aihara, K. et al., Tetrahedron 71, 4183-4191 (2015); and such); therefore, these known stapling techniques can be used to form stapling structures. For example, stapling structures can be formed by synthesizing peptides through solid-phase synthesis or such by incorporating amino acid derivatives carrying a substituent such as an alkenyl group, and then performing an olefin metathesis reaction or an intramolecular amidation reaction between the substituents of the above-mentioned amino acid derivatives. Commercially available amino acid derivatives may be used as amino acid derivatives for forming the stapling structure.

Examples of preferred stapling structures for the peptides of the present invention include structures represented by Formula (I) shown below:

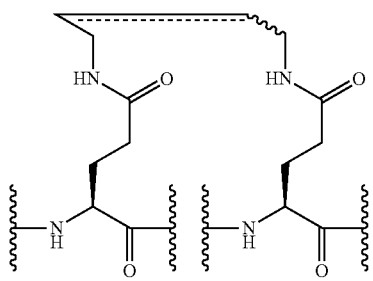

(wherein the double line drawn by a solid line and a dashed line indicates a single bond or a double bond).

Figure 1A:
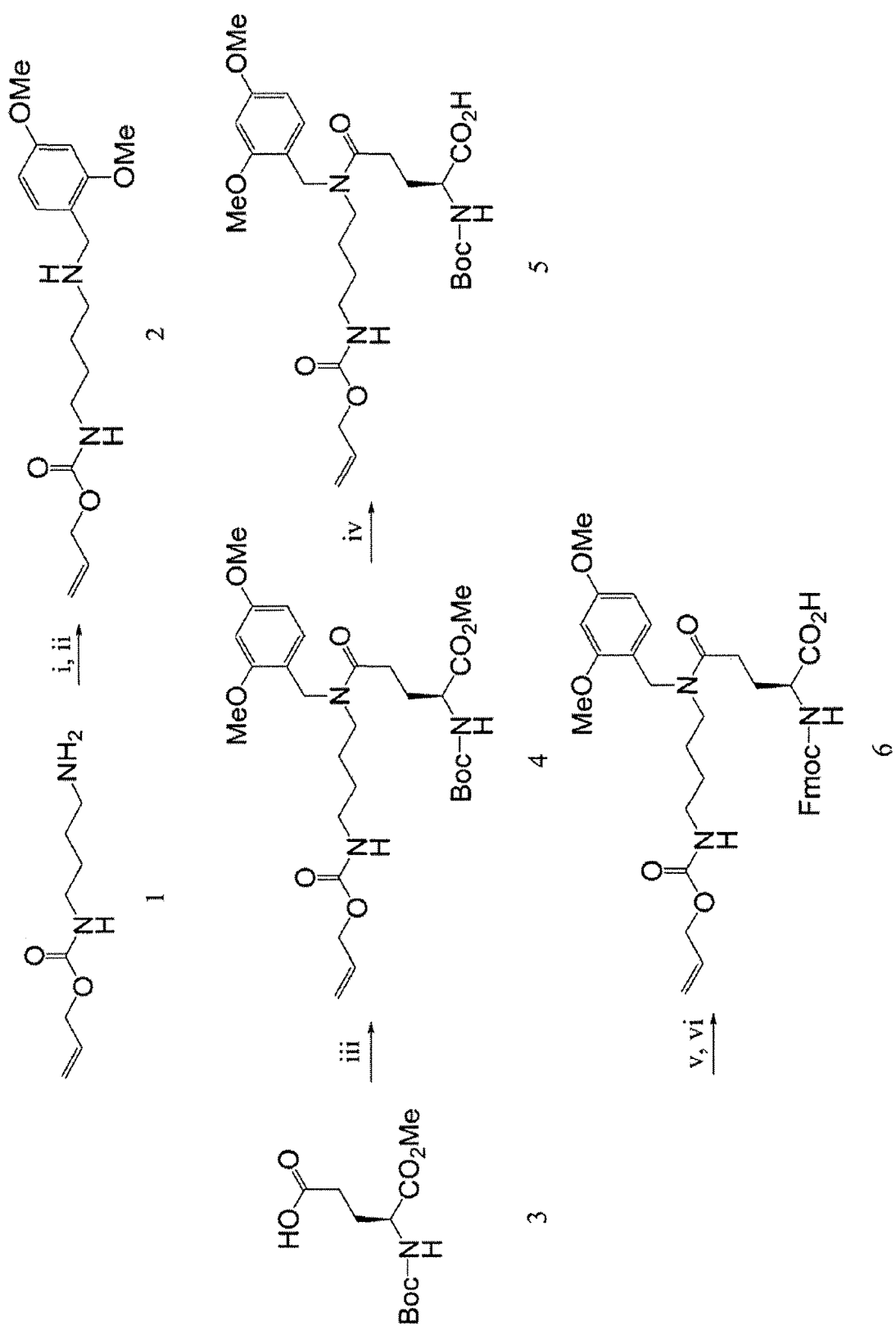
FIG. 1A shows a scheme for the synthesis of an amino acid derivative used for the synthesis of stapled ERAPs. In the figure, (i) to (vi) indicate reagents and amino acid synthesis conditions for each of the reactions: (i) 2,4-dimethoxybenzaldehyde, AcOH, MgSO$_4$, CH$_2$Cl$_2$; (ii) NaBH$_4$, MeOH, CH$_2$Cl$_2$, 87% yield (two steps); (iii) Compound 2, EDC.HCl, DIPEA, CH$_2$CH$_2$, 76% yield; (iv) LiOH.H$_2$O, THF, MeOH, H$_2$O, 92% yield; (v) TBSOTf, 2,6-lutidine, CH$_2$CH$_2$; (vi) Fmoc-OSu, Na$_2$CO$_3$, THF, H$_2$O, 90% yield (two steps).
Figure 1B:
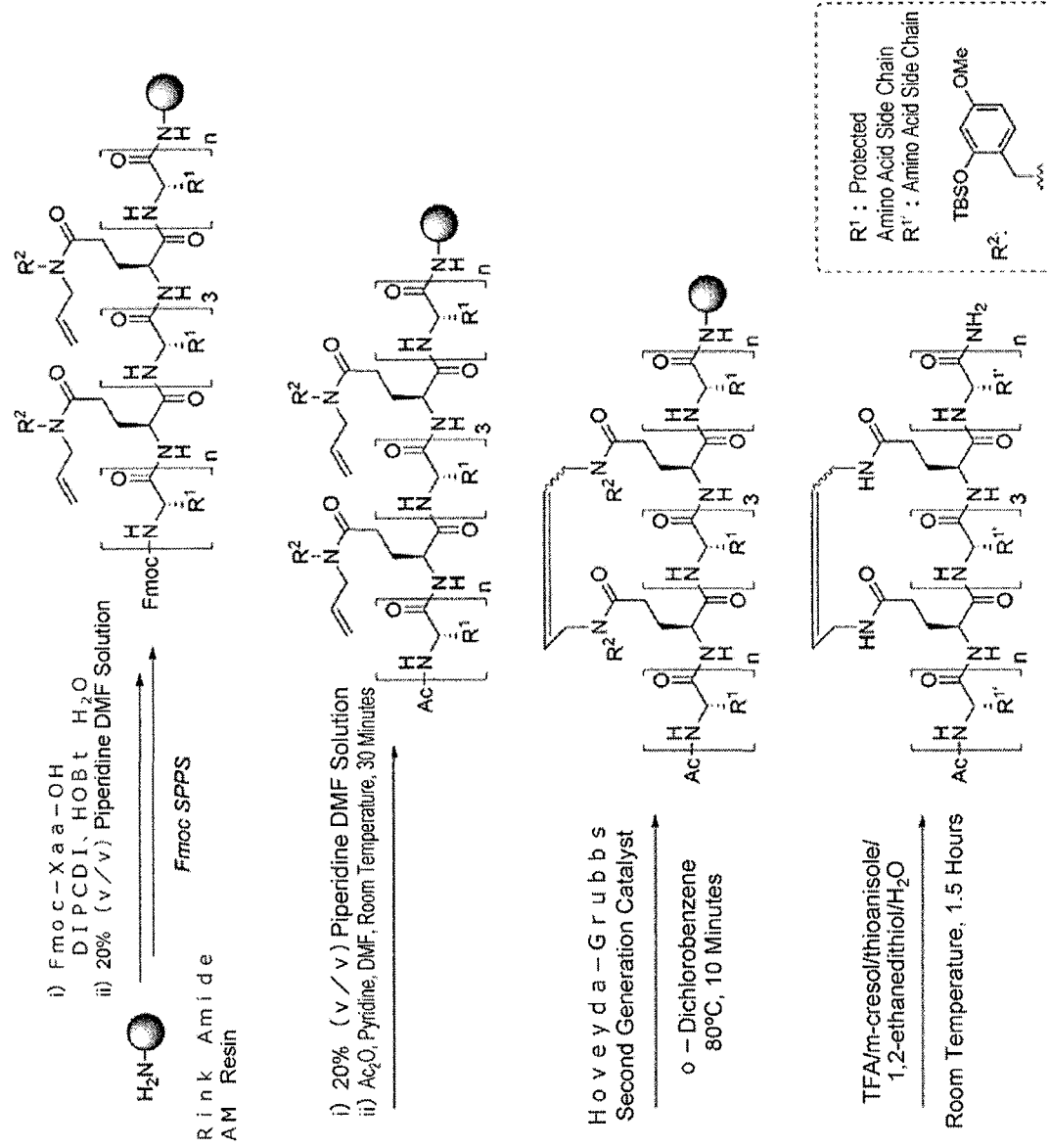
FIG. 1B shows a scheme for stapling synthesis in ERAP by ring-closing olefin metathesis.
Figure 1C:
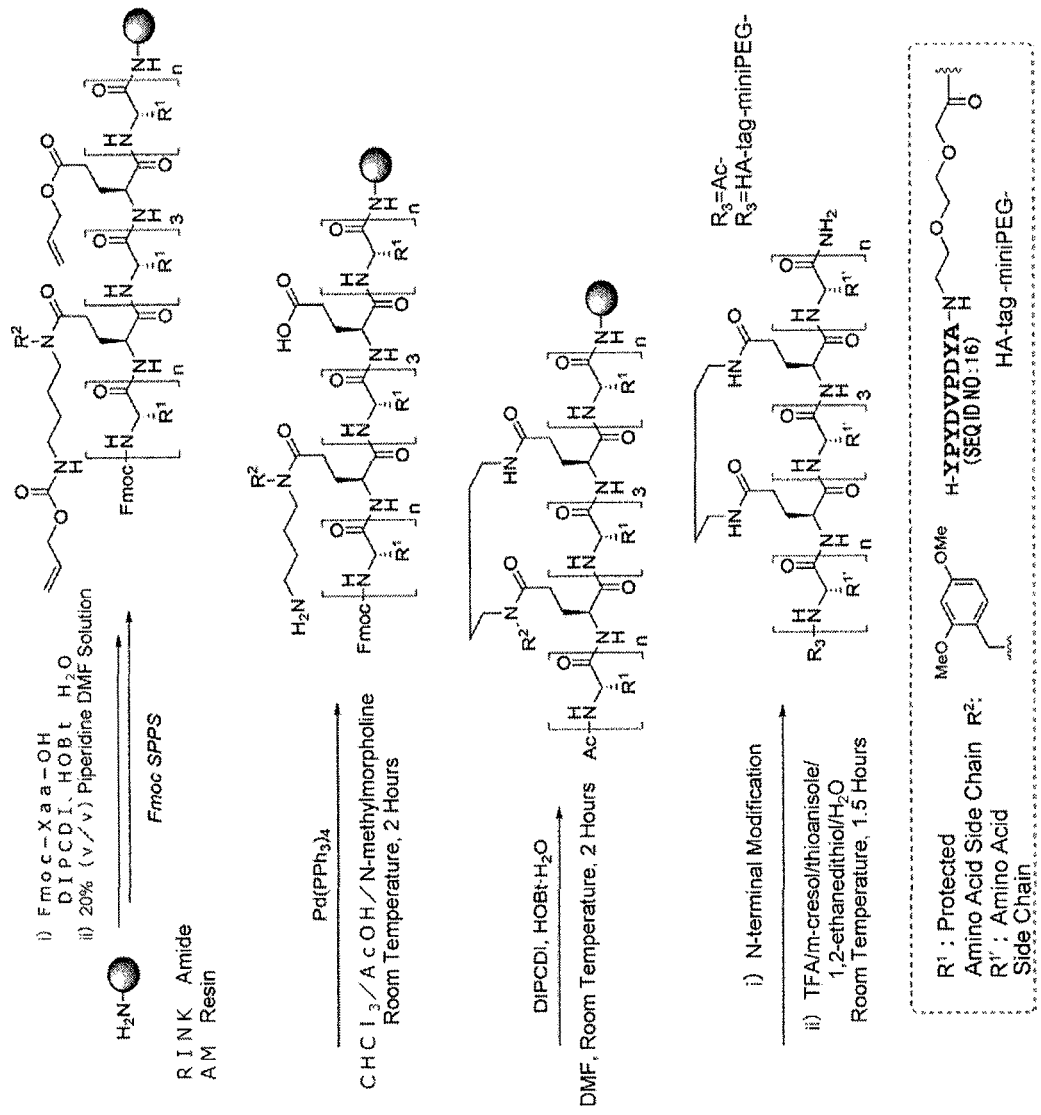
FIG. 1C shows a scheme for stapling synthesis in ERAP via intramolecular amidation.

The stapling structure of Formula (I) above can be formed, for example, according to the scheme shown in FIG. 1B or FIG. 1C. The scheme shown in FIG. 1B (hereinafter, "Scheme (I)") is an example where the stapling structure is formed by an olefin metathesis reaction. On the other hand, the scheme shown in FIG. 1C (hereinafter, "Scheme (II)") is an example where the stapling structure is formed by an intramolecular amidation reaction.

When forming a stapling structure by the olefin metathesis reaction shown in Scheme (I), the amino acid derivative used for stapling may be the glutamine derivative (4-{allyl-[2-(tert-butyl-dimethyl-silanyloxy)-4-methoxy-benzyl]-carbonyl}-2-(9H-fluoren-9-yl-methoxycarbonylamino)-butyric acid) represented by Formula (III) shown below.

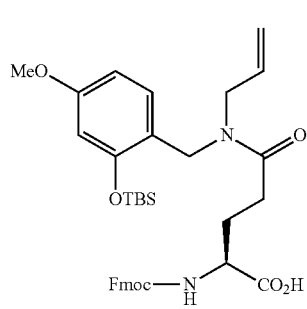

The glutamine derivative of Formula (III) can be synthesized, for example, according to Scheme (III) shown below (Aihara, K. et al., Tetrahedron 71, 4183-4191 (2015)).

Scheme (III)

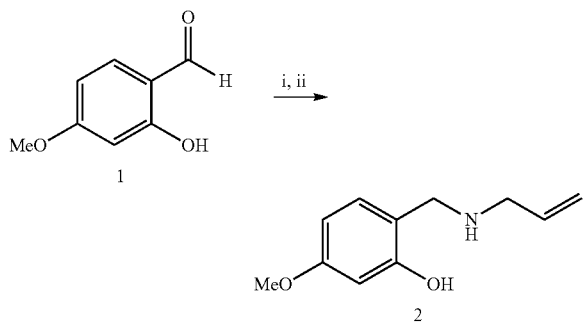

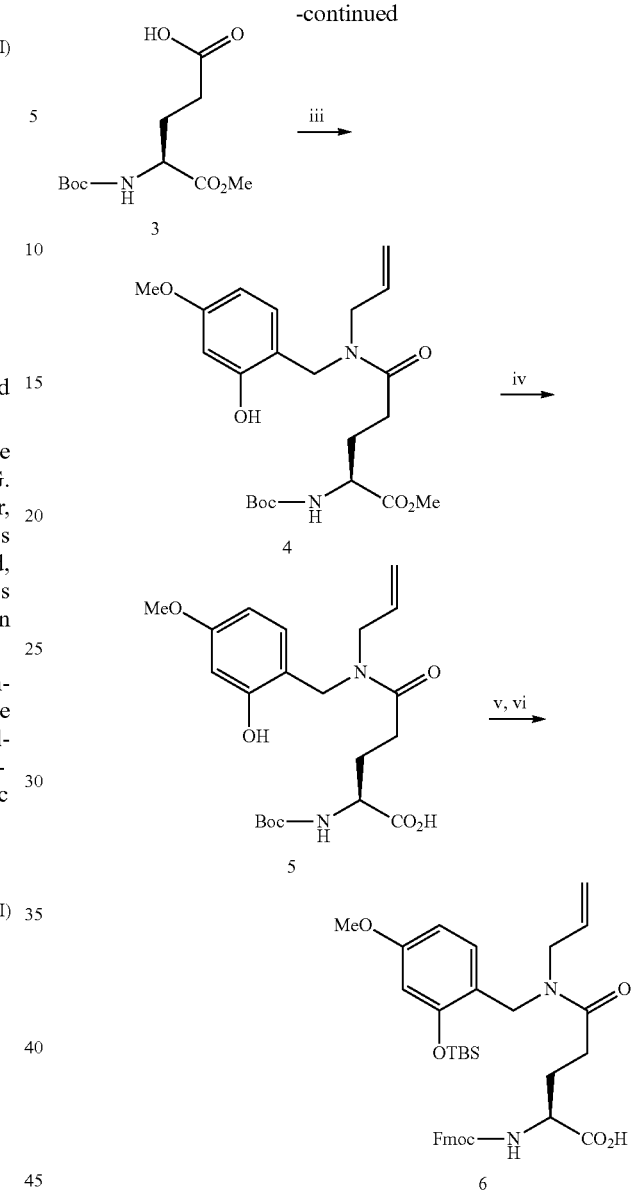

In Scheme (III) shown above, (i) to (vi) each indicate the followings: (i) 3-amino-1-propene, AcOH, MgSO$_4$, CH$_2$Cl$_2$; (ii) NaBH$_4$, MeOH, CH$_2$Cl$_2$; (iii) Compound 2, DCC, CH$_2$Cl$_2$; (iv) LiOH.H$_2$O, THF, MeOH, H$_2$O; (v) TBSOTf TBSOTf, 2,6-lutidine; and (vi) Fmoc-OSu, Na$_2$CO$_3$, THF, H$_2$O.

As shown in Scheme (III), 2-hydroxy-4-methoxybenzaldehyde (Compound 1) is reductively aminated with 3-amino-1-propene to obtain 2-allylaminomethyl-5-methoxy-phenol (Compound 2). Next, Compound 2 is coupled with N-α-(tert-butoxycarbonyl)-L-glutamic acid α-methyl ester (Compound 3) to obtain 4-[allyl-(2-hydroxy-4-methoxy-benzypcarbamoyl]-2-tert-butoxycarbonylamino-butyric acid methyl ester (Compound 4). Next, the methyl ester in Compound 4 is hydrolyzed to obtain 4-[allyl-(2-hydroxy-4-methoxy-benzyl)carbamoyl]-2-tert-butoxy-carbonylamino-butyric acid (Compound 5). Furthermore, by substituting the Boc group of Compound 5 with an Fmoc group and protecting the phenol portion of Hmb group with TBS, the glutamine derivative of Formula (III) can be obtained. Commercially available reagents can be used for all the reagents necessary to carry out Scheme (III).

On the other hand, synthesis of stapled ERAPs by Scheme (I) can be carried out using the glutamine derivative of Formula (III), for example, as described below. First, a peptide is synthesized by standard Fmoc solid-phase peptide synthesis by substituting the glutamine derivative of Formula (III) for a pair of amino acid residues positioned where one wants to form a stapling structure in the amino acid sequence of SEQ ID NO: 9 or its partial sequence. Then, after deprotection of the N terminus of the Fmoc-protected peptide followed by acetylation, the acetylated peptide is treated with Hoveyda-Grubbs' second-generation catalyst to perform an olefin metathesis reaction. Furthermore, deprotection of acid-labile protecting groups along with cleavage of peptides from resin are performed using a cocktail of TFA/m-cresol/thioanisole/1,2-ethanedithiol/H$_2$O. This allows stapled ERAPs or sh stapled ERAPs carrying the stapling structure of Formula (I) (the double line drawn by a solid line and a dashed line indicates a double bond) to be obtained. In the stapled ERAP or sh stapled ERAP synthesized by Scheme (I), the number of amino acid residues interpositioned within the stapling structure is not particularly limited, but ordinarily the preferred number is three.

Furthermore, when forming a stapling structure by the intramolecular amidation reaction shown in Scheme (II) presented in FIG. 1C, the amino acid derivatives used for stapling may be N-α-(9-fluorenylmethoxycarbonyl)-L-glutamic acid γ allyl ester represented by Formula (IV) and (S)-2-((((9H-fluoren-9-yl)methoxy)carbonyl)amino)5-((4-(((allyloxy)carbonyl)amino)butyl)(2,4-dimethoxybenzyl)amino)-5-oxopentanoic acid represented by Formula (V), shown below.

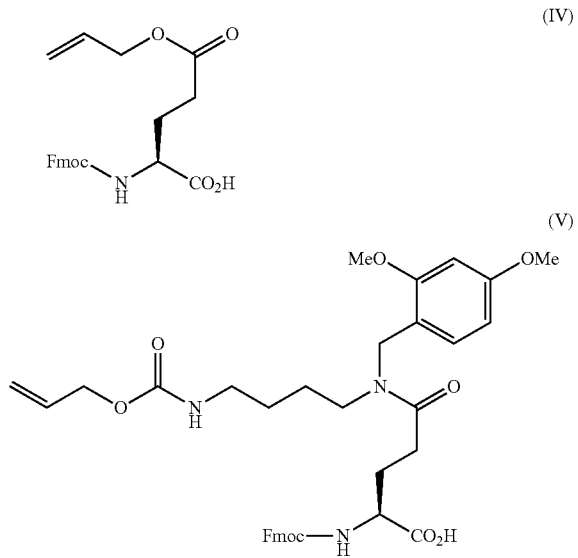

Among the two types of amino acid derivatives described above, a commercially available product may be used for the glutamic acid derivative of Formula (IV). Furthermore, the glutamine derivative of Formula (V) can be synthesized, for example, according to the scheme shown in FIG. 1A (herein below, "Scheme (IV)"). As shown in Scheme (IV), allyl(4-aminobutyl)carbamate (Compound 1) is coupled with 2,4-dimethoxybenzaldehyde to obtain allyl [4-{(2,4-dimethoxybenzyl)amino}butyl]carbamate (Compound 2). Next, Compound 2 is coupled with N-α-(tert-butoxycarbonyl)-L-glutamic acid α methyl ester (Compound 3) to obtain (5)-methyl-5-{(4-[{(allyloxy)carbonyl}amino]butyl) (2,4-dimethoxybenzyl)amino}-2-{(tert-butoxycarbonyl)amino}-5-oxopentanoate (Compound 4). Next, the methyl ester in Compound 4 is hydrolyzed to obtain (S)-5-{(4-[{(allyloxy)carbonyl}amino]butyl) (2,4-dimethoxybenzyl)amino}-2-{(tert-butoxycarbonyl)amino}-5-oxopentanoic acid (Compound 5). Furthermore, by substituting an Fmoc group for the Boc group of Compound 5, the glutamine derivative of Formula (V) can be obtained. Commercially available reagents can be used for all of the reagents necessary to carry out Scheme (IV).

On the other hand, synthesis of a stapled ERAP by Scheme (II) can be carried out using the glutamic acid derivative of Formula (IV) and the glutamine derivative of Formula (V) above, for example, as described below. First, a peptide is synthesized through standard Fmoc solid-phase peptide synthesis by substituting the glutamic acid derivative of Formula (IV) and the glutamine derivative of Formula (V) for a pair of amino acid residues positioned where one wants to form a stapling structure in the amino acid sequence of SEQ ID NO: 9 or a partial sequence thereof. Then, the Fmoc-protected peptide is mixed with a solution of tetrakis(triphenylphosphine)palladium (Pd(PPh$_3$)$_4$) in CHCl$_3$/AcOH/N-methylmorpholine to reduce the substituent of the glutamine derivative residue. Next, intramolecular amidation is carried out by using N,N-diisopropylcarbodiimide (DIPCDI) and 1-hydroxy-1H-benzotriazole hydrate (HOBt.H$_2$O) to couple the glutamine derivative residues. Furthermore, deprotection of acid-labile protecting groups along with cleavage of peptides from resin are performed using a cocktail of TFA/m-cresol/thioanisole/1,2-ethanedithiol/H$_2$O. This allows stapled ERAPs or sh stapled ERAPs carrying the stapling structure of Formula (I) (the double line drawn by a solid line and a dashed line indicates a single bond) to be obtained. In the stapled ERAP or sh stapled ERAP synthesized by Scheme (II), the number of amino acid residues interpositioned within the stapling structure is not particularly limited, but ordinarily the preferred number is three.

Specific examples of the peptides of the present invention include peptides represented by Formula (II) shown below:

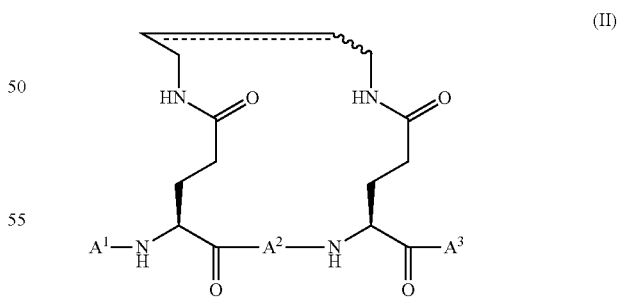

(wherein, the double line drawn by a solid line and a dashed line indicates a single bond or a double bond; and the combination of A$^1$, A$^2$, and A$^3$ is selected from the followings:
A$^1$=Q, A$^2$=LSD, and A$^3$=TLQLRQR (SEQ ID NO: 14);
A$^1$=QM, A$^2$=SDL, and A$^3$=LQLRQR (SEQ ID NO: 15);
A$^1$=QM, A$^2$=SDL, and A$^3$=—OH; and
A$^1$=Q, A$^2$=LSD, and A$^3$=T).

The peptides represented by Formula (II) above may also be referred to as peptides formed by substituting the stapling structure of Formula (I) for the pair of amino acid residues (a) or (b) below in the peptide consisting of the amino acid sequence of SEQ ID NO: 9 (QMLSDLTLQLRQR):

(a) the third (L) and seventh (T) amino acid residues from the N terminus of the amino acid sequence of SEQ ID NO: 9; or (b) the second (M) and sixth (L) amino acid residues from the N terminus of the amino acid sequence of SEQ ID NO: 9.

Alternatively, they are peptides formed by substituting the stapling structure of Formula (I) for the pair of amino acid residues (c) or (d) below in the peptide consisting of the amino acid sequence of SEQ ID NO: 13 (QMLSDLT):

(c) the third (L) and seventh (T) amino acid residues from the N terminus of the amino acid sequence of SEQ ID NO: 13; and (d) the second (M) and sixth (L) amino acid residues from the N terminus of the amino acid sequence of SEQ ID NO: 13.

Among the peptides represented by Formula (II), particularly preferred peptides include peptides in which the combination of $A^1$, $A^2$, and $A^3$ in Formula (II) is selected from the followings:

$A^1$=Q, $A^2$=LSD, and $A^3$=TLQLRQR (SEQ ID NO: 14);
$A^1$=QM, $A^2$=SDL, and $A^3$=LQLRQR (SEQ ID NO: 15); and
$A^1$=QM, $A^2$=SDL, and $A^3$=—OH.

These peptides correspond to the following peptides:

(i) peptides formed by substituting the stapling structure of Formula (I) for the pair of amino acid residues (a) or (b) below in the peptide consisting of the amino acid sequence of SEQ ID NO: 9 (QMLSDLTLQLRQR):

(a) the third (L) and seventh (T) amino acid residues from the N terminus of the amino acid sequence of SEQ ID NO: 9; and (b) the second (M) and sixth (L) amino acid residues from the N terminus of the amino acid sequence of SEQ ID NO: 9; or (ii) peptides formed by substituting the stapling structure of Formula (I) for the pair of amino acid residues below in the peptide consisting of the amino acid sequence of SEQ ID NO: 13 (QMLSDLT):

(c) the third (L) and seventh (T) amino acid residues from the N terminus of the amino acid sequence of SEQ ID NO: 13.

Peptides of the present invention encompass peptides in which either or both of the N-terminal and C-terminal amino acid residues have been modified. The types of modifications are not particularly limited, but those that do not decrease the affinity for PHB2 or cell permeability are preferred. Examples of preferred modifications include acetylation of the N-terminal amino acid residue, amidation of the C-terminal amino acid residue, addition of tag peptides such as HA-tag and FLAG-tag, and such. Furthermore, particularly preferred examples of the peptides of the present invention include peptides in which the N-terminal amino acid residue is acetylated and the C-terminal amino acid residue is amidated in the peptide represented by Formula (II) above. Amino acid residues other than the N-terminal and C-terminal amino acid residues are preferably not modified.

The peptides of the present invention are not limited to those composed of L-amino acids and may be peptides including one or more D-amino acids. The composition ratio of L-amino acids and D-amino acids in a peptide is not particularly limited, but for maintaining an α-helical structure, it is preferred that all amino acid residues are of the L-form (hereinafter, "L-form peptide") or all amino acid residues are of the D-form (hereinafter, "D-form peptide"). Therefore, in any one of the above-mentioned peptides of the present invention, peptides in which all amino acid residues have been substituted with D-form amino acid residues are also included as preferred embodiments of the peptides of the present invention. When the peptides of the present invention are D-form peptides, examples of preferred peptides may include peptides in which all amino acid residues in the peptides represented by Formula (II) have been substituted with D-form amino acid residues. When the peptides of the present invention are D-form peptides, for example, 80% or more, ordinarily 90% or more, preferably 95% or more, more preferably 98% or more, and even more preferably 99% or more of the amino acids constituting the amino acid sequences are D-form amino acid residues.

Furthermore, the peptides of the present invention may be retro-inverso forms of any of the above-mentioned peptides of the present invention. A retro-inverso form has an amino acid sequence that is reversed from that of the original peptide, and all amino acid residues are substituted with D-form amino acid residues. More specifically, a retro-inverso form is a D-form peptide having an amino acid sequence that is reversed from that of the original peptide. Therefore, peptides which are retro-inverso forms of any one of the above-mentioned peptides of the present invention are included as a preferred embodiment of the peptides of the present invention. When the peptides of the present invention are retro-inverso forms, examples of preferred peptides include peptides which are the retro-inverso forms of peptides represented by Formula (II). When the peptides of the present invention are retro-inverso forms, for example, 80% or more, ordinarily 90% or more, preferably 95% or more, more preferably 98% or more, and even more preferably 99% or more of the amino acids constituting the amino acid sequences are D-form amino acid residues.

When the peptides of the present invention are D-form peptides, D-form stapled ERAPs or sh stapled ERAPs can be synthesized by using D-amino acids instead of L-amino acids in methods as described above. In the synthesis of D-form stapled ERAPs or sh stapled ERAPs, D-form amino acid derivatives are used as the amino acid derivatives for forming stapling structures. Some of the D-form amino acid derivatives that can be used for forming stapling structures are commercially available. Therefore, such commercially available D-form amino acid derivatives may be used.

Furthermore, when synthesizing D-form stapled ERAP or sh stapled ERAP by Scheme (I) shown in FIG. 1B, a D-form optical isomer of the glutamine derivative represented by Formula (III) (hereinafter, "D-glutamine derivative of Formula (III)") may be used as the amino acid derivative for stapling. The D-glutamine derivative of Formula (III) can be synthesized by using N-α-(tert-butoxycarbonyl)-D-glutamic acid α methyl ester instead of N-α-(tert-butoxycarbonyl)-L-glutamic acid α methyl ester (Compound 3) in the above-mentioned Scheme (III). Then, a D-form stapled ERAP or sh stapled ERAP can be obtained by synthesizing a D-form peptide through standard Fmoc solid-phase peptide synthesis using D-amino acids by substituting the D-glutamine derivative of Formula (III) for a pair of amino acid residues positioned where one wants to form a stapling structure in the amino acid sequence of SEQ ID NO: 9 or a partial sequence thereof, and performing an olefin metathesis reaction according to Scheme (I). When synthesizing the retro-inverso form of a stapled ERAP or an sh stapled ERAP, solid-phase peptide synthesis can be performed based on the reversed amino acid sequence of the amino acid sequence of SEQ ID NO: 9 or a partial sequence thereof. In this case, substituting the D-glutamine derivative of Formula (III) for a pair of amino acid residues positioned where one wants to form a stapling structure and then performing an olefin metathesis reaction after synthesizing the peptide are similar to what is described above.

On the other hand, when synthesizing a D-form stapled ERAP or sh stapled ERAP by Scheme (II) shown in FIG. 1C, the D-form optical isomer of the glutamic acid derivative represented by Formula IV (hereinafter, "D-glutamic acid derivative of Formula (IV)") and the D-form optical isomer of the glutamine derivative represented by Formula (V) (hereinafter, "D-glutamine derivative of Formula (V)") can be used as the amino acid derivatives for stapling. Commercially available products can be used for the D-glutamic acid derivative of Formula (IV). Furthermore, the D-glutamine derivative of Formula (V) can be synthesized by using N-α-(tert-butoxycarbonyl)-D-glutamic acid α methyl ester instead of N-α-(tert-butoxycarbonyl)-L-glutamic acid α methyl ester (Compound 3) in Scheme (IV) shown in FIG. 1A. Furthermore, a D-form stapled ERAP or sh stapled ERAP can be obtained by synthesizing a D-form peptide through standard Fmoc solid-phase peptide synthesis using D-amino acids by substituting the D-glutamic acid derivative of Formula (IV) and the D-glutamine derivative of Formula (V) for a pair of amino acid residues positioned where one wants to form a stapling structure in the amino acid sequence of SEQ ID NO: 9 or a partial sequence thereof, and performing an intramolecular amidation reaction according to Scheme (II). When synthesizing the retro-inverso forms of stapled ERAPs or sh stapled ERAPs, solid-phase peptide synthesis can be performed based on the reversed amino acid sequence of the amino acid sequence of SEQ ID NO: 9 or partial sequences thereof. In this case, substituting the D-glutamic acid derivative of Formula (IV) and the D-glutamine derivative of Formula (V) for a pair of amino acid residues positioned where one wants to form a stapling structure and then performing an intramolecular amidation reaction after synthesizing the peptide, are similar to what is described above.

Peptides of the present invention may also be in the form of salts. The form of salts is not particularly limited, but pharmaceutically acceptable salts are preferred. Herein, the "pharmaceutically acceptable salt" refers to a salt that retains the pharmacological and pharmaceutical efficacy and characteristics of a peptide. Preferred examples of salts include salts with alkali metals (lithium, potassium, sodium and such), salts with alkaline-earth metals (calcium, magnesium and such), salts with other metals (copper, iron, zinc, manganese and such), salts with organic bases, salts with amines, salts with organic acids (acetic acid, formic acid, propionic acid, fumaric acid, maleic acid, succinic acid, tartaric acid, citric acid, malic acid, oxalic acid, benzoic acid, methanesulfonic acid, and such), salts with inorganic acids (hydrochloric acid, phosphoric acid, hydrobromic acid, sulfuric acid, nitric acid and such), and such. These salts can be prepared according to known methods.

Pharmaceutical Compositions

Peptides or salts thereof of the present invention can be formulated as pharmaceutical compositions along with pharmaceutically acceptable carriers.

Peptides of the present invention have a binding ability to PHB2, and competitively inhibit the BIG3-PHB2 interaction. The formation of BIG3-PHB2 complex enhances estrogen-dependent transcriptional activity and induces proliferation of cancer cells. Therefore, peptides of the present invention which suppress the formation of BIG3-PHB2 complex by inhibiting the BIG3-PHB2 interaction are useful as pharmaceutical compositions for cancer therapy in particular.

Enhancement of estrogen-dependent transcriptional activity by the formation of BIG3-PHB2 complex takes place mainly in estrogen receptor-positive cells. Therefore, peptides of the present invention are useful as pharmaceutical compositions for therapy of estrogen receptor-positive cancer in particular. Examples of such estrogen receptor-positive cancer include breast cancer, endometrial cancer, ovarian cancer, prostate cancer (Nelles J L, et al., Expert Rev Endocrinol Metab. 2011 May; 6(3): 437-451), and lung cancer (particularly non-small-cell lung cancer) (Stabile L P, et al., Cancer Res. 2005 Feb. 15; 65(4): 1459-70; Marquez-Garban D C, et al., Steroids. 2007 February; 72(2): 135-43), but are not limited thereto. Cancers to which pharmaceutical compositions of the present invention are applied preferably express BIG3 and PHB2, and estrogen receptor-positive cancers generally express BIG3 and PHB2. Whether a cancer is estrogen receptor-positive can be confirmed by known methods such as ELISA or immunohistochemical staining.

Furthermore, peptides of the present invention have growth suppressive effects on tamoxifen-resistant estrogen receptor-positive cancers as well. Therefore, pharmaceutical compositions of the present invention may also be applied to tamoxifen-resistant estrogen receptor-positive cancers. An example of tamoxifen-resistant estrogen receptor-positive cancers to which pharmaceutical compositions of the present invention will be applied includes tamoxifen-resistant estrogen receptor-positive breast cancer. Therefore, an example of preferred subjects to whom a pharmaceutical composition of the present invention is to be administered includes patients with tamoxifen-refractory estrogen receptor-positive breast cancer.

On the other hand, as shown in Example 3, peptides of the present invention also have suppressive effects on estrogen-independent cancer cell growth. Therefore, peptides of the present invention are also useful as pharmaceutical compositions for therapy of estrogen receptor-negative cancers. Estrogen receptor-negative cancers to which pharmaceutical compositions of the present invention are applied are not particularly limited, but they must be cancers expressing BIG3 and PHB2. Examples of such cancers include estrogen receptor-negative breast cancer and prostate cancer.

Pharmaceutical compositions of the present invention can be produced using known drug formulation techniques by mixing a peptide or a salt thereof of the present invention with a pharmaceutically acceptable carrier. Herein, "pharmaceutically acceptable carrier" refers to an inactive substance to be used as diluents or solvents for drugs. For the pharmaceutically acceptable carriers to be used in pharmaceutical compositions of the present invention, carriers generally used for pharmaceutical products can be appropriately selected according to the dosage form of the pharmaceutical compositions to be prepared.

The dosage forms of the pharmaceutical compositions of the present invention are not particularly limited, and dosage forms generally used for pharmaceutical products such as liquids, tablets, elixirs, capsules, granules, and powders can be selected appropriately. Furthermore, depending on the selected dosage form, additives such as excipients, stabilizers, suspensions, preservatives, surfactants, solubilizing agents, pH adjusters, and aggregation inhibitors can be added appropriately.

Pharmaceutical compositions of the present invention contain a pharmaceutically effective amount of peptides or salts thereof of the present invention. The pharmaceutically effective amount can be selected appropriately according to the dosage form of the pharmaceutical compositions, dosage interval, age, gender, body weight, and body surface area of subjects for administration, type of disease, and such. Examples of the content of peptides or salts thereof of the present invention in pharmaceutical compositions of the present invention include 0.001 mg to 1000 mg, 0.01 mg to 100 mg, 0.1 mg to 30 mg, or 0.1 mg to 10 mg, but are not limited thereto.

Pharmaceutical compositions of the present invention may optionally include other pharmaceutical agents. Examples of other pharmaceutical agents include anti-inflammatory agents, analgesic agents, antipyretics, other therapeutic agents for cancer, and such. Other therapeutic agents for cancer that may be used for pharmaceutical compositions of the present invention are not particularly limited, but when the pharmaceutical compositions are used for estrogen-positive cancers, examples may include hormone therapy agents such as selective ERα modulators (e.g., tamoxifen and raloxifene), ERα down-regulators (e.g., fulvestrant), aromatase inhibitors, LH-RH agonist formulations, and progesterone formulations. These pharmaceutical agents may also be mixed in the form of prodrugs and pharmaceutically acceptable salts.

Pharmaceutical compositions of the present invention can be administered to a subject by appropriately selecting a suitable administration route depending on the dosage form. The administration route is not particularly limited, but examples include oral administration, intradermal, subcutaneous, intramuscular, intraosseous, peritoneal and intravenous injection, and such. Furthermore, while either systemic administration or local administration near the diseased site is possible, local administration is preferred.

Dosage interval of pharmaceutical compositions of the present invention may also be appropriately selected according to the age, gender, body weight, and body surface area of subjects for administration, the disease type and such, as well as the dosage form, administration route, and such of the pharmaceutical compositions of the present invention. Examples of the dosage interval include every day, every four days, and every seven days, but are not limited thereto.

Dosage of pharmaceutical compositions of the present invention may also be appropriately selected according to the age, gender, body weight, and body surface area of subjects for administration, the disease type and such, as well as the dosage form, administration route, and such of the pharmaceutical compositions of the present invention. Examples of the dosage of peptides or salts thereof of the present invention include, for example, 0.001 mg/kg/day to 1000 mg/kg/day, 0.005 mg/kg/day to 500 mg/kg/day, 0.01 mg/kg/day to 250 mg/kg/day, but are not limited thereto.

Pharmaceutical compositions of the present invention may be used in combination with other pharmaceuticals depending on the condition of the administration subjects. The pharmaceuticals used in combination are not particularly limited, but when the pharmaceutical compositions are used for estrogen receptor-positive cancers, examples may include hormone therapy agents such as selective ERα modulators (e.g., tamoxifen and raloxifene), ERα down-regulators (e.g., fulvestrant), aromatase inhibitors, LH-RH agonist formulations, and progesterone formulations. Among these hormone therapy agents, particularly preferred examples include tamoxifen and fulvestrant.

When pharmaceutical compositions of the present invention are used for cancer therapy, one may examine whether the cancer to be treated is accompanied by expression of BIG3 and PHB2 before administering the pharmaceutical compositions. Whether BIG3 and PHB2 are expressed in the cancer to be treated can be confirmed by detecting transcription products or translation products of these genes in the samples collected from the subjects. Known methods can be used for detection methods, and for example, methods of detecting transcription products using probes or PCR methods (for example, cDNA microarray method, Northern blotting, and RT-PCR) and methods of detecting translation products using antibodies and such (for example, Western blotting and immunostaining) may be used.

The present invention also provides articles of manufacture or kits that comprise a pharmaceutical composition of the present invention. The articles of manufacture or kits of the present invention can include a container that houses the pharmaceutical composition of the present invention. An example of an appropriate container includes a bottle, a vial or a test tube, but is not limited thereto. The container may be formed of various materials such as glass or plastic. A label may be attached to the container, and the disease or disease state to which the pharmaceutical composition of the present invention should be used may be described in the label. The label may also indicate directions for administration and such.

The articles of manufacture or kits of the present invention may further comprise a second container that houses pharmaceutically acceptable diluents optionally, in addition to the container that houses the pharmaceutical composition of the present invention. The articles of manufacture or kits of the present invention may further comprise the other materials desirable from a commercial standpoint and the user's perspective, such as the other buffers, diluents, filters, injection needles, syringes, and package inserts with instructions for use.

As needed, the pharmaceutical composition of the present invention can be provided in a pack or dispenser device that can contain one or more units of dosage forms containing active ingredients. The pack can include, for example, a metallic foil or a plastic foil such as a blister pack. Instructions for administration can be attached to the pack or dispenser device.

In another embodiment, the present invention provides the following use, methods, and such:

(a) use of a peptide or a salt thereof of the present invention in the production of a pharmaceutical composition for cancer therapy;

(b) a peptide or a salt thereof of the present invention for use in cancer therapy;

(c) a method or process for producing a pharmaceutical composition for cancer therapy, which comprises the step of formulating a peptide or a salt thereof of the present invention with a pharmaceutically acceptable carrier;

(d) a method or process for producing a pharmaceutical composition for cancer therapy, which comprises the step of mixing a peptide or a salt thereof of the present invention with a pharmaceutically acceptable carrier; and (e) a method for cancer therapy, which comprises administering a peptide or a salt thereof of the present invention to a subject.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

All prior art documents cited herein are incorporated by reference in the present specification.

EXAMPLES

[Example 1] Synthesis of Stapled Peptides

ERAP Peptide Synthesis

A dominant negative peptide (11R-ERAP; 11R-GGG-QMLSDLTLQLRQR (SEQ ID NO: 9)) designed to specifically inhibit the BIG3-PHB2 interaction was synthesized as described previously (T. Yoshimaru, et al., Nat. Commun. 4, 2443 (2013)). All chemicals used were of analytical grade. "11R" in 11R-ERAP refers to poly-arginine (poly-R) consisting of eleven arginine residues. "GGG" present between poly-R and SEQ ID NO: 9 is three glycine residues introduced as a linker between the two. 11R was introduced to confer cell permeability to ERAP (SEQ ID NO: 9).

Amino Acid Derivatives for Stapled Peptide Synthesis

The amino acid derivatives used for the olefin-bearing stapled peptide synthesis was synthesized based on the method described in Aihara et al. (Tetrahedron, 71, 4183-4191 (2015)). The amino acids serving as the source of the amino acid derivatives were purchased from Peptide Institute, Inc. (Osaka, Japan).

Among the two amino acid derivatives used for the synthesis of stapled peptides without olefin, the glutamic acid derivative (N-α-(9-fluorenylmethoxycarbonyl)-L-glutamic acid γ-allyl ester) was obtained from Watanabe Chemical Industries, LTD. (Hiroshima, Japan). On the other hand, the glutamine derivative ((S)-2-(((((9H-fluoren-9-yl)methoxy)carbonyl)amino)5-((4-(((allyloxy)carbonyl)amino)butyl) (2,4-dimethoxybenzyl)amino)-5-oxopentanoic acid) was synthesized according to the scheme shown in FIG. 1A.

Silicagel 60N (spherical, neutral, particle size 63-210 μm) (Kanto Chemical, Tokyo, Japan) was used for column chromatography. Mass spectra were recorded on Waters MICROMASSR LCT PREMIER™ (ESI-TOF). NMR spectra were measured using a JEOL GSX300 spectrometer. For HPLC separation, a Cosmosil $5C_{18}$-AR-II analytical column (4.6×250 mm, flow rate: 1 mL/min) (Nacalai Tesque, Kyoto, Japan) and a Cosmosil $5C_{18}$-AR-II semi-preparative column (10×250 mm, flow rate: 3.0 mL/min) (Nacalai Tesque) were used, and the eluate was detected by 220 nm ultraviolet. A 0.1% (v/v) aqueous TFA solution (solvent A) and a 0.1% (v/v) TFA solution in MeCN (solvent B) were used as HPLC solutions, and the analysis was performed for 30 minutes. Optical rotation was measured with a JASCO P2200 polarimeter.

Amino acid derivatives were synthesized as shown in FIG. 1A. First, 2,4-dimethoxybenzaldehyde (781 mg, 4.70 mmol), $MgSO_4$ (2.26 g, 18.8 mmol) and AcOH (26.9 mL, 0.47 mmol) were added to a solution of allyl (4-aminobutyl) carbamate (Compound 1; 810 mg, 4.7 mmol) (M. Hurevich, et. al., J. Pept. Sci. 16, 178-185 (2010)) in methanol (47 mL). The resulting mixture was stirred at room temperature for three hours, and then filtered to remove $MgSO_4$. The obtained reaction mixture was cooled to 0° C. and $NaBH_4$ (355 mg, 9.4 mmol) was added thereto. The obtained solution was warmed to room temperature and stirred for one hour. A container carrying the reaction mixture was cooled to 4° C. by soaking it in ice-water, and a 5% (w/v) aqueous $KHSO_4$ solution was added. The obtained solution was basified using a saturated aqueous $NaHCO_3$ solution, and the reaction mixture was extracted with ethyl acetate. The organic layer was washed with a saturated salt solution (brine), dried over $MgSO_4$, and then filtered. After concentration under reduced pressure, the residue was purified by column chromatography ($CHCl_3$/MeOH=30:1 (v/v)), and 1.32 g of Compound 2 (allyl [4-{(2,4-dimethoxybenzyl)amino}butyl]carbamate; 4.09 mmol, 87%) was obtained as a pale yellow oil;

$^1$H NMR ($CDCl_3$, 300 MHz) δ=1.42-1.58 (4H, m), 2.56 (2H, t, J=6.7 Hz), 3.15 (2H, dt, J=6.0 and 6.0 Hz), 3.67 (2H, s), 3.77 (3H, s), 3.78 (3H, s), 4.52 (2H, d, J=5.5 Hz), 5.17 (1H, ddt J=10.5 and 1.5, 1.5 Hz), 5.27 (1H, ddt J=17.3, 1.5 and 1.5 Hz), 5.35 (1H, br s), 5.89 (1H, ddt, J=17.3, 10.5 and 5.5 Hz), 6.40 (1H, dd, J=8.1 and 2.4 Hz), 6.43 (1H, d, J=2.4 Hz), 7.09 (1H, d, J=8.1 Hz); $^{13}$C NMR ($CDCl_3$, 75 MHz) δ=27.4, 27.9, 41.0, 48.6, 48.9, 55.3, 55.4, 65.4, 98.6, 103.7, 117.4, 120.9, 130.5, 133.2, 156.4, 158.6, 160.1; HRMS (ESI-TOF) m/z calcd for $C_{17}H_{27}N_2O_4$ ([M+H]$^+$): 323.1971, found: 323.1963.

Compound 2 (1.22 g, 3.78 mmol), 1-(3-dimethylaminopropyl)-3-ethylcarbodiimide hydrochloride (EDC-HCl) (798 mg, 4.16 mmol), and diisopropylethylamine (DIPEA) (978 mg, 7.57 mmol) were added to a solution of N-α-(t-butoxycarbonyl)-L-glutamic acid α methyl ester (Compound 3) (989 mg, 3.78 mmol) in 1,2-dichloroethane (18.9 mL) at 0° C., and the mixture was stirred at room temperature for five hours. After addition of 5% (w/v) aqueous $KHSO_4$ solution, the reaction mixture was extracted with ethyl acetate. The organic layer was washed with brine, dried over $Na_2SO_4$, filtered, and then concentrated under reduced pressure. The residue was purified by column chromatography (hexane/ethyl acetate=1:2 (v/v)), and 1.62 g of Compound 4 ((5)-methyl-5-{(4-[{(allyloxy)carbonyl}amino]butyl) (2,4-dimethoxybenzyl)amino}-2-{(tert-butoxycarbonyl)amino}-5-oxopentanoate; 2.86 mmol, 76%) was obtained as a pale yellow oil;

$[α]^{19}_D$-5.33 (c 1.24, MeOH); $^1$H NMR (DMSO-$d_6$, 300 MHz, 80° C.) δ=1.38 (9H, s), 1.27-1.53 (2H, m), 1.27-1.53 (2H, m), 1.46-1.92 (1H, m), 1.92-2.10 (1H, m), 2.42 (2H, dt, J=4.5 and 6.6 Hz), 2.97 (2H, dt, J=6.0 and 6.3 Hz), 3.19 (2H, br t, J=7.0 Hz), 3.62 (3H, s), 3.76 (3H, s), 3.80 (3H, s), 3.94-4.14 (1H, m), 4.39 (2H, br s), 4.46 (2H, ddd, J=5.5, 1.7 and 1.3 Hz), 5.16 (1H, ddt, J=10.4, 1.8 and 1.3 Hz), 5.26 (1H, ddt, J=17.2, 1.8 and 1.7 Hz), 5.90 (1H, ddt, J=17.2, 10.4 and 5.5 Hz), 6.39-6.53 (1H, br m), 6.53-6.63 (1H, br m), 6.70-6.92 (2H, br m), 6.96 (1H, br d, 7.9 Hz); $^{13}$C NMR (DMSO-$d_6$, 75 MHz, 80° C.) δ=24.0, 25.2, 26.4, 26.5, 27.8, 28.3, 41.6, 44.4, 45.3, 46.1, 51.1, 53.1, 54.9, 55.1, 63.7, 77.9, 78.7, 98.4, 104.7, 116.3, 117.0, 128.0, 128.8, 133.5, 154.9, 155.5, 157.8, 159.5, 159.8, 171.0, 172.4; HRMS (ESI-TOF) m/z calcd for $C_{28}H_{43}N_3NaO_9$ ([M+Na]$^+$): 588.2897, found: 588.2902.

To a solution of Compound 4 in THF (5 mL), LiOH·$H_2O$ (91.8 mg, 2.18 mmol), methanol (2.5 mL), and $H_2O$ (2 mL) were added at 0° C., and the reaction mixture was stirred for two hours. A 5% (w/v) aqueous $KHSO_4$ solution was added to stop the reaction, and the reaction mixture was extracted with ethyl acetate. The organic layer was washed with brine, dried over $Na_2SO_4$, filtered, and then concentrated under reduced pressure. The residue was purified by column chromatography ($CHCl_3$/MeOH=50:1-10:1 (v/v), containing 0.1% (v/v) AcOH), and 747 mg of Compound 5 ((S)-5-{(4-[{(allyloxy)carbonyl}amino]butyl) (2,4-dimethoxybenzyl)amino}-2-{(tert-butoxycarbonyl)amino}-5-oxopentanoic acid; 1.35 mmol, 92%) was obtained as a white powder;

$[\alpha]^{18}{}_D$-0.65 (c 0.950, MeOH); $^1$H NMR (DMSO-$d_6$, 300 MHz, 80° C.) δ=1.39 (9H, s), 1.27-1.53 (2H, m), 1.27-1.53 (2H, m), 1.76-1.94 (1H, m), 1.94-2.13 (1H, m), 2.44 (2H, dt, J=7.5 and 4.2 Hz), 2.99 (2H, dt, J=6.3 and 6.1 Hz), 3.20 (2H, br t, J=7.1 Hz), 3.76 (3H, s), 3.80 (3H, s), 3.89-4.08 (1H, m), 4.41 (2H, br s), 4.47 (2H, ddd, J=5.4, 1.5 and 1.5 Hz), 5.16 (1H, ddt, J=10.5, 1.7 and 1.5 Hz), 5.26 (1H, ddt, J=17.4, 1.7 and 1.5 Hz), 5.90 (1H, ddt, J=17.4, 10.5 and 5.4 Hz), 6.38-6.53 (1H, br m), 6.56 (1H, br s), 6.66 (1H, br s), 6.78 (1H, br s), 6.98 (1H, br d, J=8.1 Hz); $^{13}$C NMR (d-DMSO, 75 MHz, 80° C.) δ=24.2, 25.3, 26.6, 26.7, 27.9, 28.6, 39.9, 41.8, 44.4, 45.4, 46.3, 53.1, 55.0, 55.2, 63.8, 77.8, 98.5, 104.8, 116.3, 117.1, 117.8, 128.1, 128.8, 133.5, 155.1, 155.6, 157.9, 159.6, 159.9, 171.3, 173.3; HRMS (ESI-TOF) m/z calcd for $C_{27}H_{41}N_3NaO_9$ ([M+Na]$^+$): 574.2741, found: 574.2740.

To a solution of Compound 5 (621 mg, 1.13 mmol) in $CH_2Cl_2$ (11.3 mL), tert-butyldimethylsilyl trifluoromethanesulfonic acid (TBSOTf) (1.04 µL, 4.5 mmol) and 2,6-lutidine (787 µL, 6.75 mmol) at 0° C. were added. The reaction mixture was slowly warmed to room temperature and stirred for four hours. The reaction solution was concentrated under reduced pressure, and then diluted with THF (8 mL). The diluted solution was neutralized using a 2M aqueous NaOH solution (2 mL) at 0° C., and then a 10% (w/v) aqueous solution of $Na_2CO_3$ (8 mL) and Fmoc-OSu (572 mg, 1.7 mmol) were added. After stirring at room temperature for 12 hours, the reaction mixture was acidified using a 1 M aqueous HCl solution and then extracted with ethyl acetate. The organic layer was washed with brine, dried over $Na_2SO_4$, filtered, and then concentrated under reduced pressure. The residue was purified by column chromatography ($CHCl_3$/MeOH=50:1-10:1 (v/v), containing 0.1% (v/v) AcOH), and 680 mg of Compound 6 ((S)-2-((((9H-fluoren-9-yl)methoxy)carbonyl)amino)5-((4-(((allyloxy)carbonyl)amino)butyl) (2,4-dimethoxybenzyl)amino)-5-oxopentanoic acid; 1.01 mmol, 90%) was obtained as a white powder;

$^1$H NMR (DMSO-$d_6$, 300 MHz, 80° C.) δ=1.29-1.61 (4H, m), 1.87-2.02 (1H, m), 2.03-2.21 (1H, m), 2.45-2.56 (2H, m), 3.00 (2H, dt, J=6.0 and 6.4 Hz), 3.23 (2H, br t, J=6.6 Hz), 3.74 (3H, s), 3.79 (3H, s), 4.05-4.18 (1H, m), 4.22 (1H, t, J=6.6 Hz), 4.31 (2H, d, J=6.6 Hz), 4.43 (1H, br s), 4.48 (2H, ddd, J=5.7, 1.7 and 1.5 Hz), 5.12 (1H, ddt, J=10.2, 1.7 and 1.5 Hz), 5.27 (1H, ddt, J=17.1, 1.7 and 1.7 Hz), 5.91 (1H, ddt, J=17.1, 10.2 and 5.7 Hz), 6.42-6.52 (1H, br m), 6.56 (1H, d, J=2.1 Hz), 6.80 (1H, br s), 6.91-7.10 (1H, br m), 7.31 (2H, t, J=7.5 Hz), 7.40 (2H, t, J=7.2 Hz), 7.70 (2H, br d, J=7.2 Hz), 7.85 (2H, d, J=7.5 Hz); $^{13}$C NMR (DMSO-$d_6$, 75 MHz, 80° C.) δ=24.2, 25.3, 26.6, 28.9, 39.9, 41.8, 44.3, 45.3, 46.6, 53.4, 54.9, 55.1, 63.8, 65.6, 98.4, 104.7, 108.6, 116.3, 117.0, 117.7, 119.6, 120.9, 124.8, 126.6, 126.6, 126.8, 127.2, 128.2, 128.5, 128.9, 133.5, 139.2, 140.4, 140.4, 143.6, 143.6, 155.6, 155.6, 157.8, 159.6, 159.9, 171.2, 173.1; HRMS (ESI-TOF) m/z calcd for $C_{37}H_{43}N_3NaO_9$ ([M+Na]$^+$): 696.2897, found: 696.2928.

Stapled ERAP Synthesis

Peptides were synthesized on a Rink Amide AM resin (0.62 mmol amine/g) using standard Fmoc solid-phase peptide synthesis. Cleavage of the Fmoc group was carried out using a solution of 20% (v/v) piperidine in DMF at room temperature for ten minutes. The resins were washed with DMF, the Fmoc-protected amino acids (Fmoc-Xaa-OH) were coupled using N,N-diisopropylcarbodiimide (DIPCDI) and 1-hydroxy-1H-benzotriazole hydrate (HOBt.$H_2O$) in DMF at room temperature for two hours, followed by washing with DMF.

Synthesis of olefin-bearing stapled peptides was carried out as shown in FIG. 1B by ring closing metathesis. After constructing the protected peptide, the N-terminal Fmoc group was cleaved, and for acetylation of the N-terminal amino group, the obtained resin was treated with an acetic anhydride solution and pyridine in DMF at room temperature for 30 minutes. The N-terminal acetylated peptide on the solid-phase carrier was treated with a 40 mM Hoveyda-Grubbs' second-generation catalyst solution in degassed o-dichlorobenzene at 80° C. for ten minutes. After peptide cleavage from the resin, the reaction was monitored by HPLC. Deprotection of the acid-labile protecting group which accompanies peptide release from the resins was performed using a cocktail of TFA/m-cresol/thioanisole/1,2-ethanedithiol/$H_2O$ (90:2.5:2.5:2.5:2.5 (v/v), 50 µL/1 mg resin) at room temperature for 90 minutes. The resin-bound peptides were washed with dichloromethane and dried under reduced pressure, and then the peptides were cleaved from the resin, purified using semi-preparative HPLC, and then freeze-dried.

Synthesis of stapled peptides without olefin was performed via intramolecular amidation as shown in FIG. 1C. The resin-bound N-terminal capped peptides were mixed with a solution of 20 mM (Pd(PPh$_3$)$_4$ in $CHCl_3$/AcOH/N-methylmorpholine (92.5:5:2.5 (v/v)), and the mixture was shaken at room temperature for two hours. Then, the resin was washed with $CH_2Cl_2$ and dried. Next, DIPCDI and HOBt.$H_2O$ were used for coupling at room temperature for two hours, followed by washing with DMF to perform intramolecular amidation. Peptide cleavage from the resin was carried out according to the above-mentioned standard Fmoc solid-phase peptide synthesis protocol. Specifically, deprotection of acid-labile protecting groups which accompanies peptide release from the resin was performed using a cocktail of TFA/m-cresol/thioanisole/1,2-ethanedithiol/$H_2O$ (90:2.5:2.5:2.5:2.5 (v/v), 50 µL/1 mg resin) at room temperature for 90 minutes. The resin-bound peptides were washed with dichloromethane and dried under reduced pressure, and then the peptides were cleaved from the resin, purified using semi-preparative HPLC, and then freeze-dried.

[Example 2] Effects of Stapled ERAP on E2-Dependent Breast Cancer Cells

Materials and Methods

Cell Lines and Culturing Conditions

Human breast cancer cell line MCF-7 and mammary epithelial cell line MCF-10A were purchased from American Type Culture Collection (ATCC, Manassas, Va., USA). Breast cancer cell line KPL-3C (J. Kurebayashi, et al., Br. J. Cancer 74, 200-207 (1996)) was kindly provided by Dr. Junichi Kurebayashi (Kawasaki Medical School). All cell lines were monolayer cultured in an appropriate medium supplemented with 10% FBS. The cells were maintained at 37° C. under humidified atmosphere containing 5% $CO_2$.

In each experiment, the respective cells were seeded in a 48-well plate ($2 \times 10^4$ cells/mL), a 6-well plate ($3 \times 10^5$ cells/mL), or a 10-cm dish ($2 \times 10^6$ cells/10 mL). MCF-7 cells were seeded in MEM (Thermo Fisher Scientific) supplemented with 10% FBS (Nichirei Biosciences Inc., Tokyo, Japan), 1% Antibiotic/Antimycotic solution (Thermo Fisher Scientific, Waltham, Mass., USA), 0.1 mM NEAA (Thermo Fisher Scientific), 1 mM sodium pyruvate (Thermo Fisher Scientific), and 10 µg/mL insulin (Sigma, St. Louis, Mo., USA). KPL-3C cells were seeded in RPMI (Thermo Fisher Scientific) supplemented with 10% FBS and 1% Antibiotic/Antimycotic solution. MCF-10A cells were seeded in MEBM (Lonza) supplemented with a Single Quots kit (BPE, hydrocortisone, hEGF, insulin, gentamycin/amphoterin-B) (Lonza, Walkersville, Md., USA) and 100 ng/mL cholera toxin. For 17β-estradiol (E2) (Sigma) stimulation, the media for MCF-7 and KPL-3C were changed to phenol red-free DMEM/F12 (Thermo Fisher Scientific) supplemented with 10% FBS, 1% Antibiotic/Antimycotic solution, 0.1 mM NEAA, 1 mM sodium pyruvate, and 10 µg/mL insulin on the day after seeding. Twenty-four hours later, the cells were treated with 10 nM E2 and a peptide (for example, 11R-ERAP or a stapled ERAP), or with 10 nM E2 alone.

When carrying out treatment with tamoxifen (Sigma) or fulvestrant (LKT laboratories, St. Paul, Minn., USA), cells were treated with 10 nM tamoxifen or 2 µM fulvestrant simultaneously with the above-mentioned treatment with E2 and a peptide or with E2 alone.

Cell Growth Assay

Cell growth assays on MCF-7, KPL-3C, and MCF-10A were carried out as described previously using a Cell Counting Kit-8 (CCK-8) (Dojindo, Kumamoto, Japan) (T. Yoshimaru, et al., Nat. Commun. 4, 2443 (2013)). The data are shown by mean±SE of three independent experiments.

Circular Dichroism (CD) Spectra Measurement

CD spectrum in the range of 185 nm to 265 nm was recorded at 25° C. using a quartz cuvette having an optical path length of 2 mm (circular dichroism spectrometer J1500: JASCO Corporation, Tokyo, Japan). Peptide concentration was set to 50 µg/mL in 10 mM sodium phosphate buffer (pH 7.0). Molar ellipticity (θ) was calculated according to the literature (T. Wieprecht, et al., Biophys. Chem. 96, 191-201 (2002)).

Antibody and Immunoblot Analyses

Immunoblot analyses were performed as described previously (T. Yoshimaru, et al., Nat. Commun. 4, 2443 (2013)). After performing SDS-PAGE, the membranes blotted with proteins were blocked with 4% BlockAce solution (Dainippon Pharmaceutical, Osaka, Japan) for three hours and then incubated with antibodies against the following proteins: BIG3 (1:1,000) (T. Yoshimaru, et al., Nat. Commun. 4, 2443 (2013)); PHB2 (1:1,000) (Abeam, Cambridge, UK); Akt, phosphorylated Akt (S473) (587F11, 1:1,000); p44/42 MAPK, phosphorylated p44/42 MAPK (T202/Y204) (1:1,000); α/β-tubulin (1:1,000) (Cell Signaling Technology, Danvers, Mass., USA); and LMNB1 (1:100) (Sigma). After incubation with an HRP-labeled secondary antibody (anti-mouse IgG-HRP, 1:5,000; anti-rat IgG-HRP; 1:5,000; or anti-rabbit IgG-HRP, 1:1,000) (Santa Cruz Biotechnology, Dallas, Tex., USA) for one hour, the blots were developed with an Enhanced Chemiluminescence (ECL) system (GE Healthcare, Buckinghamshire, UK) and scanned using an Image Reader LAS-3000 mini (Fujifilm, Tokyo, Japan). All the experiments were performed at least in triplicate.

Immunoprecipitation

Immunoprecipitation analysis was performed as described previously (T. Yoshimaru, et al., Nat. Commun. 4, 2443 (2013)). Cell lysates were pre-cleared with normal IgG and rec-Protein G Sepharose 4B (Thermo Fisher Scientific) at 4° C. for three hours. Then, the supernatants were incubated with 5 µg of an antibody against BIG3 or an antibody against PHB2 at 4° C. for twelve hours. Next, the antigen-antibody complexes were precipitated using rec-Protein G Sepharose 4B at 4° C. for one hour. The immunoprecipitated protein complexes were washed several times with a lysis buffer. Then, SDS-PAGE and immunoblot analyses were carried out as described above.

Nuclear/Cytoplasmic Fractionation

The nuclear and cytoplasmic fractionation of MCF-7 cells was carried out as described previously using NE-PER nuclear and cytoplasmic extraction reagent (Thermo Fisher Scientific) (T. Yoshimaru, et al., Nat. Commun. 4, 2443 (2013)). α/β-tubulin and lamin B were used as loading controls for the cytoplasmic fraction and the nuclear fraction, respectively.

Immunocytological Staining of PHB2 and HA-Tagged Stapled ERAP

MCF-7 cells were seeded at $5 \times 10^4$ cells/well in 8-well chambers (Laboratory-Tek II Chamber Slide System) (Nalgene, Nunc International) and then incubated for 48 hours. Then, the cells were treated with E2 and HA-tagged stapled ERAP or with E2 alone for 24 hours. The staining procedures were conducted as described previously (T. Yoshimaru, et al., Nat. Commun. 4, 2443 (2013)).

Real-Time RT-PCR

The expression of the ERα target genes (TFF1 and CCND1) was evaluated by real-time RT-PCR as described previously (T. Yoshimaru, et al., Nat. Commun. 4, 2443 (2013)). Each sample was normalized to the β2-MG mRNA content, and the results were expressed as multiples (-fold) of the expression level in untreated cells, with that level being defined as 1.0. The data represent the mean±SD of three independent experiments. The primers used for RT-PCR were as follows:

```
TFF1
                                    (SEQ ID NO: 17)
5'-GGCCTCCTTAGGCAAATGTT-3'
and
                                    (SEQ ID NO: 18)
5'-CCTCCTCTCTGCTCCAAAGG-3';

CCND1
                                    (SEQ ID NO: 19)
5'-CAGAAGTGCGAGGAGGAGGT-3'
and
                                    (SEQ ID NO: 20)
5'-CGGATGGAGTTGTCGGTGT-3';

β2-MG
                                    (SEQ ID NO: 21)
5'-AACTTAGAGGTGGGGAGCAG-3'
and
                                    (SEQ ID NO: 22)
5'-CACAACCATGCCTTACTTTATC-3'.
```

In Vivo Tumor Growth Inhibition

KPL-3C cell suspensions ($1 \times 10^7$ cells/mouse) were mixed with an equal volume of Matrigel (BD) and injected (200 µL in total) into the mammary fat pads of 6-week-old female BALB/c nude mice (Charles River Laboratories, Tokyo, Japan). The mice were housed in a pathogen-free isolation facility with a twelve-hour light/dark cycle and were fed solid rodent chow and water ad libitum. The tumors developed over several days and reached sizes of approximately 100 mm³ [calculated as ½×(width×length²)]. The mice were randomized into the following eleven treatment groups (five heads per group):

1) untreated;
2) E2 (6 µg/day, every day: same hereinafter);
3) E2+1.4 mg/kg/day 11R-ERAP every day;
4) E2+1.4 mg/kg/day 11R-ERAP every four days;

5) E2+14 mg/kg/day 11R-ERAP every day;
6) E2+14 mg/kg/day 11R-ERAP every four days;
7) E2+1.4 mg/kg/day stapled ERAP No. 12 every day;
8) E2+1.4 mg/kg/day stapled ERAP No. 12 every four days;
9) E2+14 mg/kg/day stapled ERAP No. 12 every day;
10) E2+14 mg/kg/day stapled ERAP No. 12 every four days;
11) E2+14 mg/kg/day HA-tagged stapled ERAP No. 12 every day; and
12) E2+14 mg/kg/day HA-tagged stapled ERAP No. 12 every four days.

E2 was administered via application of a solution to the neck skin, and regarding the other treatments, administration was performed via intraperitoneal injection unless other administration methods are stated. The tumor volume was measured with calipers for 28 days, and then the mice were subjected to scheduled sacrifice to remove tumors. All the experiments were performed in accordance with the guidelines of the animal facility at Tokushima University.

Microarray Analysis

Total RNA was purified using a NucleoSpin RNA II system (Takara-Clontech, Japan) according to the manufacturer's instructions. RNA amplification and labeling were performed using an Agilent Low-Input QuickAmp labeling kit (Agilent Technologies, Palo Alto, Calif., USA) according to the manufacturer's instructions. Briefly, 100 ng of total RNA from each sample was amplified using T7 RNA polymerase, with Cy3-labeled CTP being incorporated. Then, 600 ng of Cy3-labeled cRNA was fragmented, hybridized on Agilent Whole Human Genome Microarray 8×60K slides (Agilent Technologies), and incubated at 65° C. for 18 hours while rotating. Then, the slides were washed and scanned using an Agilent Microarray scanner system in an ozone protection fume hood. The scanned image files were extracted using an Agilent Feature Extraction (version 9.5) (Agilent Technologies). The data were analyzed using Gene-Spring (version 13.0). The microarray data across all chips and genes were normalized by quantile normalization, and the baseline was transformed to signal values relative to the median of all samples. Finally, quality control and filtering steps based on the expression level were carried out. To identify genes with significantly altered expression levels, the signal intensity values among each of the analyses were compared.

Statistical Analysis

Student's t-tests were used to determine the significant differences among the experimental groups. P<0.05 was considered statistically significant.

Results

Effects of Olefin-Bearing Stapled ERAP

The present inventors previously designed ERAP which is a dominant negative peptide targeting the BIG3-PHB2 interaction (T. Yoshimaru, et al., Nat. Commun. 4, 2443 (2013)). To improve both biological and biophysical properties such as long-term stability and functions of inhibiting the BIG3-PHB2 interaction, ERAP was chemically modified. As shown in FIG. 2A, a series of stapled ERAPs having a stapling structure at different positions was prepared. Then, the prepared stapled ERAPs were screened for their cell growth inhibitory activities. While stapled ERAP Nos. 1, 7, and 8 were not synthesized, other stapled ERAPs (Nos. 2 to 6) were synthesized.

In human breast cancer cell line MCF-7 (ERα-positive, BIG3-positive, and PHB2-positive), stapled ERAP Nos. 2, 3, 4, and 6 significantly reduced E2-dependent cell growth compared to 11R-ERAP ($IC_{50}$=7.97 μM) in a dose-dependent manner ($IC_{50}$=0.89 μM, 1.02 μM, 0.81 μM, and 0.68 μM, respectively) at 96 hours after the treatment with the peptides and E2 (FIG. 2B and FIG. 2D). On the other hand, stapled ERAP No. 5 showed slightly superior inhibition of E2-dependent cell growth compared to 11R-ERAP at 96 hours after the treatment ($IC_{50}$=7.89 μM) (FIG. 2B and FIG. 2D). In particular, the treatment with stapled ERAP No. 2 or 3 did not show significant effects on cell growth of normal mammary epithelial cell line MCF-10A (ERα-negative and BIG3-negative) (FIGS. 2C to E). On the other hand, the possibility that the treatment with stapled ERAP No. 4, 5, or 6 exhibited non-specific inhibitory effects on MCF-10A cell growth (FIGS. 2C to E) was suggested.

To clarify these non-specific inhibitory effects, MCF-10A cells treated with stapled ERAP No. 3 or 6 were used for DNA microarray analyses of the gene expression profiles at 24 hours and 48 hours after the treatment. Analyses of gene expression profiles using the cells at 48 hours after the treatment identified 93 and 191 transcripts that were up-regulated and down-regulated, respectively, by 100-fold or more in the cells treated with stapled ERAP No. 6 compared with the cells treated with stapled ERAP No. 3 (upper panel of FIG. 2F, Table 2).

On the other hand, only four genes were differentially expressed between stapled ERAP No. 3-treated and stapled ERAP No. 6-treated cells at 24 hours after the treatment (upper panel of FIG. 2F, Table 1). Gene annotation enrichment analysis of the 284 genes described above, which were differentially expressed between stapled ERAP No. 3-treated and stapled ERAP No. 6-treated cells at 48 hours after the treatment, using the DAVID algorithm and GeneMANIA software, identified many of a subset of extracellular matrix-associated genes (lower panel of FIG. 2F (cont.), ). This suggests that stapled ERAP Nos. 4, 5, and 6 have potential off-target effects on extracellular matrix pathways in normal mammary epithelial cells.

TABLE 1

Genes up-regulated or down-regulated by 100-fold or more in stapled ERAP No. 6-treated cells compared with stapled ERAP No. 3-treated cells, at 24 hours after the treatment

| Fold | | Gene Symbol | Gene Name |
|---|---|---|---|
| 81880 | down | TDRD6 | tudor domain containing 6 |
| 4199 | up | psiTPTE22 | TPTE pseudogene |
| 409 | down | ARL4A | ADP-ribosylation factor-like 4A |
| 137 | up | ZNF491 | zinc finger protein 491 |

TABLE 2

Genes up-regulated or down-regulated by 100-fold or more in stapled ERAP No. 6-treated cells compared with stapled ERAP No. 3-treated cells, at 48 hours after the treatment

| Fold | | Gene Symbol | Gene Name |
|---|---|---|---|
| 3325 | up | UCHL1 | ubiquitin carboxyl-terminal esterase L1 (ubiquitin thiolesterase) |
| 1710 | up | KIF1A | kinesin family member 1A |

TABLE 2-continued

Genes up-regulated or down-regulated by 100-fold or more in stapled ERAP No. 6-treated cells compared with stapled ERAP No. 3-treated cells, at 48 hours after the treatment

| Fold | | Gene Symbol | Gene Name |
|---|---|---|---|
| 1429 | down | CSF3 | colony stimulating factor 3 (granulocyte) |
| 1366 | down | TACSTD2 | tumor-associated calcium signal transducer 2 |
| 1317 | down | CADM3 | cell adhesion molecule 3 |
| 1282 | down | ARHGDIB | Rho GDP dissociation inhibitor (GDI) beta |
| 1213 | down | HSPA1A | heat shock 70 kDa protein 1A |
| 1197 | down | AKR1C1 | aldo-keto reductase family 1, member C1 (dihydrodiol dehydrogenase 1; 20-alpha (3-alpha)-hydroxysteroid dehydrogenase) |
| 1184 | down | KRT6A | keratin 6A |
| 1161 | up | BEX2 | brain expressed X-linked 2 |
| 1117 | down | OCIAD2 | OCIA domain containing 2 |
| 1102 | down | DCN | decorin |
| 1085 | up | GAL | galanin |
| 1085 | up | GSTM3 | glutathione S-transferase mu 3 |
| 1030 | down | MGP | matrix Gla protein |
| 921 | down | FN1 | fibronectin 1 |
| 917 | down | KRT5 | keratin 5 |
| 880 | down | MGMT | O-6-methylguanine-DNA methyltransferase |
| 879 | up | G0S2 | G0/G1 switch 2 |
| 835 | down | MT1M | metallothionein 1M |
| 812 | up | SNAR-D | steroidogenic acute regulatory protein |
| 811 | up | AMOT | fangiomotin |
| 810 | down | MLH1 | mutL homolog 1, colon cancer, nonpolyposis type 2 (*E. coli*) |
| 782 | down | NALCN | sodium leak channel, non-selective |
| 782 | down | SLC16A3 | solute carrier family 16, member 3 (monocarboxylic acid transporter 4) |
| 748 | down | SAA1 | serum amyloid A1 |
| 717 | down | S100A16 | S100 calcium binding protein A16 |
| 716 | down | C10orf116 | chromosome 10 open reading frame 116 |
| 714 | down | NNMT | nicotinamide N-methyltransferase |
| 690 | down | SAA2 | serum amyloid A2 |
| 689 | down | AOX1 | aldehyde oxidase 1 |
| 686 | down | GGT5 | gamma-glutamyltransferase 5 |
| 686 | up | BEX1 | brain expressed gene 1 |
| 681 | down | SPTLC3 | serine palmitoyltransferase, long chain base subunit 3 |
| 679 | down | CASP1 | caspase 1, apoptosis-related cysteine peptidase (interleukin 1, beta, convertase) |
| 674 | up | SNAR-G2 | small ILF3/NF90-associated RNA G2 |
| 668 | up | SNAR-F | small ILF3/NF90-associated RNA E A |
| 668 | down | PTGFR | prostaglandin F receptor (FP) |
| 666 | down | CASP4 | caspase 4, apoptosis-related cysteine peptidase |
| 660 | down | ANPEP | alanyl (membrane) aminopeptidase |
| 621 | down | CXCL1 | chemokine (C-X-C motif) ligand 1 (melanoma growth stimulating activity, alpha) |
| 609 | up | ARMCX6 | armadillo repeat containing, X-linked 6 |
| 600 | down | C3 | complement component 3 |
| 590 | up | NEFM | neurofilament, medium polypeptide |
| 586 | up | DPYSL5 | dihydropyrimidinase like 5 |
| 584 | down | S100A6 | S100 calcium binding protein A6 |
| 583 | down | TM4SF1 | transmembrane 4 L six family member 1 |
| 583 | down | IRX1 | iroquois homeobox 1 |
| 582 | down | AKR1C3 | aldo-keto reductase family 1, member C3 (3-alpha hydroxysteroid dehydrogenase, type II) |
| 576 | down | GPR110 | G protein-coupled receptor 110 |
| 563 | down | PPL | periplakin |
| 559 | down | MT1E | metallothionein 1E |
| 543 | up | IGF2BP1 | insulin like growth factor 2 mRNA binding protein 1 |
| 543 | down | CD44 | CD44 molecule (Indian blood group) |
| 541 | down | IPW | imprinted in Prader-Willi syndrome (non-protein coding) |
| 538 | down | KRT14 | keratin 14 |
| 535 | up | SNAR-G1 | small ILF3/NF90-associated RNA G1 |
| 535 | up | LONRF2 | LON peptidase N-terminal domain and ring finger 2 |
| 531 | down | JPH2 | junctophilin 2 |
| 526 | down | SERPINB5 | serpin peptidase inhibitor, clade B (ovalbumin), member 5 |
| 526 | up | SNAR-H | small ILF3/NF90-associated RNA E |
| 496 | down | ZG16B | zymogen granule protein 16 homolog B (rat) |
| 485 | up | BCAT1 | branched chain amino-acid transaminase 1, cytosolic |
| 485 | down | PSMB8 | proteasome (prosome, macropain) subunit, beta type, 8 (large multifunctional peptidase 7) |
| 484 | down | SNRPN | small nuclear ribonucleoprotein polypeptide N |
| 476 | down | C19orf33 | chromosome 19 open reading frame 33 |
| 471 | down | ROS1 | c-ros oncogene 1, receptor tyrosine kinase |
| 469 | up | RADIL | Ras association and DIL domains |
| 465 | down | MAL2 | mal, T-cell differentiation protein 2 (gene/pseudogene) |
| 464 | down | DARC | Duffy blood group, chemokine receptor |
| 462 | down | TGFBI | transforming growth factor, beta-induced, 68 kDa |
| 460 | down | S100A3 | S100 calcium binding protein A3 |
| 457 | down | COL12A1 | collagen, type XII, alpha 1 |
| 449 | down | COL8A1 | collagen, type VIII, alpha 1 |

TABLE 2-continued

Genes up-regulated or down-regulated by 100-fold or more in stapled ERAP No. 6-treated cells compared with stapled ERAP No. 3-treated cells, at 48 hours after the treatment

| Fold | | Gene Symbol | Gene Name |
|---|---|---|---|
| 445 | down | AREG | amphiregulin |
| 444 | down | DUSP23 | dual specificity phosphatase 23 |
| 443 | down | ABCC3 | ATP-binding cassette, sub-family C (CFTR/MRP), member 3 |
| 434 | down | CDH13 | cadherin 13, H-cadherin (heart) |
| 434 | up | HOXD13 | homeobox D13 |
| 426 | down | EMP1 | epithelial membrane protein 1 |
| 418 | up | CALCA | calcitonin-related polypeptide alpha |
| 417 | down | SPOCK1 | sparc/osteonectin, cwcv and kazal-like domains proteoglycan (testican) 1 |
| 416 | up | PCDH8 | protocadherin 8 |
| 415 | down | PRKCDBP | protein kinase C, delta binding protein |
| 414 | down | KCNK2 | potassium channel, subfamily K, member 2 |
| 406 | down | LAMB3 | laminin, beta 3 |
| 398 | down | PLEKHA6 | pleckstrin homology domain containing, family A member 6 |
| 398 | down | KCNN4 | potassium intermediate/small conductance calcium-activated channel, subfamily N, member 4 |
| 395 | down | SLC43A3 | solute carrier family 43, member 3 |
| 392 | down | TSTD1 | thiosulfate sulfurtransferase (rhodanese)-like domain containing 1 |
| 389 | up | C3orf14 | chromosome 3 open reading frame 14 |
| 372 | up | NEFL | neurofilament, light polypeptide |
| 371 | up | FAM101B | family with sequence similarity 101, member B |
| 367 | down | SLPI | secretory leukocyte peptidase inhibitor |
| 360 | up | NID1 | nidogen 1 |
| 358 | down | CCL2 | chemokine (C-C motif) ligand 2 |
| 357 | up | CADM1 | cell adhesion molecule 1 |
| 348 | up | ANKRD19P | ankyrin repeat domain 19, pseudogene |
| 345 | up | NPTX1 | euronal pentraxin I |
| 343 | down | FMO3 | flavin containing monooxygenase 3 |
| 341 | up | IGDCC3 | immunoglobulin superfamily, DCC subclass, member 3 |
| 337 | down | MLKL | mixed lineage kinase domain-like |
| 326 | down | MYOF | myoferlin |
| 324 | up | C11orf96 | chromosome 11 open reading frame 96 |
| 315 | up | SULT4A1 | sulfotransferase family 4A member 1 |
| 314 | down | FAP | fibroblast activation protein, alpha |
| 314 | down | TNS4 | tensin 4 |
| 309 | up | SNAR-A3 | small ILF3/NF90-associated RNA A3 |
| 308 | down | BIRC3 | baculoviral IAP repeat containing 3 |
| 307 | down | EMR2 | egf-like module containing, mucin-like, hormone receptor-like 2 |
| 303 | down | ADH1C | alcohol dehydrogenase 1C (class I), gamma polypeptide |
| 300 | down | S100A2 | S100 calcium binding protein A2 |
| 299 | up | PRDM13 | PR domain containing 13 |
| 296 | down | ITGB4 | integrin, beta 4 |
| 290 | down | PKP3 | plakophilin 3 |
| 289 | down | DKK1 | dickkopf 1 homolog (*Xenopus laevis*) |
| 275 | down | ITGA10 | integrin, alpha 10 |
| 271 | up | DACH1 | dachshund family transcription factor 1 |
| 271 | up | FOXG1 | forkhead box G1 |
| 270 | down | LGALS1 | lectin, galactoside-binding, soluble, 1 |
| 268 | down | IFI44 | interferon-induced protein 44 |
| 262 | down | PLP2 | proteolipid protein 2 (colonic epithelium-enriched) |
| 254 | down | GSTT2 | glutathione S-transferase theta 2 |
| 250 | down | CDCP1 | CUB domain containing protein 1 |
| 250 | down | CALHM2 | calcium homeostasis modulator 2 |
| 249 | down | DNAJC15 | DnaJ (Hsp40) homolog, subfamily C, member 15 |
| 247 | up | CA2 | carbonic anhydrase II |
| 247 | down | HSD11B1 | hydroxysteroid (11-beta) dehydrogenase 1 |
| 246 | down | AKR1CL1 | aldo-keto reductase family 1, member C-like 1 |
| 245 | down | CSRP1 | cysteine and glycine-rich protein 1 |
| 244 | down | RAET1E | retinoic acid early transcript 1E |
| 240 | down | MIR100HG | mir-100-let-7a-2 cluster host gene (non-protein coding) |
| 240 | up | MTAP | methylthioadenosine phosphorylase |
| 235 | up | C7orf29 | chromosome 7 open reading frame, humanC7orf29 |
| 230 | down | SFN | stratifin |
| 226 | up | POU3F2 | POU domain, class 3, transcription factor 2 |
| 225 | up | TESC | tescalcin |
| 224 | down | ABCA12 | ATP-binding cassette, sub-family A (ABC1), member 12 |
| 224 | up | LRRC34 | eucine rich repeat containing 34 |
| 223 | up | HOXB5 | homeobox B5 |
| 221 | down | S100A8 | S100 calcium binding protein A8 |
| 221 | up | TRO | trophinin |
| 219 | up | FAM155B | family with sequence similarity 155 member B |
| 216 | down | CYP4B1 | cytochrome P450, family 4, subfamily B, polypeptide 1 |
| 216 | up | PRTFDC1 | phosphoribosyl transferase domain containing 1 |
| 215 | down | DNER | delta/notch-like EGF repeat containing |
| 214 | down | ANXA1 | annexin A1 |
| 212 | down | ABLIM3 | actin binding LIM protein family, member 3 |

TABLE 2-continued

Genes up-regulated or down-regulated by 100-fold or more in stapled ERAP No. 6-treated cells compared with stapled ERAP No. 3-treated cells, at 48 hours after the treatment

| Fold | | Gene Symbol | Gene Name |
|---|---|---|---|
| 211 | up | ZNF22 | zinc finger protein 22 |
| 210 | up | RPRML | reprimo-like |
| 208 | down | KDR | kinase insert domain receptor (a type III receptor tyrosine kinase) |
| 208 | down | KRT6C | keratin 6C |
| 202 | down | LAMC2 | laminin, gamma 2 |
| 201 | down | C2CD2 | C2 calcium-dependent domain containing 2 |
| 201 | down | COL16A1 | collagen, type XVI, alpha 1 |
| 201 | down | LTBR | lymphotoxin beta receptor (TNFR superfamily, member 3) |
| 201 | down | IL18 | interleukin 18 (interferon-gamma-inducing factor) |
| 198 | down | C5orf38 | chromosome 5 open reading frame 38 |
| 198 | down | PID1 | phosphotyrosine interaction domain containing 1 |
| 197 | up | ALDH2 | aldehyde dehydrogenase 2 family |
| 195 | down | TNFAIP6 | tumor necrosis factor, alpha-induced protein 6 |
| 194 | down | SHISA9 | shisa homolog 9 (*Xenopus laevis*) |
| 193 | down | PLA2R1 | phospholipase A2 receptor 1, 180 kDa |
| 193 | down | IGFBP6 | insulin-like growth factor binding protein 6 |
| 190 | up | HOXB6 | homeobox B6 |
| 189 | down | IFI44L | interferon-induced protein 44-like |
| 188 | down | ITGB8 | integrin, beta 8 |
| 187 | down | OPLAH | 5-oxoprolinase (ATP-hydrolysing) |
| 187 | up | RUNX3 | runt-related transcription factor 3 |
| 185 | down | CFH | complement factor H |
| 185 | down | MT1L | metallothionein 1L (gene/pseudogene) |
| 185 | down | PTGR1 | prostaglandin reductase 1 |
| 183 | up | HOXA11-AS1 | HOXA11 antisense RNA |
| 182 | down | FAM198B | family with sequence similarity 198, member B |
| 181 | down | ARHGEF5 | Rho guanine nucleotide exchange factor (GEF) 5 |
| 181 | down | MLPH | melanophilin |
| 181 | up | POU4F1 | POU domain, class 4, transcription factor 1 |
| 178 | up | SERP2 | stress-associated endoplasmic reticulum protein family member 2 |
| 177 | up | BMP7 | bone morphogenetic protein 7 |
| 176 | down | LRRC3 | leucine rich repeat containing 3 |
| 176 | down | MT1B | metallothionein 1B |
| 176 | down | SCNN1A | sodium channel, nonvoltage-gated 1 alpha |
| 174 | up | COCH | cochlin |
| 173 | down | POSTN | periostin, osteoblast specific factor |
| 172 | down | PCDHB10 | protocadherin beta 10 |
| 172 | down | VSTM2L | V-set and transmembrane domain containing 2 like |
| 169 | down | FPR1 | formyl peptide receptor 1 |
| 168 | up | HOXD10 | homeobox D10 |
| 168 | down | IL20RB | interleukin 20 receptor beta |
| 168 | down | KRT17 | keratin 17 |
| 166 | down | RHOD | ras homolog gene family, member D |
| 165 | down | CFHR3 | complement factor H-related 3 |
| 164 | down | VNN1 | vanin 1 |
| 163 | up | ELOVL2 | ELOVL fatty acid elongase 2 |
| 162 | down | TNFSF14 | tumor necrosis factor (ligand) superfamily, member 14 |
| 162 | down | IRX2 | iroquois homeobox 2 |
| 161 | up | KIAA0408 | KIAA0408 |
| 160 | up | QPCT | glutaminyl-peptide cyclotransferase |
| 159 | down | ANXA8L2 | annexin A8-like 2 |
| 158 | up | CDKN2A | cyclin-dependent kinase inhibitor 2A |
| 155 | down | F2RL2 | coagulation factor II (thrombin) receptor-like 2 |
| 155 | up | CELF2 | CUGBP, Elav-like family member 2 |
| 155 | up | FBLL1 | fibrillarin-like 1 |
| 153 | up | KCNJ8 | potassium channel, inwardly rectifying subfamily J, member 8 |
| 152 | down | MIR205HG | MIR205 host gene (non-protein coding) |
| 150 | down | PEG10 | paternally expressed 10 |
| 150 | down | PLEK2 | pleckstrin 2 |
| 149 | down | MT1H | metallothionein 1H |
| 149 | up | C4orf49 | chromosome 4 open reading frame, humanC4orf29 |
| 148 | up | ONECUT2 | one cut domain, family member 2 |
| 146 | up | CNPY1 | canopy FGF signaling regulator 1 |
| 146 | down | ADH1A | alcohol dehydrogenase 1A (class I), alpha polypeptide |
| 145 | down | DSEL | dermatan sulfate epimerase-like |
| 145 | down | SAMD9L | sterile alpha motif domain containing 9-like |
| 144 | down | SNURF | SNRPN upstream reading frame |
| 144 | down | PCDHA11 | protocadherin alpha 11 |
| 143 | down | DPT | dermatopontin |
| 142 | up | ZIC3 | zinc finger protein of the cerebellum 3 |
| 140 | up | TSHZ3 | teashirt zinc finger family member 3 |
| 139 | down | IFIT2 | interferon-induced protein with tetratricopeptide repeats 2 |
| 138 | down | KRT16P2 | keratin 16 pseudogene 2 |
| 137 | down | VASN | vasorin |
| 137 | up | MPP2 | membrane protein, palmitoylated 2 |

TABLE 2-continued

Genes up-regulated or down-regulated by 100-fold or more in stapled ERAP No. 6-treated cells compared with stapled ERAP No. 3-treated cells, at 48 hours after the treatment

| Fold | | Gene Symbol | Gene Name |
|---|---|---|---|
| 137 | down | PARP12 | poly (ADP-ribose) polymerase family, member 12 |
| 136 | down | SQRDL | sulfide quinone reductase-like (yeast) |
| 133 | up | RBP1 | retinol binding protein 1 |
| 131 | down | EFEMP1 | EGF containing fibulin-like extracellular matrix protein 1 |
| 130 | down | PARP14 | poly (ADP-ribose) polymerase family, member 14 |
| 130 | down | CTGF | connective tissue growth factor |
| 130 | down | RIN1 | Ras and Rab interactor 1 |
| 129 | up | ZFHX4 | zinc finger homeobox 4 |
| 128 | down | PDZK1IP1 | PDZK1 interacting protein 1 |
| 128 | down | TRIM29 | tripartite motif containing 29 |
| 128 | down | AHNAK2 | AHNAK nucleoprotein 2 |
| 128 | up | EPDR1 | ependymin related 1 |
| 127 | up | NCAM1 | neural cell adhesion molecule 1 |
| 126 | down | H19 | H19, imprinted maternally expressed transcript (non-protein coding) |
| 126 | down | IL8 | interleukin 8 |
| 125 | down | ANGPTL4 | angiopoietin-like 4 |
| 125 | up | FOXD3 | forkhead box D3 |
| 125 | down | TMEM173 | transmembrane protein 173 |
| 123 | down | MT1X | metallothionein 1X |
| 123 | up | ID4 | nhibitor of DNA binding 4, dominant negative helix-loop-helix protein |
| 122 | down | C1S | complement component 1, s subcomponent |
| 122 | up | SLC35F1 | solute carrier family 35 member F1 |
| 121 | up | KRTAP19-1 | keratin associated protein 19-1 |
| 121 | up | PLAC1 | placenta specific 1 |
| 120 | down | DRAM1 | DNA-damage regulated autophagy modulator 1 |
| 120 | down | KLRC4 | killer cell lectin-like receptor subfamily C, member 4 |
| 119 | down | WWC3 | WWC family member 3 |
| 118 | up | COLEC11 | collectin subfamily member 11 |
| 118 | up | CYBA | cytochrome b-245, alpha polypeptide |
| 117 | up | TBX1 | T-box 1 |
| 117 | up | COL2A1 | collagen, type II, alpha 1 |
| 116 | down | NPR3 | natriuretic peptide receptor C/guanylate cyclase C (atrionatriuretic peptide receptor C) |
| 116 | down | C1R | complement component 1, r subcomponent |
| 115 | down | IRX4 | iroquois homeobox 4 |
| 113 | down | ST8SIA1 | ST8 alpha-N-acetyl-neuraminide alpha-2,8-sialyltransferase 1 |
| 113 | down | TLR3 | toll-like receptor 3 |
| 112 | down | CFI | complement factor I |
| 112 | up | SMO | smoothened, frizzled class receptor |
| 111 | down | CASP5 | caspase 5, apoptosis-related cysteine peptidase |
| 111 | up | ATF3 | activating transcription factor 3 |
| 111 | down | EBI3 | Epstein-Barr virus induced 3 |
| 110 | down | IFI16 | interferon, gamma-inducible protein 16 |
| 110 | up | SH2D3C | SH2 domain containing 3C |
| 110 | up | FOXN4 | forkhead box N4 |
| 107 | down | KRT83 | keratin 83 |
| 107 | down | PTRF | polymerase I and transcript release factor |
| 107 | up | ERC2 | ELKS/RAB6-interacting/CAST family member 2 |
| 107 | up | C15orf27 | chromosome 10 open reading frame, humanC15orf27 |
| 107 | down | NT5E | 5'-nucleotidase, ecto (CD73) |
| 107 | down | GSTT2B | glutathione S-transferase theta 2B (gene/pseudogene) |
| 106 | down | LSP1 | lymphocyte-specific protein 1 |
| 106 | down | TENC1 | tensin like C1 domain containing phosphatase (tensin 2) |
| 106 | down | GNA15 | guanine nucleotide binding protein (G protein), alpha 15 (Gq class) |
| 105 | down | CDH11 | cadherin 11, type 2, OB-cadherin (osteoblast) |
| 104 | down | PYCARD | PYD and CARD domain containing |
| 103 | down | TGFBR2 | transforming growth factor, beta receptor II (70/80 kDa) |
| 103 | up | RRAGD | Ras-related GTP binding D |
| 103 | up | RNF182 | ring finger protein 182 |
| 101 | down | CLIC3 | chloride intracellular channel 3 |
| 100 | down | CAV1 | caveolin 1, caveolae protein, 22 kDa |
| 130 | down | RIN1 | Ras and Rab interactor 1 |
| 129 | up | ZFHX4 | zinc finger homeobox 4 |
| 128 | down | PDZK1IP1 | PDZK1 interacting protein 1 |
| 128 | down | TRIM29 | tripartite motif containing 29 |
| 128 | down | AHNAK2 | AHNAK nucleoprotein 2 |
| 128 | up | EPDR1 | ependymin related 1 |
| 127 | up | NCAM1 | neural cell adhesion molecule 1 |
| 126 | down | H19 | H19, imprinted maternally expressed transcript (non-protein coding) |
| 126 | down | IL8 | interleukin 8 |
| 125 | down | ANGPTL4 | angiopoietin-like 4 |
| 125 | up | FOXD3 | forkhead box D3 |
| 125 | down | TMEM173 | transmembrane protein 173 |
| 123 | down | MT1X | metallothionein 1X |
| 123 | up | ID4 | inhibitor of DNA binding 4, dominant negative helix-loop-helix protein |
| 122 | down | C1S | complement component 1, s subcomponent |

TABLE 2-continued

Genes up-regulated or down-regulated by 100-fold or more in stapled ERAP No. 6-treated cells compared with stapled ERAP No. 3-treated cells, at 48 hours after the treatment

| Fold | | Gene Symbol | Gene Name |
|---|---|---|---|
| 122 | up | SLC35F1 | solute carrier family 35 member F1 |
| 121 | up | KRTAP19-1 | keratin associated protein 19-1 |
| 121 | up | PLAC1 | placenta specific 1 |
| 120 | down | DRAM1 | DNA-damage regulated autophagy modulator 1 |
| 120 | down | KLRC4 | killer cell lectin-like receptor subfamily C, member 4 |
| 119 | down | WWC3 | WWC family member 3 |
| 118 | up | COLEC11 | rcollectin subfamily member 11 |
| 118 | up | CYBA | cytochrome b-245, alpha polypeptide |
| 117 | up | TBX1 | T-box 1 |
| 117 | up | COL2A1 | collagen, type II, alpha 1 |
| 116 | down | NPR3 | natriuretic peptide receptor C/guanylate cyclase C (atrionatriuretic peptide receptor C) |
| 116 | down | C1R | complement component 1, r subcomponent |
| 115 | down | IRX4 | iroquois homeobox 4 |
| 113 | down | ST8SIA1 | ST8 alpha-N-acetyl-neuraminide alpha-2,8-sialyltransferase 1 |
| 113 | down | TLR3 | toll-like receptor 3 |
| 112 | down | CFI | complement factor I |
| 112 | up | SMO | smoothened, frizzled class receptor |
| 111 | down | CASP5 | caspase 5, apoptosis-related cysteine peptidase |
| 111 | up | ATF3 | activating transcription factor 3 |
| 111 | down | EBI3 | Epstein-Barr virus induced 3 |
| 110 | down | IFI16 | interferon, gamma-inducible protein 16 |
| 110 | up | SH2D3C | SH2 domain containing 3C |
| 110 | up | FOXN4 | forkhead box N4 |
| 107 | down | KRT83 | keratin 83 |
| 107 | down | PTRF | polymerase I and transcript release factor |
| 107 | up | ERC2 | ELKS/RAB6-interacting/CAST family member 2 |
| 107 | up | C15orf27 | chromosome 10 open reading frame, human C15orf27 |
| 107 | down | NT5E | 5'-nucleotidase, ecto (CD73) |
| 107 | down | GSTT2B | glutathione S-transferase theta 2B (gene/pseudogene) |
| 106 | down | LSP1 | lymphocyte-specific protein 1 |
| 106 | down | TENC1 | tensin like C1 domain containing phosphatase (tensin 2) |
| 106 | down | GNA15 | guanine nucleotide binding protein (G protein), alpha 15 (Gq class) |
| 105 | down | CDH11 | cadherin 11, type 2, OB-cadherin (osteoblast) |
| 104 | down | PYCARD | PYD and CARD domain containing |
| 103 | down | TGFBR2 | transforming growth factor, beta receptor II (70/80 kDa) |
| 103 | up | RRAGD | Ras-related GTP binding D |
| 103 | up | RNF182 | ring finger protein 182 |
| 101 | down | CLIC3 | chloride intracellular channel 3 |
| 100 | down | CAV1 | caveolin 1, caveolae protein, 22 kDa |

Next, co-immunoprecipitation experiments using an anti-BIG3 antibody were performed to examine whether stapled ERAP Nos. 2 and 3 inhibit the BIG3-PHB2 interaction. The results showed that stapled ERAP Nos. 2 and 3 inhibit complex formation between the endogenous BIG3 and PHB2 in ERα-positive breast cancer cell line MCF-7 in a dose-dependent manner, similarly to 11R-ERAP (FIG. 2G).

Subsequently, direct inhibition of the BIG3-PHB2 interaction by stapled ERAP Nos. 2 and 3 was examined. Surface plasmon resonance (BiAcore) interaction analysis revealed that stapled ERAP No. 2 ($K_D$=4.68 μM) and No. 3 ($K_D$=3.52 μM) show high affinity for His-tagged recombinant PHB2 in comparison to 11R-ERAP ($K_D$=12.80 μM) (FIG. 2H). These data suggest that stapled ERAP Nos. 2 and 3 directly bind to PHB2 to specifically inhibit BIG3-PHB2 complex formation.

Furthermore, to investigate the biophysical properties of stapled ERAP Nos. 2 and 3, their conformational properties were analyzed by CD spectroscopy. Importantly, stapled ERAP No. 3 was shown to have such a highly α-helical structure (FIG. 2I) as having the helical content of 41.7% (calculated from the value at 222 nm) according to CD spectroscopy. This suggests that stapling via olefin metathesis enhanced the stability of the α-helical structure of stapled ERAP No. 3. Furthermore, when effects of the treatment with stapled ERAP No. 2 or 3 on ERα target gene expression was investigated in MCF-7 cells, during the 96 hours after the peptide treatment, E2-dependent expressions of the ERα target genes TFF1 and CCND1 were significantly suppressed (FIG. 2J). Considering cell growth inhibition and long-term inhibition of ERα target gene expression as well as retention of high α-helicity, stapled ERAP No. 3 has the most critical stapling structure, whereas stapled ERAP No. 2 also yields significant decrease of cell growth by specific inhibition of the BIG3-PHB2 interaction. Taken together, these findings suggest that the inhibitory effect of stapled ERAP No. 3 on E2-dependent cell growth of ERα-positive breast cancer cells is far higher and lasts longer than that of 11R-ERAP.

Effects of Stapled ERAP without Olefin

Ruthenium-catalyzed olefin metathesis is costly; therefore, a stapled ERAP without olefin (stapled ERAP No. 12) which serves as a substitute for stapled ERAP No. 3 was newly synthesized via intramolecular amidation (FIG. 3A). This stapled ERAP No. 12 also maintained a helicity of 42.5% which is comparable to that of stapled ERAP No. 3 (FIG. 3B) and showed significant long-term inhibition of the BIG3-PHB2 interaction and E2-dependent growth of MCF-7 cells (FIGS. 3C and 3D). On the other hand, stapled ERAP No. 12 did not inhibit the growth of MCF-10A cells (FIG. 3C). Furthermore, inhibitory effects of stapled ERAP No. 12 on the expression of ERα target genes TFF1 and CCND1 were maintained at a high level compared to that of 11R-ERAP, even at 96 hours after the treatment (FIG. 3E).

Next, to investigate the intracellular distribution of stapled ERAP No. 12, HA-tagged stapled ERAP No. 12 in which an HA-tag is attached to the N terminus of stapled ERAP No. 12 (FIG. 3A) was prepared. When MCF-7 cells were treated with 10 µM HA-tagged stapled ERAP No. 12 in the absence of E2, HA-tagged stapled ERAP No. 12 localized in the cytoplasm in only one hour after the treatment (FIG. 3F). This shows the rapid cell permeability of the stapled conformation. On the other hand, in the presence of E2, HA-tagged stapled ERAP No. 12 was translocated to the nucleus along with endogenous PHB2 in only one hour after the treatment and continued to exist in the nucleus for 24 hours after the treatment (FIGS. 3F and 3G). Furthermore, HA-tagged stapled ERAP No. 12 suppressed E2-dependent MCF-7 cell growth (FIG. 3H). On the other hand, ERAP without poly-R did not show effects on E2-dependent MCF-7 cell growth (FIG. 3I). These results show that introduction of a stapling structure enhances the cell permeability of ERAP and this causes a stapled ERAP to rapidly permeate into cells and inhibit E2-dependent cell growth.

Next, tamoxifen-resistant (TAM-R) MCF-7 cells were used to investigate the ability of stapled ERAP No. 12 to inhibit E2-dependent cell growth. As shown in FIG. 3J, treatment with stapled ERAP No. 12 significantly decreased tamoxifen-resistant MCF-7 cell growth for 96 hours after the treatment in the presence of E2 and tamoxifen. On the other hand, inhibitory effects of 11R-ERAP were maintained only for 24 hours. Combination effects of stapled ERAP No. 12 (0.5 µM) with tamoxifen (selective ERα modulator, 10 nM) or with fulvestrant (ERα down-regulator, 2 µM) on E2-dependent cell growth were each examined. Treatments using both combinations of stapled ERAP No. 12 with tamoxifen and that with fulvestrant significantly suppressed E2-dependent cell growth in MCF-7 cells in comparison to the treatment singly with stapled ERAP No. 12, tamoxifen, or fulvestrant (FIG. 3K). Remarkable synergistic inhibitory effects were observed particularly in the treatment using a combination of stapled ERAP No. 12 with tamoxifen. This suggests that stapled ERAP No. 12 enhances the responsiveness of ERα-positive breast cancer cells to tamoxifen.

In Vivo Tumor Growth Inhibitory Effects of Stapled ERAP

To investigate in vivo antitumor effects of stapled ERAP No. 12, KPL-3C orthotopic breast cancer xenografts were developed in nude mice. Once the tumor was fully established, stapled ERAP No. 12 (1.4 and 14 mg/kg), 11R-ERAP (1.4 and 14 mg/kg), HA-tagged stapled ERAP No. 12 (14 mg/kg), or vehicle alone was administered every day or every four days by intraperitoneal (i.p.) injection for 28 days (FIG. 4A). The animals were also treated with E2 every day (6 µg/day). Daily E2 treatment induced the time-dependent growth of KPL-3C tumors, whereas daily treatment with stapled ERAP No. 12 or 11R-ERAP caused significant inhibition of E2-dependent tumor growth at doses of both 1.4 mg/kg and 14 mg/kg (FIGS. 4B and 4C). In particular, unlike the treatment with 11R-ERAP, the treatment with stapled ERAP No. 12 sustained significant inhibitory effects even when administered every four days (FIGS. 4B and 4C). This suggests that from a therapeutic viewpoint, stapled ERAP No. 12 has excellent therapeutic index. No toxicity or significant body weight decrease was observed (FIG. 4D). Therefore, under these conditions, it can be said that adverse side effects were not observed.

Next, to elucidate the mechanism of in vivo antitumor effects of stapled ERAP No. 12, KPL-3C orthotopic xenograft mice were treated every day or every four days with 1.4 mg/kg stapled ERAP No. 12. On the 28th day after starting the treatment, the mice were subjected to scheduled sacrifice and the tumors were removed to examine the intracellular distribution of PHB2. Tumor cells excised from the mice were fractionated into a cytoplasmic fraction and a nuclear fraction, and co-immunoprecipitation was performed on the respective fractions using an anti-PHB2 antibody. The results showed that in the presence of E2, the treatment with 11R-ERAP or stapled ERAP No. 12 induces decrease of cytoplasmic PHB2, and this leads to large increase in the amount of nuclear PHB2 (FIG. 4E). Furthermore, to investigate the intracellular distribution of stapled ERAP No. 12, tumors were removed from KPL-3C orthotopic xenograft mice treated every day or every four days with 1.4 mg/kg or 14 mg/kg HA-tagged stapled ERAP No. 12, and immunohistochemistry and co-immunoprecipitation experiments using an anti-PHB2 antibody were performed. Their results showed that HA-tagged stapled ERAP No. 12 interacts with PHB2 mainly in the nucleus, suggesting that it interacts with PHB2 in the cytoplasm and translocates into the nucleus (FIGS. 4F to H). Furthermore, tumors were removed from KPL-3C orthotopic xenograft mice treated every day or every four days with 1.4 mg/kg stapled ERAP No. 12, and the expression of ERα target genes (TFF1 and CCND1) was examined. Both treatments with stapled ERAP No. 12 significantly suppressed the E2-dependent expressions of TFF1 and CCND1 in the tumors (FIG. 4I). These findings suggest that effective inhibition of endogenous BIG3-PHB2 complex formation in tumors by stapled ERAP No. 12 results in nuclear translocation of PHB2, which causes inhibition of E2-dependent genomic activation.

Next, effects of stapled ERAP No. 12 on the activation of the non-genomic ERα signaling pathway in tumors were examined. The phosphorylation levels of Akt and MAPK were detected using an anti-phosphorylated Akt antibody and anti-phosphorylated MAPK antibody in tumors removed from KPL-3C orthotopic xenograft mice treated every day or every four days with 1.4 mg/kg stapled ERAP No. 12. As expected, remarkable suppression of Akt phosphorylation and MAPK phosphorylation was observed in both treatments with stapled ERAP No. 12 (FIG. 4J). Unlike 11R-ERAP, stapled ERAP No. 12 clearly suppressed the E2-dependent phosphorylation level even when treatment was performed every four days, and this demonstrated that stapled ERAP No. 12 has long-term and potent in vivo antitumor activity (FIG. 4J).

Furthermore, when hematoxylin-eosin staining was performed on heart, lung, liver, kidney, pancreas, and brain removed from KPL-3C orthotopic xenograft mice treated every four days with 14 mg/kg stapled ERAP No. 12, histopathological changes were hardly observed in these vital organs (FIG. 4K). When hematoxylin-eosin staining was performed on heart, lung, liver, kidney, pancreas, and brain removed from KPL-3C orthotopic xenograft mice treated every day with 14 mg/kg HA-tagged stapled ERAP No. 12, similarly, histopathological changes were hardly observed (FIG. 4L).

In addition, long-term in vivo antitumor activity of stapled ERAP No. 12 was examined using the KPL-3C orthotopic xenograft nude mouse model. Once the tumor was fully established, stapled ERAP No. 12 (0.02, 0.1, or 1 mg/kg) or vehicle alone was administered every four days or every seven days by intraperitoneal (i.p.) injection for 28 days (FIG. 4M). The animals were treated with E2 every day (6 µg/day). The every seven days treatment with stapled ERAP No. 12 at 1 mg/kg completely inhibited E2-dependent tumor growth up to day 28 (FIG. 4M). Furthermore, the every seven days treatments with stapled ERAP No. 12 at 0.1 and 0.02 mg/kg completely inhibited E2-dependent tumor growth up to day 21 and day 18, respectively. Moreover, the treatment every four days or every seven days with stapled ERAP No. 12 significantly suppressed E2-dependent expression of ERα target genes TFF1 and CCND1 in tumors as well (FIG. 4N).

[Example 3] Effects of Stapled ERAP on Prostate Cancer Cells

Materials and Methods
Cell Lines and Culturing Conditions

Human prostate cancer cell line 22Rv1 was purchased from American Type Culture Collection (ATCC, Manassas, Va., USA). 22Rv1 cells were monolayer cultured in an appropriate medium supplemented with 10% FBS. The cells were maintained at 37° C. under humidified atmosphere containing 5% $CO_2$. 22Rv1 cells were seeded in RPMI (Thermo Fisher Scientific) supplemented with 10% FBS (Thermo Fisher Scientific) and 1% Antibiotic/Antimycotic solution (Wako, Tokyo, Japan) in a 48-well plate ($3\times10^4$ cells/mL) or a 10-cm dish ($8\times10^6$ cells/dish). Forty-eight hours later, the cells were treated with 10 µM (only when performing immunoprecipitation), 20 µM, or 50 µM stapled ERAP No. 12.

Cell Growth Assay

Cell growth assay was performed by staining dead cells using trypan blue, and evaluating total cell count using Countess II (Thermo Fisher Scientific). Cell viability was measured every 24 hours using a Countess II automated cell counter (Thermo Fisher Scientific) according to the manufacturer's instructions.

Immunoprecipitation

Immunoprecipitation was performed as in Example 2.

Results

Inhibitory effects of stapled ERAP No. 12 on E2-independent cell growth were examined using 22Rv1 prostate cancer cell line (ERα-negative, BIG3-positive, and PHB2-positive). As shown in FIG. 5A, treatment with stapled ERAP No. 12 significantly suppressed 22Rv1 cell growth in a time-dependent and dose-dependent manner.

Furthermore, to investigate whether stapled ERAP No. 12 inhibits the BIG3-PHB2 interaction, co-immunoprecipitation experiment using an anti-BIG3 antibody was performed. The result showed that stapled ERAP No. 12 dose-dependently inhibits complex formation between the endogenous BIG3 and PHB2 in 22Rv1 cells (FIG. 5B).

In addition, the treatment with 10 µM, 20 µM, or 50 µM stapled ERAP No. 12 did not affect the growth of MCF-10A cells, which do not express BIG3 and ERα (FIG. 5C). This suggests that the treatments with stapled ERAP No. 12 at these concentrations do not induce non-specific inhibitory effects on MCF-10A cell growth.

[Example 4] D-Form Peptide and Retro-Inverso Form of Stapled ERAP

D-form peptide and retro-inverso form of stapled ERAP No. 12 were synthesized to identify peptides with a conformation having greater resistance to proteolysis (FIG. 6A; M. Chorev, et al., Trends. Biotechnol. 13, 438-445 (1995); C. Bonny, et al., Diabetes 50, 77-82 (2001); M. Taylor, et al., Biochemistry 49, 3261-3272 (2010); T. Weeden, et al., J. Pept. Sci. 17, 47-55 (2011)). In the retro-inverso form, not only the amino acid chirality is reversed by substituting all L-amino acids with D-amino acids, but also its amino acid sequence is reversed from that of the original peptide. The D-form peptide and retro-inverso form of stapled ERAP No. 12 were synthesized in a manner similar to the L-peptide of stapled ERAP, except that D-amino acids were used instead of L-amino acids in peptide synthesis.

The prepared D-form peptide of stapled ERAP No. 12 (hereinafter, "stapled-D-ERAP No. 12") and retro-inverso form of stapled ERAP No. 12 (hereinafter, "RI stapled ERAP No. 12") inhibited E2-dependent growth of MCF-7 cells in a dose-dependent manner at nanomolar levels (FIG. 6B, left). On the other hand, MCF-10A cell growth was not inhibited (FIG. 6B, right). The $IC_{50}$ values of stapled-D-ERAP No. 12 and RI stapled ERAP No. 12 at 96 hours after the treatment were 0.44 µM and 0.50 µM, respectively (FIG. 6C). On the other hand, the $IC_{50}$ of stapled ERAP No. 12 was 0.59 µM (FIG. 6C).

Furthermore, short stapled retro-inverso ERAP No. 12 (hereinafter, "shRI stapled ERAP No. 12"), which is a retro-inverso form of the N-terminal partial sequence of ERAP (QMLSDLT (SEQ ID NO: 13)), was synthesized (FIG. 6A). This shRI stapled ERAP No. 12 suppressed the E2-dependent growth of MCF-7 cells (IC50=0.53 µM) and this stapled peptide of the N-terminal short sequence was shown to have an ability to significantly suppress E2-dependent growth of breast cancer cells (FIGS. 6B and C).

Next, long-term inhibitory effects of the above-mentioned various stapled ERAPs on E2-dependent growth of MCF-7 cells were examined. The treatment with 1 µM stapled-D-ERAP No. 12, RI stapled ERAP No. 12, or shRI stapled ERAP No. 12 sustained significant cell growth inhibitory effects for seven days. On the other hand, stapled ERAP No. 12 sustained significant cell growth inhibitory effects for four days (FIG. 6D).

Then, to investigate whether these stapled ERAPs inhibit the BIG3-PHB2 interaction, co-immunoprecipitation experiments using an anti-BIG3 antibody were performed.

Co-immunoprecipitation was performed by using MCF-7 cells 24 hours and 96 hours after the treatments with 1 µM of each of the peptides. The results showed that even at 24 hours after the treatment, stapled-D-ERAP No. 12, RI stapled ERAP No. 12, and shRI stapled ERAP No. 12 inhibited endogenous BIG3-PHB2 complex formation in MCF-7 cells (FIG. 6E). Particularly, inhibitory effects of these stapled ERAPs on the endogenous BIG-3-PHB2 interaction sustained even at 96 hours after the treatment.

Furthermore, in vivo antitumor activity of RI stapled ERAP No. 12 was examined. Once the tumor was fully established, RI stapled ERAP No. 12 (0.02, 0.1, or 1 mg/kg) or vehicle alone was administered every four days or every seven days by intraperitoneal (i.p.) injection. The animals were also treated with E2 every day (6 µg/day). The treatment every four days or every seven days with RI stapled ERAP No. 12 at 1 mg/kg or 0.1 mg/kg almost fully inhibited E2-dependent tumor growth up to 28 days after the treatment (FIG. 6F). Furthermore, the treatment every four days or every seven days with RI stapled ERAP No. 12 (0.02, 0.1, or 1 mg/kg) significantly suppressed E2-dependent expression of ERa target genes TFF1 and CCND1 in the tumors (FIG. 6G).

[Example 5] ERAP Formed by Adding Cell-Permeable Polyarginine Residues to the C Terminus Peptides formed by adding cell-permeable polyarginine residues (8R) to the C termini of ERAP and its partial sequence were each designed (QMLSDLTLQLRQR-8R (SEQ ID NO: 10) and QMLSDLTLQL-8R (SEQ ID NO:

11); FIG. 7). When MCF-7 cells were treated with these peptides, the treatment showed inhibitory effects on E2-dependent growth of MCF-7 cells that are similar to those of 11R-ERAP (the former $IC_{50}$=7.78 μM and the latter 7.98 μM) (FIG. 7).

[Example 6] Inhibitory Effects of Stapled ERAP (No. 12) on Phosphorylation of mTOR and S6K in Tamoxifen-Resistant Breast Cancer Cell Line Tamoxifen (TAM)-resistant MCF7 cells significantly induced phosphorylation of mTOR and S6K in the presence of TAM, and showed nearly the same phosphorylation intensity as the intensity at 24-hour E2 addition, but 24-hour treatment with stapled ERAP (No. 12) and that with 11R-ERAP almost completely inhibited the respective phosphorylations, and the intensities were not more than that of the negative control (untreated cells in the absence of TAM) (FIG. 8).

Furthermore, in the presence of TAM, the mTOR and S6K phosphorylation intensities due to E2 addition for 96 hours were nearly the same as the intensities for the 24-hour reaction, but the inhibitory effects of 11R-ERAP treatment was significantly attenuated compared to that for the 24-hour reaction (FIG. 8). On the other hand, the stapled ERAP (No. 12) treatment sustained almost complete inhibitory effects even for the 96-hour reaction, and it is considered that long-term and stable suppression is possible in TAM-resistant breast cancer cases.

[Example 7] Effects of Combined Use of Stapled ERAP (No. 12) with Tamoxifen, Fulvestrant, or Everolimus on E2-Dependent Cell Growth In the 24-hour reaction, 11R-ERAP and stapled ERAP (No. 12) almost completely suppressed E2-dependent cell growth, and combined use with tamoxifen (anti-estrogen agent), fulvestrant (ER□ modulator), or everolimus (mTOR inhibitor) showed synergistic suppressing effects and decreased the number of viable cells to that observed without the treatment, or lower (FIG. 9, left).

In the 96-hour reaction, stapled ERAP (No. 12) sustained almost complete suppressive effects, and showed synergistic suppressive effects with existing inhibitors, as in the case with the 24-hour reaction (FIG. 9, right). On the other hand, while 11R-ERAP attenuated E2-dependent growth at an inhibition rate of 45%, effects of its combined use with existing inhibitors provided approximately the same number of viable cells as that of the 24-hour reaction, and were considered to possibly induce cell death at 24 hours.

[Example 8] Antitumor Effects of Tail Vein Administration of Stapled ERAP (No. 12)

To investigate in vivo antitumor effects of stapled ERAP (No. 12) administered intravenously, KPL-3C orthotopic breast cancer xenografts were grown in nude mice. Once the tumor was fully established, stapled ERAP (No. 12) (0.1, 1, or 10 mg/kg) or vehicle alone was administered by tail vein injection every day or every seven days for 35 days. E2 was also administered every day (6 μg/day). The daily E2 treatment induced the time-dependent growth of KPL-3C tumors (FIG. 10, left). On the other hand, the treatments with stapled ERAP (No. 12) both every day and every seven days significantly suppressed E2-dependent tumor growth in a dose-dependent manner, and almost complete antitumor effects were obtained at 10 mg/kg, similarly to the antitumor effects yielded so far by intraperitoneal administration (FIG. 10).

[Example 9] BIG3-PHB2 Interaction in Tumors Removed from Stapled ERAP (No. 12)-Treated Grafted Mice Effects of stapled ERAP (No. 12) on the BIG3-PHB2 interaction in tumors removed from grafted mice were examined. Tumors removed from KPL-3C orthotopic xenograft mice treated every day or every seven days with 10 mg/kg stapled ERAP (No. 12) were subjected to co-immunoprecipitation experiment using an anti-BIG3 antibody. The results showed that in the untreated group and the group subjected to daily E2 administration, BIG3 and PHB2 are strongly bound, however, co-precipitation of PHB2 was hardly detected in tumors resulting from administration of stapled ERAP (No. 12) at 10 mg/kg every day and every seven days for 35 days, indicating that stapled ERAP (No. 12) at 10 mg/kg almost completely inhibits the BIG3-PHB2 interaction and suppresses the enlargement of tumors (FIG. 11).

[Example 10] Phosphorylation of Akt and MAPK in Tumors Treated with Stapled ERAP (No. 12)

Effects of stapled ERAP (No. 12) on Akt- and MAPK-phosphorylation in tumors were examined. In tumors removed from KPL-3C orthotopic xenograft mice treated every day or every seven days with 10 mg/kg stapled ERAP (No. 12), Akt- and MAPK-phosphorylation levels were detected using an anti-phosphorylated Akt antibody and anti-phosphorylated MAPK antibody. As a result, remarkable suppression of Akt phosphorylation and MAPK phosphorylation was observed for the stapled ERAP (No. 12) treatment by administration every day and every seven days (FIG. 12).

[Example 11] In Vitro Blood-Brain Barrier Permeability Test of Stapled ERAP (No. 12)

BIG3 is expressed in the brain though expression is weak (Kim, J. W. et al., Cancer Sci. 100, 1468-1478 (2009)). Then, since there were concerns of side effects due to the transfer of stapled ERAP to the brain, blood-brain-barrier permeability test was carried out on stapled ERAP. Blood-brain-barrier permeability of stapled ERAP (No. 12) was examined by placing stapled ERAP (No. 12) to the inner side (vascular cavity side) of the insert of a blood-brain barrier permeability kit, and measuring the concentration of stapled ERAP (No. 12) that passed through a filter specialized for intracerebral transferability assay and leaked into the well (cerebral parenchyma side) of the plate in 30 minutes. The permeability coefficient (Papp) at this time was calculated (2 or less: very low permeability; 2 to 10: low permeability; 10 to 20: high permeability; and 20 or higher: very high permeability). As a result, blood-brain barrier permeability coefficient of stapled ERAP (No. 12) was showed to be 2 or less and this suggested that possibility of its transfer into the brain is low, and there is no concern of side effects due to intracerebral transfer (Table 3).

TABLE 3

| Blood-brain barrier Permeability Test | | |
| --- | --- | --- |
| | Permeability ($10^{-6}$ cm/sec) | Recovery Rate (%) |
| No. 12   10 μM | 0 | 0 |
| 30 μM | 0.177 | 0.01 |

INDUSTRIAL APPLICABILITY

The present invention provides peptides having BIG3-PHB2 interaction inhibitory effects that last longer. Peptides of the present invention have cell permeability as well as low blood-brain-barrier permeability. Pharmaceutical compositions comprising peptides or salts thereof of the present invention can be used to therapy of cancer, particularly estrogen receptor-positive cancer, and estrogen receptor-negative breast cancer and prostate cancer.

The invention claimed is:

1. A peptide comprising an amino acid sequence in which one pair of amino acid residues is substituted with one stapling structure in the amino acid sequence of SEQ ID NO: 9 or a partial sequence thereof, or a salt thereof, wherein the one pair of amino acid residues is selected from (a) or (b) below:

(a) the third and seventh amino acid residues from the N terminus of the amino acid sequence of SEQ ID NO: 9; or (b) the second and sixth amino acid residues from the N terminus of the amino acid sequence of SEQ ID NO: 9.

2. The peptide or the salt thereof of claim 1, wherein the partial sequence of the amino acid sequence of SEQ ID NO:

9 is the amino acid sequence of SEQ ID NO: 13, and wherein the one pair of amino acid residues is selected from (a) or (b) below:
(a) the third and seventh amino acid residues from the N terminus of the amino acid sequence of SEQ ID NO: 13; or
(b) the second and sixth amino acid residues from the N terminus of the amino acid sequence of SEQ ID NO: 13.

3. The peptide or the salt thereof of claim 1, wherein the stapling structure is represented by Formula (I) below:

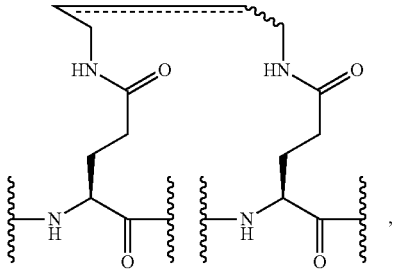

(I)

wherein the double line drawn by a solid line and a dashed line indicates a single bond or a double bond.

4. The peptide or the salt thereof of claim 3, which is represented by Formula (II) below:

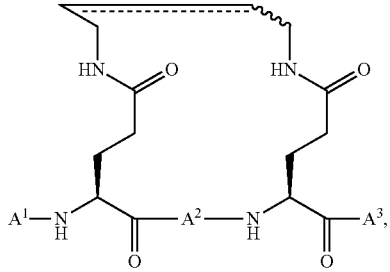

(II)

wherein the double line drawn by a solid line and a dashed line indicates a single bond or a double bond;

the combination of $A^1$, $A^2$, and $A^3$ is selected from the following:

$A^1$=Q, $A^2$=LSD, and $A^3$=TLQLRQR (SEQ ID NO: 14);

$A^1$=QM, $A^2$=SDL, and $A^3$=LQLRQR (SEQ ID NO: 15);

$A^1$=QM, $A^2$=SDL, and $A^3$=—OH; and $A^1$=Q, $A^2$=LSD, and $A^3$=T.

5. The peptide or the salt thereof of claim 1, wherein either one or both of N-terminal and C-terminal amino acid residues have been modified.

6. The peptide or the salt thereof of claim 5, wherein either one or both of N-terminal and C-terminal amino acid residues have been modified by any one or a combination of acetylation, amidation, and HA tagging.

7. The peptide or the salt thereof of claim 6, wherein the N-terminal amino acid residue is acetylated and the C-terminal amino acid residue is amidated.

8. The peptide or the salt thereof of claim 1, wherein all the amino acid residues have been substituted with D-form amino acid residues.

9. A peptide which is a retro-inverso form of the peptide of claim 1, or a salt thereof.

10. A pharmaceutical composition comprising the peptide or the salt thereof of claim 1 and a pharmaceutically acceptable carrier.

11. The pharmaceutical composition of claim 10, which is for cancer therapy.

12. The pharmaceutical composition of claim 11, wherein the cancer is breast cancer or prostate cancer.

13. The pharmaceutical composition of claim 11, wherein the cancer is estrogen receptor-positive cancer.

* * * * *

```
                        SEQUENCE LISTING

<160> NUMBER OF SEQ ID NOS: 36

<210> SEQ ID NO 1
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
      with olefin
<220> FEATURE:
<221> NAME/KEY: MISC_FEATURE
<222> LOCATION: (1)..(1)
<223> OTHER INFORMATION: Glutamine analog for stapling by olefin
      metathesis
<220> FEATURE:
<221> NAME/KEY: MISC_FEATURE
<222> LOCATION: (5)..(5)
<223> OTHER INFORMATION: Glutamine analog for stapling by olefin
      metathesis

<400> SEQUENCE: 1

Xaa Met Leu Ser Xaa Leu Thr Leu Gln Leu Arg Gln Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
      with olefin
<220> FEATURE:
<221> NAME/KEY: MISC_FEATURE
<222> LOCATION: (2)..(2)
<223> OTHER INFORMATION: Glutamine analog for stapling by olefin
      metathesis
<220> FEATURE:
<221> NAME/KEY: MISC_FEATURE
<222> LOCATION: (6)..(6)
<223> OTHER INFORMATION: Glutamine analog for stapling by olefin
      metathesis

<400> SEQUENCE: 2

Gln Xaa Leu Ser Asp Xaa Thr Leu Gln Leu Arg Gln Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
      with olefin
<220> FEATURE:
<221> NAME/KEY: MISC_FEATURE
<222> LOCATION: (3)..(3)
<223> OTHER INFORMATION: Glutamine analog for stapling by olefin
      metathesis
<220> FEATURE:
<221> NAME/KEY: MISC_FEATURE
<222> LOCATION: (7)..(7)
```

<223> OTHER INFORMATION: Glutamine analog for stapling by olefin
    metathesis

<400> SEQUENCE: 3

Gln Met Xaa Ser Asp Leu Xaa Leu Gln Leu Arg Gln Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
    with olefin
<220> FEATURE:
<221> NAME/KEY: MISC_FEATURE
<222> LOCATION: (4)..(4)
<223> OTHER INFORMATION: Glutamine analog for stapling by olefin
    metathesis
<220> FEATURE:
<221> NAME/KEY: MISC_FEATURE
<222> LOCATION: (8)..(8)
<223> OTHER INFORMATION: Glutamine analog for stapling by olefin
    metathesis

<400> SEQUENCE: 4

Gln Met Leu Xaa Asp Leu Thr Xaa Gln Leu Arg Gln Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
    with olefin
<220> FEATURE:
<221> NAME/KEY: MISC_FEATURE
<222> LOCATION: (5)..(5)
<223> OTHER INFORMATION: Glutamine analog for stapling by olefin
    metathesis
<220> FEATURE:
<221> NAME/KEY: MISC_FEATURE
<222> LOCATION: (9)..(9)
<223> OTHER INFORMATION: Glutamine analog for stapling by olefin
    metathesis

<400> SEQUENCE: 5

Gln Met Leu Ser Xaa Leu Thr Leu Xaa Leu Arg Gln Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
    with olefin
<220> FEATURE:
<221> NAME/KEY: MISC_FEATURE
<222> LOCATION: (6)..(6)
<223> OTHER INFORMATION: Glutamine analog for stapling by olefin
    metathesis
<220> FEATURE:
<221> NAME/KEY: MISC_FEATURE
<222> LOCATION: (10)..(10)
<223> OTHER INFORMATION: Glutamine analog for stapling by olefin
    metathesis

<400> SEQUENCE: 6

Gln Met Leu Ser Asp Xaa Thr Leu Gln Xaa Arg Gln Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
      with olefin
<220> FEATURE:
<221> NAME/KEY: MISC_FEATURE
<222> LOCATION: (7)..(7)
<223> OTHER INFORMATION: Glutamine analog for stapling by olefin
      metathesis
<220> FEATURE:
<221> NAME/KEY: MISC_FEATURE
<222> LOCATION: (11)..(11)
<223> OTHER INFORMATION: Glutamine analog for stapling by olefin
      metathesis

<400> SEQUENCE: 7

Gln Met Leu Ser Asp Leu Xaa Leu Gln Leu Xaa Gln Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
      with olefin
<220> FEATURE:
<221> NAME/KEY: MISC_FEATURE
<222> LOCATION: (8)..(8)
<223> OTHER INFORMATION: Glutamine analog for stapling by olefin
      metathesis
<220> FEATURE:
<221> NAME/KEY: MISC_FEATURE
<222> LOCATION: (12)..(12)
<223> OTHER INFORMATION: Glutamine analog for stapling by olefin
      metathesis

<400> SEQUENCE: 8

Gln Met Leu Ser Asp Leu Thr Xaa Gln Leu Arg Xaa Arg
1               5                   10

<210> SEQ ID NO 9
<211> LENGTH: 13
<212> TYPE: PRT
<213> ORGANISM: Artificial Sequence
<220> FEATURE:
<223> OTHER INFORMATION: PHB2-binding peptide derived from BIG3

<400> SEQUENCE: 9

Gln Met Leu Ser Asp Leu Thr Leu Gln Leu Arg Gln Arg
1               5                   10

<210> SEQ ID NO 10
<211> LENGTH: 21
<212> TYPE: PRT
<213> ORGANISM: Artificial Sequence
<220> FEATURE:
<223> OTHER INFORMATION: PHB2-binding peptide derived from BIG3 with 8R
      at the C terminal

<400> SEQUENCE: 10

Gln Met Leu Ser Asp Leu Thr Leu Gln Leu Arg Gln Arg Arg Arg Arg
1               5                   10                  15

Arg Arg Arg Arg Arg
            20

```
<210> SEQ ID NO 11
<211> LENGTH: 18
<212> TYPE: PRT
<213> ORGANISM: Artificial Sequence
<220> FEATURE:
<223> OTHER INFORMATION: Partial PHB2-binding peptide derived from BIG3
      with 8R at the C terminal

<400> SEQUENCE: 11

Gln Met Leu Ser Asp Leu Thr Leu Gln Leu Arg Arg Arg Arg Arg Arg
1               5                   10                  15

Arg Arg

<210> SEQ ID NO 12
<211> LENGTH: 13
<212> TYPE: PRT
<213> ORGANISM: Artificial Sequence
<220> FEATURE:
<223> OTHER INFORMATION: Stapled PHB2-binding peptide derived from BIG3
      without olefin
<220> FEATURE:
<221> NAME/KEY: MISC_FEATURE
<222> LOCATION: (3)..(3)
<223> OTHER INFORMATION: Glutamine analog for stapling by intramolecular
      amidation
<220> FEATURE:
<221> NAME/KEY: MISC_FEATURE
<222> LOCATION: (7)..(7)
<223> OTHER INFORMATION: Glutamine analog for stapling by intramolecular
      amidation

<400> SEQUENCE: 12

Gln Met Xaa Ser Asp Leu Xaa Leu Gln Leu Arg Gln Arg
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Short PHB2-binding peptide derived from BIG3

<400> SEQUENCE: 13

Gln Met Leu Ser Asp Leu Thr
1               5

<210> SEQ ID NO 14
<211> LENGTH: 7
<212> TYPE: PRT
<213> ORGANISM: Artificial Sequence
<220> FEATURE:
<223> OTHER INFORMATION: C-terminal sequence of PHB2-binding peptide
      derived from BIG3

<400> SEQUENCE: 14

Thr Leu Gln Leu Arg Gln Arg
1               5

<210> SEQ ID NO 15
<211> LENGTH: 6
<212> TYPE: PRT
<213> ORGANISM: Artificial Sequence
<220> FEATURE:
<223> OTHER INFORMATION: C-terminal sequence of PHB2-binding peptide
      derived from BIG3

<400> SEQUENCE: 15

Leu Gln Leu Arg Gln Arg
```

```
<210> SEQ ID NO 16
<211> LENGTH: 9
<212> TYPE: PRT
<213> ORGANISM: Artificial Sequence
<220> FEATURE:
<223> OTHER INFORMATION: an HA-tag peptide

<400> SEQUENCE: 16

Tyr Pro Tyr Asp Val Pro Asp Tyr Ala
1               5

<210> SEQ ID NO 17
<211> LENGTH: 20
<212> TYPE: DNA
<213> ORGANISM: Artificial Sequence
<220> FEATURE:
<223> OTHER INFORMATION: 5' primer for TFF1

<400> SEQUENCE: 17
ggcctcctta ggcaaatgtt                                                 20

<210> SEQ ID NO 18
<211> LENGTH: 20
<212> TYPE: DNA
<213> ORGANISM: Artificial Sequence
<220> FEATURE:
<223> OTHER INFORMATION: 3' primer for TFF1

<400> SEQUENCE: 18
cctcctctct gctccaaagg                                                 20

<210> SEQ ID NO 19
<211> LENGTH: 20
<212> TYPE: DNA
<213> ORGANISM: Artificial Sequence
<220> FEATURE:
<223> OTHER INFORMATION: 5' primer for CCND1

<400> SEQUENCE: 19
cagaagtgcg aggaggaggt                                                 20

<210> SEQ ID NO 20
<211> LENGTH: 19
<212> TYPE: DNA
<213> ORGANISM: Artificial Sequence
<220> FEATURE:
<223> OTHER INFORMATION: 3' primer for CCND1

<400> SEQUENCE: 20
cggatggagt tgtcggtgt                                                  19

<210> SEQ ID NO 21
<211> LENGTH: 20
<212> TYPE: DNA
<213> ORGANISM: Artificial Sequence
<220> FEATURE:
<223> OTHER INFORMATION: 5' primer for B2-MG

<400> SEQUENCE: 21
aacttagagg tggggagcag                                                 20

<210> SEQ ID NO 22
<211> LENGTH: 22
<212> TYPE: DNA
```

```
<213> ORGANISM: Artificial Sequence
<220> FEATURE:
<223> OTHER INFORMATION: 3' primer for B2-MG

<400> SEQUENCE: 22
cacaaccatg ccttacttta tc                                               22

<210> SEQ ID NO 23
<211> LENGTH: 14895
<212> TYPE: DNA
<213> ORGANISM: Homo sapiens
<220> FEATURE:
<221> NAME/KEY: CDS
<222> LOCATION: (172)..(6705)

<400> SEQUENCE: 23
gtggcccgcg gcatggagcg ggcgtgattc atcagcatcc gcgccggggc ggcatggggg     60
cgcgcgcggc ggccgcctag gcgcccaggg ccaggcagcg gcggcttccc cggcccggct    120
cgcccgcgct tctctccctg tgggcggcgg cccggcgcct ggaaggtcaa g atg gaa    177
                                                          Met Glu
                                                          1 gaa atc ctg agg aag ctg cag aag gag gcg tcc ggg agc aag tac aaa    225
Glu Ile Leu Arg Lys Leu Gln Lys Glu Ala Ser Gly Ser Lys Tyr Lys
        5                  10                  15 gcc atc aag gag agc tgc acc tgg gcc ctg gaa act cta ggt ggt ctg    273
Ala Ile Lys Glu Ser Cys Thr Trp Ala Leu Glu Thr Leu Gly Gly Leu
 20                  25                  30 gat acc att gtc aag atc cct cca cat gta ctg agg gag aaa tgc ctg    321
Asp Thr Ile Val Lys Ile Pro Pro His Val Leu Arg Glu Lys Cys Leu
35                  40                  45                  50 ctg cct ctc cag ttg gct ttg gaa tcc aag aat gtg aag ctg gcc caa    369
Leu Pro Leu Gln Leu Ala Leu Glu Ser Lys Asn Val Lys Leu Ala Gln
                55                  60                  65 cat gct ttg gca ggg atg cag aag ctt ctg tcg gaa gag agg ttt gta    417
His Ala Leu Ala Gly Met Gln Lys Leu Leu Ser Glu Glu Arg Phe Val
             70                  75                  80 tcc atg gaa aca gat tct gat gag aag cag ctg ctc aat cag ata ctg    465
Ser Met Glu Thr Asp Ser Asp Glu Lys Gln Leu Leu Asn Gln Ile Leu
         85                  90                  95 aat gcc gtg aaa gtg acg cct tcg ctc aac gag gac ctg cag gtg gaa    513
Asn Ala Val Lys Val Thr Pro Ser Leu Asn Glu Asp Leu Gln Val Glu
     100                 105                 110 gtg atg aag gtt tta cta tgc atc acc tac acg cca aca ttt gat ctg    561
Val Met Lys Val Leu Leu Cys Ile Thr Tyr Thr Pro Thr Phe Asp Leu
115                 120                 125                 130 aat ggg agt gcc gtg ctg aag atc gcg gag gtg tgc att gag acg tac    609
Asn Gly Ser Ala Val Leu Lys Ile Ala Glu Val Cys Ile Glu Thr Tyr
                135                 140                 145 ata agc agc tgt cac cag cgt agc ata aac act gct gtg cgg gca act    657
Ile Ser Ser Cys His Gln Arg Ser Ile Asn Thr Ala Val Arg Ala Thr
            150                 155                 160 ctc agt caa atg ctg agt gac ttg act tta cag tta cga cag agg cag    705
Leu Ser Gln Met Leu Ser Asp Leu Thr Leu Gln Leu Arg Gln Arg Gln
        165                 170                 175 gag aat acg ata att gaa aac cca gat gtc cca cag gat ttc ggg aat    753
Glu Asn Thr Ile Ile Glu Asn Pro Asp Val Pro Gln Asp Phe Gly Asn
    180                 185                 190 caa ggg tca aca gta gag tcc ctc tgt gat gat gtt gtc tct gta ctc    801
Gln Gly Ser Thr Val Glu Ser Leu Cys Asp Asp Val Val Ser Val Leu
195                 200                 205                 210
```

-continued

| | | |
|---|---|---|
| acc gtc ctg tgt gag aag ctg caa gcc gcc ata aat gac agc cag cag<br>Thr Val Leu Cys Glu Lys Leu Gln Ala Ala Ile Asn Asp Ser Gln Gln<br>                215                      220                      225 | 849 |
| ctg cag ctt ctc tac ctg gag tgc atc ctg tct gtg ctc agc agc tcc<br>Leu Gln Leu Leu Tyr Leu Glu Cys Ile Leu Ser Val Leu Ser Ser Ser<br>                230                      235                      240 | 897 |
| tcc tcc tcc atg cac ctg cac agg cgc ttc acg gac ctg atc tgg aaa<br>Ser Ser Ser Met His Leu His Arg Arg Phe Thr Asp Leu Ile Trp Lys<br>            245                      250                      255 | 945 |
| aac ctc tgc cct gct ctc atc gtg atc ttg ggg aat cca att cat gac<br>Asn Leu Cys Pro Ala Leu Ile Val Ile Leu Gly Asn Pro Ile His Asp<br>260                      265                      270 | 993 |
| aaa acc atc acc tct gct cac acc agc agc acc agt acc agc ctg gag<br>Lys Thr Ile Thr Ser Ala His Thr Ser Ser Thr Ser Thr Ser Leu Glu<br>275                      280                      285                      290 | 1041 |
| tcg gac tct gcg tct ccg gga gtg tct gac cac ggc cga gga tca ggc<br>Ser Asp Ser Ala Ser Pro Gly Val Ser Asp His Gly Arg Gly Ser Gly<br>                295                      300                      305 | 1089 |
| tgc tcc tgc act gcg ccg gcc ctg agc gga cct gtg gct cgg act atc<br>Cys Ser Cys Thr Ala Pro Ala Leu Ser Gly Pro Val Ala Arg Thr Ile<br>            310                      315                      320 | 1137 |
| tat tac atc gca gcc gag ctg gtc cgg ctg gtg ggg tct gtg gac tcc<br>Tyr Tyr Ile Ala Ala Glu Leu Val Arg Leu Val Gly Ser Val Asp Ser<br>                325                      330                      335 | 1185 |
| atg aag ccc gtg ctc cag tcc ctc tac cac cga gtg ctg ctc tac ccc<br>Met Lys Pro Val Leu Gln Ser Leu Tyr His Arg Val Leu Leu Tyr Pro<br>340                      345                      350 | 1233 |
| cca ccc cag cac cgg gtg gaa gcc atc aaa ata atg aaa gag ata ctt<br>Pro Pro Gln His Arg Val Glu Ala Ile Lys Ile Met Lys Glu Ile Leu<br>355                      360                      365                      370 | 1281 |
| ggg agc cca cag cgt ctc tgt gac ttg gca gga ccc agc tcc act gaa<br>Gly Ser Pro Gln Arg Leu Cys Asp Leu Ala Gly Pro Ser Ser Thr Glu<br>                375                      380                      385 | 1329 |
| tca gag tcc aga aaa aga tca att tca aaa aga aag tct cat ctg gat<br>Ser Glu Ser Arg Lys Arg Ser Ile Ser Lys Arg Lys Ser His Leu Asp<br>            390                      395                      400 | 1377 |
| ctc ctc aaa ctc atc atg gat ggc atg acc gaa gca tgc atc aag ggt<br>Leu Leu Lys Leu Ile Met Asp Gly Met Thr Glu Ala Cys Ile Lys Gly<br>                405                      410                      415 | 1425 |
| ggc atc gaa gct tgc tat gca gcc gtg tcc tgt gtc tgc acc ttg ctg<br>Gly Ile Glu Ala Cys Tyr Ala Ala Val Ser Cys Val Cys Thr Leu Leu<br>420                      425                      430 | 1473 |
| ggt gcc ctg gat gag ctc agc cag ggg aag ggc ttg agc gaa ggt cag<br>Gly Ala Leu Asp Glu Leu Ser Gln Gly Lys Gly Leu Ser Glu Gly Gln<br>435                      440                      445                      450 | 1521 |
| gtg caa ctg ctg ctt ctg cgc ctt gag gag ctg aag gat ggg gct gag<br>Val Gln Leu Leu Leu Leu Arg Leu Glu Glu Leu Lys Asp Gly Ala Glu<br>                455                      460                      465 | 1569 |
| tgg agc cga gat tcc atg gag atc aat gag gct gac ttc cgc tgg cag<br>Trp Ser Arg Asp Ser Met Glu Ile Asn Glu Ala Asp Phe Arg Trp Gln<br>            470                      475                      480 | 1617 |
| cgg cga gtg ctg tcc tca gaa cac acg ccg tgg gag tca ggg aac gag<br>Arg Arg Val Leu Ser Ser Glu His Thr Pro Trp Glu Ser Gly Asn Glu<br>                485                      490                      495 | 1665 |
| agg agc ctt gac atc agc atc agt gtc acc aca gac aca ggc cag acc<br>Arg Ser Leu Asp Ile Ser Ile Ser Val Thr Thr Asp Thr Gly Gln Thr<br>500                      505                      510 | 1713 |
| act ctc gag gga gag ttg ggt cag act aca ccc gag gac cat tcg gga<br>Thr Leu Glu Gly Glu Leu Gly Gln Thr Thr Pro Glu Asp His Ser Gly<br>515                      520                      525                      530 | 1761 |

```
aac cac aag aac agt ctc aag tcg cca gcc atc cca gag ggt aag gag    1809
Asn His Lys Asn Ser Leu Lys Ser Pro Ala Ile Pro Glu Gly Lys Glu
            535                 540                 545 acg ctg agc aaa gta ttg gaa aca gag gcg gta gac cag cca gat gtc    1857
Thr Leu Ser Lys Val Leu Glu Thr Glu Ala Val Asp Gln Pro Asp Val
        550                 555                 560 gtg cag aga agc cac acg gtc cct tac cct gac ata act aac ttc ctg    1905
Val Gln Arg Ser His Thr Val Pro Tyr Pro Asp Ile Thr Asn Phe Leu
        565                 570                 575 tca gta gac tgc agg aca agg tcc tat gga tct agg tat agt gag agc    1953
Ser Val Asp Cys Arg Thr Arg Ser Tyr Gly Ser Arg Tyr Ser Glu Ser
        580                 585                 590 aat ttt agc gtt gat gac caa gac ctt tct agg aca gag ttt gat tcc    2001
Asn Phe Ser Val Asp Asp Gln Asp Leu Ser Arg Thr Glu Phe Asp Ser
595                 600                 605                 610 tgt gat cag tac tct atg gca gca gaa aag gac tcg ggc agg tcc gac    2049
Cys Asp Gln Tyr Ser Met Ala Ala Glu Lys Asp Ser Gly Arg Ser Asp
                615                 620                 625 gtg tca gac att ggg tcg gac aac tgt tca cta gcc gat gaa gag cag    2097
Val Ser Asp Ile Gly Ser Asp Asn Cys Ser Leu Ala Asp Glu Glu Gln
        630                 635                 640 aca ccc cgg gac tgc cta ggc cac cgg tcc ctg cga act gcc gcc ctg    2145
Thr Pro Arg Asp Cys Leu Gly His Arg Ser Leu Arg Thr Ala Ala Leu
        645                 650                 655 tct cta aaa ctg ctg aag aac cag gag gcg gat cag cac agc gcc agg    2193
Ser Leu Lys Leu Leu Lys Asn Gln Glu Ala Asp Gln His Ser Ala Arg
        660                 665                 670 ctg ttc ata cag tcc ctg gaa ggc ctc ctc cct cgg ctc ctg tct ctc    2241
Leu Phe Ile Gln Ser Leu Glu Gly Leu Leu Pro Arg Leu Leu Ser Leu
675                 680                 685                 690 tcc aat gta gag gag gtg gac acc gct ctg cag aac ttt gcc tct act    2289
Ser Asn Val Glu Glu Val Asp Thr Ala Leu Gln Asn Phe Ala Ser Thr
                695                 700                 705 ttc tgc tca ggc atg atg cac tct cct ggc ttt gac ggg aat agc agc    2337
Phe Cys Ser Gly Met Met His Ser Pro Gly Phe Asp Gly Asn Ser Ser
        710                 715                 720 ctc agc ttc cag atg ctg atg aac gca gac agc ctc tac aca gct gca    2385
Leu Ser Phe Gln Met Leu Met Asn Ala Asp Ser Leu Tyr Thr Ala Ala
        725                 730                 735 cac tgc gcc ctg ctc ctc aac ctg aag ctc tcc cac ggt gac tac tac    2433
His Cys Ala Leu Leu Leu Asn Leu Lys Leu Ser His Gly Asp Tyr Tyr
        740                 745                 750 agg aag cgg ccg acc ctg gcg cca ggc gtg atg aag gac ttc atg aag    2481
Arg Lys Arg Pro Thr Leu Ala Pro Gly Val Met Lys Asp Phe Met Lys
755                 760                 765                 770 cag gtg cag acc agc ggc gtg ctg atg gtc ttc tct cag gcc tgg att    2529
Gln Val Gln Thr Ser Gly Val Leu Met Val Phe Ser Gln Ala Trp Ile
                775                 780                 785 gag gag ctc tac cat cag gtg ctc gac agg aac atg ctt gga gag gct    2577
Glu Glu Leu Tyr His Gln Val Leu Asp Arg Asn Met Leu Gly Glu Ala
        790                 795                 800 ggc tat tgg ggc agc cca gaa gat aac agc ctt ccc ctc atc aca atg    2625
Gly Tyr Trp Gly Ser Pro Glu Asp Asn Ser Leu Pro Leu Ile Thr Met
        805                 810                 815 ctg acc gat att gac ggc tta gag agc agt gcc att ggt ggc cag ctg    2673
Leu Thr Asp Ile Asp Gly Leu Glu Ser Ser Ala Ile Gly Gly Gln Leu
        820                 825                 830 atg gcc tcg gct gct aca gag tct cct ttc gcc cag agc agg aga att    2721
Met Ala Ser Ala Ala Thr Glu Ser Pro Phe Ala Gln Ser Arg Arg Ile
```

-continued

| | |
|---|---|
| gat gac tcc aca gtg gca ggc gtg gca ttt gct cgc tat att ctg gtg<br>Asp Asp Ser Thr Val Ala Gly Val Ala Phe Ala Arg Tyr Ile Leu Val<br>855                    860                    865 | 2769 |
| ggc tgc tgg aag aac ttg atc gat act tta tca acc cca ctg act ggt<br>Gly Cys Trp Lys Asn Leu Ile Asp Thr Leu Ser Thr Pro Leu Thr Gly<br>870                    875                    880 | 2817 |
| cga atg gcg ggg agc tcc aaa ggg ctg gcc ttc att ctg gga gct gaa<br>Arg Met Ala Gly Ser Ser Lys Gly Leu Ala Phe Ile Leu Gly Ala Glu<br>885                    890                    895 | 2865 |
| ggc atc aaa gag cag aac cag aag gag cgg gac gcc atc tgc atg agc<br>Gly Ile Lys Glu Gln Asn Gln Lys Glu Arg Asp Ala Ile Cys Met Ser<br>900                    905                    910 | 2913 |
| ctc gac ggg ctg cgg aaa gcc gca cgg ctg agc tgc gct cta ggc gtt<br>Leu Asp Gly Leu Arg Lys Ala Ala Arg Leu Ser Cys Ala Leu Gly Val<br>915                    920                    925                    930 | 2961 |
| gct gct aac tgc gcc tca gcc ctt gcc cag atg gca gct gcc tcc tgt<br>Ala Ala Asn Cys Ala Ser Ala Leu Ala Gln Met Ala Ala Ala Ser Cys<br>935                    940                    945 | 3009 |
| gtc caa gaa gaa aaa gaa gag agg gag gcc caa gaa ccc agt gat gcc<br>Val Gln Glu Glu Lys Glu Glu Arg Glu Ala Gln Glu Pro Ser Asp Ala<br>950                    955                    960 | 3057 |
| atc aca caa gtg aaa cta aaa gtg gag cag aaa ctg gag cag att ggg<br>Ile Thr Gln Val Lys Leu Lys Val Glu Gln Lys Leu Glu Gln Ile Gly<br>965                    970                    975 | 3105 |
| aag gtg cag ggg gtg tgg ctg cac act gcc cac gtc ttg tgc atg gag<br>Lys Val Gln Gly Val Trp Leu His Thr Ala His Val Leu Cys Met Glu<br>980                    985                    990 | 3153 |
| gcc atc ctc agc gta ggc ctg gag atg gga agc cac aac ccg gac<br>Ala Ile Leu Ser Val Gly Leu Glu Met Gly Ser His Asn Pro Asp<br>995                    1000                  1005 | 3198 |
| tgc tgg cca cac gtg ttc agg gtg tgt gaa tac gtg ggc acc ctg<br>Cys Trp Pro His Val Phe Arg Val Cys Glu Tyr Val Gly Thr Leu<br>1010                   1015                  1020 | 3243 |
| gag cac aac cac ttc agc gat ggt gcc tcg cag ccc cct ctg acc<br>Glu His Asn His Phe Ser Asp Gly Ala Ser Gln Pro Pro Leu Thr<br>1025                   1030                  1035 | 3288 |
| atc agc cag ccc cag aag gcc act gga agc gct ggc ctc ctt ggg<br>Ile Ser Gln Pro Gln Lys Ala Thr Gly Ser Ala Gly Leu Leu Gly<br>1040                   1045                  1050 | 3333 |
| gac ccc gag tgt gag ggc tcg ccc ccc gag cac agc ccg gag cag<br>Asp Pro Glu Cys Glu Gly Ser Pro Pro Glu His Ser Pro Glu Gln<br>1055                   1060                  1065 | 3378 |
| ggg cgc tcc ctg agc acg gcc cct gtc gtc cag ccc ctg tcc atc<br>Gly Arg Ser Leu Ser Thr Ala Pro Val Val Gln Pro Leu Ser Ile<br>1070                   1075                  1080 | 3423 |
| cag gac ctc gtc cgg gaa ggc agc cgg ggt cgg gcc tcc gac ttc<br>Gln Asp Leu Val Arg Glu Gly Ser Arg Gly Arg Ala Ser Asp Phe<br>1085                   1090                  1095 | 3468 |
| cgc ggc ggg agc ctc atg agc ggg agc agc gcg gcc aag gtg gtg<br>Arg Gly Gly Ser Leu Met Ser Gly Ser Ser Ala Ala Lys Val Val<br>1100                   1105                  1110 | 3513 |
| ctc acc ctc tcc acg caa gcc gac agg ctc ttt gaa gat gct acg<br>Leu Thr Leu Ser Thr Gln Ala Asp Arg Leu Phe Glu Asp Ala Thr<br>1115                   1120                  1125 | 3558 |
| gat aag ttg aac ctc atg gcc ttg gga ggt ttt ctt tac cag ctg<br>Asp Lys Leu Asn Leu Met Ala Leu Gly Gly Phe Leu Tyr Gln Leu<br>1130                   1135                  1140 | 3603 |
| aag aaa gca tcg cag tct cag ctt ttc cat tct gtt aca gat aca | 3648 |

| | | | | | | | | | | | | |
|---|---|---|---|---|---|---|---|---|---|---|---|---|
| Lys | Lys | Ala | Ser | Gln | Ser | Gln | Leu | Phe | His | Ser | Val | Thr | Asp | Thr |
| 1145 | | | | 1150 | | | | | 1155 | | | |

| gtt | gat | tac | tct | ctg | gca | atg | cca | gga | gaa | gtt | aaa | tcc | act | caa | 3693 |
|---|---|---|---|---|---|---|---|---|---|---|---|---|---|---|---|
| Val | Asp | Tyr | Ser | Leu | Ala | Met | Pro | Gly | Glu | Val | Lys | Ser | Thr | Gln | |
| 1160 | | | | 1165 | | | | | 1170 | | | | | | |

| gac | cga | aaa | agc | gcc | ctc | cac | ctg | ttc | cgc | ctg | ggg | aat | gcc | atg | 3738 |
|---|---|---|---|---|---|---|---|---|---|---|---|---|---|---|---|
| Asp | Arg | Lys | Ser | Ala | Leu | His | Leu | Phe | Arg | Leu | Gly | Asn | Ala | Met | |
| 1175 | | | | 1180 | | | | | 1185 | | | | | | |

| ctg | agg | att | gtg | cgg | agc | aaa | gca | cgg | ccc | ctg | ctc | cac | gtg | atg | 3783 |
|---|---|---|---|---|---|---|---|---|---|---|---|---|---|---|---|
| Leu | Arg | Ile | Val | Arg | Ser | Lys | Ala | Arg | Pro | Leu | Leu | His | Val | Met | |
| 1190 | | | | 1195 | | | | | 1200 | | | | | | |

| cgc | tgc | tgg | agc | ctt | gtg | gcc | cca | cac | ctg | gtg | gag | gct | gct | tgc | 3828 |
|---|---|---|---|---|---|---|---|---|---|---|---|---|---|---|---|
| Arg | Cys | Trp | Ser | Leu | Val | Ala | Pro | His | Leu | Val | Glu | Ala | Ala | Cys | |
| 1205 | | | | 1210 | | | | | 1215 | | | | | | |

| cat | aag | gaa | aga | cat | gtg | tct | cag | aag | gct | gtt | tcc | ttc | atc | cat | 3873 |
|---|---|---|---|---|---|---|---|---|---|---|---|---|---|---|---|
| His | Lys | Glu | Arg | His | Val | Ser | Gln | Lys | Ala | Val | Ser | Phe | Ile | His | |
| 1220 | | | | 1225 | | | | | 1230 | | | | | | |

| gac | ata | ctg | aca | gaa | gtc | ctc | act | gac | tgg | aat | gag | cca | cct | cat | 3918 |
|---|---|---|---|---|---|---|---|---|---|---|---|---|---|---|---|
| Asp | Ile | Leu | Thr | Glu | Val | Leu | Thr | Asp | Trp | Asn | Glu | Pro | Pro | His | |
| 1235 | | | | 1240 | | | | | 1245 | | | | | | |

| ttt | cac | ttc | aat | gaa | gca | ctc | ttc | cga | cct | ttc | gag | cgc | att | atg | 3963 |
|---|---|---|---|---|---|---|---|---|---|---|---|---|---|---|---|
| Phe | His | Phe | Asn | Glu | Ala | Leu | Phe | Arg | Pro | Phe | Glu | Arg | Ile | Met | |
| 1250 | | | | 1255 | | | | | 1260 | | | | | | |

| cag | ctg | gaa | ttg | tgt | gat | gag | gac | gtc | caa | gac | cag | gtt | gtc | aca | 4008 |
|---|---|---|---|---|---|---|---|---|---|---|---|---|---|---|---|
| Gln | Leu | Glu | Leu | Cys | Asp | Glu | Asp | Val | Gln | Asp | Gln | Val | Val | Thr | |
| 1265 | | | | 1270 | | | | | 1275 | | | | | | |

| tcc | att | ggt | gag | ctg | gtt | gaa | gtg | tgt | tcc | acg | cag | atc | cag | tcg | 4053 |
|---|---|---|---|---|---|---|---|---|---|---|---|---|---|---|---|
| Ser | Ile | Gly | Glu | Leu | Val | Glu | Val | Cys | Ser | Thr | Gln | Ile | Gln | Ser | |
| 1280 | | | | 1285 | | | | | 1290 | | | | | | |

| gga | tgg | aga | ccc | ttg | ttc | agt | gcc | ctg | gaa | aca | gtg | cat | ggc | ggg | 4098 |
|---|---|---|---|---|---|---|---|---|---|---|---|---|---|---|---|
| Gly | Trp | Arg | Pro | Leu | Phe | Ser | Ala | Leu | Glu | Thr | Val | His | Gly | Gly | |
| 1295 | | | | 1300 | | | | | 1305 | | | | | | |

| aac | aag | tca | gag | atg | aag | gag | tac | ctg | gtt | ggt | gac | tac | tcc | atg | 4143 |
|---|---|---|---|---|---|---|---|---|---|---|---|---|---|---|---|
| Asn | Lys | Ser | Glu | Met | Lys | Glu | Tyr | Leu | Val | Gly | Asp | Tyr | Ser | Met | |
| 1310 | | | | 1315 | | | | | 1320 | | | | | | |

| gga | aaa | ggc | caa | gct | cca | gtg | ttt | gat | gta | ttt | gaa | gct | ttt | ctc | 4188 |
|---|---|---|---|---|---|---|---|---|---|---|---|---|---|---|---|
| Gly | Lys | Gly | Gln | Ala | Pro | Val | Phe | Asp | Val | Phe | Glu | Ala | Phe | Leu | |
| 1325 | | | | 1330 | | | | | 1335 | | | | | | |

| aat | act | gac | aac | atc | cag | gtc | ttt | gct | aat | gca | gcc | act | agc | tac | 4233 |
|---|---|---|---|---|---|---|---|---|---|---|---|---|---|---|---|
| Asn | Thr | Asp | Asn | Ile | Gln | Val | Phe | Ala | Asn | Ala | Ala | Thr | Ser | Tyr | |
| 1340 | | | | 1345 | | | | | 1350 | | | | | | |

| atc | atg | tgc | ctt | atg | aag | ttt | gtc | aaa | gga | ctg | ggg | gag | gtg | gac | 4278 |
|---|---|---|---|---|---|---|---|---|---|---|---|---|---|---|---|
| Ile | Met | Cys | Leu | Met | Lys | Phe | Val | Lys | Gly | Leu | Gly | Glu | Val | Asp | |
| 1355 | | | | 1360 | | | | | 1365 | | | | | | |

| tgt | aaa | gag | att | gga | gac | tgt | gcc | cca | gca | ccc | gga | gcc | ccg | tcc | 4323 |
|---|---|---|---|---|---|---|---|---|---|---|---|---|---|---|---|
| Cys | Lys | Glu | Ile | Gly | Asp | Cys | Ala | Pro | Ala | Pro | Gly | Ala | Pro | Ser | |
| 1370 | | | | 1375 | | | | | 1380 | | | | | | |

| aca | gac | ctg | tgc | ctc | ccg | gcc | ctg | gat | tac | ctc | agg | cgc | tgc | tct | 4368 |
|---|---|---|---|---|---|---|---|---|---|---|---|---|---|---|---|
| Thr | Asp | Leu | Cys | Leu | Pro | Ala | Leu | Asp | Tyr | Leu | Arg | Arg | Cys | Ser | |
| 1385 | | | | 1390 | | | | | 1395 | | | | | | |

| cag | tta | ttg | gcc | aaa | atc | tac | aaa | atg | ccc | ttg | aag | cca | ata | ttc | 4413 |
|---|---|---|---|---|---|---|---|---|---|---|---|---|---|---|---|
| Gln | Leu | Leu | Ala | Lys | Ile | Tyr | Lys | Met | Pro | Leu | Lys | Pro | Ile | Phe | |
| 1400 | | | | 1405 | | | | | 1410 | | | | | | |

| ctt | agt | ggg | aga | ctt | gcc | ggc | ttg | cct | cga | aga | ctt | cag | gaa | cag | 4458 |
|---|---|---|---|---|---|---|---|---|---|---|---|---|---|---|---|
| Leu | Ser | Gly | Arg | Leu | Ala | Gly | Leu | Pro | Arg | Arg | Leu | Gln | Glu | Gln | |
| 1415 | | | | 1420 | | | | | 1425 | | | | | | |

| tca | gcc | agc | agt | gag | gat | gga | att | gaa | tca | gtc | ctg | tct | gat | ttt | 4503 |
|---|---|---|---|---|---|---|---|---|---|---|---|---|---|---|---|
| Ser | Ala | Ser | Ser | Glu | Asp | Gly | Ile | Glu | Ser | Val | Leu | Ser | Asp | Phe | |
| 1430 | | | | 1435 | | | | | 1440 | | | | | | |

```
                                                      -continued
gat gat gac acc ggt ctg ata gaa gtc tgg ata atc ctg ctg gag        4548
Asp Asp Asp Thr Gly Leu Ile Glu Val Trp Ile Ile Leu Leu Glu
1445                1450                1455 cag ctg aca gcg gct gtg tcc aat tgt cca cgg cag cac caa cca        4593
Gln Leu Thr Ala Ala Val Ser Asn Cys Pro Arg Gln His Gln Pro
1460                1465                1470 cca act ctg gat tta ctc ttt gag ctg ttg aga gat gtg acg aaa        4638
Pro Thr Leu Asp Leu Leu Phe Glu Leu Leu Arg Asp Val Thr Lys
1475                1480                1485 aca cca gga cca ggg ttt ggt atc tat gca gtg gtt cac ctc ctc        4683
Thr Pro Gly Pro Gly Phe Gly Ile Tyr Ala Val Val His Leu Leu
1490                1495                1500 ctt cct gtg atg tcc gtt tgg ctc cgc cgg agc cat aaa gac cat        4728
Leu Pro Val Met Ser Val Trp Leu Arg Arg Ser His Lys Asp His
1505                1510                1515 tcc tac tgg gat atg gcc tct gcc aat ttc aag cac gct att ggt        4773
Ser Tyr Trp Asp Met Ala Ser Ala Asn Phe Lys His Ala Ile Gly
1520                1525                1530 ctg tcc tgt gag ctg gtg gtg gag cac att caa agc ttt cta cat        4818
Leu Ser Cys Glu Leu Val Val Glu His Ile Gln Ser Phe Leu His
1535                1540                1545 tca gat atc agg tac gag agc atg atc aat acc atg ctg aag gac        4863
Ser Asp Ile Arg Tyr Glu Ser Met Ile Asn Thr Met Leu Lys Asp
1550                1555                1560 ctc ttt gag ttg ctg gtc gcc tgt gtg gcc aag ccc act gaa acc        4908
Leu Phe Glu Leu Leu Val Ala Cys Val Ala Lys Pro Thr Glu Thr
1565                1570                1575 atc tcc aga gtg ggc tgc tcc tgt att aga tac gtc ctt gtg aca        4953
Ile Ser Arg Val Gly Cys Ser Cys Ile Arg Tyr Val Leu Val Thr
1580                1585                1590 gcg ggc cct gtg ttc act gag gag atg tgg agg ctt gcc tgc tgt        4998
Ala Gly Pro Val Phe Thr Glu Glu Met Trp Arg Leu Ala Cys Cys
1595                1600                1605 gcc ctg caa gat gcg ttc tct gcc aca ctc aag cca gtg aag gac        5043
Ala Leu Gln Asp Ala Phe Ser Ala Thr Leu Lys Pro Val Lys Asp
1610                1615                1620 ctg ctg ggc tgc ttc cac agc ggc acg gag agc ttc agc ggg gaa        5088
Leu Leu Gly Cys Phe His Ser Gly Thr Glu Ser Phe Ser Gly Glu
1625                1630                1635 ggc tgc cag gtg cga gtg gcg gcc ccg tcc tcc tcc cca agt gcc        5133
Gly Cys Gln Val Arg Val Ala Ala Pro Ser Ser Ser Pro Ser Ala
1640                1645                1650 gag gcc gag tac tgg cgc atc cga gcc atg gcc cag cag gtg ttt        5178
Glu Ala Glu Tyr Trp Arg Ile Arg Ala Met Ala Gln Gln Val Phe
1655                1660                1665 atg ctg gac acc cag tgc tca cca aag aca cca aac aac ttt gac        5223
Met Leu Asp Thr Gln Cys Ser Pro Lys Thr Pro Asn Asn Phe Asp
1670                1675                1680 cac gct cag tcc tgc cag ctc att att gag ctg cct cct gat gaa        5268
His Ala Gln Ser Cys Gln Leu Ile Ile Glu Leu Pro Pro Asp Glu
1685                1690                1695 aaa cca aat gga cac acc aag aaa agc gtg tct ttc agg gaa att        5313
Lys Pro Asn Gly His Thr Lys Lys Ser Val Ser Phe Arg Glu Ile
1700                1705                1710 gtg gtg agc ctg ctg tct cat cag gtg tta ctc cag aac tta tat        5358
Val Val Ser Leu Leu Ser His Gln Val Leu Leu Gln Asn Leu Tyr
1715                1720                1725 gac atc ttg tta gaa gag ttt gtc aaa ggc ccc tct cct gga gag        5403
Asp Ile Leu Leu Glu Glu Phe Val Lys Gly Pro Ser Pro Gly Glu
1730                1735                1740
```

-continued

| | | |
|---|---|---|
| gaa aag acg ata caa gtg cca gaa gcc aag ctg gct ggc ttc ctc<br>Glu Lys Thr Ile Gln Val Pro Glu Ala Lys Leu Ala Gly Phe Leu<br>1745                    1750                    1755 | 5448 |
| aga tac atc tct atg cag aac ttg gca gtc ata ttc gac ctg ctg<br>Arg Tyr Ile Ser Met Gln Asn Leu Ala Val Ile Phe Asp Leu Leu<br>1760                    1765                    1770 | 5493 |
| ctg gac tct tat agg act gcc agg gag ttt gac acc agc ccc ggg<br>Leu Asp Ser Tyr Arg Thr Ala Arg Glu Phe Asp Thr Ser Pro Gly<br>1775                    1780                    1785 | 5538 |
| ctg aag tgc ctg ctg aag aaa gtg tct ggc atc ggg ggc gcc gcc<br>Leu Lys Cys Leu Leu Lys Lys Val Ser Gly Ile Gly Gly Ala Ala<br>1790                    1795                    1800 | 5583 |
| aac ctc tac cgc cag tct gcg atg agc ttt aac att tat ttc cac<br>Asn Leu Tyr Arg Gln Ser Ala Met Ser Phe Asn Ile Tyr Phe His<br>1805                    1810                    1815 | 5628 |
| gcc ctg gtg tgt gct gtt ctc acc aat caa gaa acc atc acg gcc<br>Ala Leu Val Cys Ala Val Leu Thr Asn Gln Glu Thr Ile Thr Ala<br>1820                    1825                    1830 | 5673 |
| gag caa gtg aag aag gtc ctt ttt gag gac gac gag aga agc acg<br>Glu Gln Val Lys Lys Val Leu Phe Glu Asp Asp Glu Arg Ser Thr<br>1835                    1840                    1845 | 5718 |
| gat tct tcc cag cag tgt tca tct gag gat gaa gac atc ttt gag<br>Asp Ser Ser Gln Gln Cys Ser Ser Glu Asp Glu Asp Ile Phe Glu<br>1850                    1855                    1860 | 5763 |
| gaa acc gcc cag gtc agc ccc ccg aga ggc aag gag aag aga cag<br>Glu Thr Ala Gln Val Ser Pro Pro Arg Gly Lys Glu Lys Arg Gln<br>1865                    1870                    1875 | 5808 |
| tgg cgg gca cgg atg ccc ttg ctc agc gtc cag cct gtc agc aac<br>Trp Arg Ala Arg Met Pro Leu Leu Ser Val Gln Pro Val Ser Asn<br>1880                    1885                    1890 | 5853 |
| gca gat tgg gtg tgg ctg gtc aag agg ctg cac aag ctg tgc atg<br>Ala Asp Trp Val Trp Leu Val Lys Arg Leu His Lys Leu Cys Met<br>1895                    1900                    1905 | 5898 |
| gaa ctg tgc aac aac tac atc cag atg cac ttg gac ctg gag aac<br>Glu Leu Cys Asn Asn Tyr Ile Gln Met His Leu Asp Leu Glu Asn<br>1910                    1915                    1920 | 5943 |
| tgt atg gag gag cct ccc atc ttc aag ggc gac ccg ttc ttc atc<br>Cys Met Glu Glu Pro Pro Ile Phe Lys Gly Asp Pro Phe Phe Ile<br>1925                    1930                    1935 | 5988 |
| ctg ccc tcc ttc cag tcc gag tca tcc acc cca tcc acc ggg ggc<br>Leu Pro Ser Phe Gln Ser Glu Ser Ser Thr Pro Ser Thr Gly Gly<br>1940                    1945                    1950 | 6033 |
| ttc tct ggg aaa gaa acc cct tcc gag gat gac aga agc cag tcc<br>Phe Ser Gly Lys Glu Thr Pro Ser Glu Asp Asp Arg Ser Gln Ser<br>1955                    1960                    1965 | 6078 |
| cgg gag cac atg ggc gag tcc ctg agc ctg aag gcc ggt ggt ggg<br>Arg Glu His Met Gly Glu Ser Leu Ser Leu Lys Ala Gly Gly Gly<br>1970                    1975                    1980 | 6123 |
| gac ctg ctg ctg ccc ccc agc ccc aaa gtg gag aag aag gat ccc<br>Asp Leu Leu Leu Pro Pro Ser Pro Lys Val Glu Lys Lys Asp Pro<br>1985                    1990                    1995 | 6168 |
| agc cgg aag aag gag tgg tgg gag aat gcg ggg aac aaa atc tac<br>Ser Arg Lys Lys Glu Trp Trp Glu Asn Ala Gly Asn Lys Ile Tyr<br>2000                    2005                    2010 | 6213 |
| acc atg gca gcc gac aag acc att tca aag ttg atg acc gaa tac<br>Thr Met Ala Ala Asp Lys Thr Ile Ser Lys Leu Met Thr Glu Tyr<br>2015                    2020                    2025 | 6258 |
| aaa aag agg aaa cag cag cac aac ctg tcc gcg ttc ccc aaa gag<br>Lys Lys Arg Lys Gln Gln His Asn Leu Ser Ala Phe Pro Lys Glu | 6303 |

|  |  |  |  |  |  |  |  |  |  |  |  |  |
|---|---|---|---|---|---|---|---|---|---|---|---|---|
| | | 2030 | | | | 2035 | | | | 2040 | | |
| gtc | aaa | gtg | gag | aag | aaa | gga | gag | cca | ctg | ggt | ccc | agg | ggc | cag | 6348 |
| Val | Lys | Val | Glu | Lys | Lys | Gly | Glu | Pro | Leu | Gly | Pro | Arg | Gly | Gln | |
| 2045 | | | | | 2050 | | | | | 2055 | | | | | |
| gac | tcc | ccg | ctg | ctt | cag | cgt | ccc | cag | cac | ttg | atg | gac | caa | ggg | 6393 |
| Asp | Ser | Pro | Leu | Leu | Gln | Arg | Pro | Gln | His | Leu | Met | Asp | Gln | Gly | |
| 2060 | | | | | 2065 | | | | | 2070 | | | | | |
| caa | atg | cgg | cat | tcc | ttc | agc | gca | ggc | ccc | gag | ctg | ctg | cga | cag | 6438 |
| Gln | Met | Arg | His | Ser | Phe | Ser | Ala | Gly | Pro | Glu | Leu | Leu | Arg | Gln | |
| 2075 | | | | | 2080 | | | | | 2085 | | | | | |
| gac | aag | agg | ccc | cgc | tca | ggc | tcc | acc | ggg | agc | tcc | ctc | agt | gtc | 6483 |
| Asp | Lys | Arg | Pro | Arg | Ser | Gly | Ser | Thr | Gly | Ser | Ser | Leu | Ser | Val | |
| 2090 | | | | | 2095 | | | | | 2100 | | | | | |
| tcg | gtg | aga | gac | gca | gaa | gca | cag | atc | cag | gca | tgg | acc | aac | atg | 6528 |
| Ser | Val | Arg | Asp | Ala | Glu | Ala | Gln | Ile | Gln | Ala | Trp | Thr | Asn | Met | |
| 2105 | | | | | 2110 | | | | | 2115 | | | | | |
| gtg | cta | aca | gtt | ctc | aat | cag | att | cag | att | ctc | cca | gac | cag | acc | 6573 |
| Val | Leu | Thr | Val | Leu | Asn | Gln | Ile | Gln | Ile | Leu | Pro | Asp | Gln | Thr | |
| 2120 | | | | | 2125 | | | | | 2130 | | | | | |
| ttc | acg | gcc | ctc | cag | ccc | gca | gtg | ttc | ccg | tgc | atc | agt | cag | ctg | 6618 |
| Phe | Thr | Ala | Leu | Gln | Pro | Ala | Val | Phe | Pro | Cys | Ile | Ser | Gln | Leu | |
| 2135 | | | | | 2140 | | | | | 2145 | | | | | |
| acc | tgt | cac | gtg | acc | gac | atc | aga | gtt | cgc | cag | gct | gtg | agg | gag | 6663 |
| Thr | Cys | His | Val | Thr | Asp | Ile | Arg | Val | Arg | Gln | Ala | Val | Arg | Glu | |
| 2150 | | | | | 2155 | | | | | 2160 | | | | | |
| tgg | ctg | ggc | agg | gtg | ggc | cgt | gtc | tat | gac | atc | att | gtg | tag | | 6705 |
| Trp | Leu | Gly | Arg | Val | Gly | Arg | Val | Tyr | Asp | Ile | Ile | Val | | | |
| 2165 | | | | | 2170 | | | | | 2175 | | | | | |

```
ccgactcctg ttctactctc ccaccaaata acagtagtga gggttagagt cctgccaata      6765
cagctgttgc attttcccca ccactagccc cacttaaact actactactg tctcagagaa      6825
cagtgtttcc taatgtaaaa agcctttcca accactgatc agcattgggg ccatactaag      6885
gtttgtatct agatgacaca aacgatattc tgattttgca cattattata gaagaatcta      6945
taatccttga tatgtttcta actcttgaag tatatttccc agtgcttttg cttacagtgt      7005
tgtccccaaa tgggtcattt tcaaggatta ctcatttgaa acactatat  tgatccattt      7065
gatccatcat ttaaaaaata aatacaattc ctaaggcaat atctgctggt aagtcaagct      7125
gataaacact cagacatcta gtaccaggga ttattaattg gaggaagatt tatggttatg      7185
ggtctggctg ggaagaagac aactataaat acatattctt gggtgtcata atcaagaaag      7245
aggtgacttc tgttgtaaaa taatccagaa cacttcaaaa ttattcctaa atcattaaga      7305
ttttcaggta ttcaccaatt tccccatgta aggtactgtg ttgtaccttt atttctgtat      7365
ttctaaaaga agaagttct  ttcctagcag ggtttgaagt ctgtggctta tcagcctgtg      7425
acacagagta cccagtgaaa gtggctggta cgtagattgt caagagacat aagaccgacc      7485
agccaccctg gctgttcttg tggtgtttgt ttccatcccc aaggcaaaca aggaaaggaa      7545
aggaaagaag aaaaggtgcc ttagtccttt gttgcacttc catttccatg ccccacaatt      7605
gtctgaacat aaggtatagc atttggtttt taagaaaaca aaacattaag acgcaactca      7665
ttttatatca acacgcttgg aggaaaggga ctcaggaag  ggagcaggga gtgtgggtg      7725
gggatggatt atgatgaaat cattttcaat cttaaaatat aatacaacaa tcttgcaaaa      7785
ttatggtgtc agttacacaa gctcagtct  caaaatgaaa gtaatggaga aagacactga      7845
aatttagaaa attttgtcga tttaaaatat ttctcctatc taccaagtaa agttacccta      7905
tgtttgatgt ctttgcattc agaccaatat ttcaggtgga tatttctaag tattactaga      7965
```

-continued

```
aaatacgttt gaaagcttta tcttattatt tacagtattt ttatatttct tacattatcc    8025
taatgattga aaactcctca atcaagctta cttacacaca ttctacagag ttatttaagg    8085
catacattat aatctcccag ccccattcat aatgaataag tcacccttta aatataagac    8145
acaaattcta cagtattgaa ataaggattt aaagggtat ttgtaaactt tgccctcctt     8205
gagaaatatg gaactacctt agaggttaag aggaaggcag tgttctgact tctttaggtg    8265
atctgaaaaa aacacccta tcatccagtg taccatctag agatcaccac agaatccatt    8325
tttttcccag ttccacaaaa cactctgttt gccttcagtt tttactcact agacaataat    8385
tcaagtttag aaacaggtaa tcagctattt gatcttaaaa ggcaatgaat tgttgggata    8445
tcagtgaact atgttgtata cttttgaatt tttacatttt ataaatggaa ttgaaagttg    8505
gataactgct ttttttaaat tttccaacag aagtaacacc acagttgctt tgtttctttt    8565
tatagcttac ctgaggttca gttcttcttt gtgaacctgt gagtactcca cagtttactg    8625
ggggaaaagg cttcagtaaa gcagaggcta gaattacagt atttatacat agcaactttt    8685
cataaagtag aaaaattcaa aggaagctgt ctcaatttga gaataccagc tgggcacggt    8745
ggctcacgcc tgtaatccca gcacttactt gggaggcca aggtgggcag ataacctgcg     8805
gtcaggagtt tgagaccagg ctggacaaca tggtgaaacc tcgtctctac taaaaataca    8865
aaaattagcc aggtgtggta ggatgcacct gtaatcccag ctacttagga ggccgagaca    8925
ggagaatcgc tcgaacccag gaggcggacg ttgcagtgag ccaagattgc accattgcac    8985
tccagactgg gtgacaagag tgaaactcca tctaaaaaaa aaaaaaaaaa aaagtgaata    9045
ctgtatccca aagtatgtta gttgtttgtt tggaaatcag cattctcccc gatgctctat    9105
tatgggatcc aaaattcttg aacataagtt taccctgtac tgtgtccaaa cactgttcta    9165
gttctagcct gattatgggt cccaagaata aaaggatgag taggtgtaca gagctcttga    9225
cctacaattt tttaagagtg ttttggtacc ttcccattgt cttctctata actcagtcct    9285
aacatactct gcactcgagt taccagccat ccacactgac atcagatttc aaccagaacc    9345
atcactgagt gacagcagta cttctcagag gtatttgcag cttgatgcaa agtagtctct    9405
aatgagtagg cattcaggtg gttcttccca gcaggtggag aagaaaggga ggagatgaag    9465
aacactgaga ggggagtggc accttcccag gctgcccagc tcagtctctt gccctgttcc    9525
tgtgactcag ctgcccactc ccccaacttt gtttccctcc ctcccagtct ctgaaagtgt    9585
caggtgtttc tctcctcaca gtctcttttg cagcaacagt aagacaaaat tcaaggcagc    9645
cttttaaagt tacgaacagt tattagcatg tatttacaga cctaagcaga atgagagttt    9705
atacattgtt tttagttgcc tgtatttata gccaaaagta tattacctta aagttgagat    9765 cttttctcttc ttttcctaaa ttttggtaaa gtgtgcttca tgaaacaaac atctggaaaa    9825
ctccaagtat aagagaccct ggactgatga tggcccagcc aagtatatgg agggacagag    9885
ttctctctgt cattaatgag gacatcggtt ttcacaattg aacctcatgc actgtccaca    9945
gcatctcacc tagctcctgt atctcctgat ctgcttttaa aaatagttag ttaggctgcc   10005
tttttacacc accttctctc tctcccttg tggtaatttt ccagccttcc ccatagatat    10065
aaaactagaa caccttatg atttggggtc tatgtaatga ctgaccgata agaacccagg    10125
cagatgctaa catacttaac agctcgcatt aaaatacttt aaatcaggcg tgatggctca   10185
ttcctgtaat ctcaagcact tgggaggct aaggtgggtg gatctcttga ggtcaggagt    10245
tcgagaccaa cctggccaac gtggtgaaac cccgtctcta ctaaaaatac aaaattagcc   10305
```

```
gggcatggtg gcagctgcct gtaatcccag ctactcggga agctgaggca ggagaattgc    10365
ttgaacctgg gaggtgggga ttgcagtcag ccaagattgt tctgcagcat gggtgacaaa    10425
gtgagacttc gtctcaagta aataaaacta aaattttaa atcaaacatg acaaaaatgt     10485
taatataatt cagaagtacc ttgaaattga acatatttg tgcaatgatc attaggcttt     10545
ttgtccttgt tgttttaaaa tgaggcttat acagagtgag ttgagagtca agtagccttc    10605
gctgtgagac ggtaatgcag ttatataata gatacccttg actttgccag attcatcaca    10665
atactgctta tacaggaaag ttttctcaga aaggaaaatc cattagtatc agtcccatca    10725
agccaaacag aatgaagacc tttgatagta atagcaagag gttacaaata gcagggagga    10785
ggcgagtagt gaatgtcact gtgattgcaa acccttacct gtattatcac acgtagtcct    10845
cacaacaacc ttgtgagaca agtgttgtgt tcctcatttt ttcagagggg aacacagacc    10905
cagagaggtt aagaaatttg cccaagataa caagtaaaag gcaaagttgg ttgcaaaaga    10965
ggtgtttctg aattcaaggg ccatactctc tctctgacaa catgctctaa gtccatagag    11025
taagcactct agtatgaaaa aaagtttcaa ggaacgaggc catgaaaatg agactatttg    11085
acatctcaga tctgtctggg atgttatgga ggttttaaa aataaagttg aaaaagaaa      11145 atgaatcatg tttatacata aaaaaatcac atgtaacaca tttcaagtgt ttgaaaataa    11205
aaccaaaatc taaactttag tcttcaagca gacattcagt gttactttag aaaactcact    11265
gaattaggtg gaaatgatgg aataatacta ttcatggcca gctattaaca cagaagaaca    11325
tggcagtgtg tgtctggaac ggcatgcaca atttgtaaac ctttttcaaa tatcatttaa    11385
tcaactcaga ataaagtgcc ctgtagccaa cagtgcctct ttacttgctt ctctgggaaa    11445
tacatggtac taaattagta gcacaaagtt tgggaatatg caaaataatg gataaccatt    11505
tttcaaaatg tacattctct gaagaggaag cagctggttg acaggatttt cttgaagagc    11565
caggtgctaa gggcatcagg tcgacatcca tagtaaccat gtgccataac atctacacat    11625
ttccacttgt tttacagaca aggtaacagg cagaaggaaa atccagagtc ttgcagtaag    11685
cagatgacaa aacttcaata tgcttgggca ccacttaggt gaccccaggg agatttagtg    11745
tggccttagg aaagcaaaag agcacttttt attggaaata tgagcttgtc actgggaaag    11805
atttgtaaaa ttgatcaaga acttgattta taattatgcc tcaaaaaaaa aagttctcat    11865
ttagtagtgg agcaatctag aaaacatacc ttttttgttt gtttggaaga tcctcttttcc   11925 ctggctgtat tgtagtgttt gctatttgat gtggaaataa ctaataactt aagattttgg    11985
aacagaacac cctttagatt tccaaaacac aattcttatt tcaggaaga cagaccaaaa     12045 atatctcctg agatcattgg tttctttata aattgtggta ccactccatc attgaagaga    12105
aaccactacc acaccactag caccatacag aaccttttct ctgtatcttt gtacaatact    12165
acaaaggggt accagggagg agagagtggc tgaccacttt agtgacaaaa cagcactcca    12225
ctgctggtga atcccatcta attatggtcc ttccacccctt tcaaccacc aacaactgtt    12285 cgtactgtta attcctatcc tgaaggttta accagtggtt gtctagtatc ttctgtcttt    12345
agaacagtgg ttctcaaact ttagtacaca tcagcatcac ctggagggcc ttttttttaaa   12405 ataagacaca gattgctggg ctcatggtca gagttcccag ttaagtaaat caggaaattt    12465
gtatttctaa caagtttata ggtgaggcca atactgctgt tttgggaact atgctttgag    12525
aaccactgcc ttgaaaaaat ttccaacttc tacctttaag atcagcctga cttatcaaac    12585
gctagagaaa aactgaatct acccttgggc agatgacttg ggattggatt ctatacagca    12645
gtcttgctca atcttcccag tttccagttt tattatacca acaattggtt tttacaagct    12705
```

```
agaagacaat gaatgtataa gttctatgga acagtgagat aaatctaagc ttcttgtctt    12765
tgtatttaga aacattgatt ctatggatga tcatttgtat catgttgacc ctttgacttg    12825
tactgaaggt gattttaaat ttaagtatgt agtgtttgaa tttcttccat ccatgtcgtt    12885
ttaatgagat gtttccatgt cagctccttt acagccttgg ctcctggctt acagattttt    12945
gaatagttgt ttgcttgcca gttgttttac atctttcatt ggccaccaaa atattagcca    13005
tttgagatga gatgagacta cttgttgtac cttcatcttt catttaattt tctggcgtaa    13065
attaacattt taatttcata tatatctgta aagagtctac ccaaaggctt cacggaaatt    13125
tgcaaaatga actaattccc ttttaagcag caggtgtgcc tgttttttgac ttttcagtaa    13185 atatgttgtt tgtgcacata tctacatggt ggagaccata ttcattattt catcttccaa    13245
ataatgggaa aaatataaaa gtgaatcagt gtgctttggg aattcagtga atcatgttta    13305
actcatatag aggggccctt agtttatctc ttctttactg aattaattag ttttggaaat    13365
tcttttacca ttaaaaaaaa ttaaggacca tacagagaat gatttaagaa aaaacaagtc    13425
acttaaaaat catcacctat ttataaactg tattaattac acataatgct tattgattca    13485
atgaggtttc tctaaaagact tctgcttaat aaatatgctg acttcattta aattagttta    13545
gactattgta ggaatggaag gaaatgatta tatttactag aattagtgag atcagaaagc    13605
atatcagaat gttgatgata tcaaggagac aatctcagaa gttttgcct ctgtggatgg    13665 aaataagggt gttttttttt ggttttttttt ttactttagt ttcccataat ttttggaaat    13725
tatgtgtgca tttagttctt ttagtaacac tgattttaaa attaaatttc aaaagtcaat    13785
ctctaagagt aatttatttt tgttttacca accagtgcca aaaggagag gagggaatcc    13845 aaaagccaat cttttgaacc aatgtgtaaa agattatgtt ttttcttaaa gttagggagg    13905
ctcgggccct gacactgcca gccccagtga gcatccctgg ctacctcggg attatgtgca    13965
agctgctttg tcctacattt cttttcatctg gttcttattg ggagtgcttc tctctaataa    14025
aaattgattt cccacaaaat aggcaaagct gaacaaagat gaatgctttt gataagttgg    14085
gtttcacttc agttgaaaca atgtgataga atatccaggt gtggcatgat ggggcaggag    14145
gaggtgccta gagggaaaag ttatttttgt ttccttagtgt tgtgttgtgg ggatgggaca    14205
gataagaata agatgtttat tgccctaatc atgctaagag actattattc aatatgcttt    14265
tcccgctttt ctaagaggaa taaacttaga caaattcat tataaacagt tcccctacta    14325
ctatctccca ctctagataa agccagtggg tggtatgggt cctttattc cttatagtat    14385 tatgccaaag aatcaactta ttttcattga agattataaa taaatgaagc ttgttatagc    14445
cataatgatt tgagtcagta taccattta cctataaaat gcaaaattca tccttgcaac    14505
cccattcacc aggagccttg aagcattttg tttactccaa aggccttgtc aaggaagcat    14565
aattttttgt tttgccttct tatttagtca gtttggtcat atttacttaa aaaacaaac    14625 tgaaaatcac actcctttat atgttgatat aactgatttt atagaatctg tctgttcttt    14685
gtttaacagg tctctgtaag caagcttgca agtgtatttt gtgtacattt tatctgaggt    14745
ggaaatgaaa attctaaaga gaaatatttt taaaagatat tgtatttatg ttgcttgtgt    14805
tgtagaataa agattcaaat gcattaaaaa tctggtacat gaaacaattg tgtttactga    14865
ataaatatat ataaataaaa aaaaaaaaa                                        14895
```

<210> SEQ ID NO 24
<211> LENGTH: 2177
<212> TYPE: PRT

<213> ORGANISM: Homo sapiens

<400> SEQUENCE: 24

```
Met Glu Glu Ile Leu Arg Lys Leu Gln Lys Glu Ala Ser Gly Ser Lys
1               5                   10                  15

Tyr Lys Ala Ile Lys Glu Ser Cys Thr Trp Ala Leu Glu Thr Leu Gly
            20                  25                  30

Gly Leu Asp Thr Ile Val Lys Ile Pro Pro His Val Leu Arg Glu Lys
        35                  40                  45

Cys Leu Leu Pro Leu Gln Leu Ala Leu Glu Ser Lys Asn Val Lys Leu
    50                  55                  60

Ala Gln His Ala Leu Ala Gly Met Gln Lys Leu Leu Ser Glu Glu Arg
65                  70                  75                  80

Phe Val Ser Met Glu Thr Asp Ser Asp Glu Lys Gln Leu Leu Asn Gln
                85                  90                  95

Ile Leu Asn Ala Val Lys Val Thr Pro Ser Leu Asn Glu Asp Leu Gln
            100                 105                 110

Val Glu Val Met Lys Val Leu Leu Cys Ile Thr Tyr Thr Pro Thr Phe
        115                 120                 125

Asp Leu Asn Gly Ser Ala Val Leu Lys Ile Ala Glu Val Cys Ile Glu
    130                 135                 140

Thr Tyr Ile Ser Ser Cys His Gln Arg Ser Ile Asn Thr Ala Val Arg
145                 150                 155                 160

Ala Thr Leu Ser Gln Met Leu Ser Asp Leu Thr Leu Gln Leu Arg Gln
                165                 170                 175

Arg Gln Glu Asn Thr Ile Ile Glu Asn Pro Asp Val Pro Gln Asp Phe
            180                 185                 190

Gly Asn Gln Gly Ser Thr Val Glu Ser Leu Cys Asp Asp Val Val Ser
        195                 200                 205

Val Leu Thr Val Leu Cys Glu Lys Leu Gln Ala Ala Ile Asn Asp Ser
    210                 215                 220

Gln Gln Leu Gln Leu Leu Tyr Leu Glu Cys Ile Leu Ser Val Leu Ser
225                 230                 235                 240

Ser Ser Ser Ser Met His Leu His Arg Arg Phe Thr Asp Leu Ile
                245                 250                 255

Trp Lys Asn Leu Cys Pro Ala Leu Ile Val Ile Leu Gly Asn Pro Ile
            260                 265                 270

His Asp Lys Thr Ile Thr Ser Ala His Thr Ser Ser Thr Ser Ser
        275                 280                 285

Leu Glu Ser Asp Ser Ala Ser Pro Gly Val Ser Asp His Gly Arg Gly
    290                 295                 300

Ser Gly Cys Ser Cys Thr Ala Pro Ala Leu Ser Gly Pro Val Ala Arg
305                 310                 315                 320

Thr Ile Tyr Tyr Ile Ala Ala Glu Leu Val Arg Leu Val Gly Ser Val
                325                 330                 335

Asp Ser Met Lys Pro Val Leu Gln Ser Leu Tyr His Arg Val Leu Leu
            340                 345                 350

Tyr Pro Pro Pro Gln His Arg Val Glu Ala Ile Lys Ile Met Lys Glu
        355                 360                 365

Ile Leu Gly Ser Pro Gln Arg Leu Cys Asp Leu Ala Gly Pro Ser Ser
    370                 375                 380

Thr Glu Ser Glu Ser Arg Lys Arg Ser Ile Ser Lys Arg Lys Ser His
385                 390                 395                 400
```

```
Leu Asp Leu Leu Lys Leu Ile Met Asp Gly Met Thr Glu Ala Cys Ile
            405                 410                 415
Lys Gly Gly Ile Glu Ala Cys Tyr Ala Ala Val Ser Cys Val Cys Thr
        420                 425                 430
Leu Leu Gly Ala Leu Asp Glu Leu Ser Gln Gly Lys Gly Leu Ser Glu
            435                 440                 445
Gly Gln Val Gln Leu Leu Leu Arg Leu Glu Glu Leu Lys Asp Gly
450                 455                 460
Ala Glu Trp Ser Arg Asp Ser Met Glu Ile Asn Glu Ala Asp Phe Arg
465                 470                 475                 480
Trp Gln Arg Arg Val Leu Ser Ser Glu His Thr Pro Trp Glu Ser Gly
                485                 490                 495
Asn Glu Arg Ser Leu Asp Ile Ser Ile Ser Val Thr Thr Asp Thr Gly
                500                 505                 510
Gln Thr Thr Leu Glu Gly Glu Leu Gly Gln Thr Thr Pro Glu Asp His
            515                 520                 525
Ser Gly Asn His Lys Asn Ser Leu Lys Ser Pro Ala Ile Pro Glu Gly
            530                 535                 540
Lys Glu Thr Leu Ser Lys Val Leu Glu Thr Glu Ala Val Asp Gln Pro
545                 550                 555                 560
Asp Val Val Gln Arg Ser His Thr Val Pro Tyr Pro Asp Ile Thr Asn
                565                 570                 575
Phe Leu Ser Val Asp Cys Arg Thr Arg Ser Tyr Gly Ser Arg Tyr Ser
                580                 585                 590
Glu Ser Asn Phe Ser Val Asp Asp Gln Asp Leu Ser Arg Thr Glu Phe
            595                 600                 605
Asp Ser Cys Asp Gln Tyr Ser Met Ala Ala Glu Lys Asp Ser Gly Arg
            610                 615                 620
Ser Asp Val Ser Asp Ile Gly Ser Asp Asn Cys Ser Leu Ala Asp Glu
625                 630                 635                 640
Glu Gln Thr Pro Arg Asp Cys Leu Gly His Arg Ser Leu Arg Thr Ala
                645                 650                 655
Ala Leu Ser Leu Lys Leu Leu Lys Asn Gln Glu Ala Asp Gln His Ser
                660                 665                 670
Ala Arg Leu Phe Ile Gln Ser Leu Glu Gly Leu Leu Pro Arg Leu Leu
            675                 680                 685
Ser Leu Ser Asn Val Glu Glu Val Asp Thr Ala Leu Gln Asn Phe Ala
            690                 695                 700
Ser Thr Phe Cys Ser Gly Met Met His Ser Pro Gly Phe Asp Gly Asn
705                 710                 715                 720
Ser Ser Leu Ser Phe Gln Met Leu Met Asn Ala Asp Ser Leu Tyr Thr
                725                 730                 735
Ala Ala His Cys Ala Leu Leu Asn Leu Lys Leu Ser His Gly Asp
                740                 745                 750
Tyr Tyr Arg Lys Arg Pro Thr Leu Ala Pro Gly Val Met Lys Asp Phe
            755                 760                 765
Met Lys Gln Val Gln Thr Ser Gly Val Leu Met Val Phe Ser Gln Ala
            770                 775                 780
Trp Ile Glu Glu Leu Tyr His Gln Val Leu Asp Arg Asn Met Leu Gly
785                 790                 795                 800
Glu Ala Gly Tyr Trp Gly Ser Pro Glu Asp Asn Ser Leu Pro Leu Ile
                805                 810                 815
Thr Met Leu Thr Asp Ile Asp Gly Leu Glu Ser Ser Ala Ile Gly Gly
```

-continued

```
                820                 825                 830
Gln Leu Met Ala Ser Ala Ala Thr Glu Ser Pro Phe Ala Gln Ser Arg
            835                 840                 845
Arg Ile Asp Asp Ser Thr Val Ala Gly Val Ala Phe Ala Arg Tyr Ile
        850                 855                 860
Leu Val Gly Cys Trp Lys Asn Leu Ile Asp Thr Leu Ser Thr Pro Leu
865                 870                 875                 880
Thr Gly Arg Met Ala Gly Ser Ser Lys Gly Leu Ala Phe Ile Leu Gly
                885                 890                 895
Ala Glu Gly Ile Lys Glu Gln Asn Gln Lys Glu Arg Asp Ala Ile Cys
            900                 905                 910
Met Ser Leu Asp Gly Leu Arg Lys Ala Ala Arg Leu Ser Cys Ala Leu
            915                 920                 925
Gly Val Ala Ala Asn Cys Ala Ser Ala Leu Ala Gln Met Ala Ala Ala
            930                 935                 940
Ser Cys Val Gln Glu Glu Lys Glu Glu Arg Glu Ala Gln Glu Pro Ser
945                 950                 955                 960
Asp Ala Ile Thr Gln Val Lys Leu Lys Val Glu Gln Lys Leu Glu Gln
                965                 970                 975
Ile Gly Lys Val Gln Gly Val Trp Leu His Thr Ala His Val Leu Cys
                980                 985                 990
Met Glu Ala Ile Leu Ser Val Gly Leu Glu Met Gly Ser His Asn Pro
            995                 1000                 1005
Asp Cys Trp Pro His Val Phe Arg Val Cys Glu Tyr Val Gly Thr
        1010                1015                1020
Leu Glu His Asn His Phe Ser Asp Gly Ala Ser Gln Pro Pro Leu
        1025                1030                1035
Thr Ile Ser Gln Pro Gln Lys Ala Thr Gly Ser Ala Gly Leu Leu
        1040                1045                1050
Gly Asp Pro Glu Cys Glu Gly Ser Pro Pro Glu His Ser Pro Glu
        1055                1060                1065
Gln Gly Arg Ser Leu Ser Thr Ala Pro Val Val Gln Pro Leu Ser
        1070                1075                1080
Ile Gln Asp Leu Val Arg Glu Gly Ser Arg Gly Arg Ala Ser Asp
        1085                1090                1095
Phe Arg Gly Gly Ser Leu Met Ser Gly Ser Ser Ala Ala Lys Val
        1100                1105                1110
Val Leu Thr Leu Ser Thr Gln Ala Asp Arg Leu Phe Glu Asp Ala
        1115                1120                1125
Thr Asp Lys Leu Asn Leu Met Ala Leu Gly Gly Phe Leu Tyr Gln
        1130                1135                1140
Leu Lys Lys Ala Ser Gln Ser Gln Leu Phe His Ser Val Thr Asp
        1145                1150                1155
Thr Val Asp Tyr Ser Leu Ala Met Pro Gly Glu Val Lys Ser Thr
        1160                1165                1170
Gln Asp Arg Lys Ser Ala Leu His Leu Phe Arg Leu Gly Asn Ala
        1175                1180                1185
Met Leu Arg Ile Val Arg Ser Lys Ala Arg Pro Leu Leu His Val
        1190                1195                1200
Met Arg Cys Trp Ser Leu Val Ala Pro His Leu Val Glu Ala Ala
        1205                1210                1215
Cys His Lys Glu Arg His Val Ser Gln Lys Ala Val Ser Phe Ile
        1220                1225                1230
```

-continued

```
His Asp Ile Leu Thr Glu Val Leu Thr Asp Trp Asn Glu Pro Pro
1235                1240                1245

His Phe His Phe Asn Glu Ala Leu Phe Arg Pro Phe Glu Arg Ile
1250                1255                1260

Met Gln Leu Glu Leu Cys Asp Glu Asp Val Gln Asp Gln Val Val
1265                1270                1275

Thr Ser Ile Gly Glu Leu Val Glu Val Cys Ser Thr Gln Ile Gln
1280                1285                1290

Ser Gly Trp Arg Pro Leu Phe Ser Ala Leu Glu Thr Val His Gly
1295                1300                1305

Gly Asn Lys Ser Glu Met Lys Glu Tyr Leu Val Gly Asp Tyr Ser
1310                1315                1320

Met Gly Lys Gly Gln Ala Pro Val Phe Asp Val Phe Glu Ala Phe
1325                1330                1335

Leu Asn Thr Asp Asn Ile Gln Val Phe Ala Asn Ala Ala Thr Ser
1340                1345                1350

Tyr Ile Met Cys Leu Met Lys Phe Val Lys Gly Leu Gly Glu Val
1355                1360                1365

Asp Cys Lys Glu Ile Gly Asp Cys Ala Pro Ala Pro Gly Ala Pro
1370                1375                1380

Ser Thr Asp Leu Cys Leu Pro Ala Leu Asp Tyr Leu Arg Arg Cys
1385                1390                1395

Ser Gln Leu Leu Ala Lys Ile Tyr Lys Met Pro Leu Lys Pro Ile
1400                1405                1410

Phe Leu Ser Gly Arg Leu Ala Gly Leu Pro Arg Arg Leu Gln Glu
1415                1420                1425

Gln Ser Ala Ser Ser Glu Asp Gly Ile Glu Ser Val Leu Ser Asp
1430                1435                1440

Phe Asp Asp Asp Thr Gly Leu Ile Glu Val Trp Ile Ile Leu Leu
1445                1450                1455

Glu Gln Leu Thr Ala Ala Val Ser Asn Cys Pro Arg Gln His Gln
1460                1465                1470

Pro Pro Thr Leu Asp Leu Leu Phe Glu Leu Leu Arg Asp Val Thr
1475                1480                1485

Lys Thr Pro Gly Pro Gly Phe Gly Ile Tyr Ala Val Val His Leu
1490                1495                1500

Leu Leu Pro Val Met Ser Val Trp Leu Arg Arg Ser His Lys Asp
1505                1510                1515

His Ser Tyr Trp Asp Met Ala Ser Ala Asn Phe Lys His Ala Ile
1520                1525                1530

Gly Leu Ser Cys Glu Leu Val Val Glu His Ile Gln Ser Phe Leu
1535                1540                1545

His Ser Asp Ile Arg Tyr Glu Ser Met Ile Asn Thr Met Leu Lys
1550                1555                1560

Asp Leu Phe Glu Leu Leu Val Ala Cys Val Ala Lys Pro Thr Glu
1565                1570                1575

Thr Ile Ser Arg Val Gly Cys Ser Cys Ile Arg Tyr Val Leu Val
1580                1585                1590

Thr Ala Gly Pro Val Phe Thr Glu Glu Met Trp Arg Leu Ala Cys
1595                1600                1605

Cys Ala Leu Gln Asp Ala Phe Ser Ala Thr Leu Lys Pro Val Lys
1610                1615                1620
```

```
Asp Leu Leu Gly Cys Phe His Ser Gly Thr Glu Ser Phe Ser Gly
    1625                1630                1635

Glu Gly Cys Gln Val Arg Val Ala Ala Pro Ser Ser Ser Pro Ser
    1640                1645                1650

Ala Glu Ala Glu Tyr Trp Arg Ile Arg Ala Met Ala Gln Gln Val
    1655                1660                1665

Phe Met Leu Asp Thr Gln Cys Ser Pro Lys Thr Pro Asn Asn Phe
    1670                1675                1680

Asp His Ala Gln Ser Cys Gln Leu Ile Ile Glu Leu Pro Pro Asp
    1685                1690                1695

Glu Lys Pro Asn Gly His Thr Lys Lys Ser Val Ser Phe Arg Glu
    1700                1705                1710

Ile Val Val Ser Leu Leu Ser His Gln Val Leu Leu Gln Asn Leu
    1715                1720                1725

Tyr Asp Ile Leu Leu Glu Glu Phe Val Lys Gly Pro Ser Pro Gly
    1730                1735                1740

Glu Glu Lys Thr Ile Gln Val Pro Glu Ala Lys Leu Ala Gly Phe
    1745                1750                1755

Leu Arg Tyr Ile Ser Met Gln Asn Leu Ala Val Ile Phe Asp Leu
    1760                1765                1770

Leu Leu Asp Ser Tyr Arg Thr Ala Arg Glu Phe Asp Thr Ser Pro
    1775                1780                1785

Gly Leu Lys Cys Leu Leu Lys Lys Val Ser Gly Ile Gly Gly Ala
    1790                1795                1800

Ala Asn Leu Tyr Arg Gln Ser Ala Met Ser Phe Asn Ile Tyr Phe
    1805                1810                1815

His Ala Leu Val Cys Ala Val Leu Thr Asn Gln Glu Thr Ile Thr
    1820                1825                1830

Ala Glu Gln Val Lys Lys Val Leu Phe Glu Asp Asp Glu Arg Ser
    1835                1840                1845

Thr Asp Ser Ser Gln Gln Cys Ser Ser Glu Asp Glu Asp Ile Phe
    1850                1855                1860

Glu Glu Thr Ala Gln Val Ser Pro Pro Arg Gly Lys Glu Lys Arg
    1865                1870                1875

Gln Trp Arg Ala Arg Met Pro Leu Leu Ser Val Gln Pro Val Ser
    1880                1885                1890

Asn Ala Asp Trp Val Trp Leu Val Lys Arg Leu His Lys Leu Cys
    1895                1900                1905

Met Glu Leu Cys Asn Asn Tyr Ile Gln Met His Leu Asp Leu Glu
    1910                1915                1920

Asn Cys Met Glu Glu Pro Pro Ile Phe Lys Gly Asp Pro Phe Phe
    1925                1930                1935

Ile Leu Pro Ser Phe Gln Ser Glu Ser Ser Thr Pro Ser Thr Gly
    1940                1945                1950

Gly Phe Ser Gly Lys Glu Thr Pro Ser Glu Asp Asp Arg Ser Gln
    1955                1960                1965

Ser Arg Glu His Met Gly Glu Ser Leu Ser Leu Lys Ala Gly Gly
    1970                1975                1980

Gly Asp Leu Leu Leu Pro Pro Ser Pro Lys Val Glu Lys Lys Asp
    1985                1990                1995

Pro Ser Arg Lys Lys Glu Trp Trp Glu Asn Ala Gly Asn Lys Ile
    2000                2005                2010

Tyr Thr Met Ala Ala Asp Lys Thr Ile Ser Lys Leu Met Thr Glu
```

|  |  |
|---|---:|
| Tyr Lys Lys Arg Lys Gln Gln His Asn Leu Ser Ala Phe Pro Lys<br>      2030                        2035                           2040 | |
| Glu Val Lys Val Glu Lys Lys Gly Glu Pro Leu Gly Pro Arg Gly<br>      2045                        2050                          2055 | |
| Gln Asp Ser Pro Leu Leu Gln Arg Pro Gln His Leu Met Asp Gln<br>      2060                        2065                          2070 | |
| Gly Gln Met Arg His Ser Phe Ser Ala Gly Pro Glu Leu Leu Arg<br>      2075                        2080                          2085 | |
| Gln Asp Lys Arg Pro Arg Ser Gly Ser Thr Gly Ser Ser Leu Ser<br>      2090                        2095                          2100 | |
| Val Ser Val Arg Asp Ala Glu Ala Gln Ile Gln Ala Trp Thr Asn<br>      2105                        2110                          2115 | |
| Met Val Leu Thr Val Leu Asn Gln Ile Gln Ile Leu Pro Asp Gln<br>      2120                        2125                          2130 | |
| Thr Phe Thr Ala Leu Gln Pro Ala Val Phe Pro Cys Ile Ser Gln<br>      2135                        2140                          2145 | |
| Leu Thr Cys His Val Thr Asp Ile Arg Val Arg Gln Ala Val Arg<br>      2150                        2155                          2160 | |
| Glu Trp Leu Gly Arg Val Gly Arg Val Tyr Asp Ile Ile Val<br>      2165                        2170                          2175 | |

```
<210> SEQ ID NO 25
<211> LENGTH: 1457
<212> TYPE: DNA
<213> ORGANISM: Homo sapiens
<220> FEATURE:
<221> NAME/KEY: CDS
<222> LOCATION: (211)..(1110)

<400> SEQUENCE: 25
```

| | |
|---|---:|
| tccgtatgcg cgattcctgt gcgcgaagtt cgggtccgta gtgggctaag ggggagggtt | 60 |
| tcaaagggag cgcacttccg ctgccctttc tttcgccagc cttacgggcc cgaaccctcg | 120 |
| tgtgaagggt gcagtaccta agccggagcg gggtagaggc gggccggcac ccccttctga | 180 |
| cctccagtgc cgccggcctc aagatcagac atg gcc cag aac ttg aag gac ttg<br>                                                 Met Ala Gln Asn Leu Lys Asp Leu<br>                                                  1                      5 | 234 |
| gcg gga cgg ctg ccc gcc ggg ccc cgg ggc atg ggc acg gcc ctg aag<br>Ala Gly Arg Leu Pro Ala Gly Pro Arg Gly Met Gly Thr Ala Leu Lys<br>      10                       15                      20 | 282 |
| ctg ttg ctg ggg gcc ggc gcc gtg gcc tac ggt gtg cgc gaa tct gtg<br>Leu Leu Leu Gly Ala Gly Ala Val Ala Tyr Gly Val Arg Glu Ser Val<br>25                      30                      35                      40 | 330 |
| ttc acc gtg gaa ggc ggg cac aga gcc atc ttc ttc aat cgg atc ggt<br>Phe Thr Val Glu Gly Gly His Arg Ala Ile Phe Phe Asn Arg Ile Gly<br>                        45                      50                      55 | 378 |
| gga gtg cag cag gac act atc ctg gcc gag ggc ctt cac ttc agg atc<br>Gly Val Gln Gln Asp Thr Ile Leu Ala Glu Gly Leu His Phe Arg Ile<br>      60                       65                        70 | 426 |
| cct tgg ttc cag tac ccc att atc tat gac att cgg gcc aga cct cga<br>Pro Trp Phe Gln Tyr Pro Ile Ile Tyr Asp Ile Arg Ala Arg Pro Arg<br>            75                      80                      85 | 474 |
| aaa atc tcc tcc cct aca ggc tcc aaa gac cta cag atg gtg aat atc<br>Lys Ile Ser Ser Pro Thr Gly Ser Lys Asp Leu Gln Met Val Asn Ile<br>      90                       95                       100 | 522 |
| tcc ctg cga gtg ttg tct cga ccc aat gct cag gag ctt cct agc atg<br>Ser Leu Arg Val Leu Ser Arg Pro Asn Ala Gln Glu Leu Pro Ser Met | 570 |

|  |  |  |  |  |  |  |  |  |  |  |  |  |  |  |  |
|---|---|---|---|---|---|---|---|---|---|---|---|---|---|---|---|
| | | 105 | | | | 110 | | | | 115 | | | | 120 | |

```
tac cag cgc cta ggg ctg gac tac gag gaa cga gtg ttg ccg tcc att      618
Tyr Gln Arg Leu Gly Leu Asp Tyr Glu Glu Arg Val Leu Pro Ser Ile
                125                 130                 135 gtc aac gag gtg ctc aag agt gtg gtg gcc aag ttc aat gcc tca cag      666
Val Asn Glu Val Leu Lys Ser Val Val Ala Lys Phe Asn Ala Ser Gln
            140                 145                 150 ctg atc acc cag cgg gcc cag gta tcc ctg ttg atc cgc cgg gag ctg      714
Leu Ile Thr Gln Arg Ala Gln Val Ser Leu Leu Ile Arg Arg Glu Leu
            155                 160                 165 aca gag agg gcc aag gac ttc agc ctc atc ctg gat gat gtg gcc atc      762
Thr Glu Arg Ala Lys Asp Phe Ser Leu Ile Leu Asp Asp Val Ala Ile
        170                 175                 180 aca gag ctg agc ttt agc cga gag tac aca gct gct gta gaa gcc aaa      810
Thr Glu Leu Ser Phe Ser Arg Glu Tyr Thr Ala Ala Val Glu Ala Lys
185                 190                 195                 200 caa gtg gcc cag cag gag gcc cag cgg gcc caa ttc ttg gta gaa aaa      858
Gln Val Ala Gln Gln Glu Ala Gln Arg Ala Gln Phe Leu Val Glu Lys
                205                 210                 215 gca aag cag gaa cag cgg cag aaa att gtg cag gcc gag ggt gag gcc      906
Ala Lys Gln Glu Gln Arg Gln Lys Ile Val Gln Ala Glu Gly Glu Ala
                220                 225                 230 gag gct gcc aag atg ctt gga gaa gca ctg agc aag aac cct ggc tac      954
Glu Ala Ala Lys Met Leu Gly Glu Ala Leu Ser Lys Asn Pro Gly Tyr
            235                 240                 245 atc aaa ctt cgc aag att cga gca gcc cag aat atc tcc aag acg atc     1002
Ile Lys Leu Arg Lys Ile Arg Ala Ala Gln Asn Ile Ser Lys Thr Ile
        250                 255                 260 gcc aca tca cag aat cgt atc tat ctc aca gct gac aac ctt gtg ctg     1050
Ala Thr Ser Gln Asn Arg Ile Tyr Leu Thr Ala Asp Asn Leu Val Leu
265                 270                 275                 280 aac cta cag gat gaa agt ttc acc agg gga agt gac agc ctc atc aag     1098
Asn Leu Gln Asp Glu Ser Phe Thr Arg Gly Ser Asp Ser Leu Ile Lys
                285                 290                 295 ggt aag aaa tga gcctagtcac caagaactcc accccagag gaagtggatc          1150
Gly Lys Lys tgcttctcca gttttgagg agccagccag gggtccagca cagccctacc ccgcccagt     1210 atcatgcgat ggtccccac accggttccc tgaacccctc ttggattaag gaagactgaa    1270
gactagcccc ttttctgggg aattactttc ctcctccctg tgttaactgg ggctgttggg   1330
gacagtgcgt gatttctcag tgatttccta cagtgttgtt ccctcccctca aggctgggag  1390 gagataaaca ccaacccagg aattctcaat aaattttat tacttaacct gaaaaaaaaa    1450
aaaaaaa                                                             1457

<210> SEQ ID NO 26
<211> LENGTH: 299
<212> TYPE: PRT
<213> ORGANISM: Homo sapiens

<400> SEQUENCE: 26

Met Ala Gln Asn Leu Lys Asp Leu Ala Gly Arg Leu Pro Ala Gly Pro
1               5                   10                  15

Arg Gly Met Gly Thr Ala Leu Lys Leu Leu Gly Ala Gly Ala Val
                20                  25                  30

Ala Tyr Gly Val Arg Glu Ser Val Phe Thr Val Glu Gly Gly His Arg
            35                  40                  45
```

Ala Ile Phe Phe Asn Arg Ile Gly Gly Val Gln Gln Asp Thr Ile Leu
 50                  55                  60

Ala Glu Gly Leu His Phe Arg Ile Pro Trp Phe Gln Tyr Pro Ile Ile
 65                  70                  75                  80

Tyr Asp Ile Arg Ala Arg Pro Arg Lys Ile Ser Ser Pro Thr Gly Ser
                 85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
            115                 120                 125

Glu Glu Arg Val Leu Pro Ser Ile Val Asn Glu Val Leu Lys Ser Val
130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
            195                 200                 205

Arg Ala Gln Phe Leu Val Glu Lys Ala Lys Gln Glu Gln Arg Gln Lys
210                 215                 220

Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
            275                 280                 285

Arg Gly Ser Asp Ser Leu Ile Lys Gly Lys Lys
290                 295

<210> SEQ ID NO 27
<211> LENGTH: 1343
<212> TYPE: DNA
<213> ORGANISM: Homo sapiens
<220> FEATURE:
<221> NAME/KEY: CDS
<222> LOCATION: (211)..(996)

<400> SEQUENCE: 27
tccgtatgcg cgattcctgt gcgcgaagtt cgggtccgta gtgggctaag ggggagggtt      60
tcaaagggag cgcacttccg ctgcccttc tttcgccagc cttacgggcc cgaaccctcg     120
tgtgaagggt gcagtaccta agccggagcg gggtagaggc gggccggcac cccttctga    180 cctccagtgc cgccggcctc aagatcagac atg gcc cag aac ttg aag gac ttg     234
                                    Met Ala Gln Asn Leu Lys Asp Leu
                                      1               5 gcg gga cgg ctg ccc gcc ggg ccc cgg ggc atg ggc acg gcc ctg aag     282
Ala Gly Arg Leu Pro Ala Gly Pro Arg Gly Met Gly Thr Ala Leu Lys
     10                  15                  20 ctg ttg ctg ggg gcc ggc gcc gtg gcc tac ggt gtg cgc gaa tct gtg     330
Leu Leu Leu Gly Ala Gly Ala Val Ala Tyr Gly Val Arg Glu Ser Val
 25                  30                  35                  40 ttc acc gtg gaa ggc ggg cac aga gcc atc ttc ttc aat cgg atc ggt     378
Phe Thr Val Glu Gly Gly His Arg Ala Ile Phe Phe Asn Arg Ile Gly

| | | | | | | | | | | | | | | | |
|---|---|---|---|---|---|---|---|---|---|---|---|---|---|---|---|
| | | | | 45 | | | | | 50 | | | | | 55 | |

```
gga gtg cag cag gac act atc ctg gcc gag ggc ctt cac ttc agg atc      426
Gly Val Gln Gln Asp Thr Ile Leu Ala Glu Gly Leu His Phe Arg Ile
             60                  65                  70 cct tgg ttc cag tac ccc att atc tat gac att cgg gcc aga cct cga      474
Pro Trp Phe Gln Tyr Pro Ile Ile Tyr Asp Ile Arg Ala Arg Pro Arg
         75                  80                  85 aaa atc tcc tcc cct aca ggc tcc aaa gac cta cag atg gtg aat atc      522
Lys Ile Ser Ser Pro Thr Gly Ser Lys Asp Leu Gln Met Val Asn Ile
     90                  95                 100 tcc ctg cga gtg ttg tct cga ccc aat gct cag gag ctt cct agc atg      570
Ser Leu Arg Val Leu Ser Arg Pro Asn Ala Gln Glu Leu Pro Ser Met
105                 110                 115                 120 tac cag cgc cta ggg ctg gac tac gag gaa cga gtg ttg ccg tcc att      618
Tyr Gln Arg Leu Gly Leu Asp Tyr Glu Glu Arg Val Leu Pro Ser Ile
             125                 130                 135 gtc aac gag gtg ctc aag agt gtg gtg gcc aag ttc aat gcc tca cag      666
Val Asn Glu Val Leu Lys Ser Val Val Ala Lys Phe Asn Ala Ser Gln
         140                 145                 150 ctg atc acc cag cgg gcc cag gta tcc ctg ttg atc cgc cgg gag ctg      714
Leu Ile Thr Gln Arg Ala Gln Val Ser Leu Leu Ile Arg Arg Glu Leu
     155                 160                 165 aca gag agg gcc aag gac ttc agc ctc atc ctg gat gat gtg gcc atc      762
Thr Glu Arg Ala Lys Asp Phe Ser Leu Ile Leu Asp Asp Val Ala Ile
170                 175                 180 aca gag ctg agc ttt agc cga gag tac aca gct gct gta gaa gcc aaa      810
Thr Glu Leu Ser Phe Ser Arg Glu Tyr Thr Ala Ala Val Glu Ala Lys
185                 190                 195                 200 caa gtg gca ctg agc aag aac cct ggc tac atc aaa ctt cgc aag att      858
Gln Val Ala Leu Ser Lys Asn Pro Gly Tyr Ile Lys Leu Arg Lys Ile
             205                 210                 215 cga gca gcc cag aat atc tcc aag acg atc gcc aca tca cag aat cgt      906
Arg Ala Ala Gln Asn Ile Ser Lys Thr Ile Ala Thr Ser Gln Asn Arg
         220                 225                 230 atc tat ctc aca gct gac aac ctt gtg ctg aac cta cag gat gaa agt      954
Ile Tyr Leu Thr Ala Asp Asn Leu Val Leu Asn Leu Gln Asp Glu Ser
     235                 240                 245 ttc acc agg gga agt gac agc ctc atc aag ggt aag aaa tga              996
Phe Thr Arg Gly Ser Asp Ser Leu Ile Lys Gly Lys Lys
250                 255                 260 gcctagtcac caagaactcc accccagag gaagtggatc tgcttctcca gttttgagg      1056 agccagccag gggtccagca cagccctacc ccgccccagt atcatgcgat ggtcccccac      1116
accggttccc tgaacccctc ttggattaag gaagactgaa gactagcccc ttttctgggg      1176
aattactttc ctcctccctg tgttaactgg ggctgttggg gacagtgcgt gatttctcag      1236
tgatttccta cagtgttgtt ccctccctca aggctgggag gagataaaca ccaacccagg      1296
aattctcaat aaattttat tacttaacct gaaaaaaaaa aaaaaaa                    1343

<210> SEQ ID NO 28
<211> LENGTH: 261
<212> TYPE: PRT
<213> ORGANISM: Homo sapiens

<400> SEQUENCE: 28

Met Ala Gln Asn Leu Lys Asp Leu Ala Gly Arg Leu Pro Ala Gly Pro
1               5                   10                  15

Arg Gly Met Gly Thr Ala Leu Lys Leu Leu Leu Gly Ala Gly Ala Val
            20                  25                  30
```

Ala Tyr Gly Val Arg Glu Ser Val Phe Thr Val Glu Gly Gly His Arg
            35                  40                  45

Ala Ile Phe Phe Asn Arg Ile Gly Gly Val Gln Gln Asp Thr Ile Leu
 50                  55                  60

Ala Glu Gly Leu His Phe Arg Ile Pro Trp Phe Gln Tyr Pro Ile Ile
 65                  70                  75                  80

Tyr Asp Ile Arg Ala Arg Pro Arg Lys Ile Ser Ser Pro Thr Gly Ser
                    85                  90                  95

Lys Asp Leu Gln Met Val Asn Ile Ser Leu Arg Val Leu Ser Arg Pro
                100                 105                 110

Asn Ala Gln Glu Leu Pro Ser Met Tyr Gln Arg Leu Gly Leu Asp Tyr
                115                 120                 125

Glu Glu Arg Val Leu Pro Ser Ile Val Asn Glu Val Leu Lys Ser Val
130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
                180                 185                 190

Tyr Thr Ala Ala Val Glu Ala Lys Gln Val Ala Leu Ser Lys Asn Pro
                195                 200                 205

Gly Tyr Ile Lys Leu Arg Lys Ile Arg Ala Ala Gln Asn Ile Ser Lys
                210                 215                 220

Thr Ile Ala Thr Ser Gln Asn Arg Ile Tyr Leu Thr Ala Asp Asn Leu
225                 230                 235                 240

Val Leu Asn Leu Gln Asp Glu Ser Phe Thr Arg Gly Ser Asp Ser Leu
                245                 250                 255

Ile Lys Gly Lys Lys
                260

<210> SEQ ID NO 29
<211> LENGTH: 6330
<212> TYPE: DNA
<213> ORGANISM: Homo sapiens
<220> FEATURE:
<221> NAME/KEY: CDS
<222> LOCATION: (235)..(2022)

<400> SEQUENCE: 29
aggagctggc ggagggcgtt cgtcctggga ctgcacttgc tcccgtcggg tcgcccggct      60
tcaccggacc cgcaggctcc cggggcaggg ccggggccag agctcgcgtg tcggcgggac     120
atgcgctgcg tcgcctctaa cctcgggctg tgctcttttt ccaggtggcc cgccggtttc     180
tgagccttct gccctgcggg gacacggtct gcaccctgcc cgcggccacg gacc atg      237
                                                                Met
                                                                 1 acc atg acc ctc cac acc aaa gca tct ggg atg gcc cta ctg cat cag     285
Thr Met Thr Leu His Thr Lys Ala Ser Gly Met Ala Leu Leu His Gln
          5                  10                  15 atc caa ggg aac gag ctg gag ccc ctg aac cgt ccg cag ctc aag atc     333
Ile Gln Gly Asn Glu Leu Glu Pro Leu Asn Arg Pro Gln Leu Lys Ile
         20                  25                  30 ccc ctg gag cgg ccc ctg ggc gag gtg tac ctg gac agc agc aag ccc     381
Pro Leu Glu Arg Pro Leu Gly Glu Val Tyr Leu Asp Ser Ser Lys Pro
 35                  40                  45

```
gcc gtg tac aac tac ccc gag ggc gcc tac gag ttc aac gcc gcg      429
Ala Val Tyr Asn Tyr Pro Glu Gly Ala Ala Tyr Glu Phe Asn Ala Ala
50              55                  60                  65 gcc gcc gcc aac gcg cag gtc tac ggt cag acc ggc ctc ccc tac ggc  477
Ala Ala Ala Asn Ala Gln Val Tyr Gly Gln Thr Gly Leu Pro Tyr Gly
                70                  75                  80 ccc ggg tct gag gct gcg gcg ttc ggc tcc aac ggc ctg ggg ggt ttc  525
Pro Gly Ser Glu Ala Ala Ala Phe Gly Ser Asn Gly Leu Gly Gly Phe
            85                  90                  95 ccc cca ctc aac agc gtg tct ccg agc ccg ctg atg cta ctg cac ccg  573
Pro Pro Leu Asn Ser Val Ser Pro Ser Pro Leu Met Leu Leu His Pro
        100                 105                 110 ccg ccg cag ctg tcg cct ttc ctg cag ccc cac ggc cag cag gtg ccc  621
Pro Pro Gln Leu Ser Pro Phe Leu Gln Pro His Gly Gln Gln Val Pro
    115                 120                 125 tac tac ctg gag aac gag ccc agc ggc tac acg gtg cgc gag gcc ggc  669
Tyr Tyr Leu Glu Asn Glu Pro Ser Gly Tyr Thr Val Arg Glu Ala Gly
130             135                 140                 145 ccg ccg gca ttc tac agg cca aat tca gat aat cga cgc cag ggt ggc  717
Pro Pro Ala Phe Tyr Arg Pro Asn Ser Asp Asn Arg Arg Gln Gly Gly
                150                 155                 160 aga gaa aga ttg gcc agt acc aat gac aag gga agt atg gct atg gaa  765
Arg Glu Arg Leu Ala Ser Thr Asn Asp Lys Gly Ser Met Ala Met Glu
            165                 170                 175 tct gcc aag gag act cgc tac tgt gca gtg tgc aat gac tat gct tca  813
Ser Ala Lys Glu Thr Arg Tyr Cys Ala Val Cys Asn Asp Tyr Ala Ser
        180                 185                 190 ggc tac cat tat gga gtc tgg tcc tgt gag ggc tgc aag gcc ttc ttc  861
Gly Tyr His Tyr Gly Val Trp Ser Cys Glu Gly Cys Lys Ala Phe Phe
    195                 200                 205 aag aga agt att caa gga cat aac gac tat atg tgt cca gcc acc aac  909
Lys Arg Ser Ile Gln Gly His Asn Asp Tyr Met Cys Pro Ala Thr Asn
210             215                 220                 225 cag tgc acc att gat aaa aac agg agg aag agc tgc cag gcc tgc cgg  957
Gln Cys Thr Ile Asp Lys Asn Arg Arg Lys Ser Cys Gln Ala Cys Arg
                230                 235                 240 ctc cgc aaa tgc tac gaa gtg gga atg atg aaa ggt ggg ata cga aaa  1005
Leu Arg Lys Cys Tyr Glu Val Gly Met Met Lys Gly Gly Ile Arg Lys
            245                 250                 255 gac cga aga gga ggg aga atg ttg aaa cac aag cgc cag aga gat gat  1053
Asp Arg Arg Gly Gly Arg Met Leu Lys His Lys Arg Gln Arg Asp Asp
        260                 265                 270 ggg gag ggc agg ggt gaa gtg ggg tct gct gga gac atg aga gct gcc  1101
Gly Glu Gly Arg Gly Glu Val Gly Ser Ala Gly Asp Met Arg Ala Ala
    275                 280                 285 aac ctt tgg cca agc ccg ctc atg atc aaa cgc tct aag aag aac agc  1149
Asn Leu Trp Pro Ser Pro Leu Met Ile Lys Arg Ser Lys Lys Asn Ser
290             295                 300                 305 ctg gcc ttg tcc ctg acg gcc gac cag atg gtc agt gcc ttg ttg gat  1197
Leu Ala Leu Ser Leu Thr Ala Asp Gln Met Val Ser Ala Leu Leu Asp
                310                 315                 320 gct gag ccc ccc ata ctc tat tcc gag tat gat cct acc aga ccc ttc  1245
Ala Glu Pro Pro Ile Leu Tyr Ser Glu Tyr Asp Pro Thr Arg Pro Phe
            325                 330                 335 agt gaa gct tcg atg atg ggc tta ctg acc aac ctg gca gac agg gag  1293
Ser Glu Ala Ser Met Met Gly Leu Leu Thr Asn Leu Ala Asp Arg Glu
        340                 345                 350 ctg gtt cac atg atc aac tgg gcg aag agg gtg cca ggc ttt gtg gat  1341
Leu Val His Met Ile Asn Trp Ala Lys Arg Val Pro Gly Phe Val Asp
    355                 360                 365
```

```
ttg acc ctc cat gat cag gtc cac ctt cta gaa tgt gcc tgg cta gag    1389
Leu Thr Leu His Asp Gln Val His Leu Leu Glu Cys Ala Trp Leu Glu
370                 375                 380                 385 atc ctg atg att ggt ctc gtc tgg cgc tcc atg gag cac cca ggg aag    1437
Ile Leu Met Ile Gly Leu Val Trp Arg Ser Met Glu His Pro Gly Lys
                390                 395                 400 cta ctg ttt gct cct aac ttg ctc ttg gac agg aac cag gga aaa tgt    1485
Leu Leu Phe Ala Pro Asn Leu Leu Leu Asp Arg Asn Gln Gly Lys Cys
            405                 410                 415 gta gag ggc atg gtg gag atc ttc gac atg ctg ctg gct aca tca tct    1533
Val Glu Gly Met Val Glu Ile Phe Asp Met Leu Leu Ala Thr Ser Ser
        420                 425                 430 cgg ttc cgc atg atg aat ctg cag gga gag gag ttt gtg tgc ctc aaa    1581
Arg Phe Arg Met Met Asn Leu Gln Gly Glu Glu Phe Val Cys Leu Lys
    435                 440                 445 tct att att ttg ctt aat tct gga gtg tac aca ttt ctg tcc agc acc    1629
Ser Ile Ile Leu Leu Asn Ser Gly Val Tyr Thr Phe Leu Ser Ser Thr
450                 455                 460                 465 ctg aag tct ctg gaa gag aag gac cat atc cac cga gtc ctg gac aag    1677
Leu Lys Ser Leu Glu Glu Lys Asp His Ile His Arg Val Leu Asp Lys
                470                 475                 480 atc aca gac act ttg atc cac ctg atg gcc aag gca ggc ctg acc ctg    1725
Ile Thr Asp Thr Leu Ile His Leu Met Ala Lys Ala Gly Leu Thr Leu
            485                 490                 495 cag cag cag cac cag cgg ctg gcc cag ctc ctc ctc atc ctc tcc cac    1773
Gln Gln Gln His Gln Arg Leu Ala Gln Leu Leu Leu Ile Leu Ser His
        500                 505                 510 atc agg cac atg agt aac aaa ggc atg gag cat ctg tac agc atg aag    1821
Ile Arg His Met Ser Asn Lys Gly Met Glu His Leu Tyr Ser Met Lys
    515                 520                 525 tgc aag aac gtg gtg ccc ctc tat gac ctg ctg ctg gag atg ctg gac    1869
Cys Lys Asn Val Val Pro Leu Tyr Asp Leu Leu Leu Glu Met Leu Asp
530                 535                 540                 545 gcc cac cgc cta cat gcg ccc act agc cgt gga ggg gca tcc gtg gag    1917
Ala His Arg Leu His Ala Pro Thr Ser Arg Gly Gly Ala Ser Val Glu
                550                 555                 560 gag acg gac caa agc cac ttg gcc act gcg ggc tct act tca tcg cat    1965
Glu Thr Asp Gln Ser His Leu Ala Thr Ala Gly Ser Thr Ser Ser His
            565                 570                 575 tcc ttg caa aag tat tac atc acg ggg gag gca gag ggt ttc cct gcc    2013
Ser Leu Gln Lys Tyr Tyr Ile Thr Gly Glu Ala Glu Gly Phe Pro Ala
        580                 585                 590 acg gtc tga gagctccctg gctcccacac ggttcagata atccctgctg            2062
Thr Val
    595 cattttaccc tcatcatgca ccactttagc caaattctgt ctcctgcata cactccggca   2122 tgcatccaac accaatggct ttctagatga gtggccattc atttgcttgc tcagttctta   2182 gtggcacatc ttctgtcttc tgttgggaac agccaaaggg attccaaggc taaatctttg   2242 taacagctct cttttccccct tgctatgtta ctaagcgtga ggattcccgt agctcttcac   2302 agctgaactc agtctatggg ttggggctca gataactctg tgcatttaag ctacttgtag   2362 agacccaggc ctgagagta gacattttgc ctctgataag cacttttaa atggctctaa    2422 gaataagcca cagcaaagaa tttaaagtgg ctcctttaat tggtgacttg gagaaagcta   2482 ggtcaagggt ttattatagc accctcttgt attcctatgg caatgcatcc ttttatgaaa   2542 gtggtacacc ttaaagcttt tatatgactg tagcagagta tctggtgatt gtcaattcat   2602
```

```
tcccccctata ggaatacaag gggcacacag ggaaggcaga tccccctagtt ggcaagacta    2662 ttttaacttg atacactgca gattcagatg tgctgaaagc tctgcctctg gctttccggt    2722
catgggttcc agttaattca tgcctcccat ggacctatgg agagcagcaa gttgatctta    2782
gttaagtctc cctatatgag ggataagttc ctgattttttg tttttatttt tgtgttacaa    2842
aagaaagccc tccctccctg aacttgcagt aaggtcagct tcaggacctg ttccagtggg    2902
cactgtactt ggatcttccc ggcgtgtgtg tgccttacac agggggtgaac tgttcactgt    2962 ggtgatgcat gatgagggta aatggtagtt gaaaggagca ggggccctgg tgttgcattt    3022
agccctgggg catggagctg aacagtactt gtgcaggatt gttgtggcta ctagagaaca    3082
agagggaaag tagggcagaa actggataca gttctgaggc acagccagac ttgctcaggg    3142
tggccctgcc acaggctgca gctacctagg aacattcctt gcagaccccg cattgccctt    3202
tgggggtgcc ctgggatccc tggggtagtc cagctcttct tcatttccca gcgtggccct    3262
ggttggaaga agcagctgtc acagctgcta tagacagctg tgttcctaca attggcccag    3322
caccctgggg cacgggagaa gggtgggggac cgttgctgtc actactcagg ctgactgggg    3382
cctggtcaga ttacgtatgc ccttggtggt ttagagataa tccaaaatca gggtttggtt    3442
tggggaagaa aatcctcccc cttcctcccc cgccccgttc cctaccgcct ccactcctgc    3502
cagctcattt ccttcaattt cctttgacct ataggctaaa aagaaaggc tcattccagc    3562 cacagggcag ccttccctgg gcctttgctt ctctagcaca attatgggtt acttcctttt    3622
tcttaacaaa aagaatgtt tgatttcctc tgggtgacct tattgtctgt aattgaaacc    3682
ctattgagag gtgatgtctg tgttagccaa tgacccaggt gagctgctcg ggcttctctt    3742
ggtatgtctt gtttggaaaa gtggatttca ttcatttctg attgtccagt aagtgatca    3802 ccaaaggact gagaatctgg gagggcaaaa aaaaaaaaaa agtttttatg tgcacttaaa    3862
tttggggaca atttttatgta tctgtgttaa ggatatgttt aagaacataa ttcttttgtt    3922
gctgtttgtt taagaagcac cttagtttgt ttaagaagca ccttatatag tataatatat    3982
atttttttga aattacattg cttgttttatc agacaattga atgtagtaat tctgttctgg    4042
atttaatttg actgggttaa catgcaaaaa ccaaggaaaa atatttagtt ttttttttt    4102 tttttgtata cttttcaagc taccttgtca tgtatacagt catttatgcc taaagcctgg    4162
tgattattca tttaaatgaa gatcacattt catatcaact tttgtatcca cagtagacaa    4222
aatagcacta atccagatgc ctattgttgg atactgaatg acagacaatc ttatgtagca    4282
aagattatgc ctgaaaagga aaattattca gggcagctaa ttttgctttt accaaaatat    4342
cagtagtaat attttttggac agtagctaat gggtcagtgg gttcttttta atgtttatac    4402 ttagatttc ttttaaaaaa attaaaataa aacaaaaaaa aatttctagg actagacgat    4462
gtaataccag ctaaagccaa acaattatac agtggaaggt tttacattat tcatccaatg    4522
tgtttctatt catgttaaga tactactaca tttgaagtgg gcagagaaca tcagatgatt    4582
gaaatgttcg cccagggtc tccagcaact ttggaaatct ctttgtattt ttacttgaag    4642
tgccactaat ggacagcaga tattttctgg ctgatgttgg tattgggtgt aggaacatga    4702
tttaaaaaaa aactcttgcc tctgctttcc cccactctga ggcaagttaa aatgtaaaag    4762
atgtgattta tctgggggc tcaggtatgg tggggaagtg gattcaggaa tctggggaat    4822
ggcaaatata ttaagaagag tattgaaagt atttggagga aaatggttaa ttctgggtgt    4882
gcaccagggt tcagtagagt ccacttctgc cctggagacc acaaatcaac tagctccatt    4942
tacagccatt tctaaaatgg cagcttcagt tctagagaag aaagaacaac atcagcagta    5002
```

```
aagtccatgg aatagctagt ggtctgtgtt tcttttcgcc attgcctagc ttgccgtaat    5062
gattctataa tgccatcatg cagcaattat gagaggctag gtcatccaaa gagaagaccc    5122
tatcaatgta ggttgcaaaa tctaaccctc aaggaagtgc agtctttgat ttgatttccc    5182
tagtaacctt gcagatatgt ttaaccaagc catagcccat gccttttgag ggctgaacaa    5242
ataagggact tactgataat ttactttgta tcacattaag gtgttctcac cttgaaatct    5302
tatacactga aatggccatt gatttaggcc actggcttag agtactcctt cccctgcatg    5362
acactgatta caaatacttt cctattcata ctttccaatt atgagatgga ctgtgggtac    5422
tgggagtgat cactaacacc atagtaatgt ctaatattca caggcagatc tgcttgggga    5482
agctagttat gtgaaaggca aatagagtca tacagtagct caaaaggcaa ccataattct    5542
ctttggtgca ggtcttggga gcgtgatcta gattacactg caccattccc aagttaatcc    5602
cctgaaaact tactctcaac tggagcaaat gaactttggt cccaaatatc catcttttca    5662
gtagcgttaa ttatgctctg tttccaactg catttccttt ccaattgaat taaagtgtgg    5722
cctcgttttt agtcatttaa aattgttttc taagtaattg ctgcctctat tatggcactt    5782
caattttgca ctgtcttttg agattcaaga aaaatttcta ttcttttttt tgcatccaat    5842
tgtgcctgaa cttttaaaat atgtaaatgc tgccatgttc caaacccatc gtcagtgtgt    5902
gtgtttagag ctgtgcaccc tagaaacaac atattgtccc atgagcaggt gcctgagaca    5962
cagacccctt tgcattcaca gagaggtcat tggttataga acttgaatt aataagtgac    6022 attatgccag tttctgttct ctcacaggtg ataaacaatg cttttgtgc actacatact    6082 cttcagtgta gagctcttgt tttatgggaa aaggctcaaa tgccaaattg tgtttgatgg    6142
attaatatgc ccttttgccg atgcatacta ttactgatgt gactcggttt tgtcgcagct    6202
ttgctttgtt taatgaaaca cacttgtaaa cctcttttgc actttgaaaa agaatccagc    6262
gggatgctcg agcacctgta aacaattttc tcaacctatt tgatgttcaa ataaagaatt    6322
aaactaaa                                                             6330
```

<210> SEQ ID NO 30
<211> LENGTH: 595
<212> TYPE: PRT
<213> ORGANISM: Homo sapiens

<400> SEQUENCE: 30

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125
```

-continued

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val

```
                545                 550                 555                 560
Glu Glu Thr Asp Gln Ser His Leu Ala Thr Ala Gly Ser Thr Ser Ser
                    565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 31
<211> LENGTH: 2169
<212> TYPE: DNA
<213> ORGANISM: Homo sapiens
<220> FEATURE:
<221> NAME/KEY: CDS
<222> LOCATION: (469)..(2061)

<400> SEQUENCE: 31
ctcggtcttt aaaaggaaga aggggcttat cgttaagtcg cttgtgatct tttcagtttc      60
tccagctgct ggcttttgg acacccactc ccccgccagg aggcagttgc aagcgcggag      120
gctgcgagaa ataactgcct cttgaaactt gcagggcgaa gagcaggcgg cgagcgctgg    180
gccggggagg gaccacccga gctgcgacgg gctctgggc tgcggggcag ggctggcgcc     240
cggagcctga gctgcaggag gtgcgctcgc tttcctcaac aggtggcggc ggggcgcgcg    300
ccgggagacc ccccctaatg cgggaaaagc acgtgtccgc attttagaga aggcaaggcc    360
ggtgtgttta tctgcaagcc attatacttg cccacgaatc tttgagaaca ttataatgac    420
ctttgtgcct cttcttgcaa ggtgttttct cagctgttat ctcaagac atg gat ata    477
                                                    Met Asp Ile
                                                      1 aaa aac tca cca tct agc ctt aat tct cct tcc tcc tac aac tgc agt      525
Lys Asn Ser Pro Ser Ser Leu Asn Ser Pro Ser Ser Tyr Asn Cys Ser
          5                  10                  15 caa tcc atc tta ccc ctg gag cac ggc tcc ata tac ata cct tcc tcc      573
Gln Ser Ile Leu Pro Leu Glu His Gly Ser Ile Tyr Ile Pro Ser Ser
 20                  25                  30                  35 tat gta gac agc cac cat gaa tat cca gcc atg aca ttc tat agc cct      621
Tyr Val Asp Ser His His Glu Tyr Pro Ala Met Thr Phe Tyr Ser Pro
                 40                  45                  50 gct gtg atg aat tac agc att ccc agc aat gtc act aac ttg gaa ggt      669
Ala Val Met Asn Tyr Ser Ile Pro Ser Asn Val Thr Asn Leu Glu Gly
             55                  60                  65 ggg cct ggt cgg cag acc aca agc cca aat gtg ttg tgg cca aca cct      717
Gly Pro Gly Arg Gln Thr Thr Ser Pro Asn Val Leu Trp Pro Thr Pro
         70                  75                  80 ggg cac ctt tct cct tta gtg gtc cat cgc cag tta tca cat ctg tat      765
Gly His Leu Ser Pro Leu Val Val His Arg Gln Leu Ser His Leu Tyr
 85                  90                  95 gcg gaa cct caa aag agt ccc tgg tgt gaa gca aga tcg cta gaa cac      813
Ala Glu Pro Gln Lys Ser Pro Trp Cys Glu Ala Arg Ser Leu Glu His
100                 105                 110                 115 acc tta cct gta aac aga gag aca ctg aaa agg aag gtt agt ggg aac      861
Thr Leu Pro Val Asn Arg Glu Thr Leu Lys Arg Lys Val Ser Gly Asn
                 120                 125                 130 cgt tgc gcc agc cct gtt act ggt cca ggt tca aag agg gat gct cac      909
Arg Cys Ala Ser Pro Val Thr Gly Pro Gly Ser Lys Arg Asp Ala His
            135                 140                 145 ttc tgc gct gtc tgc agc gat tac gca tcg gga tat cac tat gga gtc      957
Phe Cys Ala Val Cys Ser Asp Tyr Ala Ser Gly Tyr His Tyr Gly Val
        150                 155                 160
```

```
tgg tcg tgt gaa gga tgt aag gcc ttt ttt aaa aga agc att caa gga      1005
Trp Ser Cys Glu Gly Cys Lys Ala Phe Phe Lys Arg Ser Ile Gln Gly
    165                 170                 175 cat aat gat tat att tgt cca gct aca aat cag tgt aca atc gat aaa      1053
His Asn Asp Tyr Ile Cys Pro Ala Thr Asn Gln Cys Thr Ile Asp Lys
180                 185                 190                 195 aac cgg cgc aag agc tgc cag gcc tgc cga ctt cgg aag tgt tac gaa      1101
Asn Arg Arg Lys Ser Cys Gln Ala Cys Arg Leu Arg Lys Cys Tyr Glu
                200                 205                 210 gtg gga atg gtg aag tgt ggc tcc cgg aga gag aga tgt ggg tac cgc      1149
Val Gly Met Val Lys Cys Gly Ser Arg Arg Glu Arg Cys Gly Tyr Arg
            215                 220                 225 ctt gtg cgg aga cag aga agt gcc gac gag cag ctg cac tgt gcc ggc      1197
Leu Val Arg Arg Gln Arg Ser Ala Asp Glu Gln Leu His Cys Ala Gly
        230                 235                 240 aag gcc aag aga agt ggc ggc cac gcg ccc cga gtg cgg gag ctg ctg      1245
Lys Ala Lys Arg Ser Gly Gly His Ala Pro Arg Val Arg Glu Leu Leu
    245                 250                 255 ctg gac gcc ctg agc ccc gag cag cta gtg ctc acc ctc ctg gag gct      1293
Leu Asp Ala Leu Ser Pro Glu Gln Leu Val Leu Thr Leu Leu Glu Ala
260                 265                 270                 275 gag ccg ccc cat gtg ctg atc agc cgc ccc agt gcg ccc ttc acc gag      1341
Glu Pro Pro His Val Leu Ile Ser Arg Pro Ser Ala Pro Phe Thr Glu
                280                 285                 290 gcc tcc atg atg atg tcc ctg acc aag ttg gcc gac aag gag ttg gta      1389
Ala Ser Met Met Met Ser Leu Thr Lys Leu Ala Asp Lys Glu Leu Val
            295                 300                 305 cac atg atc agc tgg gcc aag aag att ccc ggc ttt gtg gag ctc agc      1437
His Met Ile Ser Trp Ala Lys Lys Ile Pro Gly Phe Val Glu Leu Ser
        310                 315                 320 ctg ttc gac caa gtg cgg ctc ttg gag agc tgt tgg atg gag gtg tta      1485
Leu Phe Asp Gln Val Arg Leu Leu Glu Ser Cys Trp Met Glu Val Leu
    325                 330                 335 atg atg ggg ctg atg tgg cgc tca att gac cac ccc ggc aag ctc atc      1533
Met Met Gly Leu Met Trp Arg Ser Ile Asp His Pro Gly Lys Leu Ile
340                 345                 350                 355 ttt gct cca gat ctt gtt ctg gac agg gat gag ggg aaa tgc gta gaa      1581
Phe Ala Pro Asp Leu Val Leu Asp Arg Asp Glu Gly Lys Cys Val Glu
                360                 365                 370 gga att ctg gaa atc ttt gac atg ctc ctg gca act act tca agg ttt      1629
Gly Ile Leu Glu Ile Phe Asp Met Leu Leu Ala Thr Thr Ser Arg Phe
            375                 380                 385 cga gag tta aaa ctc caa cac aaa gaa tat ctc tgt gtc aag gcc atg      1677
Arg Glu Leu Lys Leu Gln His Lys Glu Tyr Leu Cys Val Lys Ala Met
        390                 395                 400 atc ctg ctc aat tcc agt atg tac cct ctg gtc aca gcg acc cag gat      1725
Ile Leu Leu Asn Ser Ser Met Tyr Pro Leu Val Thr Ala Thr Gln Asp
    405                 410                 415 gct gac agc agc cgg aag ctg gct cac ttg ctg aac gcc gtg acc gat      1773
Ala Asp Ser Ser Arg Lys Leu Ala His Leu Leu Asn Ala Val Thr Asp
420                 425                 430                 435 gct ttg gtt tgg gtg att gcc aag agc ggc atc tcc tcc cag cag caa      1821
Ala Leu Val Trp Val Ile Ala Lys Ser Gly Ile Ser Ser Gln Gln Gln
                440                 445                 450 tcc atg cgc ctg gct aac ctg ctg atg ctg ctg tcc cac gtc agg cat      1869
Ser Met Arg Leu Ala Asn Leu Leu Met Leu Leu Ser His Val Arg His
            455                 460                 465 gcg agt aac aag ggc atg gaa cat ctg ctc aac atg aag tgc aaa aat      1917
Ala Ser Asn Lys Gly Met Glu His Leu Leu Asn Met Lys Cys Lys Asn
```

-continued

```
                470                 475                 480
gtg gtc cca gtg tat gac ctg ctg ctg gag atg ctg aat gcc cac gtg      1965
Val Val Pro Val Tyr Asp Leu Leu Leu Glu Met Leu Asn Ala His Val
485                 490                 495 ctt cgc ggg tgc aag tcc tcc atc acg ggg tcc gag tgc agc ccg gca      2013
Leu Arg Gly Cys Lys Ser Ser Ile Thr Gly Ser Glu Cys Ser Pro Ala
500                 505                 510                 515 gag gac agt aaa agc aaa gag ggc tcc cag aac cca cag tct cag tga      2061
Glu Asp Ser Lys Ser Lys Glu Gly Ser Gln Asn Pro Gln Ser Gln
                520                 525                 530 cgcctggccc tgaggtgaac tggcccacag aggtcacagg ctgaagcgtg aactccagtg    2121
tgtcaggagc ctgggcttca tctttctgct gtgtggtccc tcatttgg                 2169

<210> SEQ ID NO 32
<211> LENGTH: 530
<212> TYPE: PRT
<213> ORGANISM: Homo sapiens

<400> SEQUENCE: 32

Met Asp Ile Lys Asn Ser Pro Ser Ser Leu Asn Ser Pro Ser Ser Tyr
1               5                   10                  15

Asn Cys Ser Gln Ser Ile Leu Pro Leu Glu His Gly Ser Ile Tyr Ile
                20                  25                  30

Pro Ser Ser Tyr Val Asp Ser His His Glu Tyr Pro Ala Met Thr Phe
            35                  40                  45

Tyr Ser Pro Ala Val Met Asn Tyr Ser Ile Pro Ser Asn Val Thr Asn
        50                  55                  60

Leu Glu Gly Gly Pro Gly Arg Gln Thr Thr Ser Pro Asn Val Leu Trp
65                  70                  75                  80

Pro Thr Pro Gly His Leu Ser Pro Leu Val Val His Arg Gln Leu Ser
                85                  90                  95

His Leu Tyr Ala Glu Pro Gln Lys Ser Pro Trp Cys Glu Ala Arg Ser
                100                 105                 110

Leu Glu His Thr Leu Pro Val Asn Arg Glu Thr Leu Lys Arg Lys Val
            115                 120                 125

Ser Gly Asn Arg Cys Ala Ser Pro Val Thr Gly Pro Gly Ser Lys Arg
        130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
            180                 185                 190

Ile Asp Lys Asn Arg Arg Lys Ser Cys Gln Ala Cys Arg Leu Arg Lys
        195                 200                 205

Cys Tyr Glu Val Gly Met Val Lys Cys Gly Ser Arg Arg Glu Arg Cys
    210                 215                 220

Gly Tyr Arg Leu Val Arg Arg Gln Arg Ser Ala Asp Glu Gln Leu His
225                 230                 235                 240

Cys Ala Gly Lys Ala Lys Arg Ser Gly Gly His Ala Pro Arg Val Arg
                245                 250                 255

Glu Leu Leu Leu Asp Ala Leu Ser Pro Glu Gln Leu Val Leu Thr Leu
            260                 265                 270

Leu Glu Ala Glu Pro Pro His Val Leu Ile Ser Arg Pro Ser Ala Pro
        275                 280                 285
```

Phe Thr Glu Ala Ser Met Met Met Ser Leu Thr Lys Leu Ala Asp Lys
    290                 295                 300

Glu Leu Val His Met Ile Ser Trp Ala Lys Lys Ile Pro Gly Phe Val
305                 310                 315                 320

Glu Leu Ser Leu Phe Asp Gln Val Arg Leu Leu Glu Ser Cys Trp Met
                325                 330                 335

Glu Val Leu Met Met Gly Leu Met Trp Arg Ser Ile Asp His Pro Gly
            340                 345                 350

Lys Leu Ile Phe Ala Pro Asp Leu Val Leu Asp Arg Asp Glu Gly Lys
        355                 360                 365

Cys Val Glu Gly Ile Leu Glu Ile Phe Asp Met Leu Leu Ala Thr Thr
370                 375                 380

Ser Arg Phe Arg Glu Leu Lys Leu Gln His Lys Glu Tyr Leu Cys Val
385                 390                 395                 400

Lys Ala Met Ile Leu Leu Asn Ser Ser Met Tyr Pro Leu Val Thr Ala
                405                 410                 415

Thr Gln Asp Ala Asp Ser Ser Arg Lys Leu Ala His Leu Leu Asn Ala
            420                 425                 430

Val Thr Asp Ala Leu Val Trp Val Ile Ala Lys Ser Gly Ile Ser Ser
        435                 440                 445

Gln Gln Gln Ser Met Arg Leu Ala Asn Leu Leu Met Leu Leu Ser His
    450                 455                 460

Val Arg His Ala Ser Asn Lys Gly Met Glu His Leu Leu Asn Met Lys
465                 470                 475                 480

Cys Lys Asn Val Val Pro Val Tyr Asp Leu Leu Leu Glu Met Leu Asn
                485                 490                 495

Ala His Val Leu Arg Gly Cys Lys Ser Ser Ile Thr Gly Ser Glu Cys
            500                 505                 510

Ser Pro Ala Glu Asp Ser Lys Ser Lys Glu Gly Ser Gln Asn Pro Gln
        515                 520                 525

Ser Gln
    530

<210> SEQ ID NO 33
<211> LENGTH: 27
<212> TYPE: PRT
<213> ORGANISM: Artificial Sequence
<220> FEATURE:
<223> OTHER INFORMATION: PHB2-binding peptide derived from BIG3 with
      11R-GGG at the N terminal

<400> SEQUENCE: 33

Arg Arg Arg Arg Arg Arg Arg Arg Arg Arg Arg Gly Gly Gly Gln Met
1               5                   10                  15

Leu Ser Asp Leu Thr Leu Gln Leu Arg Gln Arg
                20                  25

<210> SEQ ID NO 34
<211> LENGTH: 13
<212> TYPE: PRT
<213> ORGANISM: Artificial Sequence
<220> FEATURE:
<223> OTHER INFORMATION: Stapled PHB2-binding D-peptide without olefin
<220> FEATURE:
<221> NAME/KEY: MISC_FEATURE
<223> OTHER INFORMATION: all amino acids of SEQ ID NO:34 are D-amino
      Acids
<220> FEATURE:
<221> NAME/KEY: MISC_FEATURE

```
<222> LOCATION: (3)..(3)
<223> OTHER INFORMATION: Glutamine analog for stapling by intramolecular
      amidation
<220> FEATURE:
<221> NAME/KEY: MISC_FEATURE
<222> LOCATION: (7)..(7)
<223> OTHER INFORMATION: Glutamine analog for stapling by intramolecular
      amidation

<400> SEQUENCE: 34

Gln Met Xaa Ser Asp Leu Xaa Leu Gln Leu Arg Gln Arg
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Stapled PHB2-binding retroinverse peptide
      without olefin
<220> FEATURE:
<221> NAME/KEY: MISC_FEATURE
<223> OTHER INFORMATION: all amino acids of SEQ ID NO:35 are D-amino
      Acids
<220> FEATURE:
<221> NAME/KEY: MISC_FEATURE
<222> LOCATION: (7)..(7)
<223> OTHER INFORMATION: Glutamine analog for stapling by intramolecular
      amidation
<220> FEATURE:
<221> NAME/KEY: MISC_FEATURE
<222> LOCATION: (11)..(11)
<223> OTHER INFORMATION: Glutamine analog for stapling by intramolecular
      amidation

<400> SEQUENCE: 35

Arg Gln Arg Leu Gln Leu Xaa Leu Asp Ser Xaa Met Gln
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Short stapled PHB2-binding retroinverse peptide
      without olefin
<220> FEATURE:
<221> NAME/KEY: MISC_FEATURE
<223> OTHER INFORMATION: all amino acids of SEQ ID NO:36 are D-amino
      Acids
<220> FEATURE:
<221> NAME/KEY: MISC_FEATURE
<222> LOCATION: (1)..(1)
<223> OTHER INFORMATION: Glutamine analog for stapling by intramolecular
      amidation
<220> FEATURE:
<221> NAME/KEY: MISC_FEATURE
<222> LOCATION: (5)..(5)
<223> OTHER INFORMATION: Glutamine analog for stapling by intramolecular
      amidation

<400> SEQUENCE: 36

Xaa Leu Asp Ser Xaa Met Gln
1               5
```